(12) United States Patent
Yamamoto et al.

(10) Patent No.: US 6,710,060 B2
(45) Date of Patent: Mar. 23, 2004

(54) 4-HYDROXYPIPERIDINE DERIVATIVES HAVING ANTIARRHYTHMIC ACTIVITY

(75) Inventors: Ichiro Yamamoto, Shinjuku-ku (JP); Manabu Itoh, Shinjuku-ku (JP); Fumiaki Yamasaki, Shinjuku-ku (JP); Yutaka Miyazaki, Shinjuku-ku (JP); Shinichi Ogawa, Shinjuku (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 15 days.

(21) Appl. No.: 09/969,639

(22) Filed: Oct. 4, 2001

(65) Prior Publication Data

US 2002/0188006 A1 Dec. 12, 2002

Related U.S. Application Data

(63) Continuation-in-part of application No. PCT/JP00/02331, filed on Apr. 10, 2000.

(30) Foreign Application Priority Data

Apr. 9, 1999  (JP) ............................................. 11-103212

(51) Int. Cl.[7] ...................... A61K 31/445; C07D 409/06
(52) U.S. Cl. ........................ 514/326; 546/212; 546/213; 546/217; 514/327
(58) Field of Search ................................ 546/212, 213, 546/217; 514/326, 327

(56) References Cited

U.S. PATENT DOCUMENTS

| | | | |
|---|---|---|---|
| 3,350,403 A | | 10/1967 | Biel et al. |
| 3,998,834 A | * | 12/1976 | Janssen et al. ............... 546/213 |
| 4,178,377 A | | 12/1979 | Rissi et al. |
| 4,248,877 A | | 2/1981 | Rissi et al. |
| 4,508,724 A | | 4/1985 | Taylor, Jr. et al. |

FOREIGN PATENT DOCUMENTS

| | | |
|---|---|---|
| CH | 586 198 | 6/1973 |
| CH | 587 812 | 6/1973 |
| CH | 587 822 | 6/1973 |
| CH | 586 199 | 7/1973 |
| EP | 0 867 183 A1 | 9/1998 |

OTHER PUBLICATIONS

Janssen et al. "4–anilinopiperidines" CA 92:128743 (1980).*
Suh et al. "Concise and versital syntheses of n–arylalkylpiperidines . . . " CA 1128:203598 (1998).*
Shin et al. "total synthesis of sufentanil" CA 131;336918 (1999).*
Suh et al. "Concise and versatile synthesis . . . " CA 128:294668 (1998).*
"Synthesis and Pharmacological Studies of 4, 4–Disubstituted Piperidines: A New Class of Compounds With Potent Analgesic Properties" by Bruno S. Huegi et al., American Chemical Society, Aug. 21, 1982, pp. 42–50.
Suh, Y.–G.; Shin, D.–Y.; Cho, K.–H.; Ryu, J.–S.: "Concise and versatile synthesis of N–arylalkylpiperidines as potential intermediates for 4–anilidopiperidine analgesics" Heterocycles, Elsevier Science Publishers B.V. Amsterdam, NL, vol. 48, No. 2, 1998, pp. 239–242, XP001063134.

* cited by examiner

Primary Examiner—Ceila Chang
(74) Attorney, Agent, or Firm—Oliff & Berridge, PLC

(57) ABSTRACT

The present invention relates to a compound represented by the following formula (I) or a salt thereof, or a pharmaceutical composition containing the compound as an effective ingredient:

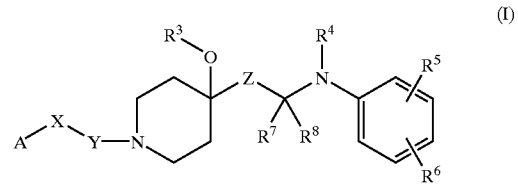

(wherein A represents, for example, phenyl group substituted with $R^1$ and $R^2$ or unsubstituted thienyl group; $R^1$ and $R^2$ each independently represent, for example, hydrogen atom, halogen atom or lower alkoxycarbonyl group; $R^3$ represents, for example, hydrogen atom; $R^4$ represents, for example, lower alkyl group; $R^5$ represents, for example, lower alkoxy group; $R^6$ represents, for example, hydrogen atom; $R^7$ and $R^8$ each represent, for example, hydrogen atom, respectively; X represents, for example, a single bond; Y represents, for example, methylene group or benzylidene group substituted with $R^1$; and Z represents, for example, methylene group.) The compounds according to the present invention that do not suppress the transient sodium current of the cardiac muscle and do not manifest proarrhythimic activity is useful as a therapeutic agent for preventing and/or treating arrhythimia and for preventing sudden death.

10 Claims, No Drawings

4-HYDROXYPIPERIDINE DERIVATIVES HAVING ANTIARRHYTHMIC ACTIVITY

BACKGROUND OF THE INVENTION

1. Field of the Invention

The present invention relates to novel 4-hydroxypiperidine derivatives, a method for manufacturing thereof, and a pharmaceutical composition comprising at least one of the derivatives as active ingredients, in particular an antiarrythmic agent capable of oral administration.

2. Description of Related Art

The heart can regularly beat when the excitation initiated at the sinus node conducts in a correct order. Arrythmia is generated when abnormal excitation and conduction to the heart are caused. Accordingly, the mechanism of onset of arrythmia is categorized into three groups of (1) abnormal excitation (2) abnormal conduction of excitation and (3) a combination of abnormal excitation and abnormal conduction of excitation.

Vaughan Williams, Singh and Houswirth have categorized antiarrythmic agents into four classes based on their action in the first half of 1970's. Since then, this classification—namely the Vaughan Williams classification—has been utilized as a standard classification of the antiarrythmic agents. This classification method is excellent in that it briefly expresses features of pharmacological action of various antiarrythmic agents, and has been utilized by many physicians. This classification method roughly classifies the antiarrythmic agents into four classes of the class I to class IV.

The antiarrythmic agents classified into the class I are medicines which have mainly a sodium channel blocking activity, and reduce the maximum upstroke velocity of depolarization at the 0-th phase of the action potential, thereby reducing the conduction speed. The class I agents are further classified into sub-classes of Ia, Ib and Ic based on their effects on the action potential duration. The class I agents are featured in reduction of the cardiac contractility as a result of reduced intracellular calcium concentration due to activation of a sodium/calcium exchange mechanism, because the intracellular sodium concentration is reduced by blocking the sodium channel. Reduction of the cardiac contractility is one of crucial adverse effects of the class I antiarrythmic agents comparable to a proarrhythmic activity directly related to suppression of conduction due to the sodium channel blocking activity.

The antiarrythmic agents belonging to the class II are medicines which mainly have a β-receptor blocking activity. Stimulation of the β ($β_1$)-receptor in the cardiac muscle cells with catecholamines activates adenylate cyclase, enhances production of cyclic AMP and increases the inward calcium current. As a result, physiological automaticity of the sinus node as well as abnormal automaticity in the morbid cardiac muscle are exacerbated. Action potential duration is also shortened by activating various ion channels related to repolarization. Although the class II antiarrythmic agents are effective against the arrhythimia related to the sympathetic nerve by their antagonistic activity against the action of catecholamines, adverse effects such as suppression of cardiac function due to β-receptor blocking activity is worried.

The antiarrythmic agents belonging to the class III are defined as the medicines with a primary action to retard repolarization and prolong of the action potential duration. These agents suppress arrythmia by prolonging refractory period as a result of prolongation of the action potential duration. It was made clear from recent studies that blocking action on the potassium channel is mainly responsible for the principal action of such agent, and a term "pottasium channel blocker" is currently synonymous with the class III agent. The class III agents are advantageous over the class I agents in that the former shows no suppression on cardiac contractility. On the other hand, "torsades de pointes" as a result of a prolonged QT interval is a crucial and potentially lethal adverse effect common to the class III agents.

The antiarrythmic agents classified into the class IV is defined as medicines the main action of which is the blocking of the calcium channel. Although the agents are used for treating arrythmia caused by acceleration of automaticity in the sinus node and arrythmia related to the atrioventricular node, an antiarrythmic agent, for example, verapamil may weaken contraction force of the cardiac muscle.

In the Cardiac Arrythmia Suppression Trial (CAST) operated in 1989 in USA, Flecainide and Encainide belonging to the class I antarrythmic agents were used for postmyocardial infarction patients with silent and mild symptoms of ventricular extrasystole, and it was found that incidence of sudden death increases in the group administered with test drugs (Echt, D. A. et al., The new England Journal of Medicine, Vol. 324, pp.781–788, 1991). In other words, it was shown that suppression of ventricular extrasystole by the class I agents does not always suppress severe arrythmia such as ventricular fibrillation that is considered to cause sudden death. This research report aroused the need of paying attention to an appropriate use of the antiarrythmic agents, besides affording novel antiarrythmic agents to be developed. In place of conventional chemicals represented by powerful sodium channel blockers that have been used in the CAST study and suppress depolarization process of the cardiac muscle, potassium channel blockers that prolong the refractory period by prolonging the repolarization process have been expected to be the antiarrythmic agents for preventing sudden death. Clinical trials with amiodarone and sotalol at an early stage have accelerated this trend, and the potassium channel blocker without severe side-effects of amiodarone (for example, interstitial pneumonia and fibrosis of the lung) has been largely expected. However, developments of d-sotalol, E-4031 and sematilide have been suspended since it was proved that the incidence of "torsades de pointes" accompanied by the QT prolongation was unexpectedly high in clinical trials in Japan as well as those in the USA and Europe with large scale in addition to the increase of mortality by these drugs. No antiarrythmic agent that can suppress sudden death of the arrythmia patients with basal diseases such as ischemic heart diseases and heart failure while avoiding the severe side-effects of amiodarone (for example, interstitial pneumonia and fibrosis of the lung) have been discovered in the present time. The large problems involved in drug therapy of arrythmia are (1) the class I and class III agents that affect conduction velocity and action potential duration by acting on the normal cardiac muscle cannot be safe antiarrythmic agents since they have proarrythmic action, and (2) the class II and class IV agents are only effective to limited symptoms of arrythmia. Accordingly, developments of novel type of antiarrythmic agents that are highly safe while avoiding the drawbacks of the antiarrythmic agents belonging to the class I to class IV classification are desired.

The sodium current normally observed in the excitable cells is rapidly inactivated after being promptly activated by a stimulus (depolarization), and thus the observed current is a transient inward current. The class I agent suppresses this transient sodium current, and decreases the maximum upstroke velocity of depolarization at the 0-th phase of the action potential to reduce the conduction velocity. However, some kinds of the sodium current are slowly or seldom inactivated, and these currents are considered to be involved in adjustment of physiological excitability of the neurons and cardiac myocytes. This sort of current is called as a persistent sodium current. This current is suggested to be involved in abnormal excitability of the neurons (for example, epileptic attack and ischemia) and morbidity of the cardiac myocytes (for example, onset of arrythmia), as reported by Segal, M. M. et al. (Journal of Neurophysiology, Vol. 77, pp. 3021–3034, 1997) and Ju, Y-K et al. (Journal of Physiology, Vol. 497, No. 2, pp. 337–347, 1996).

While lidocaine and quinidine are reported as the compounds for suppressing the persistent sodium current in the cardiac muscle (Ju, Y-K et al., British Journal of Pharmacology, Vol. 107, pp. 311–316, 1992), these compounds belong to the class I agent, and exhibit no specificity since they suppress the persistent sodium current as well as the transient sodium current. While phenytoin is reported to suppress these currents in the neurons (Segal et al., Journal of Neurophysiology, Vol. 77, pp. 3021–3034, 1997), phenytoin also has no specificity since it is categorized in the class I antiarrythmic agent.

Although 4-hydroxypiperidine derivatives have been reported to be the compounds having an analgesic activity in Japanese Patent Application Laid-open No. Sho 50-36471, an antiarrythmic action as described in the compound according to the present invention has not been disclosed therein. Although piperidine derivatives having an antiarrythmic activity have been disclosed in Japanese Patent Application Laid-open No. Sho 59-225161, the compounds have different structures from the compounds according to the present invention, and are suspected of having side-effects adverse on the activity of the normal cardiac muscle. Therefore, the compounds of the publication have not been developed as commercially available drugs. While Japanese National Patent Publication No. Hei 6-50093 discloses 4-substituted piperidine derivatives having the calcium blocking activity as neuro protective agents, the antiarrythmic activity as disclosed in the compounds according to the present invention has not been disclosed.

Not only desired pharmaceutical activities but also long-term safety are required in the development of medicines. In addition, severe criteria in various tests on absorption, distribution, metabolism and excretion should be satisfied. For example, problems to be examined and solved include interaction among the drugs, desentitization and tolerance, absorption at the digestive tract after oral administration, transfer speed into the small intestines, absorption velocity and first pass effect, internal organ barrier, binding to proteins, induction of drug metabolizing enzymes, the excretion pathway, clearance in the body and the methods of application (application sites, methods and objects). However, compounds satisfying all these requirements can be seldom found.

The antiarrythmic agent also involves such general problems as described above in developing as a medicine. The antiarrythmic agent is further required to avoid several problems as hitherto described such as proarrythmic activity, cardiac depression, torsades de pointes accompanied by prolongation of the QT interval, and increased incidence of sudden death.

SUMMARY OF THE INVENTION

The object of the present invention is to provide a novel compounds having an antiarrythmic activities with less side-effect and high grade of safety. Another object of the present invention is to provide methods for manufacturing the compounds Ad and to provide medicines and pharmaceutical compositions containing the compounds. In particular, the object of the present invention is to provide a drug, particularly an anti-arrythmic agent, capable of orally administering to mammals including humans, wherein at least one problem in the conventional art, for example, an proarrythmic action, a cardiac depression and torsades de pointes accompanied by a prolonged QT interval involved in the conventional drugs have been conquered. The medicines also have less proarrythmic action and cardiac depression so that conduction and action potential duration of the normal cardiac myocytes are not affected, and sudden death can be prevented.

DETAILED DESCRIPTION OF THE INVENTION

The inventors of the present invention have found that, through intensive studies for obtaining chemicals having an excellent antiarrythmic action with high safety, novel 4-hydroxypiperidine derivatives and salts thereof have a suppressing action against contracture of the isolated cardiac muscle caused by veratrine, oral administration of the chemicals is effective in an ischemia-reperfusion model, have no effects on the normal activity in cardiac myocytes, and have less adverse effects while being highly safe, thereby completing the present invention.

The first embodiment of the present invention is to provide a compound represented by the formula (I):

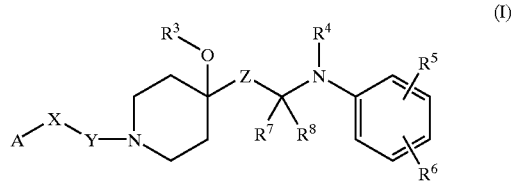

(wherein A represents a phenyl group, naphthyl group or monocyclic aromatic heterocyclic group each substituted by $R^1$ and $R^2$; $R^1$ and $R^2$ each independently represent groups arbitrarily selected from a group comprising hydrogen atom, halogen atom, trifluoromethyl group, cyano group, lower alkoxycarbonyl group, amino group unsubstituted or mono- or di-substituted by lower alkyl group, lower alkanoylamino group unsubstituted or substituted by fluorine atom, unprotected or protected hydroxyl group, lower alkoxy group, lower alkyl group, trifluoromethoxy group, nitro group, phenyl group, phenoxy group, unprotected or protected carboxyl group, carbamoyl group unsubstituted or mono- or di-substituted by lower alkyl group, lower alkanoyl group, lower alkylthio group, lower alkylsulfinyl group, lower alkylsulfonyl group and sulfamoyl group unsubstituted or mono- or di-substituted by lower alkyl group, or $R^1$ and $R^2$ together represent alkylenedioxy group; $R^3$ represents hydrogen atom or lower alkyl group; $R^4$ represents hydrogen atom, lower alkyl group or lower alkanoyl group; $R^5$ and $R^6$ each independently represent a group arbitrarily selected from a group comprising hydrogen atom, halogen atom, lower alkoxy group unsubstituted or mono-substituted by unprotected or protected hydroxyl group, lower alkyl group unsubstituted or mono-substituted by unprotected or protected hydroxyl group, phenoxy group, lower alkenyloxy group or unprotected or protected hydroxyl group; X represents a single bond, a group: —CH(OH)—, oxygen atom or carbonyl group; Y represents lower alkylene group, lower alkylidene group or benzylidene group substituted by $R^1$, Y may form 5- or 6-membered ring together with X and carbon atoms on a benzene ring when A is phenyl group; Z represents a single bond or methylene group unsubstituted or substituted by a group arbitrarily selected from a group comprising a lower alkyl group, lower alkoxy group or unprotected or protected hydroxyl group; and $R^7$ and $R^8$ each independently represent hydrogen atom or lower alkyl groups, provided that a case that $R^5$ and $R^6$ simultaneously represent hydrogen atoms is excluded) and pharmaceutically acceptable salts thereof and a pharmaceutical composition containing these compounds as active ingredients.

Preferable substituents or preferable combinations thereof in the compound represented by the formula (I) are shown below. However, the present invention is by no means restricted thereto.

A is preferably phenyl group or thienyl group each substituted by $R^1$ and $R^2$, more preferably phenyl group substituted by $R^1$ and $R^2$ or an unsubstituted thienyl group. In addition, it is preferable that A is phenyl group substituted by $R^1$ and $R^2$, and $R^1$ is bound to a para-position (4-position) relative to —X—.

$R^1$ and $R^2$ each are preferably hydrogen atom, halogen atom, trifluoromethyl group, cyano group, lower alkoxycarbonyl group, lower alkanoylamino group unsubstituted or substituted by fluorine atom, lower alkoxy group, lower alkyl group, trifluoromethoxy group, nitro group or lower alkylthio group, and more preferably hydrogen atom, halogen atom, trifluoromethyl group, cyano group, lower alkoxycarbonyl group or trifluoromethoxy group.

As the combinations of $R^1$ and $R^2$, it is preferable that $R^1$ is hydrogen atom, halogen atom, trifluoromethyl group, cyano group, lower alkoxycarbonyl group, lower alkanoylamino group unsubstituted or substituted by fluorine atom, lower alkoxy group, lower alkyl group, trifluoromethoxy group, nitro group or lower alkylthio group, and $R^2$ is hydrogen atom or halogen atom. It is more preferable that $R^1$ is hydrogen atom, halogen atom, trifluoromethyl group, cyano group, lower alkoxycarbonyl group or trifluoromethoxy group, and $R^2$ is hydrogen atom or halogen atom.

$R^3$ is preferably hydrogen atom.

$R^4$ is preferably lower alkyl group or lower alkanoyl group, more preferably lower alkyl group.

$R^5$ is preferably lower alkoxy group, lower alkyl group or phenoxy group, more preferably $C_{2-6}$ alkoxy group, and further preferably straight chaine or branched $C_{2-4}$ alkoxy group.

$R^6$ is preferably hydrogen atom, halogen atom, unprotected or protected hydroxyl group or lower alkyl group unsubstituted or mono-substituted by unprotected or protected hydroxyl group, and more preferably hydrogen atom.

As the combination of $R^5$ and $R^6$, it is preferable that $R^5$ is $C_{2-6}$ alkoxy group, and $R^6$ is hydrogen atom, and it is more preferable that $R^5$ is straight chian or branched $C_{2-4}$ alkoxy group, and $R^6$ is hydrogen atom.

$R^5$ is preferably bound to a para-position (4-position) relative to —$NR^4$—.

X is preferably a single bond or a group: —CH(OH)—, and more preferably a single bond.

Y is preferably $C_{1-2}$ alkylene group or benzylidene group substituted by $R^1$, and more preferably methylene group or benzylidene group substituted by $R^1$.

Y preferably forms indanyl group when A is a phenyl group and 5- to 6-membered ring is formed together with X and carbon atoms on the benzene ring.

Z is preferably a single bond or methylene group unsubstituted or substituted by hydroxyl group, and more preferably methylene group.

$R^7$ and $R^8$ each are preferably hydrogen atoms.

As the combination of the substituents is preferable that the bonding position of $R^5$ is at the para-position (4-position) relative to the group —$NR^4$—, $R^7$ and $R^8$ each are hydrogen atom, X is a single bond, and Y is $C_{1-2}$ alkylene group or benzylidene group substituted by $R^1$.

It is preferable that A is phenyl group or thienyl group each substituted by $R^1$ and $R^2$, $R^4$ is lower alkyl group, and Z is a single bond or methylene group.

It is preferable that $R^1$ is hydrogen atom, halogen atom, trifluoromethyl group, cyano group, lower alkoxycarbonyl group or trifluoromethoxy group, $R^2$ is hydrogen atom or halogen atom, $R^3$ is hydrogen atom, $R^5$ is $C_{2-6}$ alkoxy group, $R^6$ is hydrogen atom, and Y is methylene group benzylidene group substituted by $R^1$.

The compounds according to the present invention are the compounds represented by the formula (I) or salts thereof. Concrete examples of the compounds having combinations of preferable substituents are as follows.

In the formula (I), it is shown a compound or a salt thereof in which A is phenyl group substituted by $R^1$ and $R^2$ or unsubstituted thienyl group; $R^1$ is hydrogen atom, halogen atom, trifluoromethyl group, cyano group, lower alkoxycarbonyl group or trifluoromethoxy group; $R^2$ is hydrogen atom or halogen atom; $R^3$ is hydrogen atom; $R^4$ is methyl group; $R^5$ is straight chain or branched $C_{2-4}$ alkoxy group with its bonding position at the para-position (4-position) relative to the group —$NR^4$—; $R^6$ is hydrogen atom; $R^7$ is hydrogen atom; $R^8$ is hydrogen atom; X is a single bond; Y is methylene group or benzylidene group substituted by $R^1$; and Z is methylene group. In this case, the formula (I) may be expressed by the formula (II):

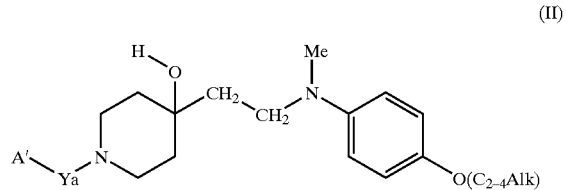

(II)

(wherein A' represents a phenyl group substituted by $R^1$ and $R^2$ or unsubstituted thienyl group, —$O(C_{2-4}$ Alk) represents straight chain or branched $C_{2-4}$ alkoxy group, and Ya represents methylene group or benzylidene group substituted by $R^1$).

The second embodiment of the present invention is to provide a pharmaceutical composition comprising the compound represented by the formula (I) or a pharmaceutically acceptable salt thereof as active ingredients.

The third embodiment of the present invention is to provide an antiarrythmic agent comprising the compound represented by the formula (I) or a pharmaceutically acceptable salt thereof as acective ingredients. The antiarrythmic agent is capable of oral administration.

The fourth embodiment of the present invention is to provide a method for manufacturing a compound represented by the formula (I)-a or a salt thereof which both $R^7$ and $R^8$ in the formula (I) are hydrogen atoms:

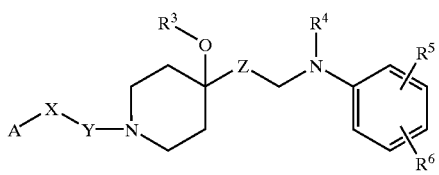

(I)-a (wherein A, R³, R⁴, R⁵, R⁶, X, Y and Z have the same meanings as defined above), comprising the following process (a) or (b).

Process (a)

A process characterized by reacting the compound represented by the formula (VI):

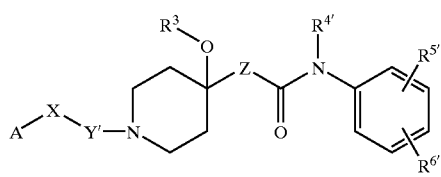

(VI)

(wherein A, R³, X and Z have the same meanings as defined above, R⁴' represents hydrogen atom or lower alkyl group, R⁵' and R⁶' have the same meanings as defined in R⁵ and R⁶, or represent lower alkoxycarbonyl group, and Y' has the same meaning as defined in Y, or represents $C_{1-2}$ alkylenecarbonyl group or carbonyl group) under reducing conditions.

Process (b)

A process characterized by reacting a compound represented by the formula (VIII):

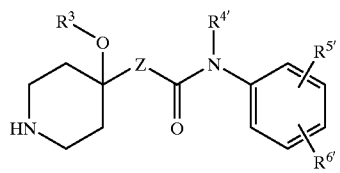

(VIII)

(wherein R³, R⁴', R⁵', R⁶' and Z have the same meanings as defined above) under reducing conditions to form a compound represented by the formula (X):

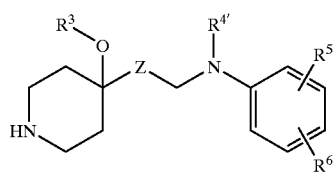

(X)

(wherein R³, R⁴', R⁵, R⁶ and Z have the same meanings as defined above) and reacting the obtained compound of the formula (X) with a compound represented by the formula (IX):

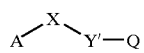

(IX)

(wherein A, X and Y' have the same meaning as defined above, and Q represent hydrogen atom, hydroxyl group, halogen atom or lower alkyl group) in the presence or absence of a base when —Y' and -Q together represent halogenated alkyl, in the presence or absence of an acid catalyst under reducing conditions when —Y' and -Q together represent aldehyde or ketone, or using a condensation agent when —Y' and -Q together represent carboxylic acid, followed by reduction reaction.

The fifth embodiment of the present invention is to provide a method for manufacturing a compound represented by the following formula (I)-b or a salt thereof which R⁷ and R⁸ in the formula (I) are simultaneously hydrogen atom and Z is Z':

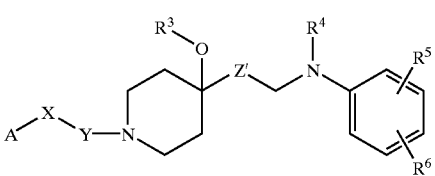

(I)-b (wherein A, R³, R⁴, R⁵, R⁶, X and Y have the same meanings as defined above, and Z' represents methylene group unsubstituted or substituted by a group arbitrarily selected from a group comprising lower alkyl group, lower alkoxy group or unprotected or protected hydroxyl group), and uses the following process (c) or (d).

Process (c)

A process characterized by adding a compound represented by the formula (XI):

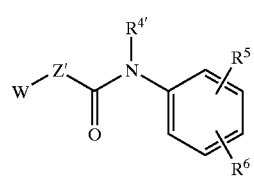

(XI)

(wherein R⁴', R⁵, R⁶ and Z' have the same meanings as defined above and W represents hydrogen atom or halogen atom) to a compound represented by the formula (XII):

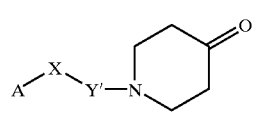

(XII)

(wherein A, X and Y' have the same meanings as defined above) and alkylating the generated hydroxy group according to the necessity to obtain a compound represented by the formula (VI'):

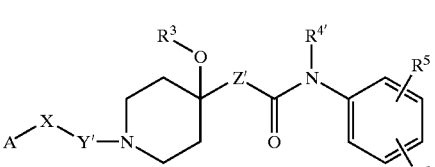

(VI')

(wherein A, R³, R⁴', R⁵, R⁶, X, Y' and Z' have the same meanings as defined above) and reacting the obtained compound (VI') under reducing conditions.

Process (d)

A process characterized by adding the compound represented by the formula (XI):

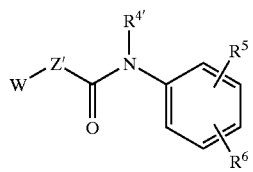 (XI)

to a compound represented by the formula (XIII):

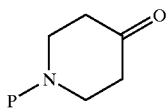 (XIII)

(wherein P represents a protective group used for an amino group) and alkylating the obtained hydroxyl group according to the necessity to obtain a compound represented by the formula (VII'):

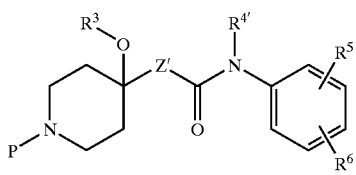 (VII')

(wherein $R^3$, $R^{4'}$, $R^5$, $R^6$, Z' and P have the same meanings as defined above), and followed by deprotection and reduction reactions to obtain a compound represented by the formula (X'):

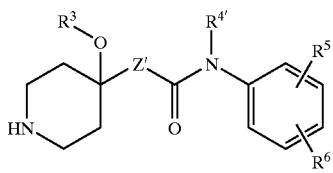 (X')

(wherein $R^3$, $R^{4'}$, $R^5$, $R^6$ and Z' have the same meaning as defined above), which is allowed to react with a compound represented by the formula (IX):

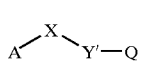 (IX)

in the presence or absence of a base when —Y' and -Q together represent halogenated alkyl, in the presence or absence of an acid catalyst under a reducing condition when —Y' and -Q together represent aldehyde or ketone groups, or using a condensation agent when —Y' and -Q together represent carboxylic acid, followed by conducting reduction reaction.

BEST MODE FOR CARRYING OUT THE INVENTION

The present invention will be described in detail hereinafter. The compounds according to the present invention are compounds represented by the formula (I) or pharmaceutically acceptable salts thereof:

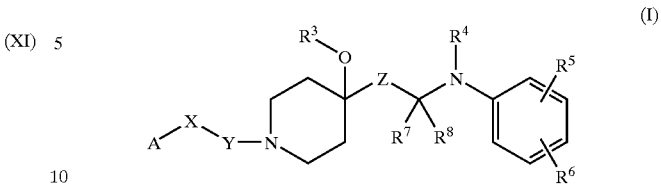 (I)

(wherein A represents phenyl group, naphthyl group or monocyclic aromatic heterocyclic group each substituted by $R^1$ and $R^2$; $R^1$ and $R^2$ each independently represent groups arbitrarily selected from a group comprising hydrogen atom, halogen atom, trifluoromethyl group, cyano group, lower alkoxycarbonyl group, amino group unsubstituted or mono- or di-substituted by lower alkyl group, lower alkanoylamino group unsubstituted or substituted by fluorine atom, unprotected or protected hydroxyl group, lower alkoxy group, lower alkyl group, trifluoromethoxy group, nitro group, phenyl group, phenoxy group, unprotected or protected carboxyl group, carbamoyl group unsubstituted or mono- or di-substituted by lower alkyl group, lower alkanoyl group, lower alkylthio group, lower alkylsulfinyl group, lower alkylsulfonyl group and sulfamoyl group unsubstituted or mono- or di-substituted by lower alkyl group, or $R^1$ and $R^2$ together represent alkylenedioxy group; $R^3$ represents hydrogen atom or lower alkyl group; $R^4$ represents a hydrogen atom, lower alkyl group or lower alkanoyl group; $R^5$ and $R^6$ each independently represent a group arbitrarily selected from a group comprising hydrogen atom, halogen atom, lower alkoxy group unsubstituted or mono-substituted by unprotected or protected hydroxyl group, lower alkyl group unsubstituted or mono-substituted by unprotected or protected hydroxyl group, phenoxy group, lower alkenyloxy group or unprotected or protected hydroxyl group; X represents a single bond, a group: —CH(OH)—, oxygen atom or carbonyl group; Y represents lower alkylene group, lower alkylidene group or benzylidene group substituted by $R^1$, Y may form 5 or 6-membered ring together with X and carbon atom on a benzene ring when A is phenyl group; Z represents a single bond or methylene group unsubstituted or substituted by a group arbitrarily selected from a group comprising a lower alkyl group, lower alkoxy group or unprotected or protected hydroxyl group; and $R^7$ and $R^8$ each independently represent hydrogen atom or lower alkyl groups, provided that a case that $R^5$ and $R^6$ simultaneously represent hydrogen atoms is excluded).

In the definitions of the groups in the structural formula according to the present invention, the "monocyclic aromatic heterocyclic" means 5 or 6-membered ring containing one or two hetero-atoms and includes, for example, pyrrolyl group, furyl group, thienyl group, imidazolyl group, oxazolyl group, thiazolyl group, pyridyl group or pyrimidinyl group.

The "halogen atom" includes fluorine atom, chlorine atom, bromine atom and iodine atom.

The term "lower" means straight, branched or cyclic carbon chain with a carbon number of 1 to 6, unless otherwise stated. Accordingly, the "lower alkyl group" includes, for example, methyl group, ethyl group, propyl group, isopropyl group, butyl group, isobutyl group, sec-butyl group, tert-butyl group, pentyl group, isopentyl group, 3-pentyl group, neopentyl group, tert-pentyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, cyclopropyl group, cyclobutyl group, cyclopentyl group, cyclohexyl group, cyclopropylmethyl group, 1-cyclopropylethyl group, 2-cyclopropylethyl group, cyclobutylmethyl group, 2-cyclobutylethyl group or cyclopentylmethyl group.

The term "lower alkyl group mono-substituted by hydroxyl group" means a group which an arbitrary hydrogen atom on the lower alkyl group is substituted by hydroxyl group. Examples of it include a hydroxymethyl group, 1-hydroxyethyl group, 2-hydroxyethyl group, 1-hydroxy-1-methylethyl group, 1-hydroxypropyl group, 2-hydroxypropyl group, 3-hydroxypropyl group, 1-hydroxy-1-methylpropyl group, 1-hydroxybutyl group, 2-hydroxybutyl group, 3-hydroxybutyl group, 4-hydroxybutyl group, 1-hydroxy-1-methylbutyl group, 1-hydroxypentyl group, 2-hydroxypentyl group, 3-hydroxypentyl group, 4-hydroxypentyl group, 5-hydroxypentyl group, 1-hydroxy-1-methylpentyl group, 1-hydroxyhexyl group, 2-hydroxyhexyl group, 3-hydroxyhexyl group, 4-hydroxyhexyl group, 5-hydroxyhexyl group, 6-hydroxyhexyl group, 1-hydroxycyclopropyl group and 1-hydroxycyclopropylmethyl group.

The "lower alkoxycarbonyl group" includes a methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, neopentyloxycarbonyl group, tert-pentyloxycarbonyl group, hexyloxycarbonyl group, cyclopropyloxycarbonyl group, cyclobutyloxycarbonyl group, cyclopentyloxycarbonyl group, cyclohexyloxycarbonyl group, cyclopropylmethyloxycarbonyl group, 1-cyclopropylethyloxycarbonyl group, 2-cyclopropylethyloxycarbonyl group, cyclobutylmethyloxycarbonyl group, 2-cyclobutylethyloxycarbonyl group or cyclopentylmethyloxycarbonyl group.

The term "the amino group unsubstituted or mono- or di-substituted by lower alkyl group" means amino group in which one or two hydrogen atoms of the amino group may be substituted by the "lower alkyl group". Example of it include amino group, methylamino group, ethylamino group, propylamino group, isopropylamino group, butylamino group, isobutylamino group, pentylamino group, isopentylamino group, hexylamino group, isohexylamino group, dimethylamino group, diethylamino group, dipropylamino group, diisopropylamino group, dibutylamino group, dipentylamino group, ethylmethylamino group, methylpropylamino group, ethylpropylamino group, butylmethylamino group, butylethylamino group or butylpropylamino group.

The "lower alkanoylamino group unsubstituted or substituted by fluorine atoms" include, for example, a formylamino group, acetylamino group, monofluoroacetylamino group, difluoroacetylamino group, trifluoroacetylamino group, propionylamino group, 2-fluoroaropionylamino group, 3-fluoropropionylamino group, 2,2-difluoropropionylamino group, 2,3-difluoropropionylamino group, 3,3,3-trifluoropropionylamino group, 2,2,3,3-tetrafluoropropionylamino group, pentafluoropropionylamino group, butyrylamino group, isobutyrylamino group, valerylamino group, isovalerylamino group, pivaloylamino group or hexanoylamino group.

The "lower alkoxy group" include, for example, a methoxy group, ethoxy group, propoxy group, isopropoxy group, butoxy group, isobutoxy group, sec-butoxy group, tert-butoxy group, pentyloxy group, isopentyloxy group, 3-pentyloxy group, tert-pentyloxy group, neopentyloxy group, 2-methylbutoxy group, 1,2-dimethylpropoxy group, 1-ethylpropoxy group, hexyloxy group, cyclopropyloxy group, cyclobutyloxy group, cyclopentyloxy group, cyclohexyloxy group, cyclopropylmethyloxy group, 1-cyclopropylethyloxy group, 2-cyclopropylethyloxy group, cyclobutylmethyloxy group, 2-cyclobutylethyloxy group or cyclopentylmethyloxy group.

The "lower alkoxy group mono-substituted by hydroxyl group" means a group in which an arbitrary hydrogen atom except at the 1-position of the lower $C_{2-6}$ alkoxy group is mono-substituted by hydroxyl group. Examples of it include 2-hydroxyethoxy group, 2-hydroxy-1-methylethoxy group, 2-hydroxypropoxy group, 3-hydroxypropoxy group, 2-hydroxybutoxy group, 3-hydroxybutoxy group, 4-hydroxybutoxy group, 2-hydroxypentyloxy group, 5-hydroxypentyloxy group, 2-hydroxyhexyloxy group, 6-hydroxyhexyloxy group, 2-hydroxycyclopropyloxy group, 2-hydroxycyclobutyloxy group, 2-hydroxycyclopentyloxy group or 3-hydroxycyclopentyloxy group.

The "carbamoyl group unsubstituted or mono- or di-substituted by lower alkyl groups" means a carbamoyl group in which one or two hydrogen atoms on the nitrogen atom in the carbamoyl group may be substituted by aforesaid "lower alkyl group". Example of it include carbamoyl group, methylcarbamoyl group, ethylcarbamoyl group, propylcarbamoyl group, isopropylcarbamoyl group, cyclopropylcarbamoyl group, butylcarbamoyl group, isobutylcarbamoyl group, pentylcarbamoyl group, isopentylcarbamoyl group, hexylcarbamoyl group, isohexylcarbamoyl group, dimethylcarbamoyl group, diethylcarbamoyl group, dipropylcarbamoyl group, diisopropyl-carbamoyl group, dibutylcarbamoyl group, dipentylcarbamoyl group, ethylmethylcarbamoyl group, methylpropylcarbamoyl group, ethylpropylcarbamoyl group, butylmethylcarbamoyl group, butylethylcarbamoyl group, or butylpropylcarbamoyl group.

Examples of the "lower alkanoyl group" include formyl group, acetyl group, propionyl group, butyryl group, isobutyryl group, valeryl group, isovaleryl group, pivaloyl group or hexanoyl group.

Examples of the "lower alkylthio group" include a methylthio group, ethylthio group, propylthio group, isopropylthio group, butylthio group, isobutylthio group, sec-butylthio group, tert-butylthio group, pentylthio group, isopentylthio group, tert-pentylthio group, neopentylthio group, 2-methylbutylthio group, 1,2-dimethylpropylthio group, 1-ethylpropylthio group, hexylthio group, cyclopropylthio group, cyclobutylthio group, cyclopentylthio group, cyclohexylthio group, cyclopropylmethylthio group, 1-cyclopropylethylthio group, 2-cyclopropylethylthio group, cyclobutylmethyl-thio group, 2-cyclobutylethylthio group or cyclopentylmethylthio group.

Examples of the "lower alkylsulfinyl group" include a methylsulfinyl group, ethylsulfinyl group, propylsulfinyl group, isopropylsulfinyl group, butylsulfinyl group, isobutylsulfinyl group, sec-butylsulfinyl group, tert-butylsulfinyl group, pentylsulfinyl group, isopentylsulfinyl group, tert-pentylsulfinyl group, neopentylsulfinyl group, 2-methylbutylsulfinyl group, 1,2-dimetylpropylsulfinyl group, 1-ethylpropylsulfinyl group, hexylsulfinyl group, cyclopropylsulfinyl group, cyclobutylsulfinyl group, cyclopentylsulfinyl group, cyclohexylsulfinyl group, cyclopropylmethylsulfinyl group, 1-cyclopropylethylsulfinyl group, 2-cyclopropylethylsulfinyl group, cyclobutylmethylsulfinyl group, 2-cyclobutylethylsulfinyl group or cyclopentylmethylsulfinyl group.

Examples of the "lower alkylsulfonyl group" include a methylsulfonyl group, ethylsulfonyl group, propylsulfonyl group, isopropylsulfonyl group, butylsulfonyl group, isobutylsulfonyl group, sec-butylsulfonyl group, tert-butylsulfonyl group, pentylsulfonyl group, isopentylsulfonyl group, tert-pentylsulfonyl group, neopentylsulfonyl group, 2-methylbutylsulfonyl group, 1,2-dimethylpropylsulfonyl group, 1-ethylpropylsulfonyl group, hexylsulfonyl group, cyclopropylsulfonyl group, cyclobutylsulfonyl group, cyclopentylsulfonyl group, cyclohexylsulfonyl group, cyclopropylmethylsulfonyl group, 1-cyclopropylethylsulfonyl group, 2-cyclopropylethylsulfonyl group, cyclobutylmethylsulfonyl group, 2-cyclobutylethylsulfonyl group or cyclopentylmethlsulfonyl group.

The "sulfamoyl group unsubstituted or mono- or di-substituted by lower alkyl group" means a sulfamoyl group in which one or two hydrogen atom on the nitrogen atom in the sulfamoyl group may be substituted by said "lower alkyl group". Examples of it include sulfamoyl group, methylsulfamoyl group, ethylsulfamoyl group, propylsulfamoyl group, isopropylsulfamoyl group, cyclopropylsulfamoyl group, butylsulfamoyl group, isobutylsulfamoyl group, pentylsulfamoyl group, isopentylsulfamoyl group, hexylsulfamoyl group, isohexylsulfamoyl group, dimethylsulfamoyl group, diethylsulfamoyl group, dipropylsulfamoyl group, disopropylsulfamoyl group, dibutylsulfamoyl group, dipentylsulfamoyl group, ethylmethylsulfamoyl group, metylpropylsulfamoyl group, ethylpropylsulfamoyl group, butylmethylsulfamoyl group, butylethylsulfamoyl group and butylpropylsulfamoyl group.

Examples of the "alkylenedioxy group" include methylenedioxy group or ethylenedioxy group.

The "lower alkenyloxy group" means a group in which one of the carbon—carbon bonds in the lower $C_{3-6}$ alkoxy group is a double bond and the position of which is not at the 1-position. Examples of it include 2-propenyloxy group, 1-methyl-2-propenyloxy group, 2-methyl-2-propenyloxy group, 1,1-dimethyl-2-propenyloxy group, 1,2-dimethyl-2-propenyloxy group, 1,1,2-trimethyl-2-propenyloxy group, 2-butenyloxy group, 1-methyl-2-butenyloxy group, 2-methyl-2-butenyloxy group, 3-methyl-2-butenyloxy group, 3-butenyloxy group, 1-metyl-3-butenyloxy group, 2-pentenyloxy group, 3-pentenyloxy group, 4-pentenyloxy group, 2-cyclopentenyloxy group, 2-hexenyloxy group, 3-hexenyloxy group, 4-hexenyloxy group, 5-hexenyloxy group, 2-cyclohexenyloxy group or 3-cyclohexenyloxy group.

The "lower alkylene or alkylidene group" is $C_{1-6}$ alkylene or $C_{1-6}$ alkylidene group, and includes methylene group, ethylene group, methylmethylene group, trimethylene group, dimethylmethylene group, tetramethylene group, methyltrimethylene group, ethylethylene group, dimethylethylene group, ethylmethylmethylene group, pentamethylene group, methyltetramethylene group, dimethyltrimethylene group, trimethylethylene group, dimethylmethylene group, hexamethylene group, methylpentamethylene group or dimethyltetramethylene group, and also includes straight-chain or branched ones of these groups.

Examples of the protective group for the "unprotected or protected hydroxyl group" described in the present specification include alkyl protective group such as a methyl group, tert-butyl group, benzyl group, trityl group and methoxymethyl group; silyl protective group such as trimethylsilyl group or tert-butyidimethylsilyl group; acyl protective group such as formyl group, acetyl group or benzoyl group; and carbonate protective group such as methoxycarbonyl group or benzyloxycarbonyl group.

Examples of the protective group for the "unprotected or protected carboxyl group" described in the present specification include alkylester protective groups such as a methyl group, ethyl group, tert-butyl group, benzyl group, diphenylmethyl group or trityl group; and silyl ester protective group such as trimethylsilyl group or tert-butyldimethylsilyl group.

Preferable embodiments in the definitions of the substituents of the compound according to the present invention are as follows.

The A is preferably phenyl group, naphthyl group, furyl group, thienyl group or pyridyl group, more preferably phenyl group or thienyl group, and further preferably phenyl group.

Preferably, $R^1$ and $R^2$ each are hydrogen atom, fluorine atom, chlorine atom, bromine atom, trifluoromethyl group, cyano group, methoxycarbonyl group, ethoxycarbonyl group, propoxycarbonyl group, isopropoxycarbonyl group, dimethylamino group, trifluoroacetylamino group, hydroxyl group, methoxy group, isopropoxy group, methyl group, isopropyl group, trifluoromethoxy group, nitro group, phenyl group, phenoxy group, carboxyl group, carbamoyl group, dimethylcarbamoyl group, acetyl group, methylthio group, methylsulfinyl group, methylsulfonyl group or sulfamoyl group, respectively, or $R^1$ and $R^2$ together form methylenedioxy group. More preferably, $R^1$ and $R^2$ each are hydrogen atom, fluorine atom, chlorine atom, bromine atom, trifluoromethyl group, cyano group, methoxycarbonyl group, ethoxycarbonyl group, propoxycarbonyl group, isopropoxycarbonyl group, trifluoroacetylamino group, methoxy group, isopropoxy group, methyl group, isopropyl group, trifluoromethoxy group, nitro group or methylthio group. Further preferably, $R^1$ and $R^2$ each are hydrogen atom, fluorine atom, chlorine atom, bromine atom, trifluoromethyl group, cyano group, methoxycarbonyl group, ethoxycarbonyl group, propoxycarbonyl group, isopropoxycarbonyl group or trifluoromethoxy group.

As the combination of $R^1$ and $R^2$, it is preferable that $R^1$ is hydrogen atom, fluorine atom, chlorine atom, bromine atom, trifluoromethyl group, cyano group, methoxycarbony group, ethoxycarbonyl group, propoxycarbonyl group, isopropoxycarbonyl group, trifluoroacetylamino group, methoxy group, isopropoxy group, methyl group, isopropyl group, trifluoromethoxy group, nitro group or methylthio group, and $R^2$ is hydrogen atom or fluorine atom. More preferably, $R^1$ is hydrogen atom, fluorine atom, chlorine atom, bromine atom, trifluoromethyl group, cyano group, methoxycarbonyl group, ethoxycarbonyl group, propoxycarbonyl group, isopropoxycarbonyl group or trifluoromethoxy group, and $R^2$ is hydrogen atom or fluorine atom.

$R^3$ is preferably hydrogen atom or methyl group, more preferably hydrogen atom.

$R^4$ is preferably hydrogen atom, methyl group, ethyl group, isopropyl group or acetyl group, more preferably methyl group, ethyl group, isopropyl group or acetyl group, and further preferably methyl group, ethyl group or isopropyl group.

$R^5$ is preferably methoxy group, ethoxy group, propoxy group, isopropoxy group, butoxy group, isobutoxy group, cyclobutoxy group, cyclopropylmethyloxy group, 2-cyclopropylethyloxy group, pentyloxy group, 3-pentyloxy group, isopentyloxy group, 2-methyl-2-butoxy group, cyclohexyloxy group, 3-butenyloxy group, 3-hydroxybutyloxy group, 4-hydroxybutyloxy group, propyl group or phenoxy group; more preferably, ethoxy group, propoxy group, isopropoxy group, butoxy group, isobutoxy group, cyclobutoxy group, cyclopropylmethyloxy group, 2-cyclopropylethyloxy group, pentyloxy group, 3-pentyloxy group, isopentyloxy group, 2-methyl-2-butoxy group or cyclohexyloxy group; and further preferably ethoxy group, propoxy group, isopropoxy group, butoxy group or isobutoxy group.

$R^6$ is preferably hydrogen atom, fluorine atom, hydroxyl group or hydroxymethyl group, more preferably hydrogen atom.

As the combination of $R^5$ and $R^6$, it is preferable that $R^5$ is ethoxy group, propoxy group, isopropoxy group, butoxy group, isobutoxy group, cyclobutoxy group, cyclopropylmethyloxy group, 2-cyclopropylethyloxy group, pentyloxy group, 3-pentyloxy group, isopentyloxy group, 2-methyl-2-butoxy group or cyclohexyloxy group, and $R^6$ is hydrogen atom. More preferably, $R^5$ is ethoxy group, propoxy group, isopropoxy group, butoxy group or isobutoxy group, and $R^6$ is hydrogen atom.

It is preferable that the binding position of $R^5$ is a para-position relative to —$NR^4$—.

X is preferably a single bond, group: —CH(OH)—, oxygen atom or carbonyl group, more preferably a single bond or group: —CH(OH)—, and further preferably a single bond.

Y is preferably methylene group, ethylene group, methylmethylene group, trimethylene group, benzylidene group or 4'-fluorobenzylidene group, more preferably methylene group, ethylene group, benzylidene group or 4'-fluorobenzylidene group, and further preferably methylene group, benzylidene group or 4'-fluorobenzylidene group.

Y is preferably forms an indanyl group when A is a phenyl group and forms 5 or 6-membered rings together with X and carbon atoms on the benzene ring.

Z is preferably a single bond or methylene group unsubstituted or substituted by methoxy group or hydroxyl group, and is more preferably methylene group.

$R^7$ and $R^8$ each are preferably hydrogen atoms.

As the combination of the substituents, it is preferable that A is a phenyl group, naphthyl group, furyl group, thienyl group or pyridyl group each substituted by $R^1$ and $R^2$, wherein $R^1$ and $R^2$ each are hydrogen atom, fluorine atom, chlorine atom, bromine atom, trifluoromethyl group, cyano group, methoxycarbonyl group, ethoxycarbonyl group, propoxycarbonyl group, isopropoxycarbonyl group, dimethylamino group, trifluoroacetylamino group, hydroxyl group, methoxy group, isopropoxy group, methyl group, isopropyl group, trifluoromethoxy group, nitro group, phenyl group, phenoxy group, carboxyl group, carbamoyl group, dimethylcarbamoyl group, acetyl group, methylthio group, methylsulfinyl group, methylsulfonyl group or sulfamoyl group, or $R^1$ and $R^2$ together form methylenedioxy group; $R^3$ is hydrogen atom or methyl group; $R^4$ is hydrogen atom, methyl group, ethyl group, isopropyl group or acetyl group; $R^5$ is methoxy group, ethoxy group, propoxy group, isopropoxy group, butoxy group, isobutoxy group, cyclobutoxy group, cyclopropylmethyloxy group, 2-cyclopropylethyloxy group, pentyloxy group, 3-pentyloxy group, isopentyloxy group, 2-methyl-2-butoxy group, cyclohexyloxy group, 3-butenyloxy group, 3-hydroxybutyloxy group, 4-hydroxybutyloxy group, propyl group or phenoxy group, and the binding position of $R^5$ is at a para-position (4-position) relative to —$NR^4$—; $R^6$ is hydrogen atom, fluorine atom, hydroxyl group or hydroxymethyl group; $R^7$ is hydrogen atom; $R^8$ is hydrogen atom; X is a single bond; Y is methylene group, ethylene group, benzylidene group or 4'-fluorobenzylidene group; and Z is a single bond or methylene group unsubstituted or substitubed by methoxy group or hydroxyl group.

Further, it is preferable that A is phenyl group or thienyl group each substituted by $R^1$ and $R^2$; $R^1$ and $R^2$ each are hydrogen atom, fluorine atom, chlorine atom, bromine atom, trifluoromethyl group, cyano group, methoxycarbonyl group, ethoxycarbonyl group, propoxycarbonyl group, isopropoxycarbonyl group, dimethylamino group, trifluoroacetylamino group, hydroxyl group, methoxy group, isopropoxy group, methyl group, isopropyl group, trifluoromethoxy group, nitro group, phenyl group, phenoxy group, carboxyl group, carbamoyl group, dimethylcarbamoyl group, acetyl group, methylthio group, methylsulfinyl group, methylsulfonyl group or sulfamoyl group, or $R^1$ and $R^2$ together form methylenedioxy group; $R^3$ is hydrogen atom or methyl group; $R^4$ is methyl group, ethyl group or isopropyl group; $R^5$ is methoxy group, ethoxy group, propoxy group, isopropoxy group, butoxy group, isobutoxy group, cyclobutoxy group, cyclopropylmethyloxy group, 2-cyclopropylethyloxy group, pentyloxy group, 3-pentyloxy group, isopentyloxy group, 2-methyl-2-butoxy group, cyclohexyloxy group, 3-butenyloxy group, 3-hydroxybutyloxy group, 4-hydroxybutyloxy group, propyl group or phenoxy group; $R^6$ is hydrogen atom, fluorine atom, hydroxyl group or hydroxymethyl group; $R^7$ is hydrogen atom; $R^8$ is hydrogen atom; X is a single bond, group: —CH(OH)—, oxygen atom or carbonyl group; Y is methylene group, ethylene group, methylmethylene group, trimethylene group, benzylidene group or 4'-fluorobenzylidene group; Y may form indanyl group when A is phenyl group and forms 5- or 6-membered rings together with X and carbon atoms on the benzene ring; and Z is a single bond or methylene group.

Further, it is preferable that A is phenyl group, naphthyl group, furyl group, thienyl group or pyridyl group each substituted by $R^1$ and $R^2$; $R^1$ is hydrogen atom, fluorine atom, chlorine atom, bromine atom, trifluoromethyl group, cyano group, methoxycarbonyl group, ethoxycarbonyl group, propoxycarbonyl group, isopropoxycarbonyl group or trifluoromethoxy group; $R^2$ is hydrogen atom or fluorine atom; $R^3$ is hydrogen atom; $R^4$ is hydrogen atom, methyl group, ethyl group, isopropyl group or acetyl group; $R^5$ is ethoxy group, propoxy group, isopropoxy group, butoxy group, isobutoxy group, cyclobutoxy group, cyclopropylmethyloxy group, 2-cyclopropylethyloxy group, pentyloxy group, 3-pentyloxy group, 3-methylbutoxy group, 2-methyl-2-butoxy group or cyclohexyloxy group; $R^6$ is hydrogen atom; $R^7$ is hydrogen atom; $R^8$ is hydrogen atom; X is a single bond, group: —CH(OH)—, oxygen atom or carbonyl group; Y is a methylene group, benzylidene group or 4'-fluorobenzylidene group; and Z is a single bond or methylene group unsubstituted or substituted by methoxy group or hydroxyl group.

While the compounds according to the present invention are compounds represented by the formula (I) or salts thereof, examples of preferable combinations of the substituents are as follows.

In the compounds represented by the formula (I) or salts thereof, A is phenyl group substituted by $R^1$ and $R^2$ or unsubstituted thienyl group; $R^1$ is hydrogen atom, halogen atom, trifluoromethyl group, cyano group, lower alkoxycarbonyl group or trifluoromethoxy group; $R^2$ is hydrogen atom or halogen atom; $R^3$ is hydrogen atom; $R^4$ is methyl group; $R^5$ is straight chain or branched $C_{2-4}$ alkoxy group, and the binding position of which is at a para-position (4-position) relative to —NR⁴—; $R^6$ is hydrogen atom; $R^7$ is hydrogen atom; $R^8$ is hydrogen atom; X is a single bond; Y is methylene group or benzylidene group substituted by $R^1$; and Z is methylene group. In this case, the formula (I) may be also expressed as the formula (II):

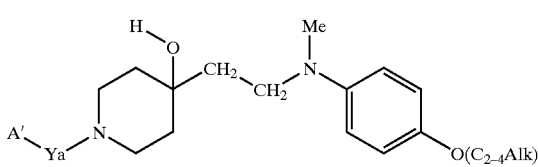

(wherein A' represents a phenyl group substituted by $R^1$ and $R^2$, or unsubstituted thienyl group; —O($C_{2-4}$Alk) represents straight chain or branched $C_{2-4}$ alkoxy group; and Ya represents methylene group or benzylidene group substituted by $R^1$).

Preferable examples of the compounds of the formula (I) include:

1-benzyl-4-[2-[N-(4-n-butoxyphenyl)-N-methylamino]ethyl]piperidin-4-ol;
1-benzyl-4-[2-[N-methyl-N-(4-n-propoxyphenyl)amino]ethyl]piperidin-4-ol;
4-[2-[N-(4-n-butoxyphenyl)-N-methylamino]ethyl]-1-(4-chlorophenylmethyl)piperidin-4-ol;
4-[2-[N-(4-n-butoxyphenyl)-N-methylamino]ethyl]-1-(4-(trifluoromethyl)phenylmethyl]piperidin-4-ol;
4-[2-[N-(4-n-butoxyphenyl)-N-methylamino]ethyl]-1-(4-cyanophenylmethyl)piperidin-4-ol;
4-[2-[N-(4-n-butoxyphenyl)-N-methylamino]ethyl]-1-(4-methoxycarbonylphenylmethyl)piperidin-4-ol;
4-[2-[N-(4-n-butoxyphenyl)-N-methylamino]ethyl]-1-(3-fluorophenylmethyl)piperidin-4-ol;
4-[2-[N-(4-n-butoxyphenyl)-N-methylamino]ethyl]-1-(3,4-diflorophenylmethyl)piperidin-4-ol;
4-[2-[N-(4-n-butoxyphenyl)-N-methylamino]ethyl]-1-(4-fluorophenylmethyl)piperidin-4-ol;
4-[2-[N-(4-n-butoxyphenyl)-N-methylamino]ethyl]-1-(2-fluorophenylmethyl)piperidin-4-ol;
1-(4-chlorophenylmethyl)-4-[2-[N-methyl-N-(4-isopropoxyphenyl)amino]ethyl]piperidin-4-ol;
1-(4-bromophenylmethyl)-4-[2-[N-methyl-N-(4-isopropoxyphenyl)amino]ethyl]piperidin-4-ol;
4-[2-[N-methyl-N-(4-isopropoxyphenyl)amino]ethyl]-1-[4-(trifluoromethyl)phenylmethyl]piperidin-4-ol;
1-(4-fluorophenylmethyl)-4-[2-[N-methyl-N-(4-isopropoxyphenyl)amino]ethyl]piperidin-4-ol;
1-(4-cyanophenylmethyl)-4-[2-[N-methyl-N-(4-isopropoxyphenyl)amino]ethyl]piperidin-4-ol;
4-[2-[N-methyl-N-(4-isopropoxyphenyl)amino]ethyl]-1-(4-nitrophenylmethyl)piperidin-4-ol;
1-[4-(methoxycarbonyl)phenylmethyl]-4-[2-[N-methyl-N-(4-isopropoxyphenyl)amino]ethyl]piperidin-4-ol;
1-[4-fluoro-3-(trifluoromethyl)phenylmethyl]-4-[2-[N-methyl-N-(4-isopropoxyphenyl)amino]ethyl]piperidin-4-ol;
1-(4-bromo-2-fluorophenylmethyl)-4-[2-[N-methyl-N-(4-isopropoxyphenyl)amino]ethyl]piperidin-4-ol;
4-[2-[N-methyl-N-(4-isopropoxyphenyl)amino]ethyl]-1-(2-thienylmethyl)piperidin-4-ol;
4-[2-[N-methyl-N-(4-isopropoxyphenyl)amino]ethyl]-1-(3-thienylmethyl)piperidin-4-ol;
1-[2-(methoxycarbonyl)phenylmethyl]-4-[2-[N-methyl-N-(4-isopropoxyphenyl)amino]ethyl]piperidin-4-ol;
1-[3-(methoxycarbonyl)phenylmethyl]-4-[2-[N-methyl-N-(4-isopropoxyphenyl)amino]ethyl]piperidin-4-ol;
4-[2-[N-methyl-N-(4-isopropoxyphenyl)amino]ethyl]-1-[4-(isopropoxycarbonyl)phenylmethyl]piperidin-4-ol;
1-[2-fluoro-4-(trifluoromethyl)phenylmethyl]-4-[2-[N-methyl-N-(4-isopropoxyphenyl)amino]ethyl]piperidin-4-ol;
4-[2-[N-methyl-N-(4-ethoxyphenyl)amino]ethyl]-1-[4-(trifluoromethyl)phenylmethyl]piperidin-4-ol;
1-diphenylmethyl-4-[2-[N-methyl-N-(4-isopropoxyphenyl)amino]ethyl]piperidin-4-ol;
1-bis(4-fluorophenyl)methyl-4-[2-[N-methyl-N-(4-isopropoxyphenyl)amino]ethyl]piperidin-4-ol; and
1-diphenylmethyl-4-[2-[N-(4-ethoxyphenyl)-N-methylamino]ethyl]piperidin-4-ol.

These compounds can form salts to be described hereinafter.

The compounds according to the present invention may contain asymmetric carbon atoms, and the present invention contains mixtures of all of optically active or inactive stereoisomers (such as enantiomers and diastereomers), geometrical isomers and tautomers, and isolated compounds thereof. The isolation and purification of the stereoisomers can be made by those skilled in the art by optical resolution using preferential crystallization and column chromatography or by asymmetric synthesis.

The compound (I) according to the present invention may form an acid addition salt. A salt with a base may be also formed depending on the kind of the substituent. The salt is not particularly restricted so long as it is pharmaceutically acceptable. Examples of the salt include acid addition salts with an inorganic acid such as hydrochloric acid, hydrobromic acid, hydroiodic acid, sulfuric acid, nitric acid or phosphoric acid; acid addition salts with an organic carboxylic acid such as acetic acid, propionic acid, oxalic acid, malonic acid, succinic acid, fumaric acid, maleic acid, lactic acid, formic acid, malic acid, tartaric acid, citric acid or mandelic acid; acid addition salts with an organic sulfonic acid such as methanesulfonic acid, ethanesulfonic acid, benzenesulfonic acid, p-toluenesulfonic acid or 2-hydroxyethanesulfonic acid; an acid addition salt with an acidic amino acid such as aspartic acid and glutamic acid; a salt with an alkali metal or alkaline earth metal such as sodium, potassium, magnesium, calcium or aluminum; a salt with an organic base such as methylamine, ethylamine, ethanolamine, pyridine, lysine, arginine or ornithine; or an ammonium salt. These salts can be formed by conventional methods, for example, mixing of an equivalent compound of the present invention with a solution containing a desired acid or base, and collecting the desired salt by filtration or evaporation of solvents. The compounds of the present invention or salts thereof may form a solvate with a solvent such as water, ethanol or glycerol.

The salts of the compounds of the present invention may contain mono-, di- or tri-salts. The compounds of the present invention may simultaneously form both acid addition salt and salt with a base depending on the substituent on the side chains of the compounds.

Further, the present invention contains hydrates, various pharmaceutically acceptable solvates and polymorphic crystals of the compound (I) may be included in the present invention. Naturally, the present invention is not restricted to the compounds to be described hereinafter and contains all the compound represented by the formula (I) or pharmaceutically acceptable salts thereof.

The manufacturing methods according to the present invention will be described hereinafter together with reaction processes thereof. Definitions of A, $R^3$, $R^4$, $R^{4'}$, $R^5$, $R^{5'}$, $R^6$, $R^{6'}$, $R^7$, $R^8$, W, P, Q, X, Y, Y', Z and Z' in the compounds represented by the formulae (I), (I)-a, (I)-b, (VI), (VI'), (VII'), (VIII), (IX), (X), (X'), (XI), (XII) and (XIII) on the reaction schemes and descriptions in the MANUFACTURING METHODs 1, 2, 3 and 4 have the same meanings as defined above, unless otherwise stated.

The compounds represented by the formula (I) according to the present invention and salts thereof can be manufactured from the compounds represented by the formula (III) (in which $R^{4'}$, $R^{5'}$ and $R^{6'}$ have the same meanings as defined above), formula (III') (in which $R^{4'}$, $R^5$ and $R^6$ have the same meanings as defined above), formula (IV) (in which A, $R^3$, X, Y' and Z have the same meanings as defined above), formula (V) (in which $R^3$, P and Z have the same meanings as defined above), formula (XI), formula (XII), formula (XIII), formula (XIV) (in which A, $R^3$, $R^7$, X, Y' and Z have the same meanings as defined above), formula (XV) (in which $R^3$, $R^7$, P and Z have the same meanings as defined above), formula (XVIII) (in which A, $R^7$, $R^8$, X and Y' have the same meanings as defined above) and formula (XIX) (in which $R^7$, $R^8$ and P have the same meanings as defined above), which may be synthesized starting from the compounds known in the art or from commertially available compounds, by each method of the MANUFACTURING METHODs 1, 2, 3 and 4, or by modifications thereof. The starting materials, intermediate products and final products may be manipulated as salts, according to the necessity.

The manufacturing methods will be described in detail hereinafter.

<MANUFACTURING METHOD 1>

The compounds which $R^7$ and $R^8$ in the formula (I) represent hydrogen atom are represented by the formula (I)-a, and the manufacturing method thereof is shown below.

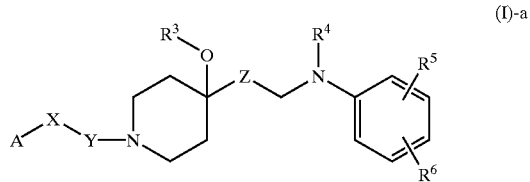

(I)-a

The compound represented by the formula (I)-a and the salt thereof can be manufactured from the compound represented by the formulae (III) and (IV), or (III) and (V) according to the processes in the reaction scheme I Reaction Scheme 1

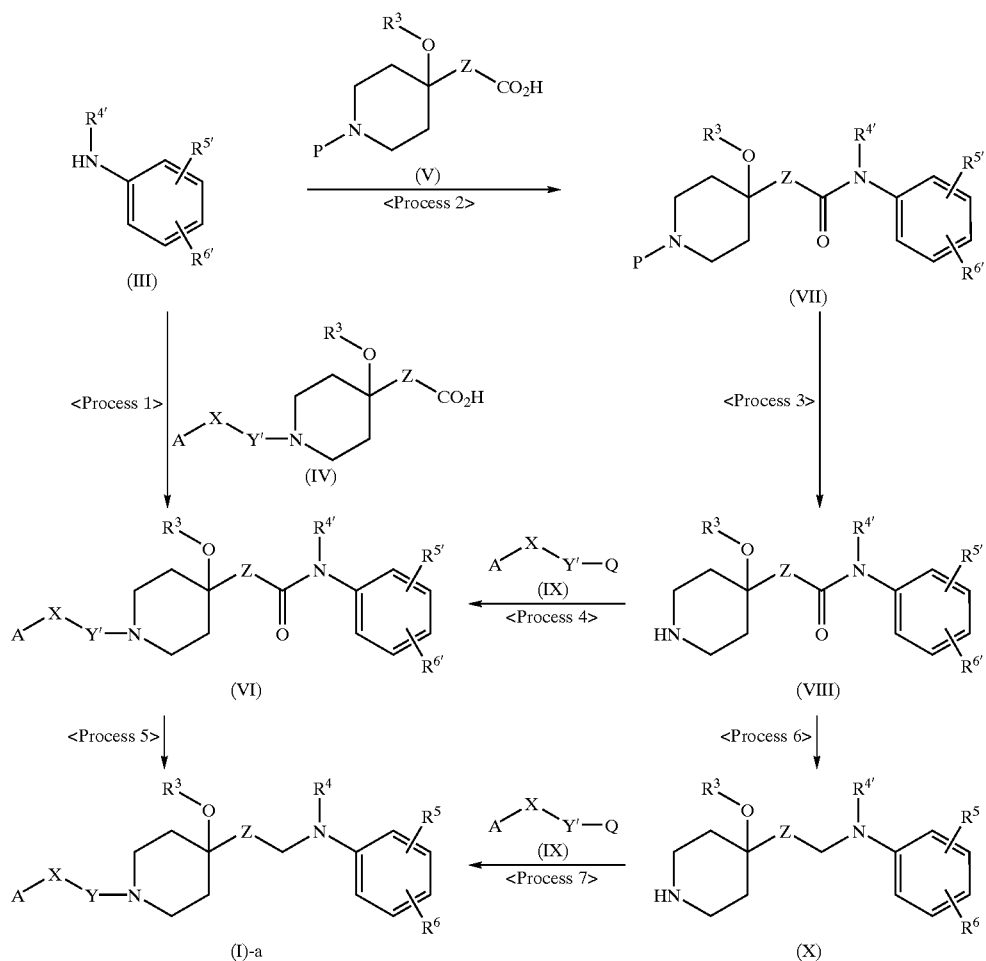

<Process 1>

The compound represented by the formula (VI) can be produced by reacting the compound represented by the formula (III) with the compound represented by the formula (IV) using a condensation agent such as 1-ethyl-3-(3-dimethylaminopropyl)carbodiimide hydrochloride (water soluble carbodiimide hydrochloride, WSC.HCl) or dicyclohexylcarbodiimide (DCC) in a solvent that does not take part in the reaction, e.g., a halogenated hydrocarbon solvent such as methylene chloride and chloroform, an ether solvent such as diethyl ether and tetrahydrofuran, a hydrocarbon solvent such as benzene and hexane, or a polar solvent such as dimethylformamide and dimethylsulfoxide in a temperature range of 0° C. to a reflux temperature of the reaction mixture.

This reaction may proceed using a dehydrating agent such as phosphorus oxychloride in the solvent that does not take part in the reaction including the halogenated hydrocarbon solvent such as methylene chloride and chloroform, ether solvent such as diethyl ether and tetrahydrofuran or the hydrocarbon solvent such as benzene and hexane in a temperature range of −20° C. to a reflux temperature of the reaction mixture in the presence of a base such as pyridine and triethylamine.

The compound represented by the formula (VI) can be also produced by converting the compound represented by the formula (IV) into an acid chloride using thionyl chloride and by reacting the acid chloride obtained with the compound represented by the formula (III) in the presence of an organic base such as triethylamine and pyridine or an inorganic base such as potassium carbonate in the halogenated hydrocarbon solvent such as methylene chloride and chloroform, ether solvent such as diethyl ether and tetrahydrofuran or hydrocarbon solvent such as benzene and hexane, or in a basic solvent such as pyridine and triethylamine in a temperature range of −20° C. to a reflux temperature of the reaction mixture.

The compound represented by the formula (VI) may be also manufactured according to the <Process 2>, <Process 3> and <Process 4> to be described hereinafter.

<Process 2>

The compound represented by the formula (VII) (in which $R^3$, $R^4$, $R^{5'}$, $R^{6'}$, P and Z have the same meaning as defined above) can be manufactured from the compound represented by the formula (III) and the compound represented by the formula (V) in accordance with the method in the <Process 1>. As the protective group P, an appropriate protective group described in the general remarks of "Protective Groups in Organic Synthesis, 3rd edition, edited by T. W. Green and P. G. M. Wuts, published by John Wiley and Sons, 1999" may be used. Such protective group includes an alkyl protective group such as a benzyl group, trityl group and methoxymethyl group, and a carbamate protective group such as a tert-butoxycarbonyl group and benzyloxycarbonyl group.

<Process 3>

The compound represented by the formula (VIII) can be produced by de-protection of the position 1 of piperidine ring of the compound represented by the formula (VII).

The position 1 of piperidine ring of the compound represented by the formula (VII) can be de-protected in accordance with the method described in the general remarks of "Protective Groups in Organic Synthesis, 3rd edition, 1999". The compound represented by the formula (VIII) can be produced by a de-protection reaction using a catalyst such as palladium on carbon or platinum oxide in an alcoholic solvent such as methanol and ethanol, or a solvent such as ethyl acetate, acetic acid and water under hydrogen atmosphere or in the presence of ammonium formate in a temperature range from 0° C. to a reflux temperature of the reaction mixture, when the protective group (P in the formula) is, for example, benzyl group or benzyloxycarbonyl group. Alternatively, the compound represented by the formula (VIII) can be produced by a de-protection reaction using an acid such as trifluoroacetic acid or hydrochloric acid in the presence or absence of anisole in a temperature range from 0° C. to a reflux temperature of the reaction mixture, when the protective group (P in the formula) is, for example, tert-butoxycarbonyl group.

<Process 4>

The compound represented by the formula (VIII) can be reacted with the compound represented by the formula (IX) by the following methods depending on the kind of —Y' and -Q.

(Method A): The compound represented by the formula (VI) can be produced by reacting the compound represented by the formula (VIII) with the compound represented by the formula (IX) in the presence or absence of the organic base such as triethylamine and pyridine or inorganic base such as potassium carbonate in a solvent that does not take part in the reaction, e.g., the halogenated hydrocarbon solvent such as methylene chloride and chloroform, ether solvent such as diethyl ether and tetrahydrofuran, hydrocarbon solvent such as benzene and hexane, or polar solvent such as dimethylformamide and dimethylsulfoxide in a temperature range from 0° C. to a reflux temperature of the reaction mixture, when —Y' and -Q together represent halogenated alkyl. Sodium iodide may be used as a catalyst thereat.

(Method B): The compound represented by the formula (VI) can be produced by reacting the compound represented by the formula (VIII) with the compound represented by the formula (IX) using an appropriate reducing agent in the presence or absence of the acid catalyst such as acetic acid in a solvent, e.g., aromatic hydrocarbon solvent such as benzene and toluene, halogenated hydrocarbon solvent such as methylene chloride and chloroform, or alcoholic solvent such as methanol and ethanol, when —Y' and -Q together represent aldehyde or ketone. While any reducing agents capable of reducing an imino group into an amino group may be generally used, sodium triacetoxyborohydride, sodium borohydride, lithium borohydride, diisobutylaluminum hydride and sodium cyanoborohydride are preferable among the reducing agents. The reducing reaction can be conducted in the temperature range from −78° C. to room temperature, preferably at room temperature and for the enough time to proceed the reaction sufficiently, concretely from 3 to 12 hours.

(Method C): The compound represented by the formula (VI) can be produced in accordance with the method in the <Process 1>, when —Y' and -Q together represent carboxylic acid.

(Process 5)

The compound represented by the formula (I)-a or a salt thereof can be manufactured by reacting the compound represented by the formula (VI) using a reducing agent such as lithium aluminum hydride, diisobutylaluminum hydride, and a borane complex represented by borane-methyl sulfide complex and borane-tetrahydrofuran complex in a solvent that does not take part in the reaction, e.g., ether solvent such as diethyl ether and tetrahydrofuran or an aromatic hydrocarbon solvent such as toluene and benzene in a temperature range from 0° C. to a reflux temperature of the reaction mixture.

When Y' represents an alkylenecarbonyl group or carbonyl group in the compound represented by the formula (VI), Y' is simultaneously reduced under the reaction condition employed to afford a compound in which Y is corresponding lower alkylene group.

When $R^5$ or $R^{6'}$ represent lower alkoxycarbonyl groups, the ester group is reduced simultaneously with the reduction of the amide bonding to be converted to a corresponding alcoholic group. The reduction can proceed by the same method after hydrolyzing the ester group to the carboxyl group. Methods known in the art, for example treating the compound in an alcoholic solvent such as methanol and ethanol in the presence of an aqueous lithium hydroxide or sodium hydroxide at a temperature from room temperature to a reflux temperature of the reaction mixture, may be used for hydrolysis.

The compound represented by the formula (I)-a or a salt thereof can be also produced using the compound represented by the formula (VIII) through the <Process 6> and <Process 7> shown below.

<Process 6>

The compound represented by the formula (X) can be produced from the compound represented by the formula (VIII) according to the method in the <Process 5>.

The compound represented by the formula (X) can be also produced by reducing the compound represented by the formula (VII) in accordance with the method in the <Process 5>, followed by de-protection of the position 1 of piperidine ring of the obtained compound in accordance with the method in the <Process 3>.

<Process 7>

The compound represented by the formula (I)-a or a salt thereof can be produced from the compounds represented by the formulae (X) and (IX). The compound represented by the formula (I)-a can be produced by the Methods A or B in the <Process 4> when —Y' and -Q together represent halogenated alkyl group, aldehyde or ketone. When —Y' and -Q together represent carboxylic acid, the compound can also be produced by reducing an amide bonding subsequently produced from the method of the Method C in the <Process 4> in accordance with the method of the <Process 5>.

<MANUFACTURING METHOD 2>

The method for manufacturing the compound represented by the formula (I)-b is described hereinafter, wherein $R^7$ and $R^8$ represent hydrogen atoms and Z is denoted by Z' in the compound represented by the formula (I).

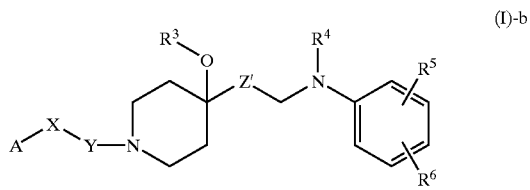

The compound represented by the formula (I)-b or a salt thereof can be manufactured from the compound represented by the formulae (XI) and (XII), or (XI) and (XIII) according to each manufacturing process in the Reaction Scheme 2.

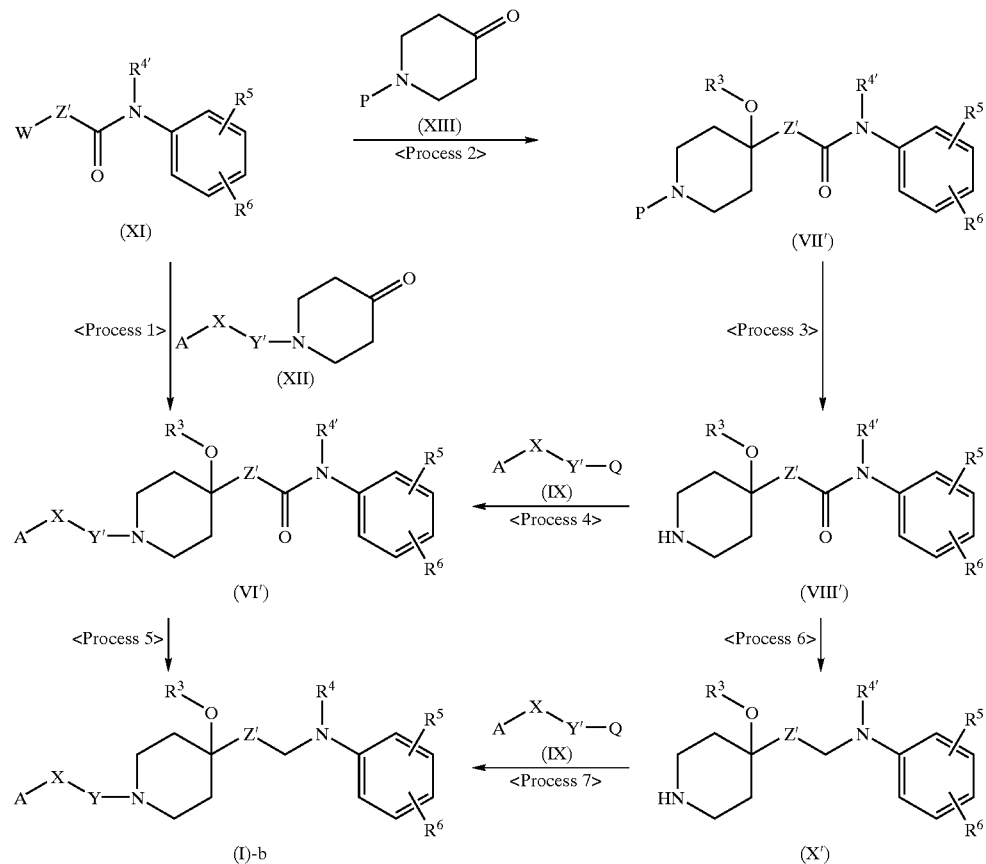

<Process 1>

The compound represented by the formula (VI') can be produced by an addition reaction between the compound represented by the formula (XI) and the compound represented by the formula (XII), followed by alkylation of the hydroxyl group produced according to the necessity. When W is hydrogen atom in the compound represented by the formula (XI), the addition reaction is performed by reacting the compound represented by the formula (XI) with a metal amide reagent such as lithium diisopropylamide, lithium hexamethyldisilazide and potassium hexamethyldisilazide, or an organometallic reagent represented by tin (II) trifulate to form a metal enolate in a solvent that does not take part in the reaction, e.g., an ether solvent such as diethyl ether and tetrahydrofuran or a hydrocarbon solvent such as benzene and hexane in a temperature range from −100° C. to room temperature, followed by reacting the reaction product with the compound represented by the formula (XII) in a temperature range from −100° C. to room temperature.

When W is halogen atom, preferably bromine atom, in the compounds represented by the formula (XI), the addition reaction is performed by reacting the compound represented by the formula (XI) with zinc powder to form a zinc compound in a solvent that does not take part in the reaction including an ether solvent such as diethyl ether and tetrahydrofuran or a hydrocarbon solvent such as benzene and hexane, followed by reacting the reaction product with the compound represented by the formula (XII).

Alkylation of the tertiary hydroxyl group produced by the addition reaction can be performed using an alkylating agent such as an alkyl halide represented by methyl iodide or an alkyl sulfate represented by dimethyl sulfate in the presence of a base such as sodium hydride in a solvent that does not take part in the reaction such as dimethylformamide or dimethylimidazolidone in a temperature range from −20° C. to a reflux temperature of the reaction mixture, preferably in a temperature range from an ice-cooled temperature to room temperature.

The compound represented by the formula (VI') can be also produced by the methods in the <Process 2>, <Process 3> and <Process 4> to be described hereinafter.

<Process 2>

The compound represented by the formula (VII') can be produced from the compounds represented by the formulae (XI) and (XIII) in accordance with the methods in the <Process 1>.

<Process 3>

The compound represented by the formula (VIII')(in which $R^3$, $R^4$, $R^5$, $R^6$ and Z' have the same meanings as defined above) can be produced from the compounds rep resented by the formula (VII') in accordance with the <Process 3> in the MANUFACTURING METHOD 1.

<Process 4>

The compound represented by the formula (VI') can be produced from the compounds represented by the formulae (VIII') and (IX) in accordance with the <Process 4> in the MANUFACTURING METHOD 1.

<Process 5>

The compound represented by the formula (I)-b or a salt thereof can be produced from the compound represented by the formula (VI') in accordance with the <Process 5> in the MANUFACTURING METHOD 1.

The compound represented by the formula (I)-b or a salt thereof can be also produced from the compound represented by the formula (VIII') in accordance with the <Process 6> and <Process 7> to be described hereinafter.

<Process 6>

The compound represented by the formula (X') can be also produced from the compound represented by the formula (VIII') in accordance with the method in the <Process 5>.

The compound represented by the formula (X') is also produced by reducing the compound represented by the formula (VII') in accordance with the method in the <Process 5>, followed by de-protection of the position 1 of piperidine ring in accordance with the method in the <Process 3>.

<Process 7>

The compound represented by the formula (I)-b or a salt thereof can be produced from the compounds represented by the formulae (X') and (IX) in accordance with the method in the <Process 7> in the MANUFACTURING METHOD 1.

<MANUFACTURING METHOD 3>

The method for manufacturing the compound represented by the formula (I)-c is described hereinafter, wherein $R^8$ in the formula (I) represents hydrogen atom.

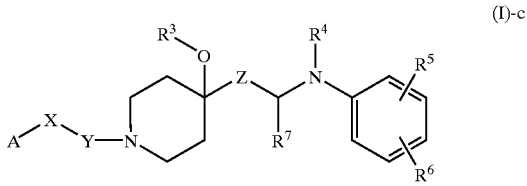

(I)-c

The compound represented by the formula (I)-c (in which A, $R^3$, $R^4$, $R^5$, $R^6$, $R^7$, X, Y and Z have the same meanings as defined above) or a salt thereof can be produced from the compounds represented by the formulae (III') and (XIV), or (III') and (XV) in accordance with each manufacturing process in the Reaction Scheme 3.

Reaction Scheme 3

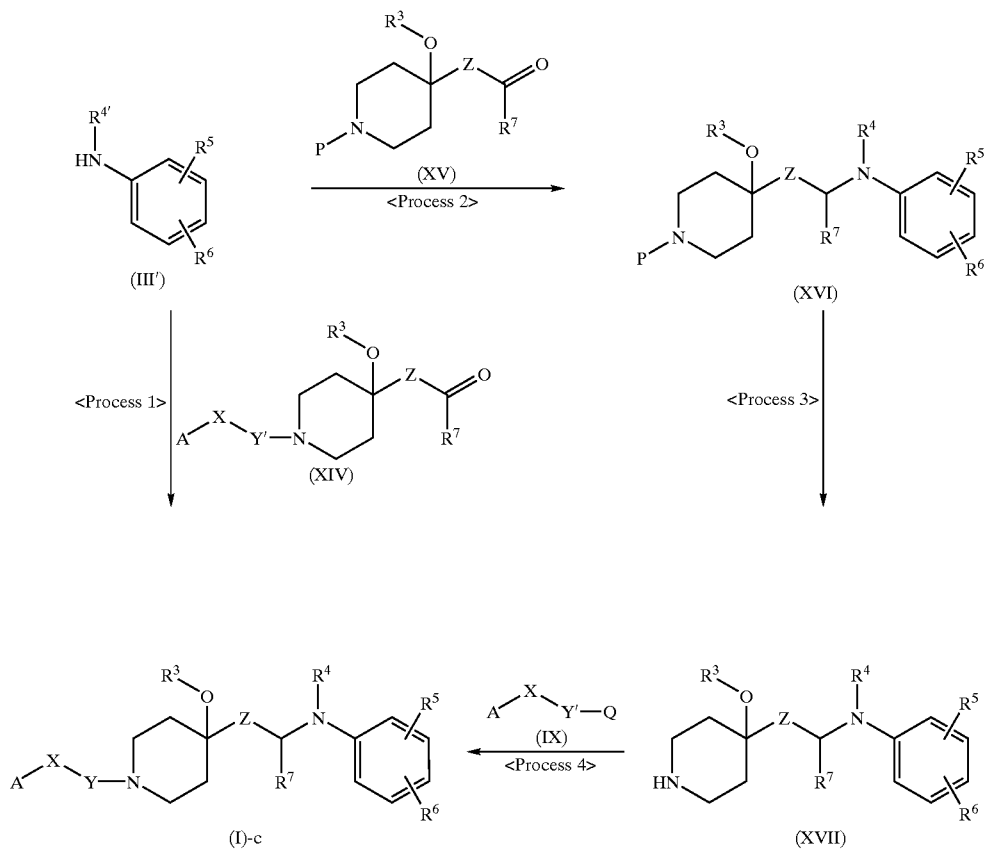

<Process 1>

The compound represented by the formula (I)-c or a salt thereof can be produced from the compounds represented by the formulae (III') and (XIV) in accordance with the Method B described in the <Process 4> of the MANUFACTURING METHOD 1.

The compound represented by the formula (I)-c can be produced by subsequently reducing the amide bonding in accordance with the method in the <Process 5> of the MANUFACTURING METHOD 1, when Y' represents alkylenecarbonyl group or carbonyl group.

The compound represented by the formula (I)-c or a salt thereof can be also produced in accordance with the <Process 2>, <Process 3> and <Process 4> to be described below.

<Process 2>

The compound represented by the formula (XVI) (in which $R^3$, $R^4$, $R^5$, $R^6$, $R^7$, P and Z have the same meanings as defined above) can be produced from the compounds represented by the formulae (III') and (XV) in accordance with the method in the <Process 1>.

<Process 3>

The compound represented by the formula (XVII) (in which $R^3$, $R^4$, $R^5$, $R^6$, $R^7$ and Z have the same meanings as defined above) can be produced from the compound represented by the formula (XVI) in accordance with the method in the <Process 3> in the MANUFACTURING METHOD 1.

<Process 4>

The compound represented by the formula (I)-c or a salt thereof can be produced from the compounds represented by the formulae (XVII) and (IX) in accordance with the method in the <Process 7> in the MANUFACTURING METHOD 1.

<MANUFACTURING METHOD 4>

The compound which Z in the formula (I) represents a single bond is represented by the formula (I)-d, and the method for manufacturing thereof will be described hereinafter.

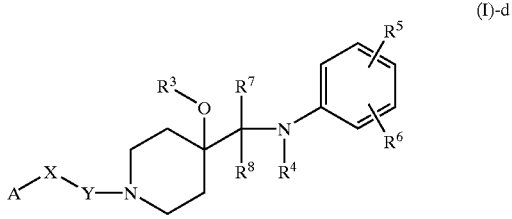

The compound represented by the formula (I)-d (in which A, $R^3$, $R^4$, $R^5$, $R^6$, $R^7$, $R^8$, X and Y have the same meaning as defined above) and a salt thereof can be produced from the compounds represented by the formulae (III') and (XVIII), or (III') and (XIX) in accordance with the manufacturing processes in the Reaction Scheme 4.

Reaction Scheme 4

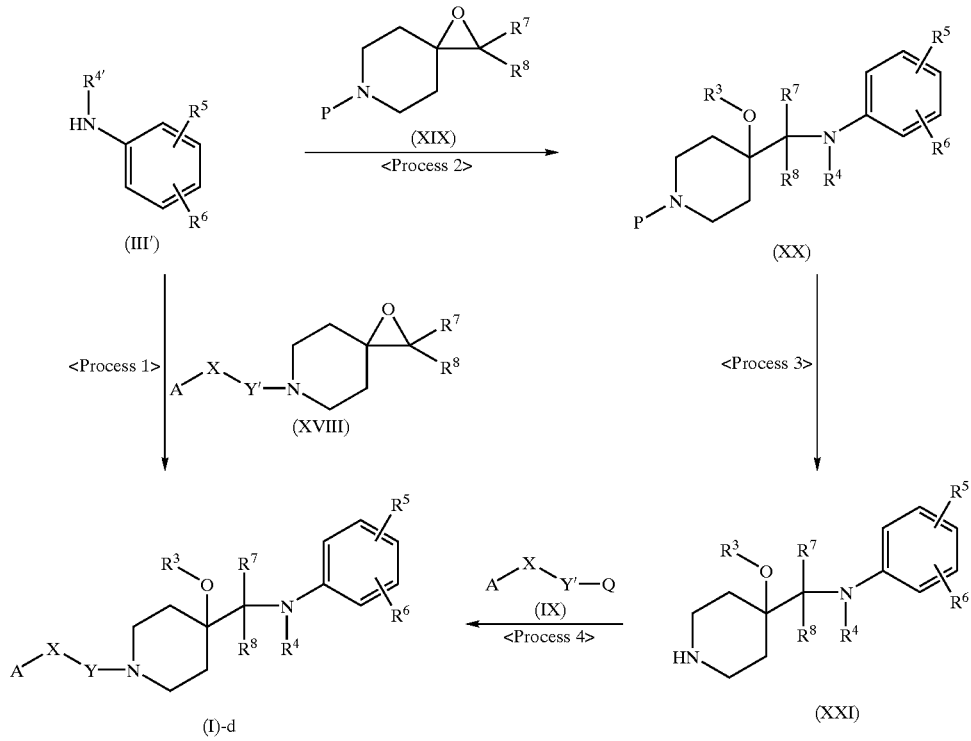

<Process 1>

The compound represented by the formula (I)-d or a salt thereof can be produced by reacting the compound represented by the formula (III') with the compound represented by the formula (XVIII) in the presence of an acid catalyst or a base catalyst in a solvent that does not take part in the reaction, e.g., halogenated hydrocarbon solvent such as methylene chloride and chloroform, an ether solvent such as diethyl ether and tetrahydrofuran, a hydrocarbon solvent such as benzene and hexane, or a polar solvent such as dimethylformamide and dimethylsulfoxide in a temperature range from 0° C. to a reflux temperature of the reaction mixture. The compound may be also produced by a reaction in accordance with the method described by Gary H. Posner et al, in Journal of the American Chemical Society, Vol. 99, pp8208–8214, 1977 in diethyl ether in the presence of neutral alumina at room temperature.

The compound represented by the formula (I)-d can be produced by succeeding reduction of the amide bonding in accordance with the method in the <Process 5> in the MANUFACTURING METHOD 1 when Y' represents an alkylenecarbonyl group or a carbonyl group.

The compound represented by the formula (I)-d or a salt thereof can be also produced in accordance with the <Process 2>, <Process 3> and <Process 4> to be described hereinafter.

<Process 2>

The compound represented by the formula (XX) (in which $R^3$, $R^4$, $R^5$, $R^6$, $R^7$, $R^8$ and P have the same meanings as defined above) can be produced from the compounds represented by the formulae (III') and (XIX) in accordance with the method in the <Process 1>.

<Process 3>

The compound represented by the formula (XXI) (in which $R^3$, $R^4$, $R^5$, $R^6$, $R^7$ and $R^8$ represent the same meanings as hitherto described) can be produced from the compound represented by the formula (XX) in accordance with the method in the <Process 3> in the MANUFACTURING METHOD 1.

<Process 4>

The compound represented by the formula (I)-d and a salt thereof can be produced from the compounds represented by the formulae (XXI) and (IX) in accordance with the method in the <Process 7> in the MANUFACTURING METHOD 1.

The compound synthesized in each manufacturing method above can be converted in each process of each manufacturing process according to the method to be described hereinafter.

Among the compounds represented by the formulae (I)-a, (I)-b, (I)-c, (I)-d, (XVI) and (XX), the compounds in which $R^4$ represents hydrogen atom can be converted to compounds in which $R^4$ is lower alkyl group using an alkylating agent such as an alkyl halide represented by methyl iodide, or an alkyl sulfate represented by dimethyl sulfate in a solvent that does not take part in the reaction, e.g., a halogenated hydrocarbon solvent such as methylene chloride and chloroform, an ether solvent such as diethyl ether and tetrahydrofuran, a hydrocarbon solvent such as benzene and hexane, or a polar solvent such as dimethylformamide and dimethylsulfoxide in the presence of an inorganic base such as potassium hydroxide, sodium hydride and potassium carbonate or an organic base such as triethylamine and pyridine in a temperature range from 0° C. to a reflux temperature of the reaction mixture. The compounds can also be converted to compounds in which $R^4$ represents a lower alkyl group using aldehyde derivative or ketone derivative by conducting reaction in accordance with the Method B described in the <Process 4> in the MANUFACTURING METHOD 1. By an acylation reaction in accordance with the method described in the <Process 1> in the MANUFACTURING METHOD 1, the compounds may be also converted to compounds in which $R^4$ represents a lower alkanoyl group using a carboxylic acid derivative. At that time, the compounds obtained by the process above may be converted to the compounds in which $R^4$ represents a lower alkyl group by subsequently applying a reduction treatment described in the <Process 5> in the MANUFACTURING METHOD 1.

Among the compounds represented by the formulae (VI), (VII), (VI') and (VII'), compounds in which $R^{4'}$ is hydrogen atom can be alkylated to be converted to compounds in which $R^{4'}$ is lower alkyl group using an alkylating agent such as an alkyl halide represented by methyl iodide or an alkyl sulfate represented by dimethyl sulfate in the presence of a base such as potassium hydroxide and sodium hydride in a solvent that does not take part in the reaction including a halogenated hydrocarbon solvent such as methylene chloride and chloroform, an ether solvent such as diethyl ether and tetrahydrofuran, a hydrocarbon solvent such as benzene and hexane, or a polar solvent such as dimethylformamide and dimethylsulfoxide in a temperature range from 0° C. to a reflux temperature of the reaction mixture.

Among the compounds represented by the formulae (I)-a, (I)-b, (I)-c, (I)-d, (VI), (VII), (VI'), (VII'), (XVI) and (XX), compounds which contain alkoxy group on the benzene ring as a substituent can be converted, after de-alkylation using boron tribromide or hydrobromic acid-acetic acid, etc., to other alkoxy substituted form in the presence of a base such as sodium hydride using the alkylating agents described above in a solvent that does not take part in the reaction such as dimethylformamide and dimethylimidazolidone in a temperature range from −20° C. to a reflux temperature of the reaction mixture, preferably from an ice-cooled temperature to room temperature. At that time, the compounds may be also converted to lower alkoxy compounds substituted by hydroxyl groups by reducing with lithium aluminum hydride, sodium borohydride or the like, after alkylation with an alkyl halide having oxygen functional group represented by bromoacetic acid ester or bromoacetone as an alkylation agent.

Among each compound produced by each method described above, compounds which X represents carbonyl group can be converted to group: —CH(OH)— by reacting the compounds in a temperature range from 0° C. to a reflux temperature of the reaction mixture in an alcoholic solvent such as methanol and ethanol using a reducing agent such as sodium borohydride according to the necessity.

Among each compound produced each method described above, compound which contain lower alkoxycarbonyl group as a substituent can be converted to a carboxyl group by conventional methods, for example, by hydrolysis in the presence of an aqueous alkali solution such as aqueous solution of lithium hydroxide or sodium hydroxide in an alcoholic solvent such as methanol and ethanol in a temperature range from room temperature to a reflux temperature of the reaction mixture. The obtained carboxyl group can be converted to a carbamoyl group that may be unsubstituted or mono- or di-substituted by lower alkyl groups by a condensation reaction in accordance with the method described in the Method C.

Among the compounds manufactured by the methods as hitherto described, compounds which contain halogen atoms, preferably bromine atoms, as substituents on the aromatic ring, the bromine atom can be converted to cyano group by conventional methods, for example, by reacting the compound using copper (I) cyanate or potassium cyanate in a solvent that does not take part in the reaction, e.g., a polar aprotic solvent such as dimethylformamide, dimethylsulfoxide and dimethylimidazolidone in a temperature range from room temperature to a reflux temperature of the reaction mixture. In this reaction, transition metal complexes such as a palladium complex represented by palladium acetate and nickel complex represented by tetrakistriphenylphosphine nickel may be used as catalysts. The cyano group can be further converted to lower alkanoyl group by reacting the compound with an organometallic compound represented by alkyl magnesium bromide and alkyl lithium in a solvent that does not take part in the reaction including ether solvents such as diethyl ether and tetrahydrofuran in a temperature range from −100° C. to room temperature.

When the compounds manufactured in each manufacturing method as hitherto described contain reactive groups such as hydroxyl group, amino group and carboxyl group, these substituents can be appropriately protected in each manufacturing process, and the protective groups can be removed at an appropriate reaction process. While these protective groups may be appropriately introduced and eliminated depending on the type of the protected group or protection group, the methods available are described, for example, in Protective Groups in Organic Synthesis, 3rd edition, 1999.

Among the intermediate compounds to be used in each manufacturing process, the compound represented by the formula (XII) may be produced in accordance with the method known in the art. For example, the compound can be produced by reacting 4-piperidone or its equivalence with the compound represented by the formula (IX) in accordance with the method described in the <Process 4> in the MANUFACTURING METHOD 1. Alternatively, Compound represented by the formula (XII) in which Y' representes Y can be produced from the compound represented by the following formula (XXII) in accordance with a reaction described by Huegi et al., in Journal of Med. Chem., Vol. 26, p42, 1983:

(XXII)

(wherein A, X and Y have the same meanings as defined above.)

The compounds represented by the formulae (IV) and (V) can be produced by reacting the compounds represented by the formulae (XII) and (XIII) with unprotected or protected acetic acid having a desired substituent in accordance with the method described in the MANUFACTURING METHOD 2.

EXPERIMENTAL EXAMPLES

While the present invention is described with reference to the examples, the present invention is by no means restricted to these examples.

Experimental Example 1

[Suppression Activity of Veratrine-Induced Contracture of Isolated Cardiac Muscle]

Rats were anesthetized with 40 mg/kg (i.p.) of pentobarbital sodium and held in supine postion, and heparin was injected through the jugular vein. After starting artificial respiration under a condition of 20 mL/kg and 54 strokes/min, the chest was open between the second and thirdcostae. A polyethylene tube filled with Krebs-Ringer-HEPES (KRH) solution (pH 7.4) containing 1 mM $CaCl_2$ was inserted through the aorta in retrograde manner, and the tube was fixed. The heart was extracted simultaneously with perfusion of the KRH solution at a hydraulic pressure of 70 cm water column. After thoroughly flushing the remaining blood by spontaneous contraction of the heart, stroke of the heart was halted by perfusion of the $Ca^{2+}$ free KRH solution for 10 minutes. The perfusion solutions described above were used after oxygenation with a mixed gas containing 95% $O_2$ and 5% $CO_2$ and keeping at a temperature of 37° C. Then, a KRH solution containing 25 μM $CaCl_2$, 0.06% collagenase and 0.1% albumin was perfused for 20 minutes at 37° C. until the heart was soften. The ventricles were cut into pieces in the collagenase solution at 37° C., followed by an enzyme treatment for 10 minutes while aerating the solution with the mixed gas of 95% $O_2$/5% $CO_2$. The cells were dispersed by pipetting, and connective tissues were removed from the dispersed cells by filtering with a stainless steel mesh. After halting the enzyme reaction by adding albumin in the filtrate, the supernatant was discarded by centrifugation. The cells were suspended in the KRH solution containing 25 μM $CaCl_2$ and 1% albumin, and the $Ca^{2+}$ concentration was increased stepwise by sequentially adding the $CaCl_2$ solution in the suspension to a final concentration of 0.5 mM. A pellet of the cells was obtained by centrifugation after allowing the suspension to stand for 10 minutes. The pellet of the cells was laid on a column (10 cm in height and 15 mm in diameter) filled with the KRH solution containing 1 mM $CaCl_2$ and 2% albumin, and the column was allowed to stand for 5 to 10 minutes. The supernatant was gently removed, and the number of rod-shaped cells in the precipitated cells was counted. The cells were re-suspended in the KRH solution containing 1 mM $CaCl_2$ and 0.1% albumin, and pipetted into each well of a 48 well multi-plate (3548, COSTER) coated with poly-L-lysine so that each well contains 0.5 mL of the cell suspension with $1 \times 10^4$ cells/well. The suspension in each well was aerated with a mixed gas of 95% $O_2$/5% $CO_2$ at 37° C. for 1 hour to allow the cells to adhere on the bottom of the well. The solution in the well was flushed with a KRH solution containing 0.025% lactic acid and 1 mM $CaCl_2$ to remove the cells that did not adhere on the bottom. Then, the medium was replaced with a KRH solution containing a test compound, 0.025% lactic acid and 1 mM $CaCl_2$, followed by aerating with a mixed gas containing 95% $O_2$/5% $CO_2$ at 37° C. for 30 minutes. After taking a photograph under a microscope, a KRH solution containing veratrine, 0.025% lactic acid and 1 mM $CaCl_2$ was added to each well so that the final concentration of veratrin becomes 100 gg/mL, followed by taking a photograph of morphological changes of the cells after 5 minutes passed from the addition. A change from the rod-shape cell to a spherical cell was defined as contraction by veratrine. Veratrine in this concentration can contract all the cells. The concentration of the test compound when half of the cells were contracted was defined as $IC_{50}$ (μmol/L) that can be calculated by a probit analysis. The results are shown in Table 1.

TABLE 1

Suppression Activity of Veratrine-induced Contracture of Isolated Cardiac Muscle

| Example No. | $IC_{50}$ (μmol/L) |
|---|---|
| 146 | 1.2 |
| 176 | 0.9 |
| 183 | 1.0 |
| 210 | 0.9 |
| 220 | 0.7 |

TABLE 1-continued

Suppression Activity of Veratrine-induced Contracture of Isolated Cardiac Muscle

| Example No. | $IC_{50}$ (μmol/L) |
|---|---|
| 221 | 0.3 |
| 236 | 0.3 |
| 240 | 0.7 |
| 278 | 0.3 |

The results above show that the compounds according to the present invention have remarkable suppressive effects on contracture of the isolated cardiac muscle cells caused by veratrine.

Experimental Example 2

[Suppression Effect on Ischemia-Reperfusion Induced Arrythmia in Rats]

The test compounds were administered to rats starved from a day before by gavage at a dosage of 10 mL/kg under an awaken condition. The rats were anesthetized with 60 mg/kg (i.p.) of sodium pentobarbital after 35 minutes passed from the administration, and were fixed on a warmed sheet in supine position. The body temperature was kept at 37° C. during the experiment, and artificial respiration was started under a condition of 15 mL/Kg and 55 strokes/minutes. A polyethylene tube for measuring the blood pressure filled with a heparin-physiological saline solution was inserted into the left common carotid artery at a depth of 2 cm and fixed. Then, the left chest was open, and the left major coronary artery at an atrium side was sewed using a needle with a thread in order to ligate the coronary artery. After stabilizing for about 10 minutes (after 60 minutes passed from the administration), the coronary artery was ligated for 5 minutes, and re-perfused for 10 minutes thereafter. The ligation of the coronary artery was conducted by inserting a suture through a snare made of a polyethylene tube and pulling the both ends of the suture, followed by pressing the snare onto the heart. The re-perfusion was conducted by removing the snare. The aortic blood pressure was measured with a pressure transducer. An electrocardiogram was led by a standard lead II. The heart rate was measured using the R—R interval on the electrocardiogram or from the blood pressure using a tachometer. Each signals were recorded with a chart recorder with verification on a monitor, while simultaneously recording on a magnetic medium using a personal computer. After the completion of the experiments, generation of ventricular fibrillation was confirmed for each individual using an analysis software running on the personal computer, and incidence (%) of the ventricular fibrillation was determined for each administration group. The results are shown in Tables 2-1 and 2-2.

TABLE 2-1

Effectiveness (1) in Ischemia-Reperfusion Induced Arrythmia Model in Rats

| Example No. | Dosage (mg/kg) | Number of animals | Incidence (%) of the ventricular fibrillation |
|---|---|---|---|
| solvent | — | 11 | 63.6 |
| 146 | 5 | 10 | 30.0 |
| 146 | 10 | 9 | 11.1 |
| 146 | 20 | 9 | 0.0 |

TABLE 2-2

Effectiveness (2) in Ischemia-Reperfusion Induced Arrythmia Model of Rat

| Example No. | Dosage (mg/kg) | Number of animals | Incidence (%) of the ventricular fibrillation |
|---|---|---|---|
| solvent | — | 7 | 57.1 |
| 233 | 5 | 7 | 28.6 |
| 240 | 5 | 7 | 0.0 |
| 278 | 5 | 8 | 0.0 |

The compounds according to the present invention were shown to suppress the incidence (%) of the ventricular fibrillation in this example.

Experimental Example 3

[Suppressive Action on Arrythmia Induced by Two Step Ligation of Canine Coronary Artery]

After anesthetizing with 30 mg/kg (i.v.) of thiopental sodium, a beagle dog was ventilated by artificial respiration under a condition of 20 mL/kg and 22 strokes/min. The fifth left intercostal space was opened under sterile condition to incise membrana pericardiac cavity, and the heart was hanged in the thoracic cavity. The left anteirior descending limb of the coronary artery was peeled at 1 cm downstream of the joint to the circumflexus branch, and the artery was wound with two strings of sutures. Blood vessel of the artery was at first ligated together with a 19G needle with a round tip, and the constriction is prepared by pulling out the needle (one step ligation). Thirty minutes after the first ligation, the artery was completely ligated with the other suture (two step ligation). A dipolar electrode was stitched on the left atrial auricle for recording atrial potential. A catheter filled with a heparin solution was inserted into the left common carotid artery for measuring the blood pressure and for sampling the blood, and another catheter was inserted into the left external jugular vein for administering test compounds. All these catheters and lead wires were hypodermically guided out of the poll. The chest was closed after administering an antibiotic (Mysyringesol for animal use), and the animal was returned to his breeding cage. The dog was hanged without being anesthetized on a hammock on a retention table at the time when 24 hours passed after the operation. The test compounds were administered at a rate of 10 mg/kg/hr when the physical conditions of the animal has been stabilized. The aortic blood pressure was measured using a pressure transducer. An electrocardiogram (standard lead II) and atrial potential were led using a bioelectric amplifier. The heart rate was measured using the R—R interval on the electrocardiogram or from the blood pressure. Each signals were recorded with a chart recorder with verification on a monitor, while simultaneously recording on a magnetic medium using a personal computer. An arrythmia ratio expressed by [Number of ventricular extrasystol/(Number of ventricular extrasystol+sinus rhythm)]×100 per one minute was used as an index of incidence of arrythmia. The results are shown in Table 3.

TABLE 3

Effective of the Test Compound of Example No. 146 on Arrythmia Model Induced by Two Step Ligation of Canine Coronary Artery

| Treatment | Arrythmia Ratio |
|---|---|
| Before Start of Administration | 100 |
| 15 Minutes after continued Injection | 49 |
| 30 Minutes after continued Injection | 21 |

The results indicate that incidence of ventricular extrasystol was suppressed by the compounds according to the present invention.

Experimental Example 4
[Effect on Electrocardiogram in Rats]

After anesthetizing with 1.5 g/kg (s.c.) of urethane, a rat was fixed on a warm plate at its supination. Polyethylene tubes for administering a test compound and for measuring the blood pressure were inserted into and fixed to the jugular vein and femoral artery, respectively. The blood pressure of the artery was measured using a pressure transducer. An electrode was attached to the animal, electrocardiograms were led by the standard lead II. The heart rate was measured by using a heart rate counter. The test compound was given by intravenous injection when the blood pressure and heat rate had been stabilized after the operation. The heart rate and blood pressure were recorded on a chart with a recorder while simultaneously recording on a magnetic medium using a personal computer. Each parameter on the electrocardiogram was processed using an analysis software running on the personal computer to calculate the rate of change as compared with that before administration. The results are shown in Table 4.

TABLE 4

Effect of Intravenous Administration of the Compound on PQ interval and QRS Width on the Electrocardiogram

| Example No. | Dose (mg/kg) | PQ Distance | QRS Width |
|---|---|---|---|
| 146 | 5 | — | — |
| 162 | 5 | — | — |
| 176 | 5 | — | — |
| 177 | 5 | — | — |
| 196 | 5 | — | — |
| 198 | 5 | — | — |
| 201 | 5 | — | — |
| 226 | 5 | — | — |
| 233 | 5 | — | — |
| 240 | 5 | — | — |
| 254 | 5 | — | — |
| 278 | 5 | — | — |

—: The rate of change at two minutes after administration is 15% or less as compared with that before administration.

It was shown in this Experimental Example that the compounds according to the present invention have few effects on the PQ interval and QRS width on the electrocardiogram.

Experimental Example 5
[Toxicity Test]

6-week aged female Crj(SD)IGS rats were orally given by gavage the compounds in the Example Nos. 146, 233 and 278 once a day for 14 days. No fatal cases were observed at daily dosages of 100 mg/kg or less of the compound in the Example No. 146, of 50 mg/kg or less of the compound in the Example No. 233 and of 20 mg/kg less of the compound in the Example No. 278. No abnormalities were also observed in the body weight and general symptoms.

It was made clear that the compounds according to the present invention can suppress contracture of the isolated cardiac muscle cells induced by veratrine. The compounds according to the present invention were able to suppress generation of ventricular fibrillation as severe arrythmia in the ischemia-reperfusion induced arrythmia model in rats, reducing mortality of the rat. Generation of ventricular extrasystol in the arrythmia model induced by two step ligation of canine coronary artery was also suppressed. No effects on the PQ interval and QRS width were observed in the compounds according to the present invention. Low toxicity of the compound according to the present invention was verified, since no abnormalities were manifested in the toxicological study.

Accordingly, the compounds according to the present invention were shown to be effective in the arrythmia model of animals with few effects on the electrocardiogram of the normal animals. Therefore, the compounds are effective for the therapy and prevention of arrythmia as medicines having no proarrythmic action.

Arrythmia is a general term of the diseases that express abnormal rhythmic function among the cardiac functions, and appears when the heart manifests abnormal excitation and conduction. While arrythmia includes ventricular arrythmia and atrial (supraventricular) arrythmia, the compounds according to the present invention are effective for both types of symptoms. In more detail, arrythmia is classified into supraventricular extrasystol, ventricular extrasystol, supraventricular tachycardia, WPW syndrome, atrial flutter/fibrillation, ventricular tachycardia and ventricular fibrillation.

Ventricular tachycardia and ventricular fibrillation are thought to be severe syndrome of arrythmia among the syndromes of ventricular arrythmia, and it is in particular suggested that these diseases may be the causes of sudden death in the patients of ischemic heart diseases such as myocardial infarction and cardiac failure. Although almost all the sudden death is caused in those suffering from some heart diseases, some of the sudden death is caused by lethal arrythmia due to overwork, although no basal diseases are observed.

The pharmaceutical composition according to the present invention is in particular effective for therapy or prevention of ventricular tachycardia and ventricular fibrillation as severe syndromes of arrythmia, or for prevention of sudden death.

In the pathological conditions of atrial flutter and fibrillation, it is known that atrial flutter and atrial fibrillation themselves induce electrical remodeling to readily cause atrial flutter and atrial fibrillation again. Chemicals that suppress electrical modeling have not been subjected to clinical medicines, and excess influx of sodium and calcium is suggested to be the cause of these syndromes. Veratrine suppresses, on the other hand, inactivation of the sodium channel in the cardiac muscle cells to generate persistent sodium current, thereby induces contracture as a result of the increased intracellular calcium concentration mediated by the sodium/calcium exchange transport system following the increased intracellular sodium concentration. Therefore, the compounds according to the present invention are thought to suppress persistent Na current. Judging from these results, suppression of excess influx of sodium due to the persistent sodium current suppressing action of the compounds according to the present invention is effective for preventing pathological conditions of atrial flutter and fibrillation from developing.

The compound according to the present invention has the activity for suppressing contracture of the isolated cardiac muscle cells induced by veratrine while suppressing persistent sodium current. Therefore, the compounds according to the present invention may be also used for therapy or amelioration of disorders such as cardiac failure, angina pectoris, myocardial infarction, injury of cardiovascular system accompanied with revascularization by PTCA/PTCR/CAGB, injury of the cardiac muscle caused by ischemia-reperfusion (except severe arrythmia), acute phase in cerebral infarction, cerebral hemorrhage, transient cerebral ischemia, subarachnoid hemorrhage, head trauma, sequela of surgical operation of the brain, cerebrovascular disease such as sequela of cerebral arteriosclerosis, failure of implanted organs after implantation, symptoms caused by temporary hemostasis at surgical operation of the organs, convulsions, epilepsy, dementia (cerebrovascular and senile), neuralgia, migraine, neuropathic pain, digitalis intoxication, monkshood poisoning and pyrethroid insecticide poisoning. The compounds according to the present invention may be also used for hyperkalemic periodic paralysis, myotonia congenita, and long QT syndrome that are congenital diseases and caused by abnormal inactivation of the sodium channel due to abnormal sodium channel genes, i.e., by generation of persistent sodium current.

The drug according to the present invention is administered as formulations of the pharmaceutical compositions.

The pharmaceutical compositions according to the present invention may comprise at least one of the compound represented by the formula (I) according to the present invention, and it may be combined with pharmaceutically acceptable additives. In more detail, the compound according to the present invention may be appropriately combined with the following additives to form various formulations: excipients (for example lactose, sucrose, mannitol, crystalline cellulose and silicic acid), binders (for example, crystalline cellulose, sugars (mannitol, sucrose, sorbitol, erythritol and xylitol), dextrine, hydroxypropyl cellulose (HPC), hydroxypropylmethyl cellulose (HPMC), polyvinylpyrrolidone (PVP) and macrogol), lubricants (for example, magnesium stearate, calcium stearate and talc), colorants, flavoring agents, disintegrants (for example corn starch and carboxymethyl cellulose), antiseptics (benzalkonium chloride and paraoxybenzoic acid ester), isotonic agents (for example, glycerine, sodium chloride, calcium chloride, mannitol and glucose), pH adjustment agents (sodium hydroxide, potassium hydroxide, sodium carbonate, hydrochloric acid, sulfuric acid and a buffer solution such as phosphate buffer), stabilizers (for example sugar, sugar alcohol and xanthan gum), dispersion agents, antioxidants (for example, ascorbic acid, butylhydroxyanisole (BHA), propyl gallate and dl-α-topcopherol), buffers, preservatives (for example, paraben, benzyl alcohol and benzalkonium chloride), aromatics (for example, vanilin, 1-menthol and rose oil), dissolution aids (for example, polyoxyethylene hardened castor oil, Polysorbate 80, polyethylene glycol, phospholipid cholesterol and triethanolamine), absorption accelerators (for example, sodium glycolate, disodium edatate, sodium caprate, acyl carnitine and limone), gelation agents, suspending agents, surface active agents or emulsifying agents, and suitable additives and solvents which are normally used.

Such formulations include tablets, capsules, granules, powers, suppository, pessary, sublingual tablets, buccal tablets, oral cavity disintegrants, mastication tablets, troches, jelly compositions, paste compositions, patch agents for tunica mucous oris, syrup (oral liquid and emulsion), inhalants, injection formulation, a nasal formulation (liquid and powder), external agents (ointment, cream, jelly, gelatium agent), stick agents (tape, patch, cataplasm), liquid formulation, suspending agents and spray formulation. These formulations may be administered to a patient orally or parenterally (for example, intravenous injection, intra-arterial injection, hypodermic administration, intramuscular injection, intrarectal administration, vaginal administration, intranasal administration, or absorption via the mucous membrane such as oral cavity mucous membrane and penial mucous membrane).

While the dosage of the compounds according to the present invention is usually 0.1 mg to 2.5 g a day for an adult, preferably 0.5 mg to 1.0 g, and more preferably 1 mg to 500 mg, it may be appropriately increased or decreased depending on disease conditions and administration route.

The entire quantity may be orally or parenterally given by two to six times administration, or may be continuously injected by intravenous drip.

EXAMPLES

While the following examples are provided for describing the present invention in more detail, the present invention is not restricted thereto. Nuclear magnetic resonance (NMR) spectra were measured by using JEOL JNM-EX270 FT-NMR (manufactured by JEOL Ltd.; data obtained by this instrument are marked by *) or JEOL JNM-LA300 FT-NMR (manufactured by JEOL Ltd.). Infra-red (IR) spectra were measured by using HORIBA FT-200 or FT-720 (manufactured by Horiba Seisakusho Co.). Melting points were measured by using Mettler FP80 or FP90 (mannufactured by Mettler Co.).

Example 1
Synthesis of 1-Benzyl-4-[2-[N-(4-methoxyphenyl)-N-methylamino]ethyl]piperidin-4-ol
<Step 1>
Synthesis of N-(4-methoxyphenyl)-N-methyl-2-(1-benzyl-4-hydroxypiperidin-4-yl)acetamide A solution of 4'-methoxy-N-methylacetanilide (12 g) in an anhydrous tetrahydrofuran (30 mL) was added to a solution in an anhydrous tetrahydrofuran (100 mL) of lithium diisopropylamide prepared from diisopropylamine (10.5 mL) and n-butyl lithium (1.53M hexane solution; 48 mL) at below −65° C., and the mixture was stirred at −78° C. for 15 minutes. An anhydrous tetrahydrofuran solution (20 mL) of 1-benzylpiperidin-4-one (12.7 g) was then added to this reaction mixture at below −65° C., and the resulting mixture was stirred at −78° C. for 10 minutes. After increasing the temperature to room temperature, water was added to the mixture, and the mixed solution was extracted with ethyl acetate. The organic layer was washed with water and saturated brine and dried over anhydrous sodium sulfate, followed by distilling off the solvent under reduced pressure. The residue obtained was recrystallized from ether-hexane to obtain the titled compound (17.2 g).
<Step 2>
Synthesis of 1-benzyl-4-[2-[N-(4-methoxyphenyl)-N-methylamino]ethyl]piperidin-4-ol A solution of borane-methyl sulfide complex (10M, 13.5 mL) was added to a solution in an anhydrous tetrahydrofuran (150 mL) of the compound (10 g) obtained in the Step 1, and the mixed solution was heated under reflux for 2 hours. After allowing the solution to cool, methanol (10 mL) and 10% hydrogen chloride in methanol (10 mL) was added to the solution, followed by heating under reflux for 2 hours. After cooling, the solvent was distilled off under reduced pressure. The solution was added with water and saturated aqueous sodium bicarbonate to make an alkaline solution and extracted with ethyl acetate. The organic layer was washed with water and saturated brine. After drying the organic layer over anhydrous sodium sulfate, the solvent was distilled off under reduced pressure. The residue obtained was purified through silica gel column chromatography (elution solvent:methylene chloride:methanol=49:1 to 9:1) to obtain the titled compound (8.2 g).

Example 2
Synthesis of 1-benzyl-4-[2-[N-(4-ethoxyphenyl)-N-methylamino]ethyl]piperidin-4-ol
<Step 1>
Synthesis of N-(4-ethoxyphenyl)-N-methyl-2-(1-benzyl-4-hydroxypiperidin-4-yl)acetamide A solution of 4'-ethoxy-N-methylacetanilide (0.97 g) in an anhydrous tetrahydrofuran (30 mL) was cooled to −78° C. under an argon atmosphere, and lithium hexamethyldisilazide (1M tetrahydrofuran solution; 6 mL) was added to the solution at below −65° C., followed by stirring at −78° C. for 15 minutes. Subsequently, 1-benzylpiperidin-4-one (1.1 g) was added to the reaction mixture at below −65° C., and the mixed solution was stirred at −78° C. for 10 minutes. After increasing the temperature to room temperature, water was added to the mixture and extracted with ethyl acetate. The organic layer was washed with water and saturated brine and dried over anhydrous sodium sulfate, and the solvent was distilled off under reduced pressure. The titled compound (1.08 g) was obtained by recrystallization of the obtained residue from hexane.
<Step 2>
Synthesis of 1-benzyl-4-[2-[N-(4-ethoxyphenyl)-N-methylamino]ethyl]piperidin-4-ol The titled compound (0.79 g) was obtained by the same method as in the Step 2 in the Example 1 by using the compound (1.0 g) obtained in the Step 1.

Example 3
Synthesis of 1-benzyl-4-[2-[N-(4-n-butoxyphenyl)-N-methylamino]ethyl]piperidin-4-ol
<Step 1>
Synthesis of N-(4-n-butoxyphenyl)-N-methyl-2-(1-benzyl-4-hydroxypiperidin-4-yl)acetamide A solution of 4'-n-butoxy-N-methylacetanilide (0.34 g) in anhydrous tetrahydrofuran (1.5 mL) was added to a solution of lithium diisopropylamide prepared from diisopropylamine (0.22 mL) and n-butyl lithium (1.58M hexane solution; 1.07 mL) in an anhydrous tetrahydrofuran (1.6 mL) under cooling with ice-water, and the mixture was stirred for 30 minutes. A solution of 1-benzylpiperidin-4-one (0.32 g) in anhydrous tetrahydrofuran solution (1.5 mL) was added to thereto under cooling with ice-water, followed by additional stirring for 30 minutes. After increasing the temperature to room temperature, water was added to the mixture and extracted with ethyl acetate. The organic layer was washed with water and saturated brine and dried over anhydrous sodium sulfate. The solvent was distilled off. The titled compound (0.33 g) was obtained by recrystallization of the residue from hexane.
<Step 2>
Synthesis of 1-benzyl-4-[2-[N-(4-n-butoxyphenyl)-N-methylamino]ethyl]piperidin-4-ol The titled compound (0.28 g) was obtained by the same method as in the Step 2 in the Example 1 using the compound (0.3 g) obtained in the Step 1.

The following compounds were synthesized by any one of the method in the Step 1 in the Examples 1 to 3, and by the same method as in the Step 2 in the Example 1.

Example 4
1-Benzyl-4-[2-[N-methyl-N-(4-isopropoxyphenyl)-amino]ethyl]piperidin-4-ol
<Step 1>
N-methyl-N-(4-isopropoxyphenyl)-2-(1-benzyl-4-hydroxypiperidin-4-yl)acetamide
<Step 2>
1-benzyl-4-[2-[N-methyl-N-(4-isopropoxyphenyl)-amino]ethyl]piperidin-4-ol

Example 5
1-Benzyl-4-[2-[N-(4-cyclohexyloxyphenyl)-N-methylamino]-ethyl]piperidin-4-ol
<Step 1>
N-(4-cyclohexyloxyphenyl)-N-methyl-2-(1-benzyl-4-hydroxypiperidin-4-yl)acetamide
<Step 22
1-benzyl-4-[2-[N-(4-cyclohexyloxyphenyl)-N-methylamino]ethyl]piperidin-4-ol

Example 6
1-Benzyl-4-[2-[N-methyl-N-(4-phenoxyphenyl) amino]ethyl]-piperidin-4-ol
<Step 1>
N-methyl-N-(4-phenoxyphenyl)-2-(1-benzyl-4-hydroxypiperidin-4-yl)acetamide
<Step 2>
1-Benzyl-4-[2-[N-methyl-N-(4-phenoxyphenyl)-amino]ethyl]piperidin-4-ol

Example 7
1-Benzyl-4-[2-[N-(3-n-butoxyphenyl)-N-methylamino]-ethyl]piperidin-4-ol
<Step 1>
N-(3-n-butoxyphenyl)-N-methyl-2-(1-benzyl-4-hydroxypiperdin-4-yl)acetamide
<Step 2>
1-Benzyl-4-[2-[N-(3-n-butoxyphenyl)-N-methylamino]ethyl]piperidin-4-ol

Example 8
1-Benzyl-4-[2-[N-(2-n-butoxyphenyl)-N-methylamino]-ethyl]piperidin-4-ol
<Step 1>
N-(2-n-butoxyphenyl)-N-methyl-2-(1-benzyl-4-hydroxypiperidin-4-yl)acetamide
<Step 2>
1-Benzyl-4-[2-[N-(2-n-butoxyphenyl)-N-methylamino]ethyl]piperidin-4-ol

Example 9
1-Benzyl-4-[2-[N-(4-n-butoxy-3-fluorophenyl)-N-methylamino]ethyl]piperidin-4-ol
<Step 1>
N-(4-n-butoxy-3-fluorophenyl)-N-methy-2-(1-benzyl-4-hydroxypiperidin-4-yl)acetamide
<Step 2>
1-Benzyl-4-[2-[N-(4-n-butoxy-3-fluorophenyl)-N-methylamino]ethyl]piperidin-4-ol

Example 10
1-Benzyl-4-[2-[N-methyl-N-(4-n-propylphenyl)amino]-ethyl]piperidin-4-ol
<Step 1>
N-methyl-N-(4-n-propylphenyl)-2-(1-benzyl-4-hydroxypiperidin-4-yl)acetamide
<Step 2>
1-Benzyl-4-[2-[N-methyl-N-(4-n-propylphenyl)-amino]ethyl]piperidin-4-ol

Example 11
1-Benzyl-4-[2-[N-(4-n-butoxyphenyl)-N-methylamino]-1-methoxyethyl]piperidin-4-ol
<Step 1>
N-(4-n-butoxyphenyl)-N-methy-2-(1-benzyl-4-hyrdoxypiperidin-4-yl)-2-methoxyacetamide
<Step 2>
1-Benzyl-4-[2-[N-(4-n-butoxyphenyl)-N-methylamino]-1-methoxyethyl]piperidin-4-ol

Example 12
Synthesis of 1-benzyl-4-[2-[N-(4-n-butoxyphenyl)-N-methylamino]-1-hydroxyethyl]piperidin-4-ol
<Step 1>
Synthesis of N-(4-n-butoxyphenyl)-N-methyl-2-tert-butyldimethylsilyloxy-2-(1-benzyl-4-hydroxypiperidin-4-yl)acetamide The titled compound (0.75 g) was obtained by the same method as in the Step 1 in the Example 1 by using 4'-n-butoxy-2-tert-butyldimethylsilyloxy-N-methylacetanilide (3.85 g).
<Step 2>
Synthesis of 1-benzyl-4-[2-[N-(4-n-butoxyphenyl)-N-methylamino]-1-hydroxyethyl]piperidin-4-ol The titled compound (0.48 g) was obtained by the same method as in the Step 2 in the Example 1 by using the compound (0.70 g) obtained in the Step 1, wherein the silyl group was simultaneously removed by treating with hydrochloric acid.

Example 13
Synthesis of 1-benzyl-4-[2-[N-(4-n-butoxyphenyl)-amino]ethyl]piperidin-4-ol
<Step 1>
Synthesis of N-(4-n-butoxyphenyl)-2-(1-benzyl-4-hydroxypiperidin-4-yl)acetamide To a solution of (1-benzyl-4-hydroxypiperidin-4-yl) acetic acid lithium salt (3.09 g) in methylene chloride (60 mL) were added 4-n-butoxyaniline (2.0 g) and pyridine (2.14 mL). Phosphorous oxychloride (1.19 mL) was added dropwise to the solution under cooling with an ice-sodium chloride, followed by stirring at 5 to 10° C. for 1 hour. The mixture was made alkaline with saturated aqueous sodium bicarbonate under cooling with an ice-water, and the solution was extracted with ethyl acetate. The organic layer was washed with water and saturated brine and dried over anhydrous sodium sulfate, and then, the solvent was distilled off under reduced pressure. The residue was purified with silica gel column chromatography (elution solvent; methylene chloride:methanol=19:1 to 9:1) to obtain the titled compound (1.15 g).
<Step 2>
Synthesis of 1-benzyl-4-[2-[N-(4-n-butoxyphenyl)amino]ethyl]piperidin-4-ol The titled compound (0.42 g) was obtained by the same method as in the Step 2 in the Example 1 by using the compound (0.5 g) obtained in the step 1.

Example 14

Synthesis of 1-benzyl-4-[2-[N-methyl-N-(4-n-propoxyphenyl)amino]ethyl]piperidin-4-ol <Step 1>
Synthesis of 1-benzyl-4-[2-[N-(4-hydroxyphenyl)-N-methylamino]ethyl]piperidin-4-ol To an acetic acid solution (51 mL) of the compound (7.12 g) obtained in the Step 2 in the Example 1, 48% hydrobromic acid (51 mL) was added, and the solution was heated under reflux for 5 hours. After concentrating the reaction solution under reduced pressure, the residue was dissolved in water. The aqueous solution was made alkaline with saturated aqueous sodium bicarbonate, and was extracted with ethyl acetate. The organic layer was washed with water and saturated brine, dried over anhydrous sodium sulfate, and the solvent was distilled off under reduced pressure. The residue obtained was purified by silica gel column chromatography [Chromatorex NH™] (elution solvent; ethyl acetate:hexane=1:1 to ethyl acetate:methanol=19:1) to obtain the titled compound (3.91 g).

<Step 2>
Synthesis of 1-benzyl-4-[2-[N-methyl-N-(4-n-propoxyphenyl)amino]ethyl]piperidin-4-ol To an anhydrous dimethylformamide solution (8 mL) of the compound (500 mg) obtained in the Step 1 was added sodium hydride (60% dispersion in oil; 70 mg) under ice-cooling, and stirred for 30 minutes. Then, n-propyl bromide (217 mg) was added and the solutionn was stirred at 10° C. for 5 hours. The mixture was poured into water, and the aqueous mixture was extracted with ethyl acetate. The organic layer was washed with water and saturated brine, dried over anhydrous sodium sulfate, the solvent was distilled off under reduced pressure. The residue obtained was purified by silica gel column chromatography [Chromatorex NH™] (elution solvent; ethyl acetate:hexane=1:3) to obtain the titled compound (82 mg).

The following compounds were obtained by the same method as in the Step 2 in the Example 14.

Example 15
1-Benzyl-4-[2-[N-methyl-N-(4-n-pentyloxyphenyl)-amino]ethyl]piperidin-4-ol

Example 16
1-Benzyl-4-[2-[N-(4-isobutoxyphenyl)-N-methylamino]-ethyl]piperidin-4-ol

Example 17
1-Benzyl-4-[2-[N-(4-cyclobutoxyphenyl)-N-methylamino]-ethyl]piperidin-4-ol

Example 18
1-Benzyl-4-[2-[N-methyl-N-(4-cyclopropylmethyloxyphenyl)-amino]ethyl]piperidin-4-ol

Example 19
Synthesis of 4-[2-[N-(4-n-butoxyphenyl)-N-methylamino]ethyl]-1-(3,4-methylenedioxyphenylmethyl)-piperidin-4-ol <Step 1>
Synthesis of 4-[2-[N-(4-n-butoxyphenyl)-N-methylamino]ethyl]piperidin-4-ol Ammonium formate (0.48 g) and 10% palladium on carbon (0.1 g) were added to a methanol solution (10 mL) of the compound (1.0 g) obtained in the Step 2 in the Example 3, and the mixture was heated under reflux for 1 hour. After cooling, the catalyst was filtered off, and the filtrate was concentrated under reduced pressure. A saturated aqueous sodium bicarbonate was added to the residue to make the solution alkaline, and the aqueous solution was extracted with methylene chloride. The organic layer was washed with water and saturated brine, and dried over anhydrous sodium sulfate. The titled compound (0.75 g) was obtained by distilling off the solvent.

<Step 2>
Synthesis of 4-[2-[N-(4-n-butoxyphenyl)-N-methylamino]ethyl]-1-(3,4-methylenedioxyphenyl-methyl)-piperidin-4-ol Piperonal (0.21 g) and acetic acid (0.14 mL), and then sodium triacetoxyborohydride (0.58 g) were added to an anhydrous methylene chloride solution (10 mL) of the compound (0.42 g) obtained in the Step 1, and the mixed solution was stirred overnight under an argon atmosphere. The reaction solution was made alkaline by adding saturated aqueous sodium bicarbonate solution, and was extracted with methylene chloride. The organic layer was washed with water and saturated brine, and dried over anhydrous sodium sulfate. The solvent was distilled off under reduced pressure. The residue was purified by silica gel column chromatography (elution solvent; methylene chloride:methanol=49:1 to 19:1) to obtain the titled compound (0.46 g)

The following compounds were synthesized by the same method as in the Step 2 in the Example 19.

Example 20
4-[2-[N-(4-n-butoxyphenyl)-N-methylamino]ethyl]-1-(4-chlorophenylmethyl)piperidin-4-ol

Example 21
4-[2-[N-(4-n-butoxyphenyl)-N-methylamino]ethyl]-1-[4-(trifluoromethyl)phenylmethyl]piperidin-4-ol

Example 22
4-[2-[N-(4-n-butoxyphenyl)-N-methylamino]ethyl]-1(4-cyanophenylmethyl)piperidin-4-ol

Example 23
4-[2-[N-(4-n-butoxyphenyl)-N-methylamino]ethyl]-1-(4-methoxycarbonylphenylmethyl)piperidin-4-ol

Example 24
4-[2-[N-(4-n-butoxyphenyl)-N-methylamino]ethyl]-1-[4-(dimethylamino)phenylmethyl]piperidin-4-ol

Example 25
4-[2-[N-(4-n-butoxyphenyl)-N-methylamino]ethyl]-1-(4-hydroxyphenylmethyl)piperidin-4-ol

Example 26
4-[2-[N-(4-n-butoxyphenyl)-N-methylamino]ethyl]-1-(4-methoxyphenylmethyl)piperidin-4-ol

Example 27
4-[2-[N-(4-n-butoxyphenyl)-N-methylamino]ethyl]-1-(3-methoxyphenylmethyl)piperidin-4-ol

Example 28
4-[2-[N-(4-n-butoxyphenyl)-N-methylamino]ethyl]-1-(2-methoxyphenylmethyl)piperidin-4-ol

Example 29
4-[2-[N-(4-n-butoxyphenyl)-N-methylamino]ethyl]-1-(3-fluorophenylmethyl)piperidin-4-ol

Example 30
4-[2-[N-(4-n-butoxyphenyl)-N-methylamino]ethyl]-1-(3,4-difluorophenylmethyl)piperidin-4-ol

Example 31
4-[2-[N-(4-n-butoxyphenyl)-N-methylamino]ethyl]-1(4-methylphenylmethyl)piperidin-4-ol

Example 32
4-[2-[N-(4-n-butoxyphenyl)-N-methylamino]ethyl]-1-(2,3-dihydro-1H-inden-2-yl)piperidin-4-ol

Example 33
Synthesis of 4-[2-[N-(4-n-butoxyphenyl)-N-methylamino] ethyl]-1-[2-(4-fluorophenyl)ethyl]piperidin-4-ol Step 1
Synthesis of 4-[2-[N-(4-n-butoxyphenyl)-N-methylamino] ethyl]-1-[(4-fluorophenyl)acetyl]-piperidin-4-ol To an anhydrous methylene chloride solution (5 mL) of the compound (0.52 g) obtained in the Step 1 in the Example 19 and 4-fluorophenylacetic acid (0.29 g) was added 1-ethyl-3-(3-dimethylaminopropyl)carbodiimide hydrochloride (0.36 g), and the mixture was stirred at room temperature for 1 hour. Water was added to the solution and then, the mixed solution was extracted with ethyl acetate. The organic layer was washed with water and saturated brine, and the organic layer was dried over anhydrous sodium sulfate. The solvent was distilled off under reduced pressure. The residue obtained was purified by silica gel column chromatography (elution solvent; methylene chloride:methanol=97:3 to 19:1) to obtain the titled compound (0.72 g).

<Step 2>
4-[2-[N-(4-n-butoxyphenyl)-N-methylamino]ethyl]-1-[2-(4-fluorophenyl)ethyl]piperidin-4-ol The titled compound (0.59 g) was obtained by the same method as in the Step 2 in the Example 1 by using the compound (0.71 g) obtained in the Step 1.

Example 34
Synthesis of 4-[2-[N-(4-n-butoxyphenyl)-N-methylamino] ethyl]-1-(4-fluorophenylmethyl)piperidin-4-ol To an anhydrous methylene chloride solution (5 mL) of the compound (0.30 g) obtained in the Step 1 in the Example 19 were added 4-fluorobenzylbromide (0.13 mL) and triethylamine (0.14 mL) under cooling with ice-water. The mixed solution was stirred under cooling with ice-water for 2 hours, and at room temperature for 2 hours. The reaction solution was poured into ice water, and the mixed solution was made alkaline by adding saturated aqueous sodium bicarbonate, followed by extraction with ethyl acetate. The organic layer was washed with water and saturated brine, and dried over anhydrous sodium sulfate. The solvent was distilled off under reduced pressure. The residue obtained was purified by silica gel column chromatography (elution solvent; methylene chloride:methanol=97:3 to 19:1) to obtain the titled compound (0.28 g).

The following compounds were synthesized by the same method as in the Example 34.

Example 35
4-[2-[N-(4-n-butoxyphenyl)-N-methylamino]ethyl]-1(1-phenylethyl)piperidin-4-ol

Example 36
4-[2-[N-(4-n-butoxyphenyl)-N-methylamino]ethyl]-1-benzoylmethylpiperidin-4-ol

Example 37
4-[2-[N-(4-n-butoxyphenyl)-N-methylamino]ethyl]-1-(4-fluorobenzoylmethyl)piperidin-4-ol

Example 38
Synthesis of 4-[2-[N-(4-n-butoxyphenyl)-N-methylamino]-1-methoxyethyl]-1-(2-phenylethyl)piperidin-4-ol
<Step 1>
Synthesis of 4-[2-[N-(4-n-butoxyphenyl)-N-methylamino]-1-methoxyethyl]piperidin-4-ol To a methanol solution (50 mL) of the compound (0.62 g) obtained in the Step 2 in the Example 11 was added 10% palladium on carbon (0.1 g), and the mixture was stirred at room temperature for 2 days under a hydrogen atmosphere. The catalyst was filtered off, and the filtrate was concentrated under reduced pressure to obtain the titled compound (0.42 g).

<Step 2>
Synthesis of 4-[2-[N-(4-n-butoxyphenyl)-N-methylamino]-1-methoxyethyl]-1-(2-phenylethyl)-piperidin-4-ol The titled compound (0.45 g) was obtained by the same method as in the Example 34 by using the compound (0.39 g) obtained in the step 1 and phenethyl bromide (0.26 g).

Example 39
Synthesis of 4-[2-[N-(4-n-butoxyphenyl)-N-methylamino]-ethyl]-1-[2-(4-methoxyphenyl)ethyl]piperidin-4-ol
<Step 1>
Synthesis of N-(4-n-butoxyphenyl)-N-methy-2-(4-hydroxypiperidin-4-yl)acetamide The crude product obtained by the same method as in the Step 1 in the Example 19 by using the compound (0.62 g) obtained in the step 1 in the Example 3 was purified by silica gel column chromatography [Chromatorex NH™] (elution solvent; methylene chloride:methanol=19:1) to obtain the titled compound (0.48 g).

<Step 2>
Synthesis of N-(4-n-butoxyphenyl)-N-methyl-2-[4-hydroxy-1-[(4-methoxyphenyl)acetyl]piperidin-4-yl] acetamide The titled compound (0.95 g) was obtained by the same method as in the Step 1 in the Example 33 by using the compound (0.71 g) obtained in the Step 1.

<Step 3>
Synthesis of 4-[2-[N-(4-n-butoxyphenyl)-N-methylamino]-ethyl]-1-[2-(4-methoxyphenyl)ethyl]piperidin-4-ol The titled compound (0.58 g) was obtained by the same method as in the Step 2 in the Example 1 by using the compound (0.95 g) obtained in the Step 2.

The following compounds were synthesized by the same methods as in the Steps 2 and 3 in the Example 39.

Example 40
4-[2-[N-(4-n-butoxyphenyl)-N-methylamino]ethyl]-1-[2-(2,4-difluorophenyl)ethyl]piperidin-4-ol
<Step 1>
N-(4-n-butoxyphenyl)-N-methyl-2-[1-(2,4-difluorophenyl) acetyl-4-hydroxypiperidin-4-yl]acetamide
<Step 2>
4-[2-[N-(4-n-butoxyphenyl)-N-methylamino]ethyl]-1-[2-(2,4-difluorophenyl)ethyl]piperidin-4-ol

Example 41
4-[2-[N-(4-n-butoxyphenyl)-N-methylamino]ethyl]-1-[2-(3,4-methylenedioxyphenyl)ethyl]piperidin-4-ol
<Step 1>
N-(4-n-butoxyphenyl)-N-methyl-2-[4-hydroxy-1-[(3,4-methylenedioxyphenyl)acetyl]piperidin-4-yl]acetamide
<Step 2>
4-[2-[N-(4-n-butoxyphenyl)-N-methylamino]ethyl]-1-[2-(3,4-methylenedioxyphenyl)ethyl]piperidin-4-ol

Example 42

4-[2-[N-(4-n-butoxyphenyl)-N-methylamino]ethyl]-1(3-phenylpropyl)piperidin-4-ol

<Step 1>

N-(4-n-butoxyphenyl)-N-methyl-2-[4-hydroxy-1-(3-phenylpropionyl)piperidin-4-yl]acetamide <Step 2>

4-[2-[N-(4-n-butoxyphenyl)-N-methylamino]ethyl]-1-(3-phenylpropyl)piperidin-4-ol

Example 43

4-[2-[N-(4-n-butoxyphenyl)-N-methylamino]ethyl]-1-(2-phenoxyethyl)piperidin-4-ol <Step 1>

N-(4-n-butoxyphenyl)-N-methyl-2-[4-hydroxy-1-(phenoxyacetyl)piperidin-4-yl]acetamide <Step 2>

4-[2-[N-(4-n-butoxyphenyl)-N-methylamino]ethyl]-1-(2-phenoxyethyl)piperidin-4-ol

Example 44

Synthesis of 4-[2-[N-(4-n-butoxyphenyl)-N-methylamino]-ethyl]-1-(2-phenylethyl)piperidin-4-ol <Step 1>

Synthesis of N-(4-n-butoxyphenyl)-N-methyl-2-[4-hydroxy-1-(phenylacetyl)piperidin-4-yl]acetamide Triethylamine (0.37 mL) and then phenylacetyl chloride (0.32 mL) were added to an anhydrous methylene chloride solution (9 mL) of the compound (0.71 g) obtained in the Step 1 in the Example 39, and the mixed solution was stirred at room temperature for 5 hours. The reaction solution was poured into ice-water, and saturated aqueous sodium bicarbonate solution was added to make the solution alkaline, followed by extraction with methylene chloride. The organic layer was washed with water and saturated brine, dried over anhydrous sodium sulfate, and the solvent was distilled off under a reduced pressure. The residue obtained was purified by silica gel column chromatography (elution solvent; ethyl acetate:hexane=3:7 to ethyl acetate) to obtain the titled compound (0.62 g).

<Step 2>

Synthesis of 4-[2-[N-(4-n-butoxyphenyl)-N-methylamino]ethyl]-1-(2-phenylethyl)piperidin-4-ol The titled compound (0.38 g) was obtained by the same method as in the step 2 in the Example 1 by using the compound (0.62 g) obtained in the Step 1.

Example 45

Synthesis of 4-[2-[N-(4-n-butoxyphenyl)amino]ethyl]-1-[2-(4-fluorophenyl)ethyl]piperidin-4-ol <Step 1>

Synthesis of N-(4-n-butoxyphenyl)amino-2-(4-hydroxypiperidin-4-yl)acetamide

The titled compound (3.0 g) was obtained by the same method as in the Step 1 in the Example 38 by using the compound (4.0 g) obtained in the Step 1 in the Example 13.

<Step 2>

Synthesis of N-(4-n-butoxyphenyl)-2-[4-hydroxy-1-[(4-fluorophenyl)acetyl]piperidin-4-yl]acetamide The titled compound (0.62 g) was obtained by the same method as in the Step 1 in the Example 33 by using the compound (0.50 g) obtained in the Step 1.

<Step 3>

Synthesis of 4-[2-[N-(4-n-butoxyphenyl)amino]ethyl]-1-[2-(4-fluorophenyl)ethyl]piperidin-4-ol The titled compound (0.49 g) was obtained by the same method as in the Step 2 in the Example 1 by using the compound (0.60 g) obtained in the Step 2.

Example 46

Synthesis of 4-[2-[N-(4-cyclobutoxyphenyl)-N-methylamino]ethyl]-1-(2-phenylethyl)piperidin-4-ol <Step 1>

Synthesis of N-(4-cyclobutoxyphenyl)-N-methyl-2-(1-benzyl-4-hydroxypiperidin-4-yl)acetamide The titled compound (1.60 g) was obtained by the same method as in the Step 1 in the Example 13 by using 4-cyclobutoxy-N-methylaniline (1.2 g).

<Step 2>

Synthesis of N-(4-cyclobutoxyphenyl)-N-methyl-2-(4-hydroxypiperidin-4-yl)acetamide The titled compound (1.25 g) was obtained by the same method as in the Step 1 in the Example 38 by using the compound (1.60 g) obtained in the Step 1.

<Step 3>

Synthesis of N-(4-cyclobutoxyphenyl)-N-methyl-2-[4-hydroxy-1-(phenylacetyl)piperidin-4-yl]acetamide The titled compound (0.43 g) was obtained by the same method as in the Step 1 in the Example 44 by using the compound (0.35 g) obtained in the Step 2.

<Step 4>

Synthesis of 4-[2-[N-(4-cyclobutoxyphenyl)-N-methylamino]ethyl]-1-(2-phenylethyl)piperidin-4-ol The titled compound (0.35 g) was obtained by the same method as in the Step 2 in the Example 1 by using the compound (0.40 g) obtained in the Step 3.

Example 47

Synthesis of 4-[2-[N-(4-cyclobutoxyphenyl)-N-methylamino]ethyl]-1-[2-(4-fluorophenyl)ethyl]piperidin-4-ol <Step 1>

N-(4-cyclobutoxyphenyl)-N-methyl-2-[1-[(4-fluorophenyl)acetyl]-4-hydroxypiperidin-4-yl]acetamide The titled compound (0.92 g) was obtained by the same method as in the Step 1 in the Example 33 by using the compound (0.82 g) obtained in the Step 2 in the Example 46.

<Step 2>

4-[2-[N-(4-cyclobutoxyphenyl)-N-methylamino]ethyl]-1-[2-(4-fluorophenyl)ethyl]piperidin-4-ol The titled compound (0.63 g) was obtained by the same method as in the Step 2 in the Example 1 by using the compound (0.91 g) obtained in the Step 1

The following compounds were obtained by the same methods as in the Steps 1 and 2 in the example 47.

Example 48

4-[2-[N-(4-cyclobutoxyphenyl)-N-methylamino]ethyl]-1-[2-(2-chlorophenyl)ethyl]piperidin-4-ol <Step 1>

N-(4-cyclobutoxyphenyl)-N-methy-2-[1-(2-chlorophenyl)acetyl-4-hydroxypiperidin-4-yl]acetamide <Step 2>

4-[2-[N-(4-cyclobutoxyphenyl)-N-methylamino]ethyl]-1-[2-(2-chlorophenyl)ethyl]piperidin-4-ol

Example 49

Synthesis of 4-[2-[N-[4-n-butoxy-3-(hydroxymethyl)phenyl]-N-methylamino]ethyl]-1-[2-(4-fluorophenyl)ethyl]piperidin-4-ol <Step 1>

Synthesis of N-(4-n-butoxy-3-methoxycarbonylphenyl)-N-methyl-2-(1-benzyl-4-hydroxypiperidin-4-yl)acetamide The titled compound (1.18 g) was obtained by the same method as in the Step 1 in the Example 13 by using lithium (1-benzyl-4-hydroxypiperidin-4-yl)acetate (2.159 g) and methyl 2-n-butoxy-5-(methylamino)benzoate (2.00 g).

<Step 2>
Synthesis of N-(4-n-butoxy-3-methoxycarbonylphenyl)-N-methyl-2-(4-hydroxypiperidin-4-yl)acetamide The titled compound (0.88 g) was obtained by the same method as in the Step 1 in the Example 19 by using the compound (1.18 g) obtained in the Step 1.

<Step 3>
Synthesis of N-(4-n-butoxy-3-methoxycarbonylphenyl)-N-methyl-2-[1-(4-fluorophenyl)acetyl-4-hydroxypiperidin-4-yl]acetamide The titled compound (1.23 g) was obtained by the same method as in the Step 1 in the Example 33 by using the compound (0.88 g) obtained in the Step 2 and 4-fluorophenyl acetic acid (0.43 g).

<Step 4>
Synthesis of N-(4-n-butoxy-3-carboxyphenyl)-N-methyl-2-[1-(4-fluorophenyl)acetyl-4-hydroxypiperidin-4-yl]acetamide An aqueous solution (2.7 mL) of lithium hydroxide monohydrate (0.20 g) was added to a methanol solution (7 mL) of the compound (1.23 g) obtained in the Step 3, and the mixture was refluxed for 10 minutes with heating. The solvent was distilled off under reduced pressure after cooling. Water was added to the residue, and the solution was washed with ethyl acetate. The aqueous layer was adjusted to pH 3 with 1N hydrochloric acid, and extracted with methylene chloride. The organic layer was washed with water and saturated brine and dried over anhydrous sodium sulfate. The titled compound (1.19 g) was obtained by distilling off the solvent.

<Step 5>
Synthesis of 4-[2-[N-[4-n-butoxy-3-(hydroxymethyl)phenyl]-N-methylamino]ethyl]-1-[2-(4-fluorophenyl)ethyl]piperidin-4-ol The titled compound (0.78 g) was obtained by the same method as in the Step 2 in the Example 1 by using the compound (1.19 g) obtained in the Step 4.

Example 50
Synthesis of 4-[2-[N-[4-n-butoxy-2-(hydroxymethyl)phenyl]-N-methylamino]ethyl]-1-[2-(3,4-methylenedioxyphenyl)ethyl]piperidin-4-ol <Step 1>
Synthesis of tert-butyl [4-hydroxy-1-[(3,4-methylenedioxyphenyl)acetyl]piperidin-4-yl]acetate The titled compound (3.25 g) was obtained by the same method as in the Step 1 in the Example 33 by using tert-butyl (4-hydroxypiperidin-4-yl)acetate (2.0 g) which is obtained from tert-butyl (4-hydroxy-1-benzylpiperidin-4-yl)acetate by the same method as in the Step 1 in the Example 38 and 3,4-methylenedioxyphenylacetic acid (2.0 g).

<Step 2>
Synthesis of [4-hydroxy-1-[(3,4-methylenedioxyphenyl)acetyl]piperidin-4-yl]acetic acid Anisole (1.5 mL) and the compound (1.6 g) obtained in the Step 1 were added to ice-cooled trifluoroacetic acid (5 mL). The mixture was stirred at room temperature for 2 hours. The reaction solution was concentrated under reduced pressure, ether was added to the residue, and the mixture was extracted with 1N aqueous sodium hydroxide solution. The aqueous layer was adjusted to pH 2 by adding conc. hydrochloric acid, and was extracted with methylene chloride. The organic layer was washed with saturated brine and dried over anhydrous sodium sulfate. The solvent was distilled off under a reduced pressure. The residue obtained was recrystallized from ether to obtain the titled compound (1.25 g).

<Step 3>
Synthesis of N-[4-n-butoxy-2-(hydroxymethyl)phenyl]-N-methyl-2-[4-hydroxy-1-[(3,4-methylenedioxyphenyl)acetyl]piperidin-4-yl]acetamide The titled compound (1.60 g) was obtained by the same method as in the Step 1 in the Example 33 by using the compound (1.2 g) obtained in the Step 2 and 4-n-butoxy-2-(hydroxymethyl)-N-methylaniline (0.94 g).

<Step 4>
Synthesis of 4-[2-[N-[4-n-butoxy-2-(hydroxymethyl)phenyl]-N-methylamino]ethyl]-1-[2-(3,4-methylenedioxyphenyl)ethyl]piperidin-4-ol The titled compound (1.02 g) was obtained by the same method as in the Step 2 in the Example 1 by using the compound (1.50 g) obtained in the Step 3.

Example 51
Synthesis of 4-[2-[N-(4-n-butoxyphenyl)-N-methylamino]-1-hydroxyethyl]-1-(2-phenylethyl)piperidin-4-ol <Step 1>
Synthesis of N-(4-n-butoxyphenyl)-N-methy-2-(1-benzyl-4-hydroxypiperidin-4-yl)-2-benzyloxyacetamide The titled compound (4.17 g) was obtained by the same method as in the Step 1 in the Example 1 by using 2-benzyloxy-4'-n-butoxy-N-methylacetanilide (3.27 g).

<Step 2>
Synthesis of N-(4-n-butoxyphenyl)-N-methyl-2-hydroxy-2-(4-hydroxypiperidin-4-yl)acetamide The titled compound (2.46 g) was obtained by the same method as in the Step 1 in the Example 38 by using the compound (4.0 g) obtained in the Step 1.

<Step 3>
Synthesis of N-(4-n-butoxyphenyl)-N-methyl-2-hydroxy-2-[4-hydroxy-1-(2-phenylethyl)piperidin-4-yl]acetamide The titled compound (1.05 g) was obtained by the same method as in the Step 1 in the Example 34 by using the compound (1.2 g) obtained in the Step 2 and phenethyl bromide (0.79 g).

<Step 4>
Synthesis of 4-[2-[N-(4-n-butoxyphenyl)-N-methylamino]-1-hydroxyethyl]-1-(2-phenylethyl)-piperidin-4-ol The titled compound (0.84 g) was obtained by the same method as in the Step 2 in the Example 1 by using the compound (1.0 g) obtained in the Step 3.

Example 52
Synthesis of 4-[2-[N-(4-n-butoxyphenyl)-N-methylamino]-1-methoxyethyl]-1-[2-(4-fluorophenyl)ethyl]piperidin-4-ol <Step 1>
Synthesis of N-(4-n-butoxyphenyl)-N-methyl-2-(4-hydroxypiperidin-4-yl)-2-methoxyacetamide The titled compound (0.58 g) was obtained by the same method as in the Step 1 in the Example 19 by using the compound (0.74 g) obtained in the Step 1 in the Example 11.

<Step 2>
Synthesis of N-(4-n-butoxyphenyl)-N-methy-2-[1-[2-(4-fluorophenyl)ethyl]-4-hydroxypiperidin-4-yl]-2-methoxyacetamide Potassium carbonate (0.34 g) and sodium iodide (61 mg) were added to an anhydrous dimethylformamide solution (7 mL) of the compound (0.57 g) obtained in the Step 1 and 2-(4-fluorophenyl)ethylchloride (0.39 g), and the mixture was stirred at 80 to 95° C. for 5 hours. After allowing to cool, the reaction mixture was poured into ice-water and was extracted with ethyl acetate. The organic layer was washed with water and saturated brine, dried over anhydrous sodium sulfate, and the solvent was distilled off under a reduced pressure. The residue obtained was purified with silica gel chromatography (elution solvent; ethyl acetate:methanol= 49:1 to 4:1) to obtain the titled compound (0.56 g).

<Step 3>
Synthesis of 4-[2-[N-(4-n-butoxyphenyl)-N-methylamino]-1-methoxyethyl]-1-[2-(4-fluorophenyl)ethyl]piperidin-4-ol The titled compound (0.43 g) was obtained by the same method as in the Step 2 in the Example 1 by using the compound (0.55 g) obtained in the Step 2.

Example 53
Synthesis of 4-[2-[N-(4-n-butoxyphenyl)-N-methylamino]-1-hydroxyethyl]-1-[2-(4-fluorophenyl)ethyl]piperidin-4-ol
<Step 1>
Synthesis of N-(4-n-butoxyphenyl)-N-methyl-2-[4-hydroxy-1-[2-(4-fluorophenyl)ethyl]piperidin-4-yl]-2-hydroxyacetamide The titled compound (0.71 g) was obtained by the same method as in the Step 2 in the Example 52 by using the compound (0.62 g) obtained in the Step 2 in the Example 51.
<Step 2>
Synthesis of 4-[2-[N-(4-n-butoxyphenyl)-N-methylamino]-1-hydroxyethyl]-1-[2-(4-fluorophenyl)ethyl]piperidin-4-ol The titled compound (0.54 g) was obtained by the same method as in the Step 2 in the Example 1 by using the compound (0.70 g) obtained in the Step 1.

Example 54
Synthesis of 4-[2-[N-(4-n-butoxyphenyl)-N-methylamino]-ethyl]-1-(2-phenyl-2-hydroxyethyl)piperidin-4-ol Sodium borohydride (54 mg) was added to a methanol solution (5 mL) of the compound (0.60 g) obtained in the Example 36 under ice-cooling, and the solution was stirred for 1 hour. Water was added to the reaction solution and extracted with ethyl acetate. The organic layer was washed with water and saturated brine and, after drying over anhydrous sodium sulfate, and the solvent was distilled off under reduced pressure. The residue obtained was crystallized from ether-hexane to obtain the titled compound (0.43 g).

The following compound was synthesized by the same method as in the Example 54.

Example 55
4-[2-[N-(4-n-butoxyphenyl)-N-methylamino]ethyl]-1-[2-(4-fluorophenyl)-2-hydroxyethyl]piperidin-4-ol

Example 56
Synthesis of 4-[2-[N-acetyl-N-(4-n-butoxyphenyl)amino]-ethyl]-1-benzylpiperidin-4-ol The titled compound (1.85 g) was obtained by the same method as in the Step 1 in the Example 33 by using the compound (2.0 g) obtained in the Step 2 in the Example 13 and acetic acid (0.36 mL).

Example 57
4-[2-[N-acetyl-N-(4-n-butoxyphenyl)amino]ethyl]-1-[2-(4-fluorophenyl)ethyl]piperidin-4-ol

Example 58
Synthesis of 1-benzyl-4-methoxy-4-[2-[N-(4-n-butoxyphenyl)-N-methylamino]ethyl]piperidine
<Step 1>
Synthesis of N-(4-n-butoxyphenyl)-N-methyl-2-(1-tert-butoxycarbonyl-4-hydroxypiperidin-4-yl)acetamide The titled compound (7.8 g) was obtained by the same method as in the Step 1 in the Example 1 by using 1-tert-butoxycarbonylpiperidin-4-one (4.5 g) and 4'-n-butoxy-N-methylacetanilide (5.0 g).
<Step 2>
Synthesis of N-(4-n-butoxyphenyl)-N-methyl-2-(1-tert-butoxycarbonyl-4-methoxypiperidin-4-yl)acetamide Sodium hydride (60% dispersion in oil; 0.29 g) was added to an anhydrous dimethylformamide solution (10 mL) of the compound (2.0 g) obtained in the Step 1 under ice-cooling, and the mixture was stirred for 1 hour. Then, methyl iodide (0.6 mL) was added and the mixture was stirred for 30 minutes, followed by additional stirring at room temperature for 3 hours. The reaction mixture was poured into water and extracted with ethyl acetate. The organic layer was washed with water and saturated brine. After drying the organic layer over anhydrous sodium sulfate, the solvent was distilled off under reduced pressure. The residue obtained was recrystallized from ether-hexane to obtain the titled compound (0.89 g).
<Step 3>
Synthesis of N-(4-n-butoxyphenyl)-N-methyl-2-(4-methoxypiperidin-4-yl)acetamide Trifluoroacetic acid (3 mL) was ice-cooled, added with the compound (0.80 g) obtained in the Step 2 and stirred for 30 minutes. The reaction solution was concentrated under reduced pressure, and 1N aqueous sodium hydroxide solution was added to the residue, followed by extraction with ethyl acetate. The organic layer was dried over anhydrous sodium sulfate, and the solvent was distilled off under reduced pressure. The residue obtained was purified by silica gel column chromatography [Chromatorex NH™) (elution solvent:methylene chloride:methanol=49:1 to 9:1) to give the titled compound (0.53 g).
<Step 4>
Synthesis of N-(4-n-butoxyphenyl)-N-methyl-2-(1-benzyl-4-methoxypiperidin-4-yl)acetamide The titled compound (0.43 g) was obtained by the same method as in the Step 2 in the Example 19 by using the compound (0.50 g) obtained in the Step 3 and benzaldehyde (0.21 g).
<Step 5>
Synthesis of 1-benzyl-4-methoxy-4-[2-[N-(4-n-butoxyphenyl)-N-methylamino]ethyl]piperidine The titled compound (0.36 g) was obtained by the same method as in the Step 2 in the Example 1 by using the compound (0.42 g) obtained in the Step 4.

Example 59
Synthesis of 1-benzyl-4-[N-(4-n-butoxyphenyl)-N-methylaminomethyl]piperidin-4-ol Activated neutral aluminum oxide 90 (activity I, made by Merck Co.) (5 g) was added to a diethyl ether solution (10 mL) of 1-benzylpiperidin-4-spiro-2'-oxirane (0.50 g) and 4-butoxy-N-methylaniline (0.53 g) and stirred at room temperature overnight. Methanol (20 mL) was added to the reaction solution and stirred at room temperature for 2 hours. The reaction solution was filtered, and the filtrate was concentrated under reduced pressure. The residue obtained was purified by silica gel column chromatography (elution solvent; ethyl acetate) to obtain the titled compound (0.71 g).

The following compounds were synthesized by the same methods as in the Step 2 in the Example 19.

Example 60
4-[2-[N-(4-n-butoxypehyl)-N-methylamino]ethyl]-1-(2-fluorophenylmethyl)piperidin-4-ol

Example 61
4-[2-[N-(4-n-butoxyphenyl)-N-methylamino]ethyl]-1-(3-methylphenylmethyl)piperidin-4-ol

Example 62
4-[2-[N-(4-n-butoxypehyl)-N-methylamino]ethyl]-1-(2-methylphenylmethyl)piperidin-4-ol

Example 63
4-[2-[N-(4-n-butoxypehyl)-N-methylamino]ethyl]-1-(3-fluoro-4-methoxyphenylmethyl)piperidin-4-ol The following compounds were synthesized by the same methods as in the Steps 1 and 2 in the Example 1.

Example 64
1-benzyl-4-[2-[N-methyl-N-[4-(2-methyl-2-butoxy)phenyl]-amino]ethyl]piperidin-4-ol
<Step 1>
N-methyl-N-[4-(2-methyl-2-butoxy)phenyl]-2-(1-benzyl-4-hydroxypiperidin-4-yl)acetamide
<Step 2>
1-benzyl-4-[2-[N-methyl-N-[4-(2-methyl-2-butoxy)phenyl]amino]ethyl]piperidin-4-ol

Example 65
1-benzyl-4-[2-[N-(4-n-butoxy-3-hydroxyphenyl)-N-methylamino]ethyl]piperidin-4-ol
<Step 1>
N-[4-n-butoxy-3-(methoxymethyloxy)phenyl]-N-methyl-2-(1-benzyl-4-hydroxypiperidin-4-yl)acetamide
<Step 2>
1-benzyl-4-[2-[N-(4-n-butoxy-3-hydroxyphenyl)-N-methylamino]ethyl]piperidin-4-ol

Example 66
1-benzyl-4-[2-[N-(4-n-butoxy-2-fluorophenyl)-N-methylamino]ethyl]piperidin-4-ol
<Step 1>
N-(4-n-butoxy-2-fluorophenyl)-N-methyl-2-(1-benzyl-4-hydroxypiperidin-4-yl)acetamide
<Step 2>
1-benzyl-4-[2-[N-(4-n-butoxy-2-fluorophenyl)-N-methylamino]ethyl]piperidin-4-ol

Example 67
1-benzyl-4-[2-[N-(4-n-butoxyphenyl)-N-isopropylamino]-ethyl]piperidin-4-ol
<Step 1>
N-(4-n-butoxyphenyl)-N-isopropyl-2-(1-benzyl-4-hydroxypiperidin-4-yl)acetamide
<Step 2>
1-benzyl-4-[2-[N-(4-n-butoxyphenyl)-N-isopropylamino]ethyl]piperidin-4-ol The following compounds were synthesized by the same method as in the Step 2 in the Example 14.

Example 68
1-benzyl-4-[2-[N-methyl-N-[4-(3-pentyloxy)phenyl]-amino]ethyl]piperidin-4-ol

Example 69
1-benzyl-4-[2-[N-methyl-N-[4-(3-methylbutoxy)phenyl]-amino]ethyl]piperidin-4-ol

Example 70
1-benzyl-4-[2-[N-[4-(2-cyclopropylethyloxy)phenyl]-N-methylamino]ethyl]piperidin-4-ol

Example 71
1-benzyl-4-[2-[N-[4-(3-butenyloxy)phenyl]-N-methylamino]ethyl]piperidin-4-ol

Example 72
Synthesis of 1-(4-chorophenylmethyl)-4-[2-[N-methyl-N-(4-isopropoxyphenyl)amino]ethyl]piperidin-4-ol
<Step 1>
Synthesis of 4-[2-[N-methyl-N-(4-isopropoxyphenyl)amino]ethyl]piperidin-4-ol The titled compound (0.31 g) was obtained by the same method as in the Step 1 in the Example 38 by using the compound (0.45 g) obtained in the Step 2 in the Example 4.

<Step 2>
Synthesis of 1-(4-chlorophenylmethyl)-4-[2-[N-methyl-N-(4-isopropoxyphenyl)amino]ethyl]piperidin-4-ol
The titled compound (0.14 g) was obtained by the same method as in the Step 2 in the Example 19 by using the compound (0.15 g) obtained in the Step 1 and 4-chlorobenzaldehyde (0.14 g).

The following compounds were synthesized by the same method as in the Step 2 in the Example 72.

Example 73
1-(4-bromophenylmethyl)-4-[2-[N-methyl-N-(4-isopropoxyphenyl)amino]ethyl]piperidin-4-ol

Example 74
4-[2-[N-methyl-N-(4-isopropoxyphenyl)amino]ethyl]-1-[4-(trifluoromethyl)phenylmethyl]piperidin-4-ol

Example 75
4-[2-[N-methyl-N-(4-isopropoxyphenyl)amino]ethylj-1-[(4-isopropylphenyl)methyl]piperidin-4-ol

Example 76
1-(4-methoxyphenylmethyl)-4-[2-[N-methyl-N-(4-isopropoxyphenyl)amino]ethyl]piperidin-4-ol

Example 77
1-(3-methoxyphenylmethyl)-4-[2-[N-methyl-N-(4-isopropoxyphenyl)amino]ethyl]piperidin-4-ol

Example 78
1-(4-fluorophenylmethyl)-4-[2-[N-methyl-N-(4-isopropoxyphenyl)amino]ethyl]piperidin-4-ol

Example 79
1-(4-cyanophenylmethyl)-4-[2-[N-methyl-N-(4-isopropoxyphenyl)amino]ethyl]piperidin-4-ol

Example 80
4-[2-[N-methyl-N-(4-isopropoxyphenyl)amino]ethyl]-1-(2-naphthylmethyl)piperidin-4-ol

Example 81
4-[2-[N-methyl-N-(4-isopropoxyphenyl)amino]ethyl]-1-[(4-isopropoxyphenyl)methyl]piperidin-4-ol

Example 82
1-(2-bromophenylmethyl)-4-[2-[N-methyl-N-(4-isopropoxyphenyl)amino]ethyl]piperidin-4-ol

Example 83
1-(3-bromophenylmethyl)-4-[2-[N-methyl-N-(4-isopropoxyphenyl)amino]ethyl]piperidin-4-ol

Example 84
4-[2-[N-methyl-N-(4-isopropoxyphenyl)amino]ethyl]-1-(4-nitrophenylmethyl)piperidin-4-ol

Example 85
4-[2-[N-methyl-N-(4-isopropoxyphenyl)amino]ethyl]-1-[3-(trifluoromethyl)phenylmethyl]piperidin-4-ol

Example 86
1-[4-(methoxycarbonyl)phenylmethyl]-4-[2-[N-methyl-N-(4-isopropoxyphenyl)amino]ethyl]piperidin-4-ol

Example 87
1-(2,4-difluorophenylmethyl)-4-[2-[N-methyl-N-(4-isopropoxyphenyl)amino]ethyl]piperidin-4-ol

Example 88
1-[4-fluoro-3-(trifluoromethyl)phenylmethyl]-4-[2-[N-methyl-N-(4-isopropoxyphenyl)amino]ethyl]piperidin-4-ol

Example 89
4-[2-[N-methyl-N-(4-isopropoxyphenyl)amino]ethyl]-1-(4-trifluoromethoxyphenylmethyl)piperidin-4-ol

Example 90
1-(2-fluoro-4-isopropoxyphenylmethyl)-4-[2-[N-methyl-N-(4-isopropoxyphenyl)amino]ethyl]piperidin-4-ol

Example 91
1-(4-biphenylmethyl)-4-[2-[N-methyl-N-(4-isopropoxyphenyl)amino]ethyl]piperidin-4-ol

Example 92
4-[2-[N-methyl-N-(4-isopropoxyphenyl)amino]ethyl]-1-(4-phenoxyphenylmethyl)piperidin-4-ol

Example 93
1-(4-bromo-2-fluorophenylmethyl)-4-[2-[N-methyl-N-(4-isopropoxyphenyl)amino]ethyl]piperidin-4-ol

Example 94
1-(3-fluorophenylmethyl)-4-[2-[N-methyl-N-(4-isopropoxyphenyl)amino]ethyl]piperidin-4-ol

Example 95
1-(2-fluorophenylmethyl)-4-[2-[N-methyl-N-(4-isopropoxyphenyl)amino]ethyl]piperidin-4-ol

Example 96
4-[2-[N-methyl-N-(4-isopropoxyphenyl)amino]ethyl]-1-(3-trifluoromethoxyphenylmethyl)piperidin-4-ol

Example 97
4-[2-[N-methyl-N-(4-isopropoxyphenyl)amino]ethyl]-1(2-trifluoromethoxyphenylmethyl)piperidin-4-ol

Example 98
1-(3-chlorophenylmethyl)-4-[2-[N-methyl-N-(4-isopropoxyphenyl)amino]ethyl]piperidin-4-ol

Example 99
1-(2-chlorophenylmethyl)-4-[2-[N-methyl-N-(4-isopropoxyphenyl)amino]ethyl]piperidin-4-ol

Example 100
1-(3-cyanophenylmethyl)-4-[2-[N-methyl-N-(4-isopropoxyphenyl)amino]ethyl]piperidin-4-ol

Example 101
1-(2-cyanophenylmethyl)-4-[2-[N-methyl-N-(4-isopropoxyphenyl)amino]ethyl]piperidin-4-ol

Example 102
4-[2-[N-methyl-N-(4-isopropoxyphenyl)amino]ethyl]-1-[2-(trifluoromethyl)phenylmethyl]piperidin-4-ol

Example 103
1-(2-methoxyphenylmethyl)-4-[2-[N-methyl-N-(4-isopropoxyphenyl)amino]ethyl]piperidin-4-ol

Example 104
4-[2-[N-methyl-N-(4-isopropoxyphenyl)amino]ethyl]-1-(3-nitrophenylmethyl)piperidin-4-ol

Example 105
4-[2-[N-methyl-N-(4-isopropoxyphenyl)amino]ethyl]-1-(2-nitrophenylmethyl)piperidin-4-ol

Example 106
1-[4-(ethoxycarbonyl)phenylmethyl]-4-[2-[N-methyl-N-(4-isopropoxyphenyl)amino]ethyl]piperidin-4-ol

Example 107
4-[2-[N-methyl-N-(4-isopropoxyphenyl]amino]ethyl]-1-(2-thienylmethyl)piperidin-4-ol

Example 108
4-[2-[N-methyl-N-(4-isopropoxyphenyl]amino]ethyl]-1-(3-thienylmethyl)piperidin-4-ol

Example 109
4-[2-[N-methyl-N-(4-isopropoxyphenyl)amino]ethyl]-1-[4-(methylthio)phenylmethyl]piperidin-4-ol

Example 110
1-[2-(methoxycarbonyl)phenylmethyl]-4-[2-[N-methyl-N-(4-isopropoxyphenyl)amino]ethyl]piperidin-4-ol

Example 111
1-[3-(methoxycarbonyl)phenylmethyl]-4-[2-[N-methyl-N-(4-isopropoxyphenyl)amino]ethyl]piperidin-4-ol

Example 112
1-(3-furylmethyl)-4-[2-[N-methyl-N-(4-isopropoxyphenyl)amino]ethyl]piperidin-4-ol

Example 113
4-[2-[N-methyl-N-(4-isopropoxyphenyl)amino]ethyl]-1-[4-(isopropoxycarbonyl)phenylmethyl]piperidin-4-ol

Example 114
4-[2-[N-methyl-N-(4-isopropoxyphenyl)amino]ethyl]-1-[4-(n-propoxycarbonyl)phenylmethyl]piperidin-4-ol

Example 115
Synthesis of 4-[2-[N-methyl-N-(4-isopropoxyphenyl)-amino]ethyl]-1-(2-phenoxyethyl)piperidin-4-ol 2-Phenoxyethyl bromide (0.2 g), potassium carbonate (0.14 g) and sodium iodide (15 mg) were added to a dimethylformamide solution (5 mL) of the compound (0.29 g) obtained in the Step 1 in the Example 72 and stirred at 100° C. for 2 hours. The reaction solution was poured into ice-water and extracted with ethyl acetate. The organic layer was washed with water and extracted with 1N aqueous hydrochloric acid. The aqueous layer was adjusted to pH 9 with sodium hydrogen carbonate, and was extracted with ethyl acetate. The organic layer obtained was washed with water and saturated brine, dried over anhydrous sodium sulfate, and the solvent was distilled off under a reduced pressure. The residue obtained was purified by silica gel column chromatography (elution solvent; methylene chloride:methanol=94:6 to 85:15) to obtain the titled compound (0.38 g).

The following compounds were synthesized by the same method as in the Example 115.

Example 116
1-[2-(4-fluorophenoxy)ethyl]-4-[2-[N-methyl-N-(4-isopropoxyphenyl)amino]ethyl]piperidin-4-ol

Example 117
4-[2-[N-methyl-N-(4-isopropoxyphenyl)amino]ethyl]-1-(3-phenylpropyl)piperidin-4-ol

Example 118
1-(3-biphenylmethyl)-4-[2-[N-methyl-N-(4-isopropoxyphenyl)amino]ethyl]piperidin-4-ol

Example 119

1-(2-biphenylmethyl)-4-[2-[N-methyl-N-(4-isopropoxyphenyl)amino]ethyl]piperidin-4-ol

Example 120

Synthesis of 1-[2-fluoro-4-(trifluoromethyl)phenylmethyl]-4-[2-[N-methyl-N-(4-isopropoxyphenyl)amino]ethyl]piperidin-4-ol <Step 1>

Synthesis of 1-[2-fluoro-4-(trifluoromethyl)benzoyl]-4-[2-[N-methyl-N-(4-isopropoxyphenyl)-amino]ethyl]piperidin-4-ol The titled compound (0.4 g) was obtained by the same method as in the Step 1 in the Example 33 by using the compound (0.3 g) obtained in the Step 1 in the Example 72.

<Step 2>

Synthesis of 1-[2-fluoro-4-(trifluoromethyl)-phenylmethyl]-4-[2-[N-methyl-N-(4-isopropoxyphenyl)-amino]ethyl]piperidin-4-ol The titled compound (0.35 g) was obtained by the same method as in the Step 2 in the Example 1 by using the compound (0.39 g) obtained in the Step 1.

Example 121

Synthesis of 4-[2-[N-methyl-N-(4-ethoxyphenyl)amino]ethyl]-1-[4-(trifluoromethyl)phenylmethyl]piperidin-4-ol <Step 1>

Synthesis of 4-[2-[N-methyl-N-(4-ethoxyphenyl)-amino]ethyl]piperidin-4-ol

The titled compound (4.10 g) was obtained by the same method as in the step 1 in the example 38 using the compound (5.48 g) obtained in the Step 2 in the Example 2.

<Step 2>

Synthesis of 4-[2-[N-methyl-N-(4-ethoxyphenyl)-amino]ethyl]-1-[4-(trifluoromethyl)phenylmethyl]-piperidin-4-ol The titled compound (0.61 g) was obtained by the same method as in the Step 2 in the Example 19 by using the compound (0.42 g) obtained in the Step 1.

Example 122

Synthesis of 1-[4-(methoxycarbonyl)phenylmethyl]-4-[2-[N-methyl-N-(3-isopropoxyphenyl)amino]ethyl]piperidin-4-ol <Step 1>

Synthesis of N-methyl-N-(3-isopropoxyphenyl)-2-(1-benzyl-4-hydroxypiperidin-4-yl)acetamide The titled compound (7.39 g) was obtained by the same method as in the Step 1 in the Example 1 by using 3'-isopropoxy-N-methylacetanilide (5.50 g).

<Step 2>

Synthesis of 1-benzyl-4-[2-[N-methyl-N-(3-isopropoxyphenyl)amino]ethyl]piperidin-4-ol An anhydrous tetrahydrofuran solution (28 mL) of the compound (7.00 g) obtained in the step 1 was cooled with ice-water under nitrogen atmosphere. A tetrahydrofuran solution of borane-tetrahydrofuran complex (1M; 70.7 mL) was added little by little. After completing the addition, the solution was heated under reflux for 2 hours. Methanol (20 mL) was added little by little under cooling with ice-water, and the solution was adjusted to below pH 1 by adding 10% hydrochloric acid-methanol solution (20 mL), followed by heat under reflux for 1.5 hour. After allowing the reaction solution to cool, the solvent was distilled off, and the residue was dissolved in 1N hydrochloric acid. After washing with ether, the aqueous layer was adjusted to pH 9 by adding potassium carbonate and extracted with ethyl acetate. The organic layer was washed with saturated brine, dried over anhydrous sodium sulfate, and the solvent was distilled off under reduced pressure. The residue obtained was purified by silica gel column chromatography [Chromatorex NH™] (elution solvent; ethyl acetate:hexane=1:4 to 2:3) to obtain the titled compound (6.52 g).

<Step 3>

Synthesis of 4-[2-[N-methyl-N-(3-isopropoxyphenyl)amino]ethyl]piperidin-4-ol

The titled compound (4.63 g) was obtained by the same method as in the Step 1 in the Example 38 by using the compound (6.00 g) obtained in the Step 2.

<Step 4>

Synthesis of 1-[4-(methoxycarbonyl)phenylmethyl]-4-[2-[N-methyl-N-(3-isopropoxyphenyl)amino]ethyl]-piperidin-4-ol The titled compound (0.74 g) was obtained by the same method as in the Step 2 in the Example 19 by using the compound (0.50 g) obtained in the Step 3 and 4-(methoxycarbonyl)benzaldehyde (0.56 g).

The following compounds were synthesized by the same method as in the Steps 1 to 4 in the Example 122.

Example 123

1-[4-(methoxycarbonyl)phenylmethyl]-4-[2-[N-methyl-N-(2-isopropoxyphenyl)amino]ethyl]piperidin-4-ol <Step 1>

N-methyl-N-(2-isopropoxyphenyl)-2-(1-benzyl-4-hydroxypiperidin-4-yl)acetamide

<Step 2>

1-benzyl-4-[2-[N-methyl-N-(2-isopropoxyphenyl)-amino]ethyl]piperidin-4-ol

<Step 3>

4-[2-[N-methyl-N-(2-isopropoxyphenyl)-amino]ethyl]piperidin-4-ol

<Step 4>

1-[4-(methoxycarbonyl)phenylmethyl]-4-[2-[N-methyl-N-(2-isopropoxyphenyl)amino]ethyl]piperidin-4-ol

Example 124

Synthesis of 4-[2-[N-(4-isopropoxyphenyl)amino]ethyl]-1-[4-(methoxycarbonyl)phenylmethyl]piperidin-4-ol <Step 1>

Synthesis of N-(4-isopropoxyphenyl)-2-(1-benzyl-4-hydroxypiperidin-4-yl)acetamide Sodium hydride (60% dispersion in oil; 1.99 g) was added to an anhydrous tetrahydrofuran solution (80 mL) of 4'-isopropoxyacetanilide (8.0 g) under nitrogen atmosphere while cooling with ice-water, followed by stirring at the intact temperature for 1 hour. The reaction solution was cooled to −50° C. and added with an anhydrous tetrahydrofuran solution (80 mL) of lithium diisopropylamide prepared from diisopropylamine (11.6 mL) and n-butyl lithium (1.6M hexane solution; 51.8 mL), followed by stirring at −50 to −30° C. for 1 hour. An anhydrous tetrahydrofuran solution (40 mL) of 1-benzylpiperidin-4-one (7.83 g) was added to the reaction solution above at −30° C., and the mixture was stirred −30° C. for 30 minutes, and under cooling with ice-water for 2 hours. The reaction solution was poured into ice-water, and the aqueous solution was extracted with ethyl acetate. The organic layer was sequentially washed with water and saturated brine, dried over anhydrous sodium sulfate, and the solution was distilled off under reduced pressure. The residue obtained was purified by silica gel column chromatography (elution solvent; methylene chloride:methanol=90:10 to 75:25) to obtain the titled compound (10.3 g).

<Step 2>
Synthesis of 1-benzyl-4-[2-[N-(4-isopropoxyphenyl)amino]ethyl]piperidin-4-ol The titled compound (4.4 g) was obtained by the same method as in the Step 2 in the Example 122 by using the compound (9.9 g) in the Step 1.
<Step 3>
Synthesis of 4-[2-[N-(4-isopropoxyphenyl)amino]-ethyl]piperidin-4-ol The titled compound (3.2 g) was obtained by the same method as in the Step 1 in the Example 38 by using the compound (4.3 g) in the Step 2.
<Step 4>
Synthesis of 4-[2-[N-(4-isopropoxyphenyl)amino]-ethyl]-1-[4-(methoxycarbonyl)phenylmethyl]piperidin-4-ol The titled compound (0.23 g) was obtained by the same method as in the Step 2 in the Example 19 by using the compound (0.42 g) in the Step 3 and 4-(methoxycarbonyl)benzaldehyde (0.25 g).

Example 125

Synthesis of 4-[2-[N-(4-isopropoxyphenyl)amino]ethyl]-1-[4-(trifluoromethyl)phenylmethyl]piperidin-4-ol The titled compound (0.21 g) was obtained by the same method as in the Step 2 in the Example 19 by using the compound (0.42 g) in the Step 3 in the Example 124 and 4-(trifluoromethyl)-benzaldehyde (0.26 g).

Example 126

Synthesis of 4-[2-[N-methyl-N-(4-isopropoxyphenyl)amino]-1-hydroxyethyl]-1-[4-trifluoromethyl)-phenylmethyl]piperidin-4-ol
<Step 1>
Synthesis of N-methyl-N-(4-isopropoxyphneyl)-2-(1-benzyl-4-hydroxypiperidin-4-yl)-2-benzyloxyacetamide The titled compound (7.35 g) was obtained by the same method as in the Step 1 in the Example 1 by using 2-benzyloxy-4'-isopropoxy-N-methylacetanilide (5.20 g).
<Step 2>
Synthesis of N-methyl-N-(4-isopropoxyphneyl)-2-hydroxy-2-(4-hydroxypiperidin-4-yl)acetamide The titled compound (2.80 g) was obtained by the same method as in the Step 1 in the Example 19 by using the compound (7.35 g) obtained in the Step 1.
<Step 3>
Synthesis of 4-[2-[N-methyl-N-(4-isopropoxyphenyl)amino]-1-hydroxyethyl]piperidin-4-ol The titled compound (0.5 g) was obtained by the same method as in the Step 2 in the Example 122 by using the compound (0.7 g) obtained in the Step 2.
<Step 4>
Synthesis of 4-[2-[N-methyl-N-(4-isopropoxphenyl)amino]-1-hydroxyethyl]-1-[4-(trifluoromethyl)phenylmethyl]piperidin-4-ol The titled compound (0.56 g) was obtained by the same method as in the Step 2 in the Example 19 by using the compound (0.46 g) obtained in the Step 3 and 4-(trifluoromethyl) benzaldehyde (0.52 g).

Example 127

Synthesis of 4-methoxy-4-[2-[N-methyl-N-(4-isopropoxyphenyl)amino]ethyl]-1-[4-(trifluoromethyl)-phenylmethyl]piperidine
<Step 1>
Synthesis of N-methyl-N-(4-isopropoxyphenyl)-2-(1-tert-butoxycarbonyl-4-hydroxypiperidin-4-yl)acetamide The titled compound (9.5 g) was obtained by the same method as in the Step 1 in the Example 1 by using 1-tert-butoxycarbonylpiperidin-4-one (6.7 g) and 4'-isopropoxy-N-methylacetanilide (7.0 g).
<Step 2>
Synthesis of N-methyl-N-(4-isopropoxyphenyl)-2-(1-tert-butoxycarbonyl-4-methoxypiperidin-4-yl)acetamide The titled compound (5.22 g) was obtained by the same method as in the Step 2 in the Example 58 by using the compound (8.50 g) obtained in the Step 1.
<Step 3>
Synthesis of 4-methoxy-4-[2-[N-methyl-N-(4-isopropoxyphenyl)amino]ethyl]piperidine The titled compound (2.52 g) was obtained by the same method as in the Step 2 of the Example 122 by using the compound (4.7 g) obtained in the Step 2.
<Step 4>
Synthesis of 4-methoxy-4-[2-[N-methyl-N-(4-isopropoxyphenyl)amino]ethyl]-1-[4-(trifluormethyl)-phenylmethyl]piperidine The titled compound (0.59 g) was obtained by the same method as in the Step 2 in the Example 19 by using the compound (0.46 g) obtained in the step 3 and 4-(trifluoromethyl)benzaldehyde (0.52 g).

Example 128

Synthesis of 4-methoxy-1-[4-(methoxycarbonyl)phenylmethyl]-4-[2-[N-methyl-N-(4-isopropoxyphenyl)-amino]ethyl]piperidine The titled compound (0.46 g) was obtained by the same method as in the Step 2 in the Example 19 by using the compound (0.40 g) obtained in the Step 3 in the Example 127 and 4-(methoxycarbonyl)benzaldehyde (0.43 g).

Example 129

Synthesis of 4-[N-methyl-N-(4-isopropoxypheny)-aminomethyl]-1-[4-(trifluoromethyl)phenylmethyl]piperidin-4-ol
<Step 1>
Synthesis of 1-benzyl-4-[N-methyl-N-(4-isopropoxypheny)aminomethyl]piperidin-4-ol The titled compound (2.43 g) was obtained by the same method as in the Example 59 by using N-methyl-4-isopropoxyaniline (3.37 g)
<Step 2>
Synthesis of 4-[N-methyl-N-(4-isopropoxypheny)-aminomethyl]piperidin-4-ol The titled compound (1.81 g) was obtained by the same method as in the Step 1 in the Example 38 by using the compound (2.40 g) obtained in the Step 1.
<Step 3>
Synthesis of 4-[N-methyl-N-(4-isopropoxypheny)-aminomethyl]-1-[4-(trifluoromethyl)phenylmethyl]-piperidin-4-ol The titled compound (0.39 g) was obtained by the same method as in the Step 2 in the Example 19 by using the compound (0.30 g) obtained in the Step 2 and 4-(trifluoromethyl)benzaldehyde (0.38 g).

Example 130

Synthesis of 1-[4-(methoxycarbonyl)phenylmethyl]-4-[N-methyl-N-(4-isopropoxyphenyl)aminomethyl]piperidin-4-ol The titled compound (0.34 g) was obtained by the same method as in the Step 2 in the Example 19 by using the compound (0.30 g) obtained in the Step 2 of the Example 129 and 4-(methoxycarbonyl)benzaldehyde (0.35 g).

Example 131
Synthesis of 1-diphenylmethyl-4-[2-[N-methyl-N-(4-isopropoxyphenyl)amino]ethyl]piperidin-4-ol Diphenylmethyl bromide (0.27 g), triethylamine (0.11 g) and sodium iodide (15 mg) were added to a tetrahydrofuran solution (4 mL) of the compound (0.30 g) obtained in the Step 1 in the Example 72 and heated under reflux for 11 hours under nitrogen atmosphere. The reaction solution was cooled, added with a saturated aqueous sodium hydrogen carbonate solution and extracted with ethyl acetate. The organic layer was washed with saturated brine, dried over anhydrous sodium sulfate, and the solvent was distilled off under reduced pressure. The residue obtained was purified by silica gel column chromatography (elution solvent; hexane:ethyl acetate=7:3) to obtain the titled compound (0.23 g).

The following compounds were synthesized by the same method as in the Example 131.

Example 132
1-bis(4-fluorophenyl)methyl-4-[2-[N-methyl-N-(4-isopropoxyphenyl)amino]ethyl]piperidin-4-ol

Example 133
1-diphenylmethyl-4-[2-[N-(4-ethoxyphenyl)-N-methylamino]ethyl]piperidin-4-ol

Example 134
1-diphenylmethyl-4-[2-[N-methyl-N-(3-isopropoxyphenyl)amino]ethyl]piperidin-4-ol

Example 135
1-diphenylmethyl-4-[2-[N-methyl-N-(2-isopropoxyphenyl)amino]ethyl]piperidin-4-ol

Example 136
1-diphenylmethyl-4-[2-[N-(4-isopropoxyphenyl)-amino]ethyl]piperidin-4-ol

Example 137
1-diphenylmethyl-4-methoxy-4-[2-[N-methyl-N-(4-isopropoxyphenyl)amino]ethyl]piperidine

Example 138
1-diphenylmethyl-4-[N-methyl-N-(4-isopropoxyphenyl)-aminomethyl]piperidin-4-ol

Example 139
Synthesis of 1-benzyl-4-[2-[N-(4-n-butoxyphenyl)-N-ethylamino]ethyl]piperidin-4-ol The titled compound (0.16 g) was obtained by the same method as in the step 2 in the example 19 using the compound (0.15 g) obtained in the step 2 in the example 13 and an excess amount of acetaldehyde.

Example 140
Synthesis of 1-(4-cyano-2-fluorophenylmehtyl)-4-[2-[N-methyl-N-(4-isopropoxyphenyl)amino]ethyl]piperidin-4-ol Copper (I) cyanide (0.1 g) was added to an anhydrous dimethylformamide solution (2 mL) of the compound (0.4 g) obtained in the Example 93 and heated under reflux for 10 hours under nitrogen atmosphere. After the reaction solution was cooled to room temperature, a solution of ethylene diamine and water (3:7) was added to the reaction solution and stirred at 50° C. under heating. Then, the reaction solution was extracted with ethyl acetate, and the organic layer obtained was sequentially washed with water and saturated brine. The organic phase was dried over anhydrous sodium sulfate, and the solvent was distilled off under reduced pressure. The residue was purified by silica gel column chromatography [Chromatorex NH™] (elution solvent; ethyl acetate:hexane=1:3) to obtain the titled compound (0.12 g).

Example 141
Synthesis of 1-(4-acetylphenylmethyl)-4-[2-[N-methyl-N-(4-isopropoxypheny)amino]ethyl]piperidin-4-ol An anhydrous tetrahydrofuran solution (5 mL) of the compound (0.50 g) obtained in the example 79 was added dropwise to an ether solution (1M; 6.1 mL) of methyl lithium while cooling with ice-water, and the mixture was stirred for 40 minutes under cooling with ice-water. Then, sulfuric acid (3M; 2.5 mL) was added to the reaction solution while cooling with ice-water, followed by stirring at room temperature for 20 minutes. The reaction solution was made alkaline by adding saturated aqueous sodium bicarbonate solution, and was extracted with ethyl acetate. The organic layer was washed with saturated brine, dried over anhydrous sodium sulfate, and the solvent was distilled off under reduced pressure. The residue was purified by silica gel column chromatography (elution solvent; methylene chloride:methanol=20:1) to obtain the titled compound (0.38 g).

Example 142
Synthesis of 4-[2-[N-methyl-N-(4-isopropoxyphenyl)-amino]ethyl]-1-[4-(trifluoroacetylamino)phenylmethyl]-piperidin-4-ol <Step 1>
Synthesis of 1-(4-aminophenylmethyl)-4-[2-[N-methyl-N-(4-isopropoxyphenyl)amino]ethyl]piperidin-4-ol The compound (0.35 g) obtained in the Example 84 was dissolved in acetic acid (4 mL), and ion powder (0.15 g) was added to the solution, followed by stirring at 70 to 80° C. for 1.5 hours. Insoluble materials were removed by filtration, and the filtrate was concentrated under reduced pressure. The residue obtained was dissolved in methylene chloride, and the solution was sequentially washed with saturated aqueous sodium bicarbonate solution and saturated brine. After drying the organic layer obtained over anhydrous sodium sulfate, the solvent was distilled off under reduced pressure. The residue obtained was purified by silica gel column chromatography [Cromatorex NH™] (elution solvent; ethyl acetate:hexane=1:2 to 2:1) to obtain the titled compound (0.23 g).

<Step 2>
Synthesis of 4-[2-[N-methyl-N-(4-isopropoxyphenyl)-amino]ethyl]-1-[4-(trifluoroacetylamino)-phenylmethyl]piperidin-4-ol The compound (0.31 g) obtained in the Step 1 and triethylamine (0.12 mL) was dissolved in methylene chloride (5 mL), and trifluoroacetic anhydride (0.12 mL) was added dropwise with stirring under cooling with ice-water. After stirring the reaction solution for 30 minutes at the same temperature and for 30 minutes at room temperature, water (2 mL) was added while cooling with ice-water again. Saturated aqueous sodium bicarbonate was added to the reaction solution, and the mixed solution was extracted with methylene chloride. The organic layer was washed with saturated brine, dried over anhydrous sodium sulfate, and the solvent was distilled off under reduced pressure. The residue obtained was purified by silica gel column chromatography (elution solvent; methylene chloride:methanol= 95:5 to 85:15) to obtain the titled compound (0.27 g).

Example 143
Synthesis of 1-(4-carboxyphenylmethyl)-4-[2-[N-methyl-N-(4-isopropoxyphenyl)amino]ethyl]piperidin-4-ol lithium salt The compound (0.44 g) obtained in the Example 86 was dissolved in methanol (20 mL), and an aqueous solution (2 mL) of lithium hydroxide monohydrate (42 mg) was added followed by heat under reflux for 18 hours. The solvent was distilled off under reduced pressure, ether was added to the residue, and the precipitated solid was filtered off to obtain the titled compound (0.35 g).

Example 144
Preparation of 1-benzyl-4-[2-[N-(4-methoxyphenyl)-N-methylamino]ethyl]piperidin-4-ol dihydrochloride After adding a 10% methanol solution (2 mL) of hydrochloric acid to a methanol solution (5 mL) of the compound (1.0 g) obtained in the Step 2 in the Example 1, the solvent was distilled off under reduced pressure. The titled compound (0.98 g) was obtained by recrystallization of the residue obtained from ether.

The following hydrochlorides were obtained by the same method as in the Example 144.

Example 145
1-benzyl-4-[2-[N-(4-ethoxyphenyl)-N-methylamino]ethyl]-piperidin-4-ol dihydrochloride

Example 146
1-benzyl-4-[2-[N-(4-n-butoxyphenyl)-N-methylamino]ethyl]piperidin-4-ol dihydrochloride

Example 147
1-benzyl-4-[2-[N-methyl-N-(4-isopropoxyphenyl)-amino]ethyl]piperidin-4-ol dihydrochloride

Example 148
1-benzyl-4-[2-[N-(4-cyclohexyloxyphenyl)-N-methylamino]ethyl]piperidin-4-ol dihydrochloride

Example 149
1-benzyl-4-[2-[N-methyl-N-(4-phenoxyphenyl)amino]ethyl]-piperidin-4-ol dihydrochloride

Example 150
1-benzyl-4-[2-[N-(3-n-butoxyphenyl)-N-methylamino]-ethyl]piperidin-4-ol dihydrochloride

Example 151
1-benzyl-4-[2-[N-(2-n-butoxyphenyl)-N-methylamino]-ethyl]piperidin-4-ol dihydrochloride

Example 152
1-benzyl-4-[2-[N-(4-n-butoxy-3-fluorophenyl)-N-methylamino]ethyl]piperidin-4-ol dihydrochloride

Example 153
1-benzyl-4-[2-[N-methyl-N-(4-n-propylphenyl)amino]-ethyl]piperidin-4-ol dihydrochloride

Example 154
1-benzyl-4-[2-[N-(4-n-butoxyphenyi)-N-methylamino]-1-methoxyethyl]piperidin-4-ol dihydrochloride

Example 155
1-benzyl-4-[2-[N-(4-n-butoxyphenyl)-N-methylamino]-1-hydroxyethyl]piperidin-4-ol dihydrochloride

Example 156
1-benzyl-4-[2-[N-(4-n-butoxyphenyl)amino]ethyl]piperidin-4-ol dihydrochloride

Example 157
1-benzyl-4-[2-[N-methyl-N-(4-n-propoxyphenyl)amino]-ethyl]piperidin-4-ol dihydrochloride

Example 158
1-benzyl-4-[2-[N-methyl-N-(4-n-pentyloxyphenyl)amino]-ethyl]piperidin-4-ol dihydrochloride

Example 159
1-benzyl-4-[2-[N-(4-isobutoxyphenyl)-N-methylamino]ethyl]piperidin-4-ol dihydrochloride

Example 160
1-benzyl-4-[2-[N-(4-cyclobutoxyphenyl)-N-methylamino]ethyl]piperidin-4-ol dihydrochloride

Example 161
1-benzyl-4-[2-[N-methyl-N-(4-cyclopropylmethyloxyphenyl)-amino]ethyl]piperidin-4-ol dihydrochloride

Example 162
4-[2-[N-(4-n-butoxyphenyl)-N-methylamino]ethyl]-1-(3,4-methylenedioxyphenylmethyl)piperidin-4-ol dihydrochloride

Example 163
4-[2-[N-(4-n-butoxyphenyl)-N-methylamino]ethyl]-1-(4-chlorophenylmethyl)piperidin-4-ol dihydrochloride

Example 164
4-[2-[N-(4-n-butoxyphenyl)-N-methylamino]ethyl]-1-[4-(trifluoromethyl)phenylmethyl]piperidin-4-ol dihydrochloride

Example 165
4-[2-[N-(4-n-butoxyphenyl)-N-methylamino]ethyl]-1-(4-cyanophenylmethyl)piperidin-4-ol dihydrochloride

Example 166
4-[2-[N-(4-n-butoxyphenyl)-N-methylamino]ethyl]-1-(4-methoxycarbonylphenylmethyl)piperidin-4-ol dihydrochloride

Example 167
4-[2-[N-(4-n-butoxyphenyl)-N-methylamino]ethyl]-1-[4-(dimethylamino)phenylmethyl]piperidin-4-ol trihydrochloride

Example 168
4-[2-[N-(4-n-butoxyphenyl)-N-methylamino]ethyl]-1-(4-hydroxyphenylmethyl)piperidin-4-ol dihydrochloride

Example 169
4-[2-[N-(4-n-butoxyphenyl)-N-methylamino]ethyl]-1(4-methoxyphenylmethyl)piperidin-4-ol dihydrochloride

Example 170
4-[2-[N-(4-n-butoxyphenyl)-N-methylamino]ethyl]-1-(3-methoxyphenylmethyl)piperidin-4-ol dihydrochloride

Example 171
4-[2-[N-(4-n-butoxyphenyl)-N-methylamino]ethyl]-1-(2-methoxyphenylmethyl)piperidin-4-ol dihydrochloride

Example 172
4-[2-[N-(4-n-butoxyphenyl)-N-methylamino]ethyl]-1-(3-fluorophenylmethyl)piperidin-4-ol dihydrochloride

Example 173
4-[2-[N-(4-n-butoxyphenyl)-N-methylamino]ethyl]-1(3,4-difluorophenylmethyl)piperidin-4-ol dihydrochloride

Example 174
4-[2-[N-(4-n-butoxyphenyl)-N-methylamino]ethyl]-1-(4-methylphenylmethyl)piperidin-4-ol dihydrochloride

Example 175
4-[2-[N-(4-n-butoxyphenyl)-N-methylamino]ethyl]-1(2,3-dihydro-1H-inden-2-yl)piperidin-4-ol dihydrochloride

Example 176
4-[2-[N-(4-n-butoxyphenyl)-N-methylamino]ethyl]-1-[2-(4-fluorophenyl)ethyl]piperidin-4-ol dihydrochloride

Example 177
4-[2-[N-(4-n-butoxyphenyl)-N-methylamino]ethyl]-1(4-fluorophenylmethyl)piperidin-4-ol dihydrochloride

Example 178
4-[2-[N-(4-n-butoxyphenyl)-N-methylamino]ethyl]-1-(1-phenylethyl)piperidin-4-ol dihydrochloride

Example 179
4-[2-[N-(4-n-butoxyphenyl)-N-methylamino]ethyl]-1-benzoylmethylpiperidin-4-ol dihydrochloride

Example 180
4-[2-[N-(4-n-butoxyphenyl)-N-methylamino]ethyl]-1-(4-fluorobenzoylmethyl)piperidin-4-ol dihydrochloride

Example 181
4-[2-[N-(4-n-butoxyphenyl)-N-methylamino]-1-methoxyethyl]-1-(2-phenylethyl)piperidin-4-ol dihydrochloride

Example 182
4-[2-[N-(4-n-butoxyphenyl)-N-methylamino]ethyl]-1-[2-(4-methoxyphenyl)ethyl]piperidin-4-ol dihydrochloride

Example 183
4-[2-[N-(4-n-butoxyphenyl)-N-methylamino]ethyl]-1-[2-(2,4-difluorophenyl)ethyl]piperidin-4-ol dihydrochloride

Example 184
4-[2-[N-(4-n-butoxyphenyl)-N-methylamino]ethyl]-1-[2-(3,4-methylenedioxyphenyl)ethyl]piperidin-4-ol dihydrochloride

Example 185
4-[2-[N-(4-n-butoxyphenyl)-N-methylamino]ethyl]-1-(3-phenylpropyl)piperidin-4-ol dihydrochloride

Example 186
4-[2-[N-(4-n-butoxyphenyl)-N-methylamino]ethyl]-1-(2-phenoxyethyl)piperidin-4-ol dihydrochloride

Example 187
4-[2-[N-(4-n-butoxyphenyl)-N-methylamino]ethyl]-1(2-phenylethyl)piperidin-4-ol dihydrochloride

Example 188
4-[2-[N-(4-n-butoxyphenyl)amino]ethyl]-1-[2-(4-fluorophenyl)ethyl]piperidin-4-ol dihydrochloride

Example 189
4-[2-[N-(4-cyclobutoxyphenyl)-N-methylamino]ethyl]-1-(2-phenylethyl)piperidin-4-ol dihydrochloride

Example 190
4-[2-[N-(4-cyclobutoxyphenyl)-N-methylamino]ethyl]-1-[2-(4-fluorophenyl)ethyl]piperidin-4-ol dihydrochloride

Example 191
4-[2-[N-(4-cyclobutoxyphenyl)-N-methylamino]ethyl]-1-[2-(2-chlorophenyl)ethyl]piperidin-4-ol dihydrochloride

Example 192
4-[2-[N-[4-n-butoxy-3-(hydroxymethyl)phenyl]-N-methylamino]ethyl]-1-[2-(4-fluorophenyl)ethyl]piperidin-4-ol dihydrochloride

Example 193
4-[2-[N-[4-n-butoxy-2-(hydroxymethyl)phenyl]-N-methylamino]ethyl]-1-[2-(3,4-methylenedioxyphenyl)-ethyl]piperidin-4-ol dihydrochloride

Example 194
4-[2-[N-(4-n-butoxyphenyl)-N-methylamino]-1-hydroxyethyl]-1-(2-phenylethyl)piperidin-4-ol dihydrochloride

Example 195
4-[2-[N-(4-n-butoxyphenyl)-N-methylamino]-1-methoxyethyl]-1-[2-(4-fluorophenyl)ethyl]piperidin-4-ol dihydrochloride

Example 196
4-[2-[N-(4-n-butoxyphenyl)-N-methylamino]-1-hydroxyethyl]-1-[2-(4-fluorophenyl)ethyl]piperidin-4-ol dihydrochloride

Example 197
4-[2-[N-(4-n-butoxyphenyl)-N-methylamino]ethyl]-1-(2-phenyl-2-hydroxyethyl)piperidin-4-ol dihydrochloride

Example 198
4-[2-[N-(4-n-butoxyphenyl)-N-methylamino]ethyl]-1-[2-(4-fluorophenyl)-2-hydroxyethyl]piperidin-4-ol dihydrochloride

Example 199
4-[2-[N-acetyl-N-(4-n-butoxyphenyl)amino]ethyl]-1-benzyl-piperidin-4-ol monohydrochloride

Example 200
4-[2-[N-acetyl-N-(4-n-butoxyphenyl)amino]ethyl]-1-[2-(4-fluorophenyl)ethyl]piperidin-4-ol monohydrochloride

Example 201
1-benzyl-4-methoxy-4-[2-[N-(4-n-butoxyphenyl)-N-methylamino]ethyl]piperidine dihydrochloride

Example 202
1-benzyl-4-[N-(4-n-butoxyphenyl)-N-methylaminomethyl]-piperidin-4-ol dihydrochloride

Example 203
4-[2-[N-(4-n-butoxyphenyl)-N-methylamino]ethyl]-1-(2-fluorophenylmethyl)piperidin-4-ol dihydrochloride

Example 204
4-[2-[N-(4-n-butoxyphenyl)-N-methylamino]ethyl]-1-(3-methylphenylmethyl)piperidin-4-ol dihydrochloride

Example 205
4-[2-[N-(4-n-butoxyphenyl)-N-methylamino]ethyl]-1(2-methylphenylmethyl)piperidin-4-ol dihydrochloride

Example 206
4-[2-[N-(4-n-butoxyphenyl)-N-methylamino]ethyl]-1-(3-fluoro-4-methoxyphenylmethyl)piperidin-4-ol dihydrochloride

Example 207
Preparation of 1-benzyl-4-[2-[N-(4-n-butoxyphenyl)-N-methylamino]ethyl]piperidin-4-ol dimaleate Maleic acid (0.23 g) was added to a 2-propanol solution (10 mL) of the compound (0.40 g) obtained in the Step 2 in the Example 3 and dissolved under heating. After allowing the solution to cool, the crystals precipitated were collected by filtration and washed with ether to obtain the titled compound (0.59 g).

Example 208
Preparation of 1-benzyl-4-[2-[N-(4-n-butoxyphenyl)-N-methylamino]ethyl]piperidin-4-ol monomaleate Maleic acid (0.10 g) was added to a methanol solution (2 mL) of the compound (0.35 g) obtained in the Step 2 in the Example 3. The titled compound (0.45 g) was obtained by removing the solvent under reduced pressure.

The following maleic acid salts were prepared by the same method as in the Example 208.

Example 209
4-[2-[N-[4-n-butoxy-2-(hydroxymethyl)phenyl]-N-methylamino]ethyl]-1-[2-(3,4-methylenedioxyphenyl)-ethyl]piperidin-4-ol monomaleate

Example 210
1-benzyl-4-[N-(4-n-butoxyphenyl)-N-methylamino]-methylpiperidin-4-ol monomaleate The following hydrochlorides were prepared by the same method as in the Example 144.

Example 211
1-benzyl-4-[2-[N-methyl-N-[4-(2-methyl-2-butoxy)phenyl]-amino]ethyl]piperidin-4-ol dihydrochloride

Example 212
1-benzyl-4-[2-[N-(4-n-butoxy-3-hydroxyphenyl)-N-methylamino]ethyl]piperidin-4-ol dihydrochloride

Example 213
1-benzyl-4-[2-[N-(4-n-butoxy-2-fluorophenyl)-N-methylamino]ethyl]piperidin-4-ol dihydrochloride

Example 214
1-benzyl-4-[2-[N-(4-n-butoxyphenyl)-N-isopropylamino]ethyl]piperidin-4-ol dihydrochloride

Example 215
1-benzyl-4-[2-[N-methyl-N-[4-(3-pentyloxy)phenyl]-amino]ethyl]piperidin-4-ol dihydrochloride

Example 216
1-benzyl-4-[2-[N-methyl-N-[4-(3-methylbutoxy)phenyl]-amino]ethyl]piperidin-4-ol dihydrochloride

Example 217
1-benzyl-4-[2-[N-[4-(2-cyclopropylethyloxy)phenyl]-N-methylamino]ethyl]piperidin-4-ol dihydrochloride

Example 218
1-benzyl-4-[2-[N-[4-(3-butenyloxy)phenyl]-N-methylamino]ethyl]piperidin-4-ol dihydrochloride

Example 219
1-(4-chlorophenylmethyl)-4-[2-[N-methyl-N-(4-isopropoxyphenyl)amino]ethyl]piperidin-4-ol dihydrochloride

Example 220
1-(4-bromophenylmethyl)-4-[2-[N-methyl-N-(4-isopropoxyphenyl)amino]ethyl]piperidin-4-ol dihydrochloride

Example 221
4-[2-[N-methyl-N-(4-isopropoxyphenyl)amino]ethyl]-1-[4-(trifluoromethyl)phenylmethyl]piperidin-4-ol dihydrochloride

Example 222
4-[2-[N-methyl-N-(4-isopropoxyphenyl)amino]ethyl]-1-[(4-isopropylphenyl)methyl]piperidin-4-ol dihydrochloride

Example 223
1-(4-methoxyphenylmethyl)-4-[2-[N-methyl-N-(4-isopropoxyphenyl)amino]ethyl]piperidin-4-ol dihydrochloride

Example 224
1-(3-methoxyphenylmethyl)-4-[2-[N-methyl-N-(4-isopropoxyphenyl)amino]ethyl]piperidin-4-ol dihydrochloride

Example 225
1-(4-fluorophenylmethyl)-4-[2-[N-methyl-N-(4-isopropoxyphenyl)amino]ethyl]piperidin-4-ol dihydrochloride

Example 226
1-(4-cyanophenylmethyl)-4-[2-[N-methyl-N-(4-isopropoxyphenyl)amino]ethyl]piperidin-4-ol dihydrochloride

Example 227
4-[2-[N-methyl-N-(4-isopropoxyphenyl)amino]ethyl]-1-(2-naphthylmethyl)piperidin-4-ol dihydrochloride

Example 228
4-[2-[N-methyl-N-(4-isopropoxyphenyl)amino]ethyl]-1-[(4-isopropoxyphenyl)methyl]piperidin-4-ol dihydrochloride

Example 229
1-(2-bromophenylmethyl)-4-[2-[N-methyl-N-(4-isopropoxyphenyl)amino]ethyl]piperidin-4-ol dihydrochloride

Example 230
1-(3-bromophenylmethyl)-4-[2-[N-methyl-N-(4-isopropoxyphenyl)amino]ethyl]piperidin-4-ol dihydrochloride

Example 231
4-[2-[N-methyl-N-(4-isopropoxyphenyl)amino]ethyl]-1-(4-nitrophenylmethyl)piperidin-4-ol dihydrochloride

Example 232
4-[2-[N-methyl-N-(4-isopropoxyphenyl)amino]ethyl]-1-[3-(trifluoromethyl)phenylmethyl]piperidin-4-ol dihydrochloride

Example 233
1-[4-(methoxycarbonyl)phenylmethyl]-4-[2-[N-methyl-N-(4-isopropoxyphenyl)amino]ethylipiperidin-4-ol dihydrochloride

Example 234
1-(2,4-difluorophenylmethyl)-4-[2-[N-methyl-N-(4-isopropoxyphenyl)amino]ethyl]piperidin-4-ol dihydrochloride

Example 235
1-[4-fluoro-3-(trifluoromethyl)phenylmethyl]-4-[2-[N-methyl-N-(4-isopropoxyphenyl)amino]ethyl]piperidin-4-ol dihydrochloride

Example 236
4-[2-[N-methyl-N-(4-isopropoxyphenyl)amino]ethyl]-1-(4-trifluoromethoxyphenylmethyl)piperidin-4-ol dihydrochloride

Example 237
1-(2-fluoro-4-isopropoxyphenylmethyl)-4-[2-[N-methyl-N-(4-isopropoxyphenyl)amino]ethyl]piperidin-4-ol dihydrochloride

Example 238
1-(4-biphenylmethyl)-4-[2-[N-methyl-N-(4-isopropoxyphenyl)amino]ethyl]piperidin-4-ol dihydrochloride

Example 239
4-[2-[N-methyl-N-(4-isopropoxyphenyl)amino]ethyl]-1-(4-phenoxyphenylmethyl)piperidin-4-ol dihydrochloride

Example 240
1-(4-bromo-2-fluorophenylmethyl)-4-[2-[N-methyl-N-(4-isopropoxyphenyl)amino]ethyl]piperidin-4-ol dihydrochloride

Example 241
1-(3-fluorophenylmethyl)-4-[2-[N-methyl-N-(4-isopropoxyphenyl)amino]ethyl]piperidin-4-ol dihydrochloride

Example 242
1-(2-fluorophenylmethyl)-4-[2-[N-methyl-N-(4-isopropoxyphenyl)amino]ethyl]piperidin-4-ol dihydrochloride

Example 243
4-[2-[N-methyl-N-(4-isopropoxyphenyl)amino]ethyl]-1-(3-trifluoromethoxyphenylmethyl)piperidin-4-ol dihydrochloride

Example 244
4-[2-[N-methyl-N-(4-isopropoxyphenyl)amino]ethyl]-1-(2-trifluoromethoxyphenylmethyl)piperidin-4-ol dihydrochloride

Example 245
1-(3-chlorophenylmethyl)-4-[2-[N-methyl-N-(4-isopropoxyphenyl)amino]ethyl]piperidin-4-ol dihydrochloride

Example 246
1-(2-chlorophenylmethyl)-4-[2-[N-methyl-N-(4-isopropoxyphenyl)amino]ethyl]piperidin-4-ol dihydrochloride

Example 247
1-(3-cyanophenylmethyl)-4-[2-[N-methyl-N-(4-isopropoxyphenyl)amino]ethyl]piperidin-4-ol dihydrochloride

Example 248
1-(2-cyanophenylmethyl)-4-[2-[N-methyl-N-(4-isopropoxyphenyl)amino]ethyl]piperidin-4-ol dihydrochloride

Example 249
4-[2-[N-methyl-N-(4-isopropoxyphenyl)amino]ethyl]-1-[2-(trifluoromethyl)phenylmethyl]piperidin-4-ol dihydrochloride

Example 250
1-(2-methoxyphenylmethyl)-4-[2-[N-methyl-N-(4-isopropoxyphenyl)amino]ethyl]piperidin-4-ol dihydrochloride

Example 251
4-[2-[N-methyl-N-(4-isopropoxyphenyl)amino]ethyl]-1(3-nitrophenylmethyl)piperidin-4-ol dihydrochloride

Example 252
4-[2-[N-methyl-N-(4-isopropoxyphenyl)amino]ethyl]-1(2-nitrophenylmethyl)piperidin-4-ol dihydrochloride

Example 253
1-[4-(ethoxycarbonyl)phenylmethyl]-4-[2-[N-methyl-N-(4-isopropoxyphenyl)amino]ethyl]piperidin-4-ol dihydrochloride

Example 254
4-[2-[N-methyl-N-(4-isopropoxyphenyl)amino]ethyl]-1(2-thienylmethyl)piperidin-4-ol dihydrochloride

Example 255
4-[2-[N-methyl-N-(4-isopropoxyphenyl)amino]ethyl]-1(3-thienylmethyl)piperidin-4-ol dihydrochloride

Example 256
4-[2-[N-methyl-N-(4-isopropoxyphenyl)amino]ethyl]-1-[4-(methylthio)phenylmethyl]piperidin-4-ol dihydrochloride

Example 257
1-[2-(methoxycarbonyl)phenylmethyl]-4-[2-[N-methyl-N-(4-isopropoxyphenyl)amino]ethyl]piperidin-4-ol dihydrochloride

Example 258
1-[3-(methoxycarbonyl)phenylmethyl]-4-[2-[N-methyl-N-(4-isopropoxyphenyl)amino]ethyl]piperidin-4-ol dihydrochloride

Example 259
1-(3-furylmethyl)-4-[2-[N-methyl-N-(4-isopropoxyphenyl)-amino]ethyl]piperidin-4-ol dihydrochloride

Example 260
4-[2-[N-methyl-N-(4-isopropoxyphenyl)amino]ethyl]-1-[4-(isopropoxycarbonyl)phenylmethyl]piperidin-4-ol dihydrochloride

Example 261
4-[2-[N-methyl-N-(4-isopropoxyphenyl)amino]ethyl]-1-[4-(n-propoxycarbonyl)phenylmethyl]piperidin-4-ol dihydrochloride

Example 262
4-[2-[N-methyl-N-(4-isopropoxyphenyl)amino]ethyl]-1-(2-phenoxyethyl)piperidin-4-ol dihydrochloride

Example 263
1-[2-(4-fluorophenoxy)ethyl]-4-[2-[N-methyl-N-(4-isopropoxyphenyl)amino]ethyl]piperidin-4-ol dihydrochloride

Example 264
4-[2-[N-methyl-N-(4-isopropoxyphenyl)amino]ethyl]-1-(3-phenylpropyl)piperidin-4-ol dihydrochloride

Example 265
1-(3-biphenylmethyl)-4-[2-[N-methyl-N-(4-isopropoxyphenyl)amino]ethyl]piperidin-4-ol dihydrochloride

Example 266
1-(2-biphenylmethyl)-4-[2-[N-methyl-N-(4-isopropoxyphenyl)amino]ethyl]piperidin-4-ol dihydrochloride

Example 267
1-[2-fluoro-4-(trifluoromethyl)phenylmethyl]-4-[2-[N-methyl-N-(4-isopropoxyphenyl)amino]ethyl]piperidin-4-ol dihydrochloride

Example 268
4-[2-[N-methyl-N-(4-ethoxyphenyl)amino]ethyl]-1-[4-(trifluoromethyl)phenylmethyl]piperidin-4-ol dihydrochloride

Example 269
1-[4-(methoxycarbonyl)phenylmethyl]-4-[2-[N-methyl-N-(3-isopropoxyphenyl)amino]ethyl]piperidin-4-ol dihydrochloride

Example 270
1-[4-(methoxycarbonyl)phenylmethyl]-4-[2-[N-methyl-N-(2-isopropoxyphenyl)amino]ethyl]piperidin-4-ol dihydrochloride

Example 271
4-[2-[N-(4-isopropoxyphenyl)amino]ethyl]-1-[4-(methoxycarbonyl)phenylmethyl]piperidin-4-ol dihydrochloride

Example 272
4-[2-[N-(4-isopropoxyphenyl)amino]ethyl]-1-[4-(trifluoromethyl)phenylmethyl]piperidin-4-ol dihydrochloride

Example 273
4-[2-[N-methyl-N-(4-isopropoxyphenyl)amino]-1-hydroxethyl]-1-[4-(trifluoromethyl)phenylmethyl]piperidin-4-ol dihydrochloride

Example 274
4-methoxy-4-[2-[N-methyl-N-(4-isopropoxyphenyl)amino]-ethyl]-1-[4-(trifluoromethyl)phenylmethyl]piperidine dihydrochloride

Example 275
4-methoxy-1-[4-(methoxycarbonyl)phenylmethyl]-4-[2-[N-methyl-N-(4-isopropoxyphenyl)amino]ethyl]piperidine dihydrochloride

Example 276
4-[N-methyl-N-(4-isopropoxyphenyl)aminomethyl]-1-[4-(trifluoromethyl)phenylmethyl]piperidin-4-ol dihydrochloride

Example 277
1-[4-(methoxycarbonyl)phenylmethyl]-4-[N-methyl-N-(4-isopropoxyphenyl)aminomethyl]piperidin-4-ol dihydrochloride

Example 278
1-diphenylmethyl-4-[2-[N-methyl-N-(4-isopropoxyphenyl)-amino]ethyl]piperidin-4-ol dihydrochloride

Example 279
1-bis(4-fluorophenyl)methyl-4-[2-[N-methyl-N-(4-isopropoxyphenyl)amino]ethyl]piperidin-4-ol dihydrochloride

Example 280
1-diphenylmethyl-4-[2-[N-(4-ethoxyphenyl)-N-methylamino]ethyl]piperidin-4-ol dihydrochloride

Example 281
1-diphenylmethyl-4-[2-[N-methyl-N-(3-isopropoxyphenyl)-amino]ethyl]piperidin-4-ol dihydrochloride

Example 282
1-diphenylmethyl-4-[2-[N-methyl-N-(2-isopropoxyphenyl)-amino]ethyl]piperidin-4-ol dihydrochloride

Example 283
1-diphenylmethyl-4-[2-[N-(4-isopropoxyphenyl)-amino]ethyl]piperidin-4-ol dihydrochloride

Example 284
1-diphenylmethyl-4-methoxy-4-[2-[N-methyl-N-(4-isopropoxyphenyl)amino]ethyl]piperidine dihydrochloride

Example 285
1-diphenylmethyl-4-[N-methyl-N-(4-isopropoxyphenyl)-aminomethyl]piperidin-4-ol dihydrochloride

Example 286
1-benzyl-4-[2-[N-(4-n-butoxyphenyl)-N-ethylamino]-ethyl]piperidin-4-ol dihydrochloride

Example 287
1-(4-cyano-2-fluorophenylmethyl)-4-[2-[N-methyl-N-(4-isopropoxyphenyl)amino]ethyl]piperidin-4-ol dihydrochloride

Example 288
1-(4-acetylphenylmethyl)-4-[2-[N-methyl-N-(4-isopropoxyphenyl)amino]ethyl]piperidin-4-ol dihydrochloride

Example 289
4-[2-[N-methyl-N-(4-isopropoxyphenyl)amino]ethyl]-1-[4-(trifluoroacetylamino)phenylmethyl]piperidin-4-ol dihydrochloride Data of physical properties of the compounds in the Examples 1 to 143, 146, 162, 176, 177, 183, 196, 198, 201, 207, 210, 233 and 278 are listed in Table 5.

The term "Example No. 1-1" denotes the Step 1 in the Example 1.

TABLE 5

| Example No. | I R (cm$^{-1}$) | NMR (ppm) (no mark: 300 MHz, *: 270 MHz) | melting point (° C.) |
|---|---|---|---|
| 1-1 | — | CDCl$_3$: 7.35–7.20(5H, m), 7.04(2H, d, J=9Hz), 6.91(2H, d, J=9Hz), 5.23(1H, s), 3.84(3H, s), 3.47(2H, s), 3.23(3H, s), 2.60–2.48(2H, m), 2.39(2H, ddd, J=12, 12, 3Hz), 2.16(2H, s), 1.71–1.60(2H, m), 1.38(2H, ddd, J=12, 12, 4Hz) | — |
| 1-2 | KBr: 2939, 1514, 1246, 1038, 814, 700 | CDCl$_3$*: 7.35–7.20(5H, m), 6.89(2H, d, J=9Hz), 6.84(2H, d, J=9Hz), 3.77(3H, s), 2.52(2H, s), 3.30(2H, t, J=7Hz), 2.78(3H, s), 2.66–2.56(2H, m), 2.38(2H, ddd, J=11, 11, 4Hz), 1.72–1.60(6H, m) | oil |
| 2-1 | — | CDCl$_3$: 7.35–7.20(5H, m), 7.02(2H, d, J=9Hz), 6.89(2H, d, J=9Hz), 5.24(1H, s), 4.05(2H, q, J=7Hz), 3.47(2H, s), 3.23(3H, s), 2.59–2.49(2H, m), 2.39(2H, ddd, J=12, 12, 2Hz), 2.16(2H, s), 1.71–1.61(2H, m), 1.46–1.32(2H, m), | — |
| 2-2 | liquid film: 2941, 2814, 1520, 1246, 1117, 1051 | CDCl$_3$: 7.38–7.20(5H, m), 6.88(2H, d, J=9Hz), 6.83(2H, d, J=9Hz), 3.98(2H, q, J=7Hz), 3.54(2H, s), 3.28(2H, t, J=7Hz), 2.77(3H, s), 2.67–2.58(2H, m), 2.46–2.34(2H, m), 1.72–1.63(4H, m), 1.68(2H, t, J=7Hz), 1.39(3H, t, J=7Hz) | oil |
| 3-1 | — | CDCl$_3$*: 7.33–7.19(5H, m), 7.01(2H, d, J=9Hz), 6.90(2H, d, J=9Hz), 5.24(1H, s), 3.98(2H, t, J=7Hz), 3.47(2H, s), 3.23(3H, s), 2.58–2.48(2H, m), 2.39(2H, ddd, J=12, 12, 3Hz), 2.16(2H, s), 1.85–1.74(2H, m), 1.72–1.60(2H, m), 1.38(2H, ddd, J=12, 12, 4Hz), 1.00(3H, t, J=7Hz) | — |
| 3-2 | liquid film: 3398, 2937, 1514, 1244, 814, 700 | CDCl$_3$: 7.34–7.21(5H, m), 6.88(2H, d, J=9Hz), 6.83(2H, d, J=9Hz), 3.91(2H, t, J=7Hz), 3.52(2H, s), 3.28(2H, t, J=7Hz), 2.77(3H, s), 2.66–2.57(2H, m), 2.38(2H, ddd, J=11, 11, 4Hz), 1.78–1.57(8H, m), 1.54–1.41(2H, m), 0.96(3H, t, J=7Hz) | oil |
| 4-1 | — | CDCl$_3$: 7.37–7.20(5H, m), 7.01(2H, d, J=9Hz), 6.88(2H, d, J=9Hz), 5.26(1H, s), 4.62–4.49(1H, m), 3.47(2H, s), 3.23(3H, s), 2.58–2.49(2H, m), 2.39(2H, ddd, J=11, 11, 2Hz), 2.17(2H, s), 1.71–1.61(2H, m), 1.45–1.31(2H, m), 1.37(6H, d, J=6Hz) | — |
| 4-2 | liquid film: 2976, 2939, 2818, 1516, 1242, 1117 | CDCl$_3$: 7.38–7.22(5H, m), 6.86(2H, d, J=9Hz), 6.82(2H, d, J=9Hz), 4.50–4.34(1H, m), 3.54(2H, s), 3.29(2H, t, J=7Hz), 2.78(3H, s), 2.67–2.59(2H, m), 2.46–2.34(2H, m), 1.73–1.62(6H, m), 1.30(6H, d, J=6Hz) | oil |
| 5-1 | — | CDCl$_3$*: 7.37–7.19(5H, m), 7.00(2H, d, J=9Hz), 6.90(2H, d, J=9Hz), 5.25(1H, s), 4.30–4.20(1H, m), 3.47(2H, s), 3.22(3H, s), 2.58–2.33(4H, m), 2.17(2H, s), 2.07–1.95(2H, m), 1.89–1.76(2H, m), 1.71–1.28(10H, m) | — |
| 5-2 | KBr: 2935, 2856, 1512, 1248, 1051, 831 | CDCl$_3$*: 7.34–7.20(5H, m), 6.89–6.79(4H, m), 4.16–4.02(1H, m), 3.76(1H, s), 3.52(2H, s), 3.29(2H, t, J=7Hz), 2.77(3H, s), 2.66–2.55(2H, m), 2.45–2.32(2H, m), 2.03–1.93(2H, m), 1.86–1.20(14H, m) | 68.1–70.1 |

TABLE 5-continued

| Example No. | I R (cm$^{-1}$) | NMR (ppm) (no mark: 300 MHz, *: 270 MHz) | melting point (° C.) |
|---|---|---|---|
| 6-1 | — | CDCl$_3$*: 7.46–6.97(14H, m), 5.19(1H, s), 3.48(2H, s), 3.25(3H, s), 2.61–2.35(4H, m), 2.19(2H, s), 1.72–1.60(2H, m), 1.48–1.35(2H, m) | — |
| 6-2 | liquid film: 2939, 2812, 1589, 1512, 1489, 1238 | CDCl$_3$*: 7.34–7.22(7H, m), 7.02(1H, dddd, J=7, 7, 1, 1Hz), 6.98–6.92(4H, m), 6.82(2H, d, J=9Hz), 3.52(2H, s), 3.40(2H, t, J=7Hz), 2.86(3H, s), 2.71(1H, br. s), 2.69–2.58(2H, m), 2.43–2.30(2H, m), 1.77–1.59(6H, m) | oil |
| 7-1 | — | CDCl$_3$: 7.33–7.19(6H, m), 6.92–6.85(1H, m), 6.72–6.63(2H, m), 5.21(1H, s), 3.95(2H, t, J=7Hz), 3.47(2H, s), 3.25(3H, s), 2.59–2.49(2H, m), 2.39(2H, ddd, J=12, 12, 2Hz), 2.20(2H, s), 1.84–1.61(4H, m), 1.58–1.40(2H, m), 1.39(2H, ddd, J=12, 12, 4Hz), 0.99(3H, t, J=7Hz) | — |
| 7-2 | liquid film: 2935, 2869, 2809, 1610, 1500, 1172 | CDCl$_3$: 7.38–7.20(5H, m), 7.12(1H, dd, J=8, 8Hz), 6.42–6.36(1H, m), 6.34–6.28(2H, m), 3.94(2H, t, J=7Hz), 3.52(2H, s), 3.44(2H, t, J=8Hz), 2.87(3H, s), 2.69–2.59(2H, m), 2.42–2.30(2H, m), 1.80–1.40(10H, m), 0.97(3H, t, J=7Hz) | oil |
| 8-1 | — | CDCl$_3$: 7.40–7.18(6H, m), 7.12–7.05(1H, m), 6.99–6.90(2H, m), 5.35(1H, s), 4.04–3.90(2H, m), 3.46(2H, s), 3.17(3H, s), 2.58–2.33(4H, m), 2.14(1H, d, J=16Hz), 2.06(1H, d, J=16Hz), 1.81–1.59(4H, m), 1.53–1.29(4H, m), 0.93(3H, t, J=7Hz) | — |
| 8-2 | liquid film: 2937, 2872, 2812, 1500, 1454, 1238, 744 | CDCl$_3$*: 7.35–7.18(5H, m), 7.08–7.00(2H, m), 6.92–6.83(2H, m), 5.03(1H, s), 3.99(2H, t, J=7Hz), 3.51(2H, s), 3.20(2H, t, J=6Hz), 2.69(3H, s), 2.60–2.48(2H, m), 2.41(2H, ddd, J=11, 11, 3Hz), 1.89–1.75(2H, m), 1.72–1.42(8H, m), 0.98(3H, t, J=7Hz) | oil |
| 9-1 | — | CDCl$_3$: 7.35–7.19(5H, m), 6.95(1H, dd, J=9, 9Hz), 6.92–6.81(2H, m), 5.10(1H, s), 4.06(2H, t, J=6Hz), 3.48(2H, s), 3.22(3H, s), 2.59–2.49(2H, m), 2.39(2H, ddd, J=12, 12, 2Hz), 2.17(2H, s), 1.89–1.78(2H, s), 1.71–1.47(4H, m), 1.39(2H, ddd, J=12, 12, 4Hz), 1.00(3H, t, J=7Hz) | — |
| 9-2 | liquid film: 2954, 2871, 1520, 1248, 1217 | CDCl$_3$: 7.35–7.25(5H, m), 6.87(1H, dd, J=9, 9Hz), 6.60(1H, dd, J=14, 3Hz), 6.49(1H, ddd, J=9, 3, 1Hz), 3.96(2H, t, J=7Hz), 3.52(2H, s), 3.35(2H, t, J=7Hz), 2.81(3H, s), 2.68–2.55(3H, m), 2.42–2.30(2H, m), 1.80–1.60(8H, m), 1.55–1.42(2H, m), 0.96(3H, t, J=7Hz) | oil |
| 10-1 | — | CDCl$_3$: 7.36–7.21(5H, m), 7.21(2H, d, J=8Hz), 7.02(2H, d, J=8Hz), 5.27(1H, s), 3.47(2H, s), 3.25(3H, s), 2.61(2H, t, J=8Hz), 2.58–2.48(2H, m), 2.39(2H, ddd, J=12, 12, 3Hz), 2.17(2H, s), 1.73–1.59(4H, m), 1.38(2H, ddd, J=12, 12, 4Hz), 0.97(3H, t, J=7Hz) | — |
| 10-2 | liquid film: 2929, 2870, 2811, 1616, 1522, 1365 | CDCl$_3$: 7.36–7.23(5H, m), 7.06(2H, d, J=9Hz), 6.78(2H, d, J=9Hz), 3.53(2H, s), 3.39(2H, t, J=7Hz), 2.84(3H, s), 2.67–2.57(2H, m), 2.49(2H, t, J=8Hz), 2.45–2.33(2H, m), 1.76–1.53(8H, m), 0.93(3H, t, J=7Hz) | oil |
| 11-1 | — | CDCl$_3$*: 7.35–7.20(5H, m), 7.08(2H, d, J=9Hz), 6.91(2H, d, J=9Hz), | |

TABLE 5-continued

| Example No. | I R (cm⁻¹) | NMR (ppm) (no mark: 300 MHz, *: 270 MHz) | melting point (° C.) |
|---|---|---|---|
| | | 4.25(1H, s), 3.98(2H, t, J=6Hz), 3.54(1H, s), 3.49(2H, s), 3.32(3H, s), 3.29(3H, s), 2.70–2.55(2H, m), 2.48–2.25(2H, m), 1.90–1.71(3H, m), 1.65–1.22(5H, m), 1.01(3H, t, J=7Hz) | |
| 11-2 | liquid film: 2933, 1514, 1365, 1242, 1101, 1076, 814 | CDCl₃*: 7.36–7.21(5H, m), 6.82(2H, d, J=9Hz), 6.73(2H, d, J=9Hz), 3.90(2H, t, J=6Hz), 3.55–3.46(1H, m), 3.53(2H, s), 3.38(3H, s), 3.27(1H, dd, J=14, 8Hz), 3.19(1H, dd, J=8, 3Hz), 2.92(3H, s), 2.76–2.65(3H, m), 2.41–2.29(2H, m), 1.80–1.40(8H, m), 0.97(3H, t, J=7Hz) | oil |
| 12-1 | — | CDCl₃: 7.33–7.20(5H, m), 7.10(2H, d, J=9Hz), 6.90(2H, d, J=9Hz), 4.04(1H, s), 3.98(2H, t, J=6Hz), 3.96(1H, s), 3.49(1H, d, J=13Hz), 3.46(1H, d, J=13Hz), 3.24(3H, s), 2.70–2.59(2H, m), 2.42–2.21(2H, m), 1.85–1.75(3H, m), 1.59–1.19(5H, m), 1.01(3H, t, J=7Hz), 0.88(9H, s), 0.07(3H, s), −0.05(3H, s) | — |
| 12-2 | KBr: 3460, 2949, 1518, 1244, 1045, 810 | CDCl₃*: 7.38–7.22(5H, m), 6.86(2H, d, J=9Hz), 6.83(2H, d, J=9Hz), 3.91(2H, t, J=6Hz), 3.64–3.55(1H, m), 3.57(2H, s), 3.29(1H, dd, J=13, 11Hz), 3.08(1H, dd, J=13, 3Hz), 2.82–2.68(2H, m), 2.79(3H, s), 2.50–2.32(2H, m), 1.90–1.40(8H, m), 0.97(3H, t, J=7Hz) | 79.2–80.4 |
| 13-1 | — | CDCl₃: 7.71(1H, s), 7.38–7.20(5H, m), 7.36(2H, d, J=9Hz), 6.84(2H, d, J=9Hz), 3.95(1H, s), 3.92(2H, t, J=7Hz), 3.52(2H, s), 2.65–2.56(2H, m), 2.47(2H, s), 2.43(2H, ddd, J=12, 12, 3Hz), 1.80–1.62(6H, m), 1.54–1.41(2H, m), 0.96(3H, t, J=7Hz) | — |
| 13-2 | KBr: 3263, 2937, 1512, 1242, 1074, 731 | CDCl₃*: 7.35–7.20(5H, m), 6.78(2H, d, J=9Hz), 6.63(2H, d, J=9Hz), 3.89(2H, t, J=6Hz), 3.52(2H, s), 3.27(2H, t, J=6Hz), 2.68–2.57(2H, m), 2.43–2.31(2H, m), 1.80–1.40(10H, m), 0.96(3H, t, J=7Hz) | 119.8–120.2 |
| 14-1 | — | DMSO-d₆*: 8.53(1H, s), 7.35–7.20(5H, m), 6.60(2H, d, J=9Hz), 6.56(2H, d, J=9Hz), 4.13(1H, s), 3.42(2H, s), 3.30–3.20(2H, m), 2.69(3H, s), 2.46–2.20(4H, m), 1.52–1.40(6H, m) | — |
| 14-2 | liquid film: 2937, 1512, 1473, 1454, 1242, 822, 700 | CDCl₃*: 7.36–7.18(5H, m), 6.88(2H, d, J=10Hz), 6.83(2H, d, J=10Hz), 3.87(2H, t, J=7Hz), 3.52(2H, s), 3.28(2H, t, J=7Hz), 2.77(3H, s), 2.67–2.57(2H, m), 2.36(2H, ddd, J=11, 11, 4Hz), 1.85–1.52(8H, m), 1.02(3H, t, J=7Hz) | oil |
| 15 | KBr: 2939, 1512, 1242, 1030, 824 | CDCl₃*: 7.36–7.20(5H, m), 6.88(2H, d, J=9Hz), 6.83(2H, d, J=9Hz), 3.90(2H, t, J=7Hz), 3.52(2H, s), 3.28(2H, t, J=7Hz), 2.77(3H, s), 2.67–2.57(2H, m), 2.36(2H, ddd, J=11, 11, 4Hz), 1.81–1.30(12H, m), 0.92(3H, t, J=7Hz) | 58.5–60.3 |
| 16 | KBr: 2937, 1516, 1470, 1248, 1036, 814 | CDCl₃*: 7.35–7.20(5H, m), 6.88(2H, d, J=9Hz), 6.83(2H, d, J=9Hz), 3.91(1H, s), 3.67(2H, d, J=7Hz), 3.52(2H, s), 3.28(2H, t, J=7Hz), 2.77(3H, s), 2.67–2.57(2H, m), 2.38(2H, ddd, J=11, 11, 4Hz), 2.13–1.98(1H, m), 1.73–1.52(6H, m), 1.01(6H, d, J=7Hz) | 50.6–52.5 |
| 17 | KBr: 3369, 2931, 1512, 1248, 818 | CDCl₃*: 7.35–7.20(5H, m), 6.85(2H, d, J=9Hz), 6.75(2H, d, J=9Hz), 4.62–4.50(1H, m), 3.52(2H, s), | 68.6–69.8 |

TABLE 5-continued

| Example No. | I R (cm$^{-1}$) | NMR (ppm) (no mark: 300 MHz, *: 270 MHz) | melting point (° C.) |
|---|---|---|---|
| 18 | liquid film: 2939, 1512, 1238, 1028, 812, 700 | 3.28(2H, t, J=7Hz), 2.77(3H, s), 2.66–2.55(2H, m), 2.48–2.30(4H, m), 2.23–2.03(2H, m), 1.90–1.55(8H, m) CDCl$_3$*: 7.36–7.20(5H, m), 6.87(2H, d, J=9Hz), 6.83(2H, d, J=9Hz), 3.78(1H, s), 3.74(2H, d, J=7Hz), 3.52(2H, s), 3.29(2H, t, J=7Hz), 2.77(3H, s), 2.68–2.56(2H, m), 2.38(2H, ddd, J=11, 11, 5Hz), 1.74–1.56(6H, m), 1.33–1.18(1H, m), 0.67–0.58(2H, m), 0.36–0.29(2H, m) | oil |
| 19-1 | — | CDCl$_3$: 6.90(2H, d, J=9Hz), 6.84(2H, d, J=9Hz), 3.91(2H, t, J=7Hz), 3.29(2H, t, J=7Hz), 3.00(2H, ddd, J=12, 12, 3Hz), 2.83(2H, ddd, J=12, 4, 4Hz), 2.78(3H, s), 1.79–1.42(10H, m), 0.97(3H, t, J=7Hz) | — |
| 19-2 | KBr: 1512, 1487, 1244, 1041, 822 | CDCl$_3$: 6.92–6.72(7H, m), 5.94(2H, s), 3.91(2H, t, J=7Hz), 3.46(2H, s), 3.28(2H, t, J=7Hz), 2.77(3H, s), 2.68–2.57(2H, m), 2.46–2.32(2H, m), 1.80–1.58(8H, m), 1.55–1.40(2H, m), 0.96(3H, t, J=7Hz) | 72.4–74.2 |
| 20 | KBr: 2951, 2926, 1512, 1242, 825 | CDCl$_3$: 7.26(4H, s), 6.89(2H, d, J=9Hz), 6.83(2H, d, J=9Hz), 4.00(1H, s), 3.91(2H, t, J=7Hz), 3.48(2H, s), 3.28(2H, t, J=7Hz), 2.77(3H, s), 2.63–2.53(2H, m), 2.37(2H, ddd, J=11, 11, 3Hz), 1.80–1.40(10H, m), 0.96(3H, t, J=7Hz) | 67.7–68.3 |
| 21 | KBr: 2951, 2933, 1516, 1331, 1242, 1161, 1122, 1066 | CDCl$_3$: 7.56(2H, d, J=8Hz), 7.45(2H, d, J=8Hz), 6.90(2H, d, J=9Hz), 6.83(2H, d, J=9Hz), 3.91(2H, t, J=7Hz), 3.57(2H, s), 3.28(2H, t, J=7Hz), 2.77(3H, s), 2.63–2.54(2H, m), 2.41(2H, ddd, J=11, 11, 3Hz), 1.79–1.42(10H, m), 0.96(3H, t, J=7Hz) | 77.4–78.2 |
| 22 | KBr: 2937, 2227, 1516, 1242, 824 | CDCl$_3$*: 7.60(2H, d, J=8Hz), 7.45(2H, d, J=8Hz), 6.90(2H, d, J=9Hz), 6.84(2H, d, J=9Hz), 3.91(2H, t, J=7Hz), 3.56(2H, s), 3.28(2H, t, J=7Hz), 2.77(3H, s), 2.62–2.50(2H, m), 2.42(2H, ddd, J=11, 11, 3Hz), 1.80–1.40(10H, m), 0.97(3H, t, J=7Hz) | 83.5–85.5 |
| 23 | KBr: 3527, 2937, 1716, 1518, 1282, 1232 | CDCl$_3$: 7.98(2H, d, J=8Hz), 7.41(2H, d, J=8Hz), 6.89(2H, d, J=9Hz), 6.83(2H, d, J=9Hz), 3.91(2H, t, J=6Hz), 3.91(3H, s), 3.57(2H, s), 3.28(2H, t, J=7Hz), 2.77(3H, s), 2.66–2.53(2H, m), 2.48–2.34(2H, m), 1.80–1.40(10H, m), 0.96(3H, t, J=7Hz) | 82.5–82.8 |
| 24 | KBr: 2951, 2927, 1612, 1512, 1240, 814 | CDCl$_3$: 7.17(2H, d, J=9Hz), 6.87(2H, d, J=9Hz), 6.83(2H, d, J=9Hz), 6.70(2H, d, J=9Hz), 3.91(2H, t, J=7Hz), 3.84(1H, s), 3.43(2H, s), 3.28(2H, t, J=7Hz), 2.93(6H, s), 2.77(3H, s), 2.66–2.55(2H, m), 2.34(2H, ddd, J=11, 11, 4Hz), 1.80–1.40(10H, m), 0.96(3H, t, J=7Hz) | 71.3–73.0 |
| 25 | KBr: 2931, 2870, 1614, 1514, 1471, 1244 | CDCl$_3$*: 7.09(2H, d, J=9Hz), 6.89(2H, d, J=9Hz), 6.83(2H, d, J=9Hz), 6.63(2H, d, J=9Hz), 3.91(2H, t, J=7Hz), 3.48(2H, s), 3.27(2H, t, J=6Hz), 2.76(3H, s), 2.72–2.63(2H, m), 2.48–2.35(2H, m), 1.80–1.40(10H, m), 0.96(3H, t, J=7Hz) | oil |
| 26 | liquid film: 2935, 1612, 1514, 1468, 1244, 1036 | CDCl$_3$*: 7.24(2H, d, J=9Hz), 6.92–6.80(6H, m), 3.91(2H, t, J=6Hz), 3.80(3H, s), 3.48(2H, s), 3.28(2H, t, J=7Hz) 2.77(3H, s), 2.70–2.55(2H, m), 2.46–2.30(2H, m), 1.80–1.40(10H, m), 0.96(3H, t, J=7Hz) | oil |

TABLE 5-continued

| Example No. | I R (cm⁻¹) | NMR (ppm) (no mark: 300 MHz, *: 270 MHz) | melting point (° C.) |
|---|---|---|---|
| 27 | KBr: 2937, 1512, 1468, 1244, 1047 | CDCl₃*: 7.22(1H, dd, J=8, 8Hz), 6.96–6.75(7H, m), 3.91(2H, t, J=7Hz), 3.81(3H, s), 3.50(2H, s), 3.29(2H, t, J=7Hz), 2.77(3H, s), 2.67–2.56(2H, m), 2.38(2H, ddd, J=11, 11, 4Hz), 1.80–1.40(10H, m), 0.96(3H, t, J=7Hz) | oil |
| 28 | KBr: 2937, 1512, 1464, 1242, 756 | CDCl₃*: 7.35(1H, dd, J=7, 2Hz), 7.22(1H, ddd, J=8, 8, 2Hz), 6.96–6.78(6H, m), 3.91(2H, t, J=7Hz), 3.81(3H, s), 3.77(1H, s), 3.58(2H, s), 3.29(2H, t, J=7Hz), 2.78(3H, s), 2.71–2.60(2H, m), 2.53–2.38(2H, m), 1.80–1.40(10H, m), 0.96(3H, t, J=7Hz) | oil |
| 29 | KBr: 2943, 2922, 1512, 1242, 825 | CDCl₃: 7.30–7.21(1H, m), 7.10–7.04(2H, m), 6.97–6.88(1H, m), 6.89(2H, d, J=9Hz), 6.83(2H, d, J=9Hz), 3.91(2H, t, J=7Hz), 3.51(2H, s), 3.28(2H, t, J=7Hz), 2.77(3H, s), 2.64–2.55(2H, m), 2.39(2H, ddd, J=11, 11, 4Hz), 1.79–1.57(8H, m), 1.54–1.41(2H, m), 0.96(3H, t, J=7Hz) | 46.7–47.2 |
| 30 | KBr: 2947, 2922, 1512, 1284, 1242, 825 | CDCl₃: 7.17(1H, ddd, J=12, 8, 2Hz), 7.13–6.97(2H, m), 6.90(2H, d, J=9Hz), 6.83(2H, d, J=9Hz), 3.91(2H, t, J=7Hz), 3.46(2H, s), 3.28(2H, t, J=7Hz), 2.77(3H, s), 2.62–2.53(2H, m), 2.38(2H, ddd, J=11, 11, 3Hz), 1.79–1.41(10H, m), 0.96(3H, t, J=7Hz) | 49.8–50.5 |
| 31 | KBr: 2920, 2872, 1514, 1475, 1242, 824 | CDCl₃*: 7.23(2H, d, J=8Hz), 7.13(2H, d, J=8Hz), 6.88(2H, d, J=9Hz), 6.83(2H, d, J=9Hz), 3.91(2H, t, J=6Hz), 3.54(2H, s), 3.27(2H, t, J=7Hz), 2.76(3H, s), 2.74–2.60(2H, m), 2.50–2.35(2H, m), 2.33(3H, s), 1.80–1.62(8H, m), 1.55–1.40(2H, m), 0.96(3H, t, J=7Hz) | 73.3–75.0 |
| 32 | KBr: 2937, 1512, 1244, 1124, 743 | CDCl₃*: 7.22–7.08(4H, m), 6.90(2H, d, J=9Hz), 6.84(2H, d, J=9Hz), 4.06(1H, s), 3.92(2H, t, J=6Hz), 3.33–3.04(5H, m), 2.91(2H, dd, J=15, 9Hz), 2.80–2.70(2H, m), 2.78(3H, s), 2.47(2H, ddd, J=11, 11, 3Hz), 1.80–1.60(8H, m), 1.55–1.41(2H, m), 0.97(3H, t, J=7Hz) | 94.4–94.6 |
| 33-1 | — | CDCl₃*: 7.21(2H, dd, J=9, 5Hz), 7.00(2H, dd, J=9, 9Hz), 6.93(2H, d, J=9Hz), 6.84(2H, d, J=9Hz), 4.42–4.33(1H, m), 3.92(2H, t, J=6Hz), 3.70(2H, s), 3.67–3.57(1H, m), 3.42(1H, ddd, J=13, 13, 3Hz), 3.22(2H, t, J=6Hz), 3.08(1H, ddd, J=13, 13, 3Hz), 2.74(3H, s), 1.80–1.36(9H, m), 1.19(1H, ddd, J=13, 13, 5Hz), 0.97(3H, t, J=7Hz) | — |
| 33-2 | KBr: 2929, 1512, 1471, 1242, 1217, 814 | CDCl₃*: 7.16(2H, dd, J=9, 6Hz), 6.96(2H, dd, J=9, 9Hz), 6.92(2H, d, J=9Hz), 6.84(2H, d, J=9Hz), 3.92(2H, t, J=7Hz), 3.29(2H, t, J=7Hz), 2.84–2.68(4H, m), 2.78(3H, s), 2.64–2.55(2H, m), 2.45(2H, ddd, J=11, 11, 3Hz), 1.80–1.60(8H, m), 1.55–1.42(2H, m), 0.97(3H, t, J=7Hz) | 75.5–75.8 |
| 34 | KBr: 2935, 2870, 2814, 1512, 1242, 1221 | CDCl₃: 7.29(2H, dd, J=9, 6Hz), 6.99(2H, dd, J=9, 9Hz), 6.89(2H, d, J=9Hz), 6.83(2H, d, J=9Hz), 3.91(2H, t, J=7Hz), 3.50(2H, s), 3.28(2H, t, J=7Hz), 2.77(3H, s), 2.66–2.56(2H, m), 2.46–2.34(2H, m), 1.80–1.62(8H, m), 1.57–1.41(2H, m), 0.96(3H, t, J=7Hz) | oil |

TABLE 5-continued

| Example No. | I R (cm⁻¹) | NMR (ppm) (no mark: 300 MHz, *: 270 MHz) | melting point (° C.) |
|---|---|---|---|
| 35 | KBr: 2956, 2933, 1512, 1242, 702 | CDCl₃*: 7.33–7.18(5H, m), 6.85(2H, d, J=9Hz), 6.82(2H, d, J=9Hz), 3.90(2H, t, J=6Hz), 3.42(1H, q, J=7Hz), 3.27(2H, t, J=7Hz), 2.80–2.71(1H, m), 2.76(3H, s), 2.56–2.46(1H, m), 2.42–2.26(2H, m), 1.79–1.40(10H, m), 1.38(3H, d, J=7Hz), 0.96(3H, t, J=7Hz) | oil |
| 36 | liquid film: 2935, 1695, 1514, 1242, 1221 | CDCl₃*: 8.02–7.98(2H, m), 7.60–7.40(3H, m) 6.91(2H, d, J=9Hz), 6.84(2H, d, J=9Hz), 3.91(2H, t, J=6Hz), 3.85(2H, s), 3.29(2H, t, J=6Hz), 2.83–2.73(2H, m), 2.78(3H, s), 2.53(2H, ddd, J=11, 11, 4Hz), 1.82–1.64(8H, m), 1.55–1.41(2H, m), 0.97(3H, t, J=7Hz) | oil |
| 37 | liquid film: 2958, 2935, 1599, 1514, 1240 | CDCl₃*: 8.05(2H, dd, J=9, 5Hz), 7.12(2H, dd, J=9, 9Hz), 6.92(2H, d, J=9Hz), 6.84(2H, d, J=9Hz), 3.91(2H, t, J=6Hz), 3.84(2H, s), 3.28(2H, t, J=6Hz), 2.86–2.72(2H, m), 2.77(3H, s), 2.58(2H, ddd, J=11, 11, 5Hz), 1.83–1.65(8H, m), 1.55–1.40(2H, m), 0.97(3H, t, J=7Hz) | oil |
| 38-1 | — | CDCl₃*: 6.83(2H, d, J=9Hz), 6.76(2H, d, J=9Hz), 3.91(2H, t, J=7Hz), 3.50(1H, dd, J=14, 3Hz), 3.40(3H, s), 3.27(1H, dd, J=14, 8Hz), 3.18(1H, dd, J=8, 3Hz), 3.06–2.83(4H, m), 2.92(3H, s), 1.80–1.40(8H, m), 0.97(3H, t, J=7Hz) | — |
| 38-2 | KBr: 2933, 2821, 1514, 1244, 1103, 808 | CDCl₃: 7.32–7.16(5H, m), 6.83(2H, d, J=9Hz), 6.75(2H, d, J=9Hz), 3.91(2H, t, J=7Hz), 3.52(1H, dd, J=14, 3Hz), 3.40(3H, s), 3.28(1H, dd, J=14, 8Hz), 3.21(1H, dd, J=8, 3Hz), 2.93(3H, s), 2.88–2.78(4H, m), 2.68–2.60(2H, m), 2.48–2.37(2H, m), 1.85–1.58(6H, m), 1.55–1.42(2H, m), 0.97(3H, t, J=7Hz) | 70.8–71.9 |
| 39-1 | — | CDCl₃*: 7.04(2H, d, J=9Hz), 6.91(2H, d, J=9Hz), 5.30(1H, s), 3.98(2H, t, J=6Hz), 3.24(3H, s), 2.99(2H, ddd, J=12, 12, 3Hz), 2.69(2H, ddd, J=12, 4, 4Hz), 2.18(2H, s), 1.87–1.43(6H, m), 1.37–1.25(2H, m), 1.00(3H, t, J=7Hz) | — |
| 39-2 | — | CDCl₃: 7.13(2H, d, J=9Hz), 6.98(2H, d, J=9Hz), 6.92(2H, d, J=9Hz), 6.82(2H, d, J=9Hz), 4.37–4.28(1H, m), 3.99(2H, t, J=6Hz), 3.79(3H, s), 3.63(2H, s), 3.61–3.52(1H, m), 3.46–3.34(1H, m), 3.22(3H, s), 3.03(1H, ddd, J=13, 13, 3Hz), 2.09(1H, d, J=16Hz), 2.08(1H, d, J=16Hz), 1.86–1.45(6H, m), 1.19(1H, ddd, J=13, 13, 5Hz), 1.00(3H, t, J=7Hz), 0.94(1H, ddd, J=13, 13, 5Hz) | — |
| 39-3 | KBr: 2935, 1512, 1464, 1246, 1103, 1028, 827 | CDCl₃*: 7.12(2H, d, J=9Hz), 6.90(2H, d, J=9Hz), 6.84(2H, d, J=9Hz), 6.83(2H, d, J=9Hz), 3.92(2H, t, J=6Hz), 3.78(3H, s), 3.29(2H, t, J=7Hz), 2.82–2.66(4H, m), 2.78(3H, s), 2.64–2.54(2H, m), 2.52–2.38(2H, m), 1.80–1.60(8H, m), 1.56–1.40(2H, m), 0.97(3H, t, J=7Hz | 61.1–61.4 |
| 40-1 | — | CDCl₃*: 7.28–7.17(1H, m), 7.01(2H, d, J=9Hz), 6.93(2H, d, J=9Hz), 6.86–6.75(2H, m), 5.43(1H, s), 4.38–4.27(1H, m), 3.99(2H, t, J=6Hz), 3.71–3.41(4H, m), 3.23(3H, s), 3.12–3.00(1H, m), 2.13(2H, s), | — |

TABLE 5-continued

| Example No. | I R (cm$^{-1}$) | NMR (ppm) (no mark: 300 MHz, *: 270 MHz) | melting point (° C.) |
|---|---|---|---|
| | | 1.86–1.44(6H, m), 1.29–1.05(2H, m), 1.00(3H, t, J=7Hz) | |
| 40-2 | liquid film: 2939, 1510, 1244, 1136, 964 | CDCl$_3$*: 7.22–7.10(1H, m), 6.95–6.72(6H, m), 3.92(2H, t, J=6Hz), 3.29(2H, t, J=6Hz), 2.86–2.65(4H, m), 2.78(3H, s), 2.65–2.40(4H, m), 1.80–1.41(10H, m), 0.97(3H, t, J=7Hz) | oil |
| 41-1 | — | CDCl$_3$*: 7.00(2H, d, J=9Hz), 6.92(2H, d, J=9Hz), 6.73(1H, d, J=2Hz), 6.72(1H, d, J=8Hz), 6.64(1H, dd, J=8, 2Hz), 5.94–5.91(2H, m), 5.39(1H, s), 4.38–4.28(1H, m), 3.98(2H, t, J=6Hz), 3.61–3.35(2H, m), 3.59(2H, s), 3.23(3H, s), 3.04(1H, ddd, J=13, 13, 3), 2.10(2H, s), 1.86–1.73(2H, m), 1.71–1.44(4H, m), 1.21(1H, ddd, J=13, 13, 5Hz), 1.07–0.93(1H, m), 1.00(3H, t, J=7Hz) | — |
| 41-2 | KBr: 3361, 2935, 1514, 1246, 1039, 814 | CDCl$_3$: 6.90(2H, d, J=9Hz), 6.84(2H, d, J=9Hz), 6.75–6.62(3H, m), 5.91(2H, s), 3.91(2H, t, J=7Hz), 3.29(2H, t, J=7Hz), 2.79–2.67(4H, m, 2.78(3H, s), 2.62–2.53(2H, m), 2.44(2H, ddd, J=11, 11, 3), 1.80–1.59(8H, m), 1.55–1.41(2H, m), 0.97(3H, t, J=7Hz) | 55.1–55.5 |
| 42-1 | — | CDCl$_3$*: 7.33–7.07(5H, m), 7.02(2H, d, J=9Hz), 6.94(2H, d, J=9Hz), 5.41(1H, s), 4.40–4.29(1H, m), 3.99(2H, t, J=6Hz), 3.53–3.30(2H, m), 3.24(3H, s), 3.07–2.89(3H, m), 2.62–2.53(2H, m), 2.10(2H, s), 1.86–1.72(2H, m), 1.710–1.43(4H, m), 1.18(1H, ddd, J=13, 13, 5Hz), 0.99(3H, t, J=7Hz), 0.94(1H, ddd, J=13, 13, 5Hz) | — |
| 42-2 | liquid film: 2937, 2870, 1514, 1471, 1242 | CDCl$_3$*: 7.32–7.13(5H, m), 6.89(2H, d, J=9Hz), 6.83(2H, d, J=9Hz), 3.91(2H, t, J=6Hz), 3.28(2H, t, J=7Hz), 2.77(3H, s), 2.68–2.57(2H, m), 2.45–2.28(4H, m), 1.91–1.40(12H, m), 0.97(3H, t, J=7Hz) | oil |
| 43-1 | — | CDCl$_3$*: 7.31–7.23(2H, m), 7.04–6.85(7H, m), 4.66(1H, d, J=13Hz), 4.63(1H, d, J=13Hz), 4.36–4.24(1H, m), 3.98(2H, t, J=6Hz), 3.75–3.64(1H, m), 3.56–3.43(1H, m), 3.24(3H, s), 3.15–3.02(1H, m), 2.13(2H, s), 1.86–1.44(6H, m), 1.32–1.16(2H, m), 1.00(3H, t, J=7Hz) | — |
| 43-2 | liquid film: 2935, 1514, 1471, 1244, 1038, 754 | CDCl$_3$*: 7.32–7.25(2H, m), 6.98–6.80(7H, m), 4.12(2H, t, J=6Hz), 3.91(2H, t, J=6Hz), 3.29(2H, t, J=6Hz), 2.84(2H, t, J=6Hz), 2.80–2.68(2H, m), 2.78(3H, s), 2.54(2H, ddd, J=11, 11, 4Hz), 1.80–1.58(8H, m), 1.56–1.40(2H, m), 0.97(3H, t, J=7Hz) | oil |
| 44-1 | — | CDCl$_3$*: 7.33–7.17(5H, m), 6.98(2H, d, J=9Hz), 6.92(2H, d, J=9Hz), 5.38(1H, s), 4.38–4.28(1H, m), 3.99(2H, t, J=6Hz), 3.69(2H, s), 3.61–3.51(1H, m), 3.46–3.34(1H, m), 3.22(3H, s), 3.04(1H, ddd, J=13, 13, 3Hz), 2.08(2H, s), 1.86–1.73(2H, m), 1.71–1.43(4H, m), 1.30–1.14(1H, m), 1.00(3H, t, J=7Hz), 0.97–0.85(1H, m) | — |
| 44-2 | liquid film: 2953, 2937, 2870, 1514, 1244 | CDCl$_3$: 7.33–7.16(5H, m), 6.91(2H, d, J=9Hz), 6.84(2H, d, J=9Hz), 3.92(2H, t, J=6Hz), 3.30(2H, t, J=6Hz), 2.87–2.71(4H, m), 2.78(3H, s), 2.68–2.60(2H, m), 2.52–2.42(2H, | oil |

TABLE 5-continued

| Example No. | I R (cm⁻¹) | NMR (ppm) (no mark: 300 MHz, *: 270 MHz) | melting point (° C.) |
|---|---|---|---|
| | | m), 1.80–1.62(8H, m), 1.55–1.41(2H, m), 0.97(3H, t, J=7Hz) | |
| 45-1 | — | CDCl₃*: 7.71(1H, s), 7.37(2H, d, J=9Hz), 6.85(2H, d, J=9Hz), 3.94(2H, t, J=7Hz), 3.03(2H, ddd, J=13, 10, 3Hz), 2.84(2H, ddd, J=13, 4, 4Hz), 2.49(2H, s), 1.81–1.40(8H, m), 0.97(3H, t, J=7Hz) | — |
| 45-2 | — | CDCl₃: 7.46(1H, s), 7.35(2H, d, J=9Hz), 7.21(2H, dd, J=9, 5Hz), 7.00(2H, dd, J=9, 9Hz), 6.85(2H, d, J=9Hz), 4.65(1H, s), 4.45–4.35(1H, m), 3.94(2H, t, J=6Hz), 3.70(2H, s), 3.70–3.60(1H, m), 3.55–3.42(1H, m), 3.11(1H, ddd, J=13, 13, 3Hz), 2.39(2H, s), 1.82–1.65(4H, m), 1.55–1.35(3H, m), 1.30–1.14(1H, m), 0.97(3H, t, J=7Hz) | — |
| 45-3 | KBr: 3269, 2935, 1512, 1236, 825 | CDCl₃: 7.16(2H, dd, J=9, 5Hz), 6.96(2H, dd, J=9, 9Hz), 6.79(2H, d, J=9Hz), 6.65(2H, d, J=9Hz), 3.89(2H, t, J=7Hz), 3.29(2H, t, J=6Hz), 2.83–2.67(4H, m), 2.63–2.54(2H, m), 2.42(2H, ddd, J=12, 12, 4Hz), 1.80(2H, t, J=6Hz), 1.76–1.67(6H, m), 1.55–1.40(2H, m), 0.96(3H, t, J=7Hz) | 92.8–94.6 |
| 46-1 | — | CDCl₃: 7.34–7.20(5H, m), 7.00(2H, d, J=9Hz), 6.81(2H, d, J=9Hz), 5.26(1H, s), 4.69–4.58(1H, m), 3.47(2H, s), 3.22(3H, s), 2.59–2.34(6H, m), 2.28–2.12(2H, m), 2.16(2H, s), 1.97–1.61(4H, m), 1.39(2H, ddd, J=12, 12, 4Hz) | — |
| 46-2 | — | CDCl₃*: 7.02(2H, d, J=9Hz), 6.82(2H, d, J=9Hz), 5.30(1H, s), 4.70–4.57(1H, m), 3.23(3H, s), 2.99(2H, ddd, J=12, 12, 3Hz), 2.70(2H, ddd, J=12, 4, 4Hz), 2.53–2.42(2H, m), 2.28–2.11(2H, m), 2.17(2H, s), 1.97–1.55(4H, m), 1.36–1.26(2H, m) | — |
| 46-3 | — | CDCl₃: 7.34–7.18(5H, m), 6.96(2H, d, J=9Hz), 6.83(2H, d, J=9Hz), 5.38(1H, s), 4.71–4.59(1H, m), 4.40–4.30(1H, m), 3.70(2H, s), 3.60–3.51(1H, m), 3.40(1H, ddd, J=13, 13, 2Hz), 3.21(3H, m), 3.04(1H, ddd, J=13, 13, 3Hz), 2.55–2.42(2H, m), 2.28–2.12(2H, m), 2.09(1H, d, J=16Hz), 2.07(1H, d, J=16Hz), 1.97–1.51(4H, m), 1.20(1H, ddd, J=13, 13, 5Hz), 0.93(1H, ddd, J=13, 13, 5Hz) | — |
| 46-4 | liquid film: 1514, 1469, 1454, 1354, 1246 | CDCl₃*: 7.35–7.20(5H, m), 6.89(2H, d, J=9Hz), 6.75(2H, d, J=9Hz), 4.65–4.50(1H, m), 3.98(1H, s), 3.30(2H, t, J=8Hz), 2.84–2.57(6H, m), 2.78(3H, s), 2.53–2.37(4H, m), 2.22–2.06(2H, m), 1.90–1.60(8H, m) | oil |
| 47-1 | — | CDCl₃*: 7.18(2H, dd, J=9, 5Hz), 7.02–6.93(4H, m), 6.83(2H, d, J=9Hz), 5.40(1H, s), 4.71–4.58(1H, m), 4.38–4.28(1H, m), 3.66(2H, s), 3.60–3.50(1H, m), 3.42(1H, ddd, J=13, 13, 3Hz), 3.21(3H, s), 3.03(1H, ddd, J=13, 13, 3Hz), 2.56–2.42(2H, m), 2.30–2.01(4H, m), 1.98–1.83(1H, m), 1.82–1.53(3H, m), 1.19(1H, ddd, J=13, 13, 5Hz), 0.93(1H, ddd, J=13, 13, 5Hz) | — |
| 47-2 | liquid film: 2941, 2814, 1510, 1354, 1244, 1132, 1086, 825 | CDCl₃: 7.16(2H, dd, J=8, 6Hz), 7.01–6.92(2H, m), 6.89(2H, d, J=9Hz), 6.76(2H, d, J=9Hz), 4.63–4.51(1H, m), 3.29(2H, t, J=6Hz), 2.84–2.69(4H, m), 2.78(3H, s), | oil |

TABLE 5-continued

| Example No. | I R (cm$^{-1}$) | NMR (ppm) (no mark: 300 MHz, *: 270 MHz) | melting point (° C.) |
|---|---|---|---|
| 48-1 | — | 2.64–2.56(2H, m), 2.52–2.36(4H, m), 2.23–2.07(2H, m), 1.90–1.57(8H, m) CDCl$_3$: 7.41–7.15(4H, m), 6.99(2H, d, J=9Hz), 6.84(2H, d, J=9Hz), 5.42(1H, s), 4.71–4.59(1H, m), 4.41–4.31(1H, m), 3.79(1H, d, J=16Hz), 3.76(1H, d, J=16Hz), 3.59–3.39(2H, m), 3.23(3H, s), 3.08(1H, ddd, J=13, 13, 3Hz), 2.56–2.42(2H, m), 2.28–2.12(2H, m), 2.13(2H, s), 1.97–1.61(4H, m), 1.25(1H, ddd, J=13, 13, 5Hz), 1.14(1H, ddd, J=13, 13, 5Hz) | — |
| 48-2 | KBr: 2941, 1514, 1252, 812, 750 | CDCl$_3$: 7.33(1H, dd, J=7, 2Hz), 7.26–7.10(3H, m), 6.89(2H, d, J=9Hz), 6.76(2H, d, J=9Hz), 4.62–4.51(1H, m), 3.30(2H, t, J=7Hz), 3.01–2.93(2H, m), 2.82–2.71(2H, m), 2.78(3H, s), 2.67–2.58(2H, m), 2.57–2.35(4H, m), 2.23–2.07(2H, m), 1.92–1.55(8H, m) | oil |
| 49-1 | — | CDCl$_3$: 7.56(1H, d, J=3Hz), 7.32–7.22(5H, m), 7.20(1H, dd, J=9, 3Hz), 6.98(1H, d, J=9Hz), 5.11(1H, s), 4.07(2H, t, J=6Hz), 3.90(3H, s), 3.47(2H, s), 3.23(3H, s), 2.60–2.49(2H, m), 2.44–2.34(2H, m), 2.15(2H, s), 1.92–1.79(2H, m), 1.71–1.49(4H, m), 1.39(2H, ddd, J=12, 12, 4Hz), 1.00(3H, t, J=7Hz) | — |
| 49-2 | — | CDCl$_3$*: 7.58(1H, d, J=3Hz), 7.22(1H, dd, J=9, 3Hz), 6.99(1H, d, J=9Hz), 5.17(1H, s), 4.07(2H, t, J=6Hz), 3.91(3H, s), 3.24(3H, s), 3.00(2H, ddd, J=12, 12, 3Hz), 2.77–2.67(2H, m), 2.16(2H, s), 1.91–1.48(6H, m), 1.38–1.24(2H, m), 1.00(3H, t, J=7Hz) | — |
| 49-3 | — | CDCl$_3$*: 7.54(1H, d, J=3Hz), 7.22–7.13(3H, m), 7.04–6.93(3H, m), 5.27(1H, s), 4.40–4.30(1H, m), 4.08(2H, t, J=7Hz), 3.92(3H, s), 3.66(2H, s), 3.62–3.36(2H, m), 3.23(3H, s), 3.03(1H, ddd, J=13, 13, 3Hz), 2.08(2H, s), 1.92–1.78(2H, m), 1.74–1.48(4H, m), 1.19(1H, ddd, 13, 13, 5Hz), 1.05–0.90(4H, m) | — |
| 49-4 | — | CDCl$_3$*: 7.97–7.93(1H, m), 7.32–6.92(6H, m), 5.21(1H, s), 4.40–4.25(3H, m), 3.74–3.30(2H, m), 3.66(2H, s), 3.24(3H, s), 3.10–2.96(1H, m), 2.08(2H, s), 2.02–1.82(2H, m), 1.72–1.48(4H, m), 1.30–0.92(5H, m) | — |
| 49-5 | KBr: 3365, 2953, 2929, 1508, 1238, 1227, 1211 | CDCl$_3$*: 7.14(2H, dd, J=9, 6Hz), 7.01–6.90(3H, m), 6.88–6.74(2H, m), 4.66(2H, s), 3.98(2H, t, J=6Hz), 3.91(1H, s), 3.31(2H, t, J=7Hz), 2.83–2.66(4H, m), 2.79(3H, s), 2.64–2.52(2H, m), 2.44(2H, ddd, J=11, 11, 4Hz), 1.84–1.42(10H, m), 0.98(3H, t, J=7Hz) | 129.6–130.8 |
| 50-1 | — | CDCl$_3$: 6.80–6.60(3H, m), 5.94(2H, s), 4.42–4.33(1H, m), 3.85(1H, s), 3.67–3.58(1H, m), 3.64(2H, s), 3.42(1H, ddd, J=13, 13, 3Hz), 3.07(1H, ddd, J=13, 13, 3Hz), 2.33(2H, s), 1.75–1.57(2H, m), 1.50–1.35(1H, m), 1.46(9H, s), 1.23(1H, ddd, J=13, 13, 5Hz) | — |
| 50-2 | — | DMSO-d$_6$: 6.81(1H, d, J=8Hz), 6.76(1H, d, J=2Hz), 6.65(1H, dd, J=8, 2Hz), 5.96(2H, s), 4.66(1H, s), 4.08–3.98(1H, m), 3.70–3.18(4H, m), 2.98–2.86(1H, m), 2.31(2H, s), 1.58–1.38(4H, m) | — |

TABLE 5-continued

| Example No. | I R (cm⁻¹) | NMR (ppm) (no mark: 300 MHz, *: 270 MHz) | melting point (° C.) |
|---|---|---|---|
| 50-3 | — | CDCl₃*: 7.12–7.07(1H, m), 7.00–6.82(2H, m), 6.76–6.69(2H, m), 6.67–6.61(1H, m), 5.93(2H, s), 5.32(1H, s), 4.58–4.48(2H, m), 4.39–4.27(1H, m), 4.00(2H, t, J=6Hz), 3.59(2H, s), 3.58–3.50(1H, m), 3.48–3.33(1H, m), 3.17(3H, s), 3.08–2.96(1H, m), 2.36–2.29(0.5H, m), 2.20–2.13(0.5H, m), 2.12–1.93(2H, m), 1.86–1.44(6H, m), 1.28–1.13(1H, m), 1.08–0.89(1H, m), 1.00(3H, t, J=7Hz) | — |
| 50-4 | liquid film: 2935, 2872, 1498, 1444, 1246, 1039 | CDCl₃: 7.15(1H, d, J=9Hz), 6.89–6.79(2H, m), 6.73(1H, d, J=8Hz), 6.69(1H, d, J=2Hz), 6.64(1H, dd, J=8, 2Hz), 5.92(2H, s), 4.69(2H, s), 3.94(2H, t, J=7Hz), 3.14(2H, t, J=7Hz), 2.80–2.38(6H, m), 2.63(3H, s), 1.81–1.60(6H, m), 1.56–1.42(2H, m), 0.97(3H, t, J=7Hz) | oil |
| 51-1 | — | CDCl₃*: 7.33–7.19(10H, m), 6.94(2H, d, J=9Hz), 6.81(2H, d, J=9Hz), 4.66(1H, d, J=12Hz), 4.38(1H, d, J=12Hz), 4.24(1H, s), 3.95(2H, t, J=6Hz), 3.80(1H, s), 3.48(2H, s), 3.28(3H, s), 2.68–2.55(2H, m), 2.46–2.25(2H, m), 1.97–1.70(3H, m), 1.60–1.21(5H, m), 1.00(3H, t, J=7Hz) | — |
| 51-2 | — | CDCl₃*: 7.13(2H, d, J=9Hz), 6.91(2H, d, J=9Hz), 3.97(2H, t, J=6Hz), 3.75(1H, s), 3.27(3H, s), 3.00(1H, ddd, J=12, 12, 3Hz), 2.88(1H, ddd, J=12, 12, 3Hz), 2.82–2.70(2H, m), 1.85–1.72(3H, m), 1.59–1.14(5H, m), 0.99(3H, t, J=7Hz) | — |
| 51-3 | — | CDCl₃: 7.32–7.09(7H, m), 6.91(2H, d, J=8Hz), 4.09(1H, s), 3.97(2H, t, J=6Hz), 3.75(1H, d, J=11Hz), 3.28(3H, s), 3.16(1H, d, J=11Hz), 2.87–2.54(6H, m), 2.45(1H, ddd, J=11, 11, 5Hz), 2.39–2.27(1H, m), 1.92–1.73(3H, m), 1.59–1.42(4H, m), 1.39–1.23(1H, m), 1.00(3H, t, J=7Hz) | — |
| 51-4 | KBr: 1514, 1250, 1122, 1043, 831, 698 | CDCl₃*: 7.33–7.16(5H, m), 6.88(2H, d, J=9Hz), 6.84(2H, d, J=9Hz), 3.91(2H, t, J=6Hz), 3.61(1H, dd, J=11, 4Hz), 3.31(1H, dd, J=14, 11Hz), 3.09(1H, dd, J=14, 4Hz), 2.92–2.78(4H, m), 2.81(3H, s), 2.71–2.60(2H, m), 2.55–2.39(2H, m), 1.95–1.40(8H, m), 0.97(3H, t, J=7Hz) | 56.6–57.5 |
| 52-1 | — | CDCl₃: 7.10(2H, d, J=9Hz), 6.92(2H, d, J=9Hz), 3.98(2H, t, J=7Hz), 3.56(1H, s), 3.34(3H, s), 3.30(3H, s), 3.11–2.98(1H, m), 2.95(1H, ddd, J=12, 12, 3Hz), 2.86–2.74(2H, m), 1.90–1.75(3H, m), 1.60–1.38(4H, m), 1.23(1H, ddd, J=13, 13, 5Hz), 1.00(3H, t, J=7Hz) | — |
| 52-2 | — | CDCl₃*: 7.14(2H, dd, J=9, 5Hz), 7.10(2H, d, J=9Hz), 6.96(2H, dd, J=9, 9Hz), 6.92(2H, d, J=9Hz), 4.29(1H, s), 3.98(2H, t, J=6Hz), 3.34(3H, s), 3.31(3H, s), 2.82–2.68(4H, m), 2.62–2.30(4H, m), 1.98–1.87(1H, m), 1.86–1.74(2H, m), 1.61–1.44(4H, m), 1.42–1.26(1H, m), 1.01(3H, t, J=7Hz) | — |
| 52-3 | KBr: 2935, 1514, 1240, 1215, 812 | CDCl₃*: 7.16(2H, dd, J=9, 6Hz), 6.96(2H, dd, J=9, 9Hz), 6.83(2H, d, J=9Hz), 6.75(2H, d, J=9Hz), 3.91(2H, t, J=6Hz), 3.51(1H, dd, J=14, 3Hz), 3.40(3H, s), 3.28(1H, | 66.8–67.2 |

TABLE 5-continued

| Example No. | I R (cm⁻¹) | NMR (ppm) (no mark: 300 MHz, *: 270 MHz) | melting point (° C.) |
|---|---|---|---|
| | | dd, J=14, 8Hz), 3.20(1H, dd, J=8, 3Hz), 2.92(3H, s), 2.87–2.74(4H, m), 2.64–2.54(2H, m), 2.47–2.33(2H, m), 1.84–1.40(8H, m), 0.97(3H, t, J=7Hz) | |
| 53-1 | — | CDCl₃*: 7.13(2H, dd, J=9, 5Hz), 7.13(2H, d, J=9Hz), 6.95(2H, dd, J=9, 9Hz), 6.91(2H, d, J=9Hz), 4.11(1H, s), 3.97(2H, t, J=6Hz), 3.74(1H, d, J=10Hz), 3.28(3H, s), 3.20(1H, d, J=10Hz), 2.80–2.65(4H, m), 2.60–2.50(1H, m), 2.58(1H, s), 2.44(1H, ddd, J=11, 11, 5Hz), 2.31(1H, ddd, J=12, 12, 2Hz), 1.92–1.72(3H, m), 1.59–1.42(4H, m), 1.37–1.22(1H, m), 1.00(3H, t, J=7Hz) | — |
| 53-2 | KBr: 2935, 1512, 1242, 1225, 827 | CDCl₃*: 7.16(2H, dd, J=9, 5Hz), 6.96(2H, dd, J=9, 9Hz), 6.87(2H, d, J=9Hz), 6.83(2H, d, J=9Hz), 3.91(2H, t, J=6Hz), 3.60(1H, dd, J=11, 4Hz), 3.31(1H, dd, J=13, 11Hz), 3.09(1H, dd, J=13, 4Hz), 2.87–2.74(4H, m), 2.81(3H, s), 2.64–2.55(1H, m), 2.63(1H, s), 2.48–2.33(2H, m), 1.95–1.84(1H, m), 1.80–1.67(3H, m), 1.60(2H, dd, J=8, 3Hz), 1.55–1.40(2H, m), 0.97(3H, t, J=7Hz) | 67.1–68.2 |
| 54 | KBr: 1512, 1470, 1244, 1070, 700 | CDCl₃*: 7.41–7.22(5H, m), 6.92(2H, d, J=9Hz), 6.85(2H, d, J=9Hz), 4.74(1H, dd, J=10, 4Hz), 3.92(2H, t, J=6Hz), 3.29(2H, t, J=6Hz), 2.97–2.86(1H, m), 2.81–2.68(1H, m), 2.78(3H, s), 2.62–2.40(4H, m), 1.80–1.40(10H, m), 0.97(3H, t, J=7Hz) | 104.0–104.8 |
| 55 | KBr: 2939, 1512, 1246, 1223, 835 | CDCl₃*: 7.34(2H, dd, J=9, 6Hz), 7.02(2H, dd, J=9, 9Hz), 6.92(2H, d, J=9Hz), 6.85(2H, d, J=9Hz), 4.70(1H, dd, J=10, 3Hz), 3.92(2H, t, J=6Hz), 3.29(2H, t, J=6Hz), 2.95–2.84(1H, m), 2.82–2.68(2H, m), 2.78(3H, s), 2.62–2.36(4H, m), 1.82–1.40(10H, m), 0.97(3H, t, J=7Hz) | 92.8–94.5 |
| 56 | KBr: 3408, 2953, 2931, 1637, 1510, 1248 | CDCl₃*: 7.33–7.20(5H, m), 7.07(2H, d, J=9Hz), 6.90(2H, d, J=9Hz), 3.97(2H, t, J=6Hz), 3.81(2H, t, J=7Hz), 3.51(2H, s), 2.92(1H, s), 2.63–2.55(2H, m), 2.37(2H, ddd, J=11, 11, 5Hz), 1.83–1.43(10H, m), 1.80(3H, s), 0.98(3H, t, J=7Hz) | 89.7–90.6 |
| 57 | KBr: 3415, 2953, 2933, 1637, 1512, 1250, 1219 | CDCl₃: 7.15(2H, dd, J=9, 5Hz), 7.08(2H, d, J=9Hz), 6.96(2H, dd, J=9, 9Hz), 6.92(2H, d, J=9Hz), 3.97(2H, t, J=7Hz), 3.83(2H, t, J=7Hz), 3.08(1H, s), 2.85–2.40(8H, m), 1.85–1.44(10H, m), 1.82(3H, s), 0.99(3H, t, J=7Hz) | 121.6–122.1 |
| 58-1 | — | CDCl₃: 7.04(2H, d, J=9Hz), 6.92(2H, d, J=9Hz), 5.38(1H, s), 3.80–3.65(2H, m), 3.30–3.10(2H, m), 3.24(3H, s), 2.15(2H, s), 1.85–1.74(2H, m), 1.70–1.40(4H, m), 1.43(9H, s), 1.32–1.28(2H, m), 0.97(3H, t, J=7Hz) | — |
| 58-2 | — | CDCl₃: 7.05(2H, d, J=9Hz), 6.90(2H, d, J=9Hz), 3.97(2H, t, J=7Hz), 3.87–3.67(2H, m), 3.22(3H, s), 3.09–2.89(2H, m), 3.04(3H, s), 2.34(2H, s), 1.85–1.60(6H, m), 1.60–1.40(2H, m), 1.44(9H, s), 0.99(3H, t, J=7Hz) | — |
| 58-3 | — | CDCl₃: 7.06(2H, d, J=9Hz), 6.90(2H, d, J=9Hz), 3.97(2H, t, J=7Hz), 3.22(3H, s), 3.05(3H, s), 2.92– | — |

TABLE 5-continued

| Example No. | I R (cm$^{-1}$) | NMR (ppm) (no mark: 300 MHz, *: 270 MHz) | melting point (° C.) |
|---|---|---|---|
| | | 2.75(4H, m), 2.34(2H, s), 1.85–1.60(6H, m), 1.58–1.44(2H, m), 0.99(3H, t, J=7Hz) | |
| 58-4 | — | CDCl$_3$*: 7.35–7.20(5H, m), 7.05(2H, d, J=9Hz), 6.88(2H, d, J=9Hz), 3.96(2H, t, J=6Hz), 3.46(2H, s), 3.22(3H, s), 3.05(3H, s), 2.60–2.48(2H, m), 2.33(2H, s), 2.30–2.16(2H, m), 1.84–1.62(6H, m), 1.60–1.43(2H, m), 0.9(3H, t, J=7Hz) | — |
| 58-5 | liquid film: 2937, 2871, 2817, 1514, 1242, 1078 | CDCl$_3$: 7.35–7.25(5H, m), 6.82(2H, d, J=9Hz), 6.69(2H, d, J=9Hz), 3.90(2H, t, J=7Hz), 3.49(2H, s), 3.33–3.27(2H, m), 3.17(3H, s), 2.82(3H, s), 2.62–2.51(2H, m), 2.33–2.20(2H, m), 1.85–1.40(10H, m), 0.96(3H, t, J=7Hz) | oil |
| 59 | liquid film: 2935, 1514, 1244, 1072, 814, 700 | CDCl$_3$: 7.36–7.21(5H, m), 6.84(2H, d, J=9Hz), 6.81(2H, d, J=9Hz), 3.90(2H, t, J=7Hz), 3.53(2H, s), 3.17(2H, s), 2.92(3H, s), 2.75–2.65(2H, m), 2.42–2.30(2H, m), 2.00(1H, s), 1.78–1.40(8H, m), 0.96(3H, t, J=7Hz) | oil |
| 60 | KBr: 2943, 1512, 1242, 825, 754 | CDCl$_3$*: 7.37(1H, ddd, J=7, 7, 2Hz), 7.28–7.17(1H, m), 7.09(1H, ddd, J=7, 7, 1Hz), 7.07–6.98(1H, m), 6.88(2H, d, J=9Hz), 6.83(2H, d, J=9Hz), 3.98–3.83(1H, m), 3.91(2H, t, J=6Hz), 3.60(2H, s), 3.28(2H, t, J=7Hz), 2.77(3H, s), 2.69–2.58(2H, m), 2.45(2H, ddd, J=11, 11, 4Hz), 1.80–1.40(10H, m), 0.96(3H, t, J=7Hz) | oil |
| 61 | KBr: 2937, 1512, 1470, 1242, 814 | CDCl$_3$*: 7.23–7.03(4H, m), 6.88(2H, d, J=10Hz), 6.83(2H, d, J=10Hz), 3.91(2H, t, J=7Hz), 3.85(1H, s), 3.48(2H, s), 3.28(2H, t, J=7Hz), 2.77(3H, s), 2.67–2.57(2H, m), 2.43–2.30(2H, m), 2.34(3H, s), 1.80–1.40(10H, m), 0.96(3H, t, J=7Hz) | oil |
| 62 | KBr: 2943, 2870, 1512, 1475, 1242 | CDCl$_3$*: 7.32–7.23(1H, m), 7.18–7.10(3H, m), 6.88(2H, d, J=9Hz), 6.83(2H, d, J=9Hz), 3.91(2H, t, J=7Hz), 3.47(2H, s), 3.29(2H, t, J=7Hz), 2.78(3H, s), 2.66–2.53(2H, m), 2.40(2H, ddd, J=11, 11, 3Hz), 2.35(3H, s), 1.82–1.40(10H, m), 0.96(3H, t, J=7Hz) | 77.0–78.0 |
| 63 | KBr: 2939, 1516, 1275, 1242, 1221, 1122, 1032 | CDCl$_3$*: 7.09(1H, dd, J=12Hz, 2Hz), 7.03–6.97(1H, m), 6.93–6.86(3H, m), 6.83(2H, d, J=9Hz), 3.91(2H, t, J=6Hz), 3.88(3H, s), 3.45(2H, s), 3.28(2H, t, J=7Hz), 2.77(3H, s), 2.65–2.54(2H, m), 2.37(2H, ddd, J=11, 11, 3Hz), 1.80–1.56(8H, m), 1.56–1.40(2H, m), 0.96(3H, t, J=7Hz) | 54.6–56.6 |
| 64-1 | — | CDCl$_3$: 7.34–7.20(5H, m), 7.00(4H, s), 5.26(1H, s), 3.47(2H, s), 3.24(3H, s), 2.56–2.46(2H, m), 2.39(2H, ddd, J=11, 11, 3Hz), 2.17(2H, s), 1.71(2H, q, J=8Hz), 1.70–1.62(2H, m), 1.39(2H, ddd, J=12, 12, 4Hz), 1.31(6H, s), 1.03(3H, t, J=7Hz) | — |
| 64-2 | KBr: 3363, 2974, 2937, 2922, 2810, 1508, 1236, 737 | CDCl$_3$: 7.35–7.22(5H, m), 6.87(2H, d, J=9Hz), 6.75(2H, d, J=9Hz), 3.52(2H, s), 3.36(2H, t, J=7Hz), 3.07(1H, br. s), 2.82(3H, s), 2.67–2.57(2H, m), 2.43–2.32(2H, m), 1.73–1.59(8H, m), 1.21(6H, s), 1.00(3H, t, J=7Hz) | 52.8–53.2 |
| 65-1 | — | CDCl$_3$: 7.33–7.19(5H, m), 6.90(1H, d, J=2Hz), 6.87(1H, d, J=8Hz), 6.73(1H, dd, J=8, 2Hz), 5.20(1H, | — |

TABLE 5-continued

| Example No. | I R (cm$^{-1}$) | NMR (ppm) (no mark: 300 MHz, *: 270 MHz) | melting point (° C.) |
|---|---|---|---|
| | | s), 5.19(2H, s), 4.04(2H, t, J=7Hz), 3.51(3H, s), 3.47(2H, s), 3.23(3H, s), 2.58–2.49(2H, m), 2.39(2H, ddd, J=11, 11, 2Hz), 2.19(2H, s), 1.89–1.79(2H, m), 1.70–1.61(2H, m), 1.58–1.44(2H, m), 1.40(2H, ddd, J=13, 13, 4Hz), 1.00(3H, t, J=7Hz) | |
| 65-2 | liquid film: 3398, 2956, 2939, 2872, 2819, 1516, 1252, 1217, 976, 743, 700 | CDCl$_3$: 7.37–7.20(5H, m), 6.75(1H, d, J=9Hz), 6.55(1H, d, J=3Hz), 6.35(1H, dd, J=9, 3Hz), 5.65(1H, br. s), 3.98(2H, t, J=7Hz), 3.52(2H, s), 3.31(2H, t, J=7Hz), 2.78(3H, s), 2.68–2.57(2H, m), 2.44–2.32(2H, m), 1.81–1.57(8H, m), 1.54–1.41(2H, m), 0.97(3H, t, J=7Hz) | oil |
| 66-1 | — | CDCl$_3$: 7.34–7.19(5H, m), 7.08–7.01(1H, m), 6.73–6.66(2H, m), 5.10(1H, s), 3.96(2H, t, J=6Hz), 3.47(2H, s), 3.20(3H, s), 2.60–2.48(2H, m), 2.39(2H, ddd, J=12, 12, 3Hz), 2.15(2H, s), 1.85–1.23(8H, m), 1.00(3H, t, J=7Hz) | — |
| 66-2 | liquid film: 2935, 1510, 1454, 1286, 1159 | CDCl$_3$: 7.35–7.20(5H, m), 7.06–6.98(1H, m), 6.67–6.58(2H, m), 4.87(1H, s), 3.90(2H, t, J=7Hz), 3.52(2H, s), 3.18(2H, t, J=6Hz), 2.70(3H, s), 2.63–2.55(2H, m), 2.41(2H, ddd, J=11, 11, 3Hz), 1.80–1.40(10H, m), 0.97(3H, t, J=7Hz) | oil |
| 67-1 | — | CDCl$_3$: 7.34–7.19(5H, m), 6.92(2H, d, J=9Hz), 6.90(2H, d, J=9), 5.40(1H, s), 5.04–4.90(1H, m), 3.98(2H, t, J=6Hz), 3.47(2H, s), 2.58–2.50(2H, m), 2.38(2H, ddd, J=12, 12, 2Hz), 2.02(2H, s), 1.85–1.74(2H, m), 1.68–1.58(2H, m), 1.59–1.46(2H, m), 1.36(2H, ddd, J=12, 12, 4Hz), 1.03(6H, d, J=7Hz), 1.01(3H, t, J=7Hz) | — |
| 67-2 | KBr: 3331, 2960, 2935, 2872, 2818, 1510, 1244, 1115, 825, 739 | CDCl$_3$: 7.35–7.20(5H, m), 6.99(2H, d, J=9Hz), 6.83(2H, d, J=9Hz), 5.74(1H, s), 3.92(2H, t, J=7Hz), 3.51(2H, s), 3.44–3.34(1H, m), 3.25(2H, t, J=6Hz), 2.64–2.53(2H, m), 2.38(2H, ddd, J=11, 11, 3Hz), 1.80–1.43(10H, m), 1.03(6H, d, J=7Hz), 0.97(3H, t, J=7Hz) | 79.4–79.7 |
| 68 | liquid film: 2962, 2937, 2877, 2810, 1508, 1238, 972, 814, 698 | CDCl$_3$: 7.35–7.21(5H, m), 6.86(2H, d, J=9Hz), 6.83(2H, d, J=9Hz), 4.04–3.94(1H, m), 3.52(2H, s), 3.29(2H, t, J=7Hz), 2.77(3H, s), 2.67–2.56(2H, m), 2.38(2H, ddd, J=11, 11, 4Hz), 1.73–1.57(10H, m), 0.95(6H, t, J=7Hz) | oil |
| 69 | KBr: 2951, 1515, 1246, 812, 700 | CDCl$_3$: 7.35–7.20(5H, m), 6.88(2H, d, J=9Hz), 6.83(2H, d, J=9Hz), 3.93(2H, t, J=7Hz), 3.52(2H, s), 3.28(2H, t, J=7Hz), 2.77(3H, s), 2.66–2.56(2H, m), 2.38(2H, ddd, J=11, 11, 4Hz), 1.90–1.74(1H, m), 1.72–1.56(8H, m), 0.95(6H, d, J=7Hz) | amorphous |
| 70 | liquid film: 2929, 1514, 1470, 1244, 814 | CDCl$_3$: 7.35–7.20(5H, m), 6.89(2H, d, J=9Hz), 6.85(2H, d, J=9Hz), 3.98(2H, t, J=7Hz), 3.52(2H, s), 3.29(2H, t, J=7Hz), 2.77(3H, s), 2.67–2.57(2H, m), 2.38(2H, ddd, J=11, 11, 4Hz), 1.75–1.55(8H, m), 0.92–0.77(1H, m), 0.51–0.43(2H, m), 0.14–0.07(2H, m) | oil |
| 71 | liquid film: 2949, 2920, 1512, 1242, 1041, 825 | CDCl$_3$: 7.35–7.21(5H, m), 6.87(2H, d, J=9Hz), 6.84(2H, d, J=9Hz), 5.90(1H, ddt, J=17, 10, 7Hz), 5.20–5.06(2H, m), 3.97(2H, t, J=7Hz), 3.52(2H, s), 3.29(2H, t, J=7Hz), 2.78(3H, s), 2.66–2.57(2H, m), | oil |

TABLE 5-continued

| Example No. | I R (cm⁻¹) | NMR (ppm) (no mark: 300 MHz, *: 270 MHz) | melting point (° C.) |
|---|---|---|---|
| 72-1 | — | 2.56–2.48(2H, m), 2.38(2H, ddd, J=11, 11, 4Hz), 1.73–1.54(6H, m) CDCl$_3$*: 6.88(2H, d, J=9Hz), 6.83(2H, d, J=9Hz), 4.50–4.36(1H, m), 3.30(2H, t, J=7Hz), 3.00(2H, ddd, J=12, 12, 3Hz), 2.84(2H, ddd, J=12, 4, 4Hz), 2.78(3H, s), 1.75–1.48(6H, m), 1.31(6H, d, J=6Hz) | — |
| 72-2 | KBr: 1510, 1244, 1132, 1082, 837 | CDCl$_3$: 7.26(4H, s), 6.87(2H, d, J=9Hz), 6.83(2H, d, J=9Hz), 4.49–4.36(1H, m), 3.93(1H, br. s), 3.48(2H, s), 3.29(2H, t, J=7Hz), 2.77(3H, s), 2.63–2.53(2H, m), 2.37(2H, ddd, J=11, 11, 3Hz), 1.73–1.55(6H, m), 1.31(6H, d, J=6Hz) | 96.9–97.1 |
| 73 | KBr: 1510, 1244, 1132, 1012 | CDCl$_3$: 7.43(2H, d, J=8Hz), 7.20(2H, d, J=8Hz), 6.87(2H, d, J=9Hz), 6.83(2H, d, J=9Hz), 4.49–4.37(1H, m), 3.93(1H, br. s), 3.46(2H, s), 3.29(2H, t, J=7Hz), 2.77(3H, s), 2.63–2.53(2H, m), 2.37(2H, ddd, J=11, 11, 3Hz), 1.73–1.55(6H, m), 1.31(6H, d, J=6Hz) | 104.3–105.0 |
| 74 | KBr: 1510, 1331, 1153, 1124, 1111 | CDCl$_3$: 7.56(2H, d, J=8Hz), 7.45(2H, d, J=8Hz), 6.88(2H, d, J=9Hz), 6.83(2H, d, J=9Hz), 4.50–4.36(1H, m), 4.00(1H, br. s), 3.57(2H, s), 3.29(2H, t, J=7Hz), 2.78(3H, s), 2.64–2.54(2H, m), 2.41(2H, ddd, J=11, 11, 3Hz), 1.74–1.55(6H, m), 1.31(6H, d, J=6Hz) | 109.9–110.6 |
| 75 | KBr: 2958, 1510, 1244, 829 | CDCl$_3$: 7.23(2H, d, J=8Hz), 7.17(2H, d, J=8Hz), 6.86(2H, d, J=9Hz), 6.82(2H, d, J=9Hz), 4.49–4.35(1H, m), 3.78(1H, br. s), 3.49(2H, s), 3.29(2H, t, J=7Hz), 2.97–2.82(1H, m), 2.78(3H, s), 2.67–2.57(2H, m), 2.37(2H, ddd, J=10, 10, 4Hz), 1.73–1.56(6H, m), 1.30(6H, d, J=6Hz), 1.24(6H, d, J=7Hz) | 75.5–75.9 |
| 76 | KBr: 1510, 1257, 1244, 829 | CDCl$_3$: 7.23(2H, d, J=9Hz), 6.89–6.78(6H, m), 4.48–4.36(1H, m), 3.80(3H, s), 3.46(2H, s), 3.29(2H, t, J=7Hz), 2.77(3H, s), 2.65–2.55(2H, m), 2.35(2H, ddd, J=11, 11, 4Hz), 1.30(6H, d, J=6Hz) | 50.8–52.4 |
| 77 | KBr: 1510, 1263, 1242, 1136 | CDCl$_3$: 7.22(1H, dd, J=8, 8Hz), 6.93–6.77(7H, m), 4.49–4.86(1H, m), 3.81(3H, s), 3.50(2H, s), 3.29(2H, t, J=7Hz), 2.78(3H, s), 2.67–2.57(2H, m), 2.38(2H, ddd, J=11, 11, 4Hz), 1.73–1.57(6H, m), 1.30(6H, d, J=6Hz) | 45.1–46.5 |
| 78 | KBr: 1510, 1244, 1217, 833 | CDCl$_3$: 7.28(2H, dd, J=9, 5Hz), 6.99(2H, dd, J=9, 9Hz), 6.87(2H, d, J=9Hz), 6.83(2H, d, J=9Hz), 4.49–4.36(1H, m), 3.92(1H, br. s), 3.48(2H, s), 3.29(2H, t, J=7Hz), 2.77(3H, s), 2.64–2.55(2H, m), 2.37(2H, ddd, J=11, 11, 4Hz), 1.75–1.55(6H, m), 1.31(6H, d, J=6Hz) | 69.2–70.0 |
| 79 | KBr: 3504, 2933, 2229, 1510, 1242 | CDCl$_3$: 7.60(2H, d, J=8Hz), 7.45(2H, d, J=8Hz), 6.88(2H, d, J=9Hz), 6.83(2H, d, J=9Hz), 4.50–4.37(1H, m), 3.56(2H, s), 3.29(2H, t, J=7Hz), 2.77(3H, s), 2.62–2.53(2H, m), 2.41(2H, ddd, J=11, 11, 3Hz), 1.75–1.55(6H, m), 1.31(6H, d, J=6Hz) | 108.1–109.5 |
| 80 | KBr: 1510, 1244, 1138, 960, 818 | CDCl$_3$: 7.85–7.72(4H, m), 7.52–7.41(3H, m), 6.86(2H, d, J=9Hz), 6.82(2H, d, J=9Hz), 4.49–4.36(1H, m), 3.68(2H, s), 3.29(2H, t, J=7Hz), 2.78(3H, s), 2.72–2.62(2H, m), 2.44(2H, ddd, J=10, 10, 5Hz), 1.74–1.58(6H, m), 1.30(6H, d, J=6Hz) | 76.2–76.8 |

TABLE 5-continued

| Example No. | I R (cm⁻¹) | NMR (ppm) (no mark: 300 MHz, *: 270 MHz) | melting point (° C.) |
|---|---|---|---|
| 81 | liquid film: 2976, 2935, 1510, 1371, 1240, 957 | CDCl₃: 7.21(2H, d, J=8Hz), 6.86(2H, d, J=9Hz), 6.83(2H, d, J=8Hz), 6.82(2H, d, J=9Hz), 4.58–4.35(2H, m), 3.46(2H, s), 3.29(2H, t, J=7Hz), 2.78(3H, s), 2.67–2.57(2H, m), 2.43–2.41(2H, m), 1.72–1.56(6H, m), 1.33(6H, d, J=6Hz), 1.30(6H, d, J=6Hz) | oil |
| 82 | liquid film: 2937, 1510, 1240, 1113 | CDCl₃: 7.53(1H, dd, J=8, 1Hz), 7.49–7.44(1H, m), 7.27(1H, ddd, J=8, 8, 1Hz), 7.10(1H, ddd, J=8, 8, 2Hz), 6.87(2H, d, J=9Hz), 6.83(2H, d, J=9Hz), 4.50–4.35(1H, m), 3.84(1H, br. s), 3.62(2H, s), 3.30(2H, t, J=7Hz), 2.79(3H, s), 2.70–2.60(2H, m), 2.51(2H, ddd, J=10, 10, 4Hz), 1.76–1.55(6H, m), 1.31(6H, d, J=6Hz) | oil |
| 83 | liquid film: 2935, 1510, 1238, 1113 | CDCl₃: 7.50(1H, dd, J=1Hz), 7.37(1H, ddd, J=8, 2, 2Hz), 7.28–7.22(1H, m), 7.17(1H, dd, J=8, 8Hz), 6.87(2H, d, J=9Hz), 6.83(2H, d, J=9Hz), 4.48–4.37(1H, m), 3.49(2H, s), 3.29(2H, t, J=7Hz), 2.78(3H, s), 2.65–2.54(2H, m), 2.39(2H, ddd, J=11, 11, 4Hz), 2.75–2.50(6H, m), 1.31(6H, d, J=6Hz) | oil |
| 84 | KBr: 2933, 1518, 1344, 1242, 1107, 822 | CDCl₃: 8.17(2H, d, J=9Hz), 7.51(2H, d, J=9Hz), 6.89(2H, d, J=9Hz), 6.83(2H, d, J=9Hz), 4.50–4.36(1H, m), 3.61(2H, s), 3.29(2H, t, J=7Hz), 2.78(3H, s), 2.62–2.54(2H, m), 2.47(2H, ddd, J=11, 11, 4Hz), 1.75–1.50(6H, m), 1.31(6H, d, J=6Hz) | 62.5–63.1 |
| 85 | KBr: 1510, 1327, 1244, 1174, 1134 | CDCl₃: 7.62–7.58(1H, m), 7.53–7.47(2H, m), 7.42(1H, dd, J=8Hz), 6.87(2H, d, J=9Hz), 6.83(2H, d, J=9Hz), 4.50–4.37(1H, m), 3.94(1H, br. s), 3.56(2H, s), 3.29(2H, t, J=7Hz), 2.78(3H, s), 2.63–2.54(2H, m), 2.41(2H, ddd, J=11, 11, 4Hz), 1.74–1.56(6H, m), 1.31(6H, d, J=6Hz) | 60.8–61.1 |
| 86 | KBr: 1722, 1510, 1281, 1244, 1113 | CDCl₃: 7.98(2H, d, J=8Hz), 7.40(2H, d, J=9Hz), 6.87(2H, d, J=9Hz), 6.82(2H, d, J=9Hz), 4.50–4.36(1H, m), 3.91(3H, s), 3.56(2H, s), 3.29(2H, t, J=7Hz), 2.77(3H, s), 2.64–2.54(2H, m), 2.40(2H, ddd, J=11, 11, 4Hz), 1.75–1.50(6H, m), 1.30(6H, d, J=6Hz) | 78.8–80.0 |
| 87 | KBr: 1510, 1246, 1136, 852, 825 | CDCl₃: 7.38–7.28(1H, m), 6.92–6.73(6H, m), 4.50–4.37(1H, m), 3.93(1H, br. s), 3.55(2H, s), 3.28(2H, t, J=7Hz), 2.77(3H, s), 2.66–2.56(2H, m), 2.43(2H, ddd, J=11, 11, 4Hz), 1.73–1.55(6H, m), 1.31(6H, d, J=6Hz) | 77.6–77.9 |
| 88 | KBr: 1508, 1317, 1252, 1240, 1173, 1151 | CDCl₃: 7.56(1H, dd, J=7, 2Hz), 7.52–7.46(1H, m), 7.13(1H, dd, J=9, 9Hz), 6.88(2H, d, J=9Hz), 6.83(2H, d, J=9Hz), 4.50–4.37(1H, m), 4.03(1H, br. s), 3.51(2H, s), 3.29(2H, t, J=7Hz), 2.78(3H, s), 2.62–2.52(2H, m), 2.40(2H, ddd, J=11, 11, 3Hz), 1.74–1.56(6H, m), 1.31(6H, d, J=6Hz) | 58.8–62.8 |
| 89 | KBr: 1510, 1281, 1244, 1225, 1153 | CDCl₃: 7.34(2H, d, J=9Hz), 7.15(2H, d, J=9Hz), 6.87(2H, d, J=9Hz), 6.83(2H, d, J=9Hz), 4.50–4.37(1H, m), 3.94(1H, br. s), 3.51(2H, s), 3.29(2H, t, J=7Hz), 2.78(3H, s), 2.63–2.55(2H, m), 2.39(2H, ddd, J=11, 11, 3Hz), 1.74–1.55(6H, m), 1.31(6H, d, J=6Hz) | 84.7–85.1 |

TABLE 5-continued

| Example No. | I R (cm⁻¹) | NMR (ppm) (no mark: 300 MHz, *: 270 MHz) | melting point (° C.) |
|---|---|---|---|
| 90 | KBr: 2976, 1510, 1246, 1113, 829 | CDCl₃: 7.20(1H, dd, J=9, 9Hz), 6.86(2H, d, J=9Hz), 6.82(2H, d, J=9Hz), 6.63(1H, dd, J=8, 2Hz), 6.56(1H, dd, J=12, 2Hz), 4.55–4.36(2H, m), 3.79(1H, br. s), 3.52(2H, s), 3.28(2H, t, J=7Hz), 2.77(3H, s), 2.68–2.58(2H, m), 2.41(2H, ddd, J=11, 11, 4Hz), 1.72–1.55(6H, m), 1.33(6H, 6, J=6Hz), 1.30(6H, d, J=6Hz) | 65.1–66.1 |
| 91 | KBr: 1514, 1244, 1117, 758, 694 | CDCl₃*: 7.62–7.52(4H, m), 7.47–7.28(5H, m), 6.86(2H, d, J=9Hz), 6.83(2H, d, J=9Hz), 4.50–4.36(1H, m), 3.57(2H, s), 3.30(2H, t, J=7Hz), 2.78(3H, s), 2.72–2.60(2H, m), 2.42(2H, ddd, J=11, 11, 4Hz), 1.76–1.52(6H, m) | 66.9–68.0 |
| 92 | liquid film: 2937, 1510, 1489, 1238, 1115 | CDCl₃*: 7.37–7.25(4H, m), 7.12–6.92(5H, m), 6.86(2H, d, J=9Hz), 6.83(2H, d, J=9Hz), 4.48–4.35(1H, m), 3.49(2H, s), 3.30(2H, t, J=7Hz), 2.78(3H, s), 2.68–2.57(2H, m), 2.38(2H, ddd, J=11, 11, 4Hz), 1.73–1.52(6H, m), 1.31(6H, d, J=6Hz) | oil |
| 93 | KBr: 1510, 1483, 1244, 1117, 825 | CDCl₃*: 7.32–7.18(3H, m), 6.86(2H, d, J=9Hz), 6.82(2H, d, J=9Hz), 4.50–4.35(1H, m), 3.91(1H, br. s), 3.54(2H, s), 3.28(2H, t, J=6Hz), 2.77(3H, s), 2.66–2.55(2H, m), 2.43(2H, ddd, J=11, 11, 3Hz), 1.75–1.50(6H, m), 1.30(6H, d, J=6Hz) | 99.8–100.9 |
| 94 | KBr: 1510, 1254, 1246, 1130, 1119, 955 | CDCl₃*: 7.30–6.90(4H, m), 6.87(2H, d, J=9Hz), 6.82(2H, d, J=9Hz), 4.50–4.35(1H, m), 3.52(2H, s), 3.29(2H, t, J=7Hz), 2.78(3H, s), 2.67–2.55(2H, m), 2.47–2.33(2H, m), 1.73–1.60(6H, m), 1.31(6H, d, J=6Hz) | 52.5–54.6 |
| 95 | KBr: 1510, 1244, 1117, 754 | CDCl₃: 7.41–7.33(1H, m), 7.26–6.98(3H, m), 6.86(2H, d, J=9Hz), 6.82(2H, d, J=9Hz), 4.49–4.36(1H, m), 3.60(2H, s), 3.29(2H, t, J=7Hz), 2.77(3H, s), 2.70–2.60(2H, m), 2.45(2H, ddd, J=11, 11, 4Hz), 1.72–1.57(6H, m), 1.31(6H, d, J=6Hz) | amorphous |
| 96 | KBr: 2924, 1510, 1261, 1217, 1167 | CDCl₃*: 7.36–7.19(3H, m), 7.09(1H, d, J=8Hz), 6.87(2H, d, J=9Hz), 6.83(2H, d, J=9Hz), 4.50–4.35(1H, m), 3.53(2H, s), 3.29(2H, t, J=6Hz), 2.78(3H, s), 2.64–2.54(2H, m), 2.40(2H, ddd, J=11, 11, 4Hz), 1.74–1.52(6H, m), 1.31(6H, d, J=6Hz) | oil |
| 97 | KBr: 2927, 1510, 1255, 1225, 1165 | CDCl₃: 7.57–7.50(1H, m), 7.30–7.19(3H, m), 6.87(2H, d, J=9Hz), 6.83(2H, d, J=9Hz), 4.49–4.36(1H, m), 3.59(2H, s), 3.29(2H, t, J=7Hz), 2.78(3H, s), 2.65–2.55(2H, m), 2.45(2H, ddd, J=11, 11, 4Hz), 1.74–1.53(6H, m), 1.31(6H, d, J=6Hz) | oil |
| 98 | liquid film: 2937, 1510, 1240, 1115 | CDCl₃: 7.36–7.33(1H, m), 7.26–7.17(3H, m), 6.87(2H, d, J=9Hz), 6.83(2H, d, J=9Hz), 4.50–4.36(1H, m), 3.49(2H, s), 3.29(2H, t, J=7Hz), 2.78(3H, s), 2.65–2.55(2H, m), 2.39(2H, ddd, J=11, 11, 4Hz), 1.73–1.57(6H, m), 1.31(6H, d, J=6Hz) | oil |
| 99 | KBr: 2924, 1510, 1240, 1115 | CDCl₃: 7.49–7.44(1H, m), 7.36–7.32(1H, m), 7.28–7.14(2H, m), 6.87(2H, d, J=9Hz), 6.83(2H, d, J=9Hz), 4.50–4.36(1H, m), 3.64(2H, s), 3.30(2H, t, J=7Hz), 2.79(3H, s), 2.70–2.60(2H, m), 2.50(2H, ddd, | oil |

TABLE 5-continued

| Example No. | I R (cm⁻¹) | NMR (ppm) (no mark: 300 MHz, *: 270 MHz) | melting point (° C.) |
|---|---|---|---|
| | | J=11, 11, 4Hz), 1.75–1.55(6H, m), 1.31(6H, d, J=6Hz) | |
| 100 | liquid film: 2937, 2229, 1510, 1238, 1115 | CDCl₃: 7.68–7.65(1H, m), 7.58–7.51(2H, m), 7.41(1H, dd, J=8, 8Hz), 6.88(2H, d, J=9Hz), 6.83(2H, d, J=9Hz), 4.50–4.36(1H, m), 3.53(2H, s), 3.29(2H, t, J=7Hz), 2.78(3H, s), 2.62–2.52(2H, m), 2.41(2H, ddd, J=11, 11, 3Hz), 1.74–1.56(6H, m), 1.31(6H, d, J=6Hz) | oil |
| 101 | liquid film: 2935, 2224, 1510, 1238, 1115 | CDCl₃*: 7.66–7.61(1H, m), 7.56–7.51(2H, m), 7.39–7.29(1H, m), 6.87(2H, d, J=9Hz), 6.83(2H, d, J=9Hz), 4.50–4.35(1H, m), 3.72(2H, s), 3.29(2H, t, J=7Hz), 2.78(3H, s), 2.66–2.45(4H, m), 1.75–1.55(6H, m), 1.31(6H, d, J=6Hz) | oil |
| 102 | liquid film: 1510, 1313, 1240, 1159, 1120 | CDCl₃*: 7.80(1H, d, J=8Hz), 7.61(1H, d, J=8Hz), 7.50(1H, dd, J=8, 8Hz), 7.31(1H, dd, J=8, 8Hz), 6.87(2H, d, J=9Hz), 6.83(2H, d, J=9Hz), 4.50–4.35(1H, m), 3.67(2H, s), 3.31(2H, t, J=7Hz), 2.79(3H, s), 2.64–2.52(2H, m), 2.47(2H, ddd, J=11, 11, 5Hz), 1.75–1.55(6H, m), 1.31(6H, d, J=6Hz) | oil |
| 103 | liquid film: 1510, 1493, 1466, 1240, 1117 | CDCl₃*: 7.37–7.31(1H, m), 7.27–7.18(1H, m), 6.96–6.78(6H, m), 4.50–4.35(1H, m), 3.81(3H, s), 3.58(2H, s), 3.30(2H, t, J=7Hz), 2.78(3H, s), 2.72–2.61(2H, m), 2.50–2.37(2H, m), 1.72–1.58(6H, m), 1.30(6H, d, J=6Hz) | oil |
| 104 | liquid film: 1527, 1510, 1350, 1240, 1115 | CDCl₃: 8.22(1H, dd, J=2, 2Hz), 8.13–8.08(1H, m), 7.69–7.64(1H, m), 7.47(1H, dd, J=8, 8Hz), 6.88(2H, d, J=9Hz), 6.83(2H, d, J=9Hz), 4.50–4.36(1H, m), 3.61(2H, s), 3.29(2H, t, J=7Hz), 2.78(3H, s), 2.60(2H, ddd, J=11, 4, 4Hz), 2.44(2H, ddd, J=11, 11, 4Hz), 1.74–1.56(6H, m), 1.31(6H, d, J=6Hz) | oil |
| 105 | KBr: 1527, 1510, 1367, 1240, 1115 | CDCl₃: 7.79(1H, dd, J=8, 1Hz), 7.59(1H, dd, J=8, 2Hz), 7.52(1H, ddd, J=8, 8, 1Hz), 7.38(1H, ddd, J=8, 8, 2Hz), 6.86(2H, d, J=9Hz), 6.83(2H, d, J=9Hz), 4.49–4.36(1H, m), 3.80(2H, s), 3.23(2H, t, J=7Hz), 2.77(3H, s), 2.56–2.45(2H, m), 2.44(2H, ddd, J=11, 11, 3Hz), 1.67(2H, t, J=7Hz), 1.65–1.50(4H, m), 1.31(6H, d, J=6Hz) | oil |
| 106 | KBr: 1714, 1510, 1277, 1244, 1113 | CDCl₃: 7.99(2H, d, J=8Hz), 7.40(2H, d, J=8Hz), 6.88(2H, d, J=9Hz), 6.82(2H, d, J=9Hz), 4.49–4.36(1H, m), 4.37(2H, q, J=7Hz), 3.57(2H, s), 3.29(2H, t, J=7Hz), 2.78(3H, s), 2.64–2.55(2H, m), 2.40(2H, ddd, J=11, 11, 3Hz), 1.74–1.48(6H, m), 1.39(3H, t, J=7Hz), 1.31(6H, d, J=6Hz) | 50.3–51.6 |
| 107 | liquid film: 1510, 1238, 1113, 957, 700 | CDCl₃*: 7.25–7.15(1H, m), 7.00–6.75(6H, m), 4.49–4.36(1H, m), 3.80(1H, br. s), 3.74(2H, s), 3.29(2H, t, J=7Hz), 2.78(3H, s), 2.74–2.58(2H, m), 2.50–2.37(2H, m), 1.80–1.48(6H, m), 1.30(6H, d, J=6Hz) | oil |
| 108 | liquid film: 1510, 1238, 1113, 957 | CDCl₃: 7.32–7.24(1H, m), 7.16–7.08(1H, m), 7.06(1H, dd, J=5, 1Hz), 6.87(2H, d, J=9Hz), 6.83(2H, d, J=9Hz), 4.49–4.37(1H, m), 3.88(1H, br. s), 3.55(2H, s), 3.29(2H, t, J=7Hz), 2.78(3H, s), 2.70–2.57(2H, m), 2.37(2H, ddd, J=11, 11, 4Hz), 1.70–1.48(6H, m), 1.31(6H, d, J=6Hz) | oil |

TABLE 5-continued

| Example No. | I R (cm$^{-1}$) | NMR (ppm) (no mark: 300 MHz, *: 270 MHz) | melting point (° C.) |
|---|---|---|---|
| 109 | KBr: 1510, 1244, 1115, 949, 835 | CDCl$_3$: 7.25(2H, d, J=8Hz), 7.20(2H, d, J=8Hz), 6.87(2H, d, J=9Hz), 6.82(2H, d, J=9Hz), 4.50–4.36(1H, m), 3.48(2H, s), 3.29(2H, t, J=7Hz), 2.77(3H, s), 2.66–2.56(2H, m), 2.48(3H, s), 2.37(2H, ddd, 11, 11, 4Hz), 1.73–1.57(6H, m), 1.30(6H, d, J=6Hz) | 66.2–68.0 |
| 110 | liquid film: 2937, 1724, 1510, 1240 | CDCl$_3$: 7.67(1H, d, J=8Hz), 7.44–7.37(2H, m), 7.32–7.25(1H, m), 6.85(2H, d, J=9Hz), 6.82(2H, d, J=9Hz), 4.48–4.35(1H, m), 3.87(3H, s), 3.75(2H, s), 3.28(2H, t, J=7Hz), 2.78(3H, s), 2.56–2.46(2H, m), 2.40(2H, ddd, J=11, 11, 3Hz), 1.70–1.50(4H, m), 1.67(2H, t, J=7Hz), 1.30(6H, d, J=6Hz) | oil |
| 111 | KBr: 1724, 1510, 1296, 1244, 1201, 1111 | CDCl$_3$: 8.00–7.90(2H, m), 7.57–7.52(1H, m), 7.39(1H, dd, J=8, 8Hz), 6.87(2H, d, J=9Hz), 6.83(2H, d, J=9Hz), 4.50–4.36(1H, m), 3.92(3H, s), 3.56(2H, s), 3.29(2H, t, J=Hz), 2.78(3H, s), 2.65–2.55(2H, m), 2.40(2H, ddd, J=11, 11, 4Hz), 1.72–1.55(6H, m), 1.31(6H, d, J=6Hz) | 53.8–54.7 |
| 112 | liquid film: 2937, 1510, 1240, 1113 | CDCl$_3$: 7.40–7.29(2H, m), 6.86(2H, d, J=9Hz), 6.83(2H, d, J=9Hz), 6.42–6.37(1H, m), 4.50–4.35(1H, m), 3.86(1H, br. s), 3.40(2H, s), 3.29(2H, t, J=7Hz), 2.77(3H, s), 2.71–2.58(2H, m), 2.36(2H, ddd, J=11, 11, 4Hz), 1.75–1.55(6H, m), 1.30(6H, d, J=6Hz) | oil |
| 113 | liquid film: 1714, 1510, 1277, 1240, 1103 | CDCl$_3$: 7.98(2H, d, J=8Hz), 7.39(2H, d, J=8Hz), 6.88(2H, d, J=9Hz), 6.82(2H, d, J=9Hz), 5.30–5.18(1H, m), 4.49–4.37(1H, m), 3.57(2H, s), 3.29(2H, t, J=7Hz), 2.78(3H, s), 2.63–2.54(2H, m), 2.40(2H, ddd, J=11, 11, 4Hz), 1.72–1.56(6H, m), 1.36(6H, d, J=6Hz), 1.31(6H, d, J=6Hz) | oil |
| 114 | liquid film: 1718, 1510, 1275, 1240, 1111 | CDCl$_3$: 7.99(2H, d, J=8Hz), 7.40(2H, d, J=8Hz), 6.88(2H, d, J=9Hz), 6.82(2H, d, J=9Hz), 4.49–4.37(1H, m), 4.27(2H, t, J=7Hz), 3.59(2H, s), 3.29(2H, t, J=7Hz), 2.77(3H, s), 2.66–2.57(2H, m), 2.42(2H, ddd, J=11, 10, 4Hz), 1.85–1.58(8H, m), 1.31(6H, d, J=6Hz), 1.03(3H, t, J=7Hz) | oil |
| 115 | liquid film: 2937, 1510, 1242, 1113, 754, 692 | CDCl$_3$*: 7.32–7.23(2H, m), 6.98–6.79(7H, m), 4.50–4.35(1H, m), 4.12(2H, t, J=6Hz), 3.98(1H, br. s), 3.29(2H, t, J=7Hz), 2.84(2H, t, J=6Hz), 2.80–2.70(2H, m), 2.78(3H, s), 2.54(2H, ddd, J=10, 10, 4Hz), 1.77–1.60(6H, m), 1.31(6H, d, J=6Hz) | oil |
| 116 | liquid film: 2937, 1508, 1242, 1209, 1113, 829 | CDCl$_3$*: 7.01–6.78(8H, m), 4.50–4.35(1H, m), 4.07(2H, t, J=6Hz), 3.29(2H, t, J=6Hz), 2.82(2H, t, J=6Hz), 2.80–2.67(2H, m), 2.78(3H, s), 2.52(2H, ddd, J=10, 10, 4Hz), 1.77–1.57(6H, m), 1.31(6H, d, J=6Hz) | oil |
| 117 | liquid film: 2937, 1510, 1238, 1115 | CDCl$_3$: 7.32–7.13(5H, m), 6.88(2H, d, J=9Hz), 6.83(2H, d, J=9Hz), 4.50–4.36(1H, m), 3.29(2H, t, J=6Hz), 2.80–2.60(4H, m), 2.77(3H, s), 2.52–2.36(4H, m), 1.95–1.65(8H, m), 1.31(6H, d, J=6Hz) | oil |
| 118 | liquid film: 1510, 1240, 1115, 756, 702 | CDCl$_3$: 7.63–7.25(9H, m), 6.86(2H, d, J=9Hz), 6.82(2H, d, J=9Hz), 4.50–4.35(1H, m), 3.80(1H, br. s), 3.59(2H, s), 3.29(2H, t, J=7Hz), | oil |

TABLE 5-continued

| Example No. | I R (cm⁻¹) | NMR (ppm) (no mark: 300 MHz, *: 270 MHz) | melting point (° C.) |
|---|---|---|---|
| 119 | liquid film: 2935, 1510, 1240, 752, 702 | 2.78(3H, s), 2.70–2.60(2H, m), 2.42(2H, ddd, J=11, 11, 4Hz), 1.75–1.50(6H, m), 1.30(6H, d, J=6Hz) CDCl₃*: 7.58–7.50(1H, m), 7.35–7.20(8H, m), 6.83(2H, d, J=9Hz), 6.82(2H, d, J=9Hz), 4.50–4.35(1H, m), 3.62(1H, br. s), 3.42(2H, s), 3.27(2H, t, J=7Hz), 2.77(3H, s), 2.57–2.45(2H, m), 2.27(2H, ddd, J=11, 11, 4Hz), 1.70–1.50(6H, m), 1.30(6H, d, J=6Hz) | oil |
| 120-1 | — | CDCl₃: 7.55–7.46(2H, m), 7.38(1H, d, J=9Hz), 6.94(2H, d, J=9Hz), 6.84(2H, d, J=9Hz), 5.08(1H, br. s), 4.60–4.38(2H, m), 3.60–3.20(5H, m), 2.77(3H, s), 1.90–1.50(6H, m), 1.31(6H, d, J=6Hz) | — |
| 120-2 | KBr: 2935, 1510, 1369, 1238, 1115 | CDCl₃: 7.55(1H, dd, J=8, 8Hz), 7.38(1H, d, J=8Hz), 7.32–7.26(1H, m), 6.88(2H, d, J=9Hz), 6.82(2H, d, J=9Hz), 4.50–4.36(1H, m), 4.03(1H, br. s), 3.63(2H, s), 3.29(2H, t, J=7Hz), 2.77(3H, s), 2.67–2.57(2H, m), 2.47(2H, ddd, J=11, 11, 3Hz), 1.75–1.55(6H, m), 1.31(6H, d, J=6Hz) | 100.2–101.4 |
| 121-1 | — | CDCl₃: 6.91(2H, d, J=9Hz), 6.84(2H, d, J=9Hz), 3.99(2H, q, J=7Hz), 3.29(2H, t, J=7Hz), 3.01(2H, ddd, J=12, 11, 3Hz), 2.85(2H, ddd, J=12, 4, 4Hz), 2.78(3H, s), 1.74–1.48(6H, m), 1.39(3H, t, J=7Hz) | — |
| 121-2 | KBr: 1512, 1329, 1244, 1165, 1120 | CDCl₃*: 7.56(2H, d, J=8Hz), 7.44(2H, d, J=8Hz), 6.90(2H, d, J=9Hz), 6.83(2H, d, J=9Hz), 3.98(2H, q, J=7Hz), 3.56(2H, s), 3.29(2H, t, J=6Hz), 2.77(3H, s), 2.67–2.51(2H, m), 2.48–2.32(2H, m), 1.76–1.52(6H, m), 1.39(3H, t, J=7Hz) | 83.5–84.0 |
| 122-1 | — | CDCl₃*: 7.35–7.18(6H, m), 6.90–6.83(1H, m), 6.70–6.60(2H, m), 5.20(1H, s), 4.61–4.48(1H, m), 3.47(2H, s), 3.25(3H, s), 2.60–2.32(4H, m), 2.21(2H, s), 1.71–1.30(4H, m), 1.36(6H, d, J=5Hz) | — |
| 122-2 | — | CDCl₃: 7.35–7.21(5H, m), 7.11(1H, dd, J=9, 9Hz), 6.40–6.35(1H, m), 6.33–6.28(2H, m), 4.59–4.47(1H, m), 3.52(2H, s), 3.47–3.39(2H, m), 2.87(3H, s), 2.67–2.58(2H, m), 2.35(1H, ddd, J=11, 11, 4Hz), 1.75–1.59(6H, m), 1.33(6H, d, J=6Hz) | — |
| 122-3 | — | CDCl₃: 7.13(1H, dd, J=8, 8Hz), 6.42–6.38(1H, m), 6.34–6.29(2H, m), 4.59–4.47(1H, m), 3.49–3.40(2H, m), 3.02–2.80(4H, m), 2.88(3H, s), 1.76–1.53(6H, m), 1.33(6H, d, J=6Hz) | — |
| 122-4 | liquid film: 1722, 1610, 1500, 1281, 1115 | CDCl₃: 7.99(2H, d, J=8Hz), 7.40(2H, d, J=8Hz), 7.12(1H, dd, J=9, 9Hz), 6.41–6.29(3H, m), 4.59–4.47(1H, m), 3.91(3H, s), 3.56(2H, s), 3.43(2H, t, J=7Hz), 2.87(3H, s), 2.65–2.55(2H, m), 2.37(2H, ddd, J=11, 11, 4Hz), 1.77–1.55(6H, m), 1.33(6H, d, J=6Hz) | oil |
| 123-1 | — | CDCl₃*: 7.34–7.18(6H, m), 7.11–7.04(1H, m), 6.97–6.88(2H, m), 5.34(1H, s), 4.65–4.51(1H, m), 3.47(2H, s), 3.47(2H, s), 3.16(3H, s), 2.58–2.45(2H, m), 2.39(2H, ddd, J=11, 11, 3Hz), 2.16(1H, d, J=16Hz), 2.07(1H, d, J=16Hz), 1.73–1.25(4H, m), 1.32(3H, d, J=6Hz), 1.30(3H, d, J=6Hz) | — |

TABLE 5-continued

| Example No. | I R (cm$^{-1}$) | NMR (ppm) (no mark: 300 MHz, *: 270 MHz) | melting point (° C.) |
|---|---|---|---|
| 123-2 | — | CDCl$_3$: 7.34–7.19(5H, m), 7.08–7.00(2H, m), 6.90–6.83(2H, m), 4.66–4.54(1H, m), 3.51(2H, s), 3.19(2H, t, J=6Hz), 2.67(3H, s), 2.60–2.51(2H, m), 2.41(2H, ddd, J=11, 11, 3Hz), 1.72–1.48(6H, m), 1.36(6H, d, J=6Hz) | — |
| 123-3 | — | CDCl$_3$*: 7.09–7.00(2H, m), 6.92–6.83(2H, m), 4.68–4.53(1H, m), 3.20(2H, t, J=6Hz), 3.04(2H, ddd, J=12, 12, 3Hz), 2.85–2.76(2H, m), 2.68(3H, s), 1.74–1.40(6H, m), 1.36(6H, d, J=6Hz) | — |
| 123-4 | liquid film: 1722, 1497, 1279, 1115 | CDCl$_3$*: 7.97(2H, d, J=8Hz), 7.40(2H, d, J=8Hz), 7.08–6.99(2H, m), 6.91–6.82(2H, m), 4.67–4.52(1H, m), 3.90(3H, s), 3.55(2H, s), 3.19(2H, t, J=6Hz), 2.67(3H, s), 2.58–2.37(4H, m), 1.72–1.46(6H, m), 1.36(6H, d, J=6Hz) | oil |
| 124-1 | — | CDCl$_3$*: 7.72(1H, br. s), 7.38–7.21(7H, m), 6.84(2H, d, J=9Hz), 4.55–4.42(1H, m), 3.93(1H, br. s), 3.53(2H, s), 2.63–2.40(4H, s), 2.47(2H, s), 1.82–1.60(4H, m), 1.31(6H, d, J=6Hz) | — |
| 124-2 | — | CDCl$_3$: 7.35–7.22(5H, m), 6.78(2H, d, J=9Hz), 6.63(2H, d, J=9Hz), 4.45–4.32(1H, m), 3.52(2H, s), 3.27(2H, t, J=6Hz), 2.68–2.58(2H, m), 2.42–2.30(2H, m), 1.78(2H, t, J=6Hz), 1.74–1.60(4H, m), 1.29(6H, d, J=6Hz) | — |
| 124-3 | — | CDCl$_3$: 6.79(2H, d, J=9Hz), 6.63(2H, d, J=9Hz), 4.45–4.32(1H, m), 3.47(1H, s), 3.28(2H, t, J=6Hz), 2.97(2H, ddd, J=12, 12, 3Hz), 2.84(2H, ddd, J=12, 4, 4Hz), 1.79(2H, t, J=6Hz), 1.70–1.48(4H, m), 1.29(6H, d, J=6Hz) | — |
| 124-4 | KBr: 3277, 1726, 1512, 1277, 1113 | CDCl$_3$*: 7.98(2H, d, J=8Hz), 7.40(2H, d, J=8Hz), 6.78(2H, d, J=9Hz), 6.63(2H, d, J=9Hz), 4.45–4.30(1H, m), 3.91(3H, s), 3.57(2H, s), 3.28(2H, t, J=6Hz), 2.65–2.55(2H, m), 2.44–2.32(2H, m), 1.78(2H, t, J=6Hz), 1.72–1.63(4H, m), 1.29(6H, d, J=6Hz) | 134.8–135.9 |
| 125 | KBr: 1510, 1333, 1232, 1159, 1122, 1099, 1066 | CDCl$_3$*: 7.57(2H, d, J=8Hz), 7.45(2H, d, J=8Hz), 6.79(2H, d, J=9Hz), 6.63(2H, d, J=9Hz), 4.44–4.31(1H, m), 3.57(2H, s), 3.28(2H, t, J=6Hz), 2.67–2.55(2H, m), 2.45–2.32(2H, m), 1.79(2H, t, J=6Hz), 1.72–1.63(4H, m), 1.29(6H, d, J=6Hz) | 152.3–153.1 |
| 126-1 | — | CDCl$_3$: 7.45–7.15(10H, m), 6.94(2H, d, J=8Hz), 6.80(2H, d, J=8Hz), 4.66(1H, d, J=12Hz), 4.58–4.46(1H, m), 4.38(1H, d, J=12Hz), 4.28(1H, s), 3.81(1H, s), 3.48(2H, s), 3.28(3H, s), 2.68–2.58(2H, m), 2.46–2.27(2H, m), 1.96–1.87(1H, m), 1.57–1.23(9H, m) | — |
| 126-2 | — | CDCl$_3$: 7.12(2H, d, J=9Hz), 6.90(2H, d, J=9Hz), 4.62–4.47(1H, m), 3.77(1H, s), 3.27(3H, s), 3.00(1H, ddd, J=12, 12, 3Hz), 2.89(1H, ddd, J=12, 12, 3Hz), 2.82–2.72(2H, m), 1.82–1.73(1H, m), 1.50–1.15(3H, m), 1.36(6H, d, J=6Hz) | — |
| 126-3 | — | CDCl$_3$: 6.87(2H, d, J=9Hz), 6.82(2H, d, J=9Hz), 4.49–4.36(1H, m), 3.60(1H, dd, J=10, 4Hz), 3.31(1H, dd, J=14, 10Hz), 3.11(1H, dd, J=14, 4Hz), 3.05–2.80(4H, m), 2.81(3H, | — |

| Example No. | I R (cm⁻¹) | NMR (ppm) (no mark: 300 MHz, *: 270 MHz) | melting point (° C.) |
|---|---|---|---|
| | | s), 1.85–1.76(1H, m), 1.66–1.40(3H, m), 1.30(6H, d, J =6Hz) | |
| 126-4 | KBr: 1514, 1331, 1246, 1159, 1120, 1066 | CDCl₃: 7.57(2H, d, J=8Hz), 7.45(2H, d, J=8Hz), 6.87(2H, d, J=9Hz), 6.82(2H, d, J=9Hz), 4.49–4.37(1H, m), 3.60(1H, dd, J=10, 3Hz), 3.57(2H, s), 3.32(1H, dd, J=13, 10Hz), 3.27(1H, s), 3.08(1H, dd, J=13, 3Hz), 2.81(3H, s), 2.73–2.62(2H, m), 2.46–2.32(2H, m), 2.26(1H, br. s), 1.90–1.80(1H, m), 1.72(1H, ddd, J=13, 13, 5Hz), 1.62–1.50(2H, m), 1.30(6H, d, J=6Hz) | 109.0–110.1 |
| 127-1 | — | CDCl₃: 7.03(2H, d, J=9Hz), 6.90(2H, d, J=9Hz), 4.62–4.50(1H, m), 3.90–3.65(2H, m), 3.24(3H, s), 3.25–3.10(2H, m), 2.16(2H, s), 1.68–1.58(2H, m), 1.43(9H, s), 1.37(6H, d, J=6Hz), 1.35–1.18(2H, m) | — |
| 127-2 | — | CDCl₃: 7.05(2H, d, J=9Hz), 6.89(2H, d, J=9Hz), 4.61–4.49(1H, m), 3.90–3.65(2H, m), 3.22(3H, s), 3.10–2.87(2H, m), 3.04(3H, s), 2.35(2H, s), 1.80–1.64(4H, m), 1.44(9H, s), 1.36(6H, d, J=6Hz) | — |
| 127-3 | — | CDCl₃: 6.83(2H, d, J=9Hz), 6.69(2H, d, J=9Hz), 4.45–4.32(1H, m), 3.38–3.27(2H, m), 3.19(3H, s), 2.96–2.72(4H, m), 2.84(3H, s), 1.82–1.62(4H, m), 1.59–1.38(2H, m), 1.30(6H, d, J=6Hz) | — |
| 127-4 | liquid film: 1510, 1325, 1240, 1161, 1122, 1066 | CDCl₃*: 7.56(2H, d, J=8Hz), 7.44(2H, d, J=8Hz), 6.82(2H, d, J=9Hz), 6.68(2H, d, J=9Hz), 4.45–4.31(1H, m), 3.53(2H, s), 3.35–3.27(2H, m), 3.17(3H, s), 2.83(3H, s), 2.60–2.48(2H, m), 2.36–2.22(2H, m), 1.86–1.48(6H, m), 1.30(6H, d, J=6Hz) | oil |
| 128 | liquid film: 1722, 1510, 1279, 1238, 1111 | CDCl₃: 7.98(2H, d, J=8Hz), 7.40(2H, d, J=8Hz), 6.83(2H, d, J=9Hz), 6.68(2H, d, J=9Hz), 4.44–4.32(1H, m), 3.91(3H, s), 3.54(2H, s), 3.35–3.27(2H, m), 3.17(3H, s), 2.83(3H, s), 2.58–2.50(2H, m), 2.35–2.24(2H, m), 1.85–1.49(6H, m), 1.30(6H, d, J=6Hz) | oil |
| 129-1 | liquid film: 1510, 1369, 1240, 1113 | CDCl₃: 7.37–7.21(5H, m), 6.84(2H, d, J=9Hz), 6.80(2H, d, J=9Hz), 4.45–4.32(1H, m), 3.53(2H, s), 3.17(2H, s), 2.92(3H, s), 2.74–2.65(2H, m), 2.36(2H, ddd, J=11, 11, 4Hz), 1.98(1H, s), 1.78–1.60(4H, m), 1.29(6H, d, J=6Hz) | oil |
| 129-2 | — | CDCl₃: 6.86(2H, d, J=9Hz), 6.81(2H, d, J=9Hz), 4.46–4.32(1H, m), 3.17(2H, s), 3.06–2.85(4H, m), 2.94(3H, s), 1.70–1.52(4H, m), 1.29(6H, d, J=6Hz) | — |
| 129-3 | liquid film: 1510, 1325, 1240, 1161, 1122, 1066 | CDCl₃*: 7.57(2H, d, J=8Hz), 7.45(2H, d, J=8Hz), 6.85(2H, d, J=10Hz), 6.80(2H, d, J=10Hz), 4.45–4.31(1H, m), 3.58(2H, s), 3.18(2H, s), 2.93(3H, s), 2.71–2.62(2H, m), 2.39(2H, ddd, J=11, 11, 4Hz), 2.00(1H, s), 1.78–1.60(4H, m), 1.29(6H, d, J=6Hz) | oil |
| 130 | liquid film: 1722, 1510. 1281, 1240, 1113 | CDCl₃: 7.99(2H, d, J=8Hz), 7.41(2H, d, J=8Hz), 6.85(2H, d, J=9Hz), 6.80(2H, d, J=9Hz), 4.45–4.33(1H, m), 3.91(3H, s), 3.58(2H, s), 3.18(2H, s), 2.93(3H, s), 2.72–2.62(2H, m), 2.39(2H, dd, J=11, 11, 4Hz), 1.77–1.60(4H, m), 1.29(6H, d, J=6Hz) | oil |
| 131 | KBr: 1510, 1242, 1122, | CDCl₃*: 7.41(4H, d, J=7Hz), 7.30–7.12(6H, m), 6.83(2H, d, J=9Hz), | 88.6–89.4 |

TABLE 5-continued

| Example No. | I R (cm⁻¹) | NMR (ppm) (no mark: 300 MHz, *: 270 MHz) | melting point (° C.) |
|---|---|---|---|
|  | 708 | 6.81(2H, d, J=9Hz), 4.48–4.34(1H, m), 4.27(1H, s), 3.59(1H, br. s), 3.29(2H, t, J=7Hz), 2.77(3H, s), 2.65–2.50(2H, m), 2.37–2.22(2H, m), 1.75–1.50(6H, m), 1.30(6H, d, J=6Hz) |  |
| 132 | KBr: 1512, 1504, 1238, 1223, 1113, 841 | CDCl₃*: 7.33(4H, dd, J=9, 5Hz), 6.96(4H, dd, J=9, 9Hz), 6.85(2H, d, J=9Hz), 6.81(2H, d, J=9Hz), 4.48–4.34(1H, m), 4.26(1H, s), 3.80(1H, br. s), 3.28(2H, t, J=7Hz), 2.77(3H, s), 2.58–2.48(2H, m), 2.33–2.20(2H, m), 1.73–1.50(6H, m), 1.30(6H, d, J=6Hz) | oil |
| 133 | KBr: 1514, 1248, 816, 704 | CDCl₃: 7.44–7.38(4H, m), 7.30–7.22(4H, m), 7.19–7.13(2H, m), 6.86(2H, d, J=9Hz), 6.81(2H, d, J=9Hz), 4.27(1H, s), 3.97(2H, q, J=7Hz), 3.68(1H, br. s), 3.28(2H, t, J=7Hz), 2.76(3H, s), 2.63–2.52(2H, m), 2.37–2.21(2H, m), 1.73–1.55(6H, m), 1.38(3H, t, J=7Hz) | 94.3–95.8 |
| 134 | liquid film: 1610, 1498, 1236, 1117, 706 | CDCl₃: 7.44–7.36(4H, m), 7.30–7.23(4H, m), 7.20–7.08(3H, m), 6.40–6.25(3H, m), 4.58–4.46(1H, m), 4.26(1H, s), 3.43(2H, t, J=8Hz), 2.86(3H, s), 2.66–2.53(2H, m), 2.25(2H, ddd, J=11, 11, 2Hz), 1.80–1.52(6H, m), 1.32(6H, d, J=6Hz) | oil |
| 135 | liquid film: 1495, 1452, 1275, 1232, 744, 706 | CDCl₃*: 7.43–7.35(4H, m), 7.28–7.10(6H, m), 7.05–6.95(2H, m), 6.88–6.79(2H, m), 4.63–4.50(1H, m), 4.26(1H, s), 3.18(2H, t, J=6Hz), 2.66(3H, s), 2.55–2.44(2H, m), 2.33(2H, ddd, J=11, 11, 3Hz), 1.74–1.48(6H, m), 1.34(6H, d, J=6Hz) | oil |
| 136 | KBr: 1512, 1234, 708 | CDCl₃*: 7.44–7.36(4H, m), 7.30–7.13(6H, m), 6.77(2H, d, J=9Hz), 6.60(2H, d, J=9Hz), 4.43–4.30(1H, m), 4.27(1H, s), 3.26(2H, t, J=6Hz), 2.65–2.53(2H, m), 2.33–2.20(2H, m), 1.78–1.50(6H, m), 1.28(6H, d, J=6Hz) | 170.0–171.2 |
| 137 | liquid film: 1510, 1238, 1076, 706 | CDCl₃: 7.43–7.37(4H, m), 7.29–7.22(4H, m), 7.19–7.12(2H, m), 6.82(2H, d, J=9Hz), 6.67(2H, d, J=9Hz), 4.44–4.32(1H, m), 4.22(1H, s), 3.34–3.25(2H, m), 3.14(3H, s), 2.83(3H, s), 2.58–2.47(2H, m), 2.25–2.12(2H, m), 1.76–1.49(6H, m), 1.30(6H, d, J=6Hz) | oil |
| 138 | KBr: 1510, 1240, 1113, 706 | CDCl₃: 7.45–7.38(4H, m), 7.30–7.22(4H, m), 7.20–7.13(2H, m), 6.84(2H, d, J=10Hz), 6.80(2H, d, J=10Hz), 4.45–4.26(1H, m), 4.28(1H, s), 3.18(2H, s), 2.92(3H, s), 2.72–2.63(2H, m), 2.32–2.20(2H, m), 1.80–1.53(6H, m), 1.29(6H, d, J=6Hz) | amorphous |
| 139 | liquid film: 3386, 2958, 2935, 2872, 2814, 1512, 1242, 812, 741 | CDCl₃: 7.35–7.20(5H, m), 6.94(2H, d, J=9Hz), 6.83(2H, d, J=9Hz), 3.92(2H, t, J=7Hz), 3.52(2H, s), 3.24(2H, t, J=6Hz), 3.10(2H, q, J=7Hz), 2.66–2.55(2H, m), 2.40(2H, ddd, J=11, 11, 3Hz), 1.79–1.42(10H, m), 0.97(3H, t, J=7Hz), 0.97(3H, t, J=7Hz) | oil |
| 140 | liquid film: 2233, 1510, 1240, 1113 | CDCl₃: 7.57(1H, dd, J=8, 8Hz), 7.42(1H, dd, J=8, 2Hz), 7.32(1H, dd, J=9, 2Hz), 6.88(2H, d, J=9Hz), 6.83(2H, d, J=9Hz), 4.50–4.35(1H, m), 3.63(2H, s), 3.28(2H, t, J=7Hz), 2.77(3H, s), 2.65–2.55(2H, m), 2.48(2H, ddd, J=11, 11, 3Hz), 1.77–1.56(6H, m), 1.31(6H, d, J=6Hz) | oil |

TABLE 5-continued

| Example No. | I R (cm$^{-1}$) | NMR (ppm) (no mark: 300 MHz, *: 270 MHz) | melting point (° C.) |
|---|---|---|---|
| 141 | KBr: 1672, 1605, 1512, 1365, 1271, 1238, 1113 | CDCl$_3$: 7.91(2H, d, J=8Hz), 7.43(2H, d, J=8Hz), 6.88(2H, d, J=9Hz), 6.82(2H, d, J=9Hz), 4.50–4.36(1H, m), 3.98(1H, br. s), 3.57(2H, s), 3.29(2H, t, J=7Hz), 2.78(3H, s), 2.60(3H, s), 2.67–2.53(2H, m), 2.41(2H, ddd, J=11, 11, 3Hz), 1.76–1.50(6H, m), 1.31(6H, d, J=6Hz) | 82.8–84.1 |
| 142-1 | — | CDCl$_3$: 7.09(2H, d, J=8Hz), 6.86(2H, d, J=9Hz), 6.81(2H, d, J=9Hz), 6.64(2H, d, J=8Hz), 4.48–4.36(1H, m), 3.61(2H, br. s), 3.41(2H, s), 3.29(2H, t, J=7Hz), 2.78(3H, s), 2.65–2.55(2H, m), 2.33(2H, ddd, J=11, 11, 4Hz), 1.71–1.55(6H, m), 1.30(6H, d, J=6Hz) | — |
| 142-2 | KBr: 1720, 1512, 1242, 1157 | CDCl$_3$: 7.86(1H, br. s), 7.51(2H, d, J=9Hz), 7.36(2H, d, J=9Hz), 6.88(2H, d, J=9Hz), 6.82(2H, d, J=9Hz), 4.49–4.37(1H, m), 3.52(2H, s), 3.29(2H, t, J=7Hz), 2.77(3H, s), 2.66–2.53(2H, m), 2.39(2H, ddd, J=11, 11, 3Hz), 1.74–1.56(6H, m), 1.31(6H, d, J=6Hz) | 38.7–40.1 |
| 143 | KBr: 1599, 1554, 1510, 1406, 1240 | CD$_3$OD: 7.91(2H, d, J=8Hz), 7.33(2H, d, J=8Hz), 6.80(2H, d, J=9Hz), 6.76(2H, d, J=9Hz), 4.47–4.33(1H, m), 3.61(2H, s), 3.40–3.28(2H, m), 2.79(3H, s), 2.70–2.43(4H, m), 1.70–1.56(6H, m), 1.25(6H, d, J=6Hz) | amorphous |
| 146 | KBr: 3355, 2948, 2364, 1512, 1252 | CD$_3$OD: 7.55–7.47(7H, m), 7.09(2H, d, J=9Hz), 4.31(2H, s), 4.01(2H, t, J=6Hz), 3.73–3.68(2H, m), 3.31–3.24(4H, m), 3.25(3H, s), 1.85–1.44(10H, m), 0.98(3H, t, J=7Hz) | 132.8 |
| 162 | KBr: 3435, 2527, 1512, 1495, 1257, 1038 | CD$_3$OD*: 7.61(2H, d, J=9Hz), 7.19–7.00(4H, m), 6.93(1H, d, J=8Hz), 6.04(2H, s), 4.25(2H, s), 4.06(2H, t, J=6Hz), 3.75(2H, t, J=8Hz), 3.50–3.02(4H, m), 3.30(3H, s), 2.13–1.44(10H, m), 1.01(3H, t, J=7Hz) | 211 dec |
| 176 | KBr: 3450, 2956, 2935, 1514, 1259, 837 | DMSO-d$_6$*: 7.84–7.45(2H, m), 7.30(2H, dd, J=9, 6Hz), 7.16(2H, dd, J=9, 9Hz), 7.15–6.98(2H, m), 3.98(2H, t, J=6Hz), 3.57–2.90(13H, m), 2.03–1.29(10H, m), 0.92(3H, t, J=7Hz) | 207 dec |
| 177 | KBr: 3367, 2937, 1514, 1255, 1226, 839 | CD$_3$OD*: 7.69–7.56(4H, m), 7.25(2H, dd, J=9, 9Hz), 7.13(2H, d, J=9Hz), 4.35(2H, s), 4.06(2H, t, J=6Hz), 3.75(2H, t, J=8Hz), 3.38–3.22(4H, m), 3.30(3H, s), 2.16–1.44(10H, m), 1.01(3H, t, J=7Hz) | 209 dec |
| 183 | KBr: 3290, 2567, 1512, 1470, 1255, 839 | CD$_3$OD*: 7.63(2H, d, J=9Hz), 7.49–7.33(1H, m), 7.13(2H, d, J=9Hz), 7.06–6.89(2H, m), 4.05(2H, t, J=6Hz), 3.77(2H, t, J=8Hz), 3.59–3.45(2H, m), 3.45–3.20(4H, m), 3.30(3H, s), 3.19–3.03(2H, m), 2.14–1.42(10H, m), 1.00(3H, t, J=7Hz) | 209 dec |
| 196 | KBr: 3261, 2960, 2575, 1512, 1255, 1225, 835 | CD$_3$OD*: 7.59(2H, d, J=9Hz), 7.31(2H, dd, J=9, 5Hz), 7.12(2H, d, J=9Hz), 7.06(2H, dd, J=9, 9Hz), 4.04(2H, t, J=6Hz), 3.95–3.85(1H, m), 3.69–3.46(3H, m), 3.37–3.19(4H, m), 3.28(3H, s), 3.16–3.03(3H, m), 2.08–1.43(8H, m), 0.99(3H, t, J=7Hz) | 191.2–198.7 |
| 198 | KBr: 3412, 2958, 2468, 1512, 1261, 1221, 835 | CD$_3$OD*: 7.59(2H, d, J=9Hz), 7.47(2H, dd, J=9, 5Hz), 7.12(2H, dd, J=9, 9Hz), 7.12(2H, d, J=9Hz), 5.14(1H, t, J=7Hz), 4.04(2H, t, J=6Hz), 3.75(2H, t, J=8Hz), 3.72–3.46(2H, m), 3.41–3.26(2H, m), | 174.9–184.5 |

TABLE 5-continued

| Example No. | I R (cm$^{-1}$) | NMR (ppm) (no mark: 300 MHz, *: 270 MHz) | melting point (° C.) |
|---|---|---|---|
| | | 3.29(3H, s), 3.25(2H, d, J=7Hz), 2.04–1.44(10H, m), 0.99(3H, t, J=7Hz) | |
| 201 | KBr: 3431, 2567, 2492, 1514, 1470, 1255, 1070 | CD$_3$OD: 6.59(2H, d, J=9Hz), 7.55–7.44(5H, m), 7.11(2H, d, J=9Hz), 4.30(2H, s), 4.02(2H, t, J=6Hz), 3.68–3.55(2H, m), 3.36–3.04(4H, m), 3.27(3H, s), 3.10(3H, s), 2.16–1.42(10H, m), 0.98(3H, t, J=7Hz) | 215 dec |
| 207 | KBr: 1583, 1514, 1385, 1365, 1252, 864 | CD$_3$OD*: 7.49(5H, s), 7.15(2H, d, J=9Hz), 6.94(2H, d, J=9Hz), 6.27(4H, s), 4.32(2H, s), 3.95(2H, t, J=7Hz), 3.58–3.45(2H, m), 3.37–3.22(4H, m), 3.02(3H, s), 1.90–1.60(8H, m), 1.55–1.40(2H, m), 0.97(3H, t, J=7Hz) | 68.0–70.0 |
| 210 | liquid film: 1583, 1516, 1456, 1356, 1246 | CDCl$_3$*: 7.47–7.37(5H, m), 6.86(2H, d, J=9Hz), 6.83(2H, d, J=9Hz), 6.34(2H, s), 4.17(2H, s), 3.90(2H, t, J=7Hz), 3.45–3.33(2H, m), 3.21(2H, s), 3.18–3.02(2H, m), 2.91(3H, s), 2.12–1.98(2H, m), 1.85–1.40(6H, m), 0.96(3H, t, J=7Hz) | oil |
| 220 | KBr: 1510, 1255, 1109, 1012, 955 | CD$_3$OD: 7.65(2H, d, J=8Hz), 7.57(2H, d, J=9Hz), 7.49(2H, d, J=8Hz), 7.08(2H, d, J=9Hz), 4.74–4.58(1H, m), 4.30(2H, s), 3.72(2H, t, s), 2.10–1.50(6H, m), 1.32(6H, d, J=6Hz) | 224.4–226.2 |
| 221 | KBr: 1510, 1325, 1257, 1169, 1130, 1068 | CD$_3$OD: 7.79(2H, d, J=9Hz), 7.77(2H, d, J=9Hz), 7.53(2H, d, J=9Hz), 7.08(2H, d, J=9Hz), 4.72–4.58(1H, m), 4.42(2H, s), 3.71(2H, t, J=8Hz), 3.35–3.23(4H, m), 3.26(3H, s), 2.10–1.50(6H, m), 1.32(6H, d, J=6Hz) | 241.2–242.6 |
| 226 | KBr: 2231, 1510, 1257, 1109, 953 | CD$_3$OD: 7.85(2H, d, J=8Hz), 7.76(2H, d, J=8Hz), 7.58(2H, d, J=9Hz), 7.08(2H, d, J=9Hz), 4.73–4.58(1H, m), 4.41(2H, s), 3.71(2H, t, J=8Hz), 3.50–3.10(4H, m), 3.26(3H, s), 2.10–1.50(6H, m), 1.32(6H, d, J=6Hz) | 220.8–222.2 |
| 233 | KBr: 1722, 1512, 1282, 1255, 1109 | CD$_3$OD: 8.11(2H, d, J=8Hz), 7.67(2H, d, J=8Hz), 7.52(2H, d, J=8Hz), 7.08(2H, d, J=9Hz), 4.72–4.48(1H, m), 4.40(2H, s), 3.92(3H, s), 3.80–3.63(2H, m), 3.50–3.40(4H, m), 3.26(3H, s), 2.10–1.50(6H, m), 1.31(6H, d, J=6Hz) | 218.5–219.2 |
| 236 | KBr: 1512, 1263, 1223, 1207, 1169 | CD$_3$OD: 7.68(2H, d, J=9Hz), 7.55(2H, d, J=9Hz), 7.42(2H, d, J=9Hz), 7.08(2H, d, J=9Hz), 4.73–4.58(1H, m), 4.36(2H, s), 3.72(2H, t, J=8Hz), 3.50–3.10(4H, m), 3.26(3H, s), 2.10–1.50(6H, m), 1.32(6H, d, J=6Hz) | 233.2–234.9 |
| 240 | KBr: 1608, 1510, 1489, 1255, 1120, 1109, 953, 881 | CD$_3$OD: 7.63–7.48(5H, m), 7.07(2H, d, J=9Hz), 4.74–4.58(1H, m), 4.38(2H, s), 3.72(2H, t, J=8Hz), 3.50–3.10(4H, m), 3.27(3H, s), 2.10–1.50(6H, m), 1.32(6H, d, J=6Hz) | 228.3–229.1 |
| 254 | KBr: 1512, 1255, 1184, 1109, 953, 839 | CD$_3$OD: 7.63(1H, dd, J=5, 1Hz), 7.58(2H, d, J=9Hz), 7.37(1H, dd, J=4, 1Hz), 7.14(1H, dd, J=5, 4Hz), 7.08(2H, d, J=9Hz), 4.74–4.58(1H, m), 4.58(2H, s), 3.72(2H, t, J=8Hz), 3.50–3.10(4H, m), 3.27(3H, s), 2.10–1.50(6H, m), 1.32(6H, d, J=6Hz) | 216.5–217.5 |
| 278 | KBR: 1510, 1456, 1255, 1109, 710 | CD$_3$OD: 7.77–7.71(4H, m), 7.62–7.36(8H, m), 7.08(2H, d, J=9Hz), 5.45(1H, s), 4.75–4.60(1H, m), 3.71(2H, t, J=8Hz), 3.38–3.04(4H, | 162.7 dec |

TABLE 5-continued

| Example No. | I R (cm⁻¹) | NMR (ppm) (no mark: 300 MHz, *: 270 MHz) | melting point (° C.) |
|---|---|---|---|
| | | m), 3.26(3H, s), 2.17–1.50(6H, m), 1.32(6H, d, J=6Hz) | |

Chemical structures of the compounds in Examples 1 to 289 are shown in Table 7. The abbreviations of the substituents used in the chemical structures in Table 7 respectively represent substituents shown in Table 6.

TABLE 6

| Abbreviation | Substituent |
|---|---|
| —Me | —$CH_3$ |
| —tBu | —$C(CH_3)_3$ |
| —Ac | —$COCH_3$ |
| —Boc | —$COOC(CH_3)_3$ |
| —Ph | 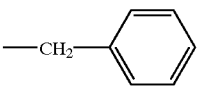 |

TABLE 6-continued

| Abbreviation | Substituent |
|---|---|
| —Bn | 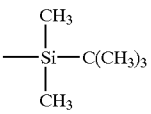 |
| —TBDMS | 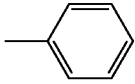 |

TABLE 7 (1)

Example 1 Step 1

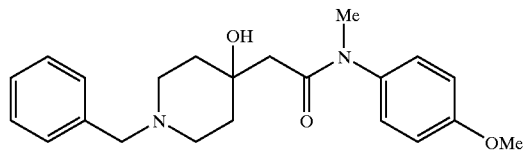

Example 1 Step 2

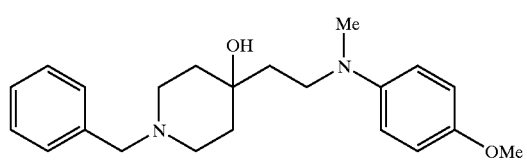

Example 2 Step 1

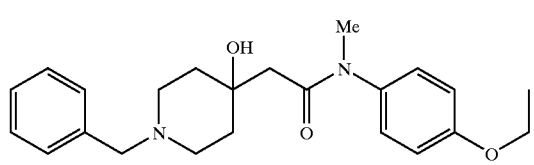

Example 2 Step 2

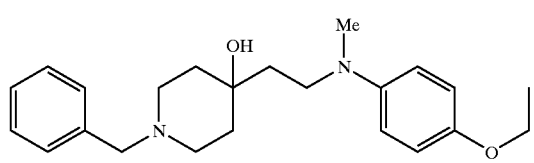

Example 3 Step 1

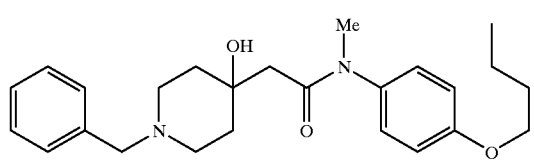

TABLE 7 (1)-continued
Example 3 Step 2
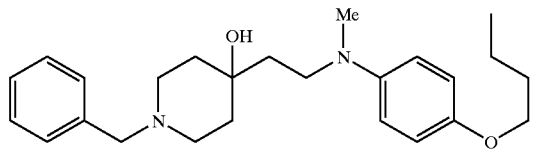
Example 4 Step 1
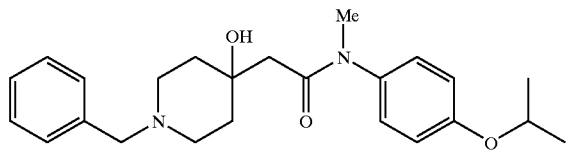
Example 4 Step 2
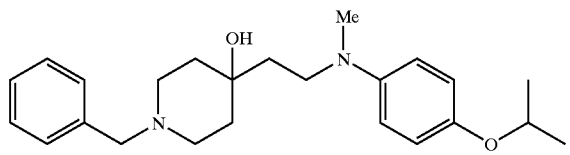
Example 5 Step 1
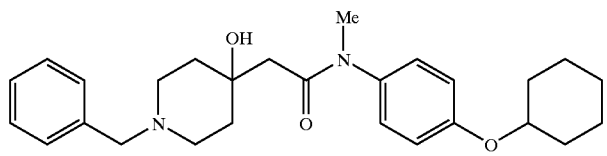
Example 5 Step 2
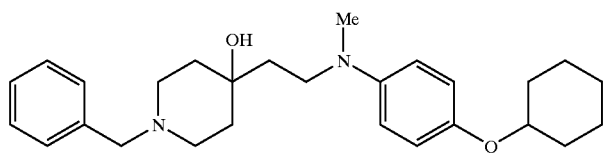
Example 6 Step 1
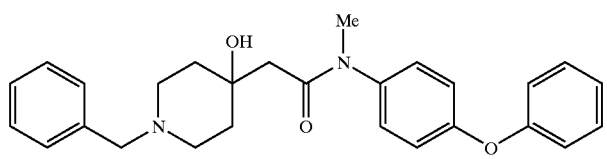
Example 6 Step 2
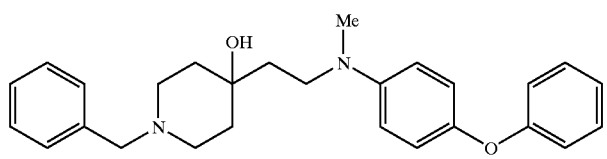
Example 7 Step 1
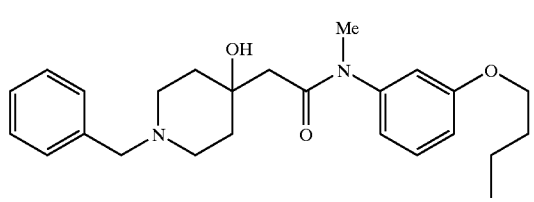
Example 7 Step 2
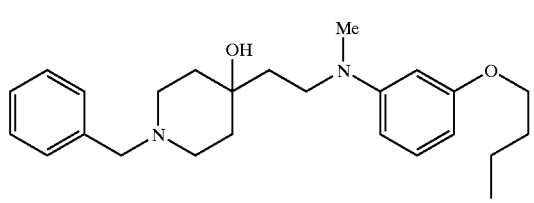

TABLE 7 (1)-continued
Example 8 Step 1
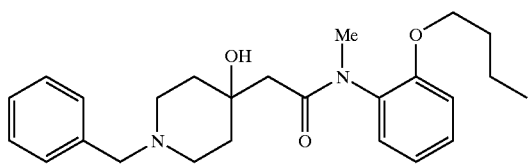
Example 8 Step 2
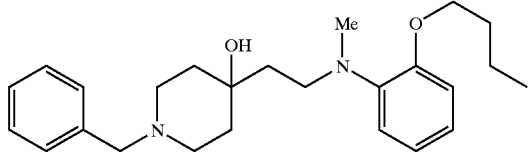
Example 9 Step 1
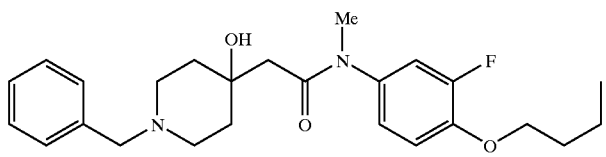
Example 9 Step 2
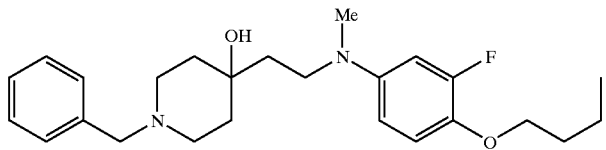
Example 10 Step 1
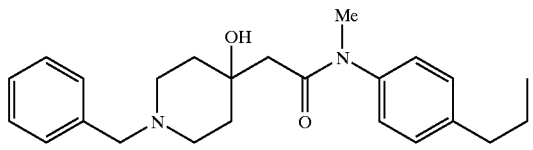
Example 10 Step 2
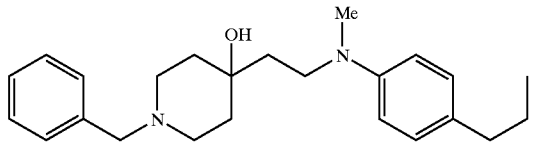
Example 11 Step 1
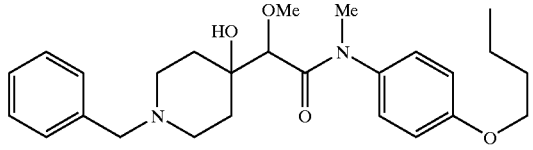
Example 11 Step 2
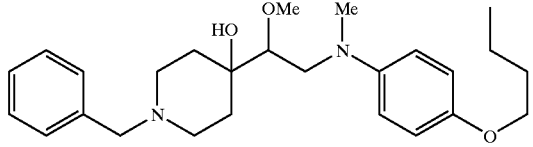
Example 12 Step 1
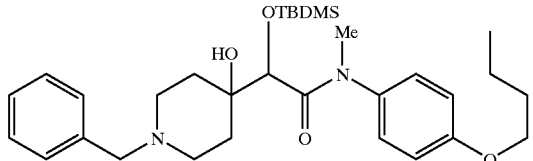

TABLE 7 (1)-continued
| Example 12 Step 2 | 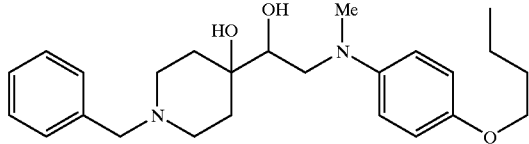 |
| Example 13 Step 1 | 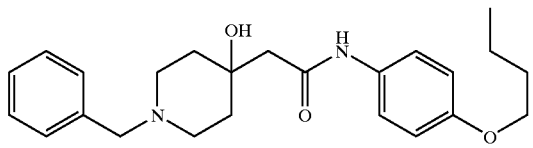 |
| Example 13 Step 2 | 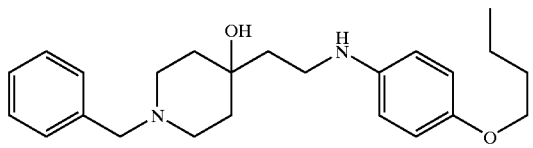 |
| Example 14 Step 1 | 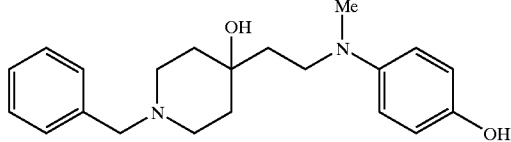 |
| Example 14 Step 2 | 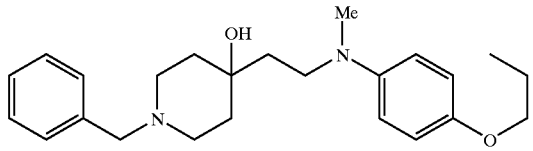 |
| Example 15 | 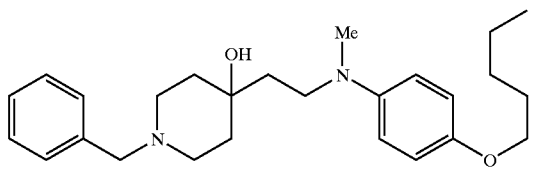 |
| Example 16 | 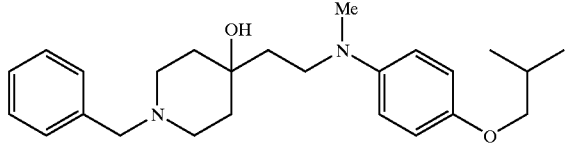 |
| Example 17 | 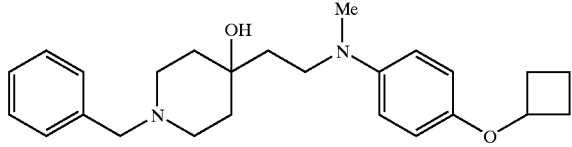 |
| Example 18 | 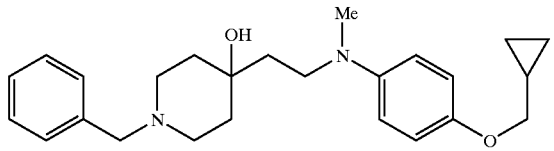 |

TABLE 7 (1)-continued
Example 19 Step 1
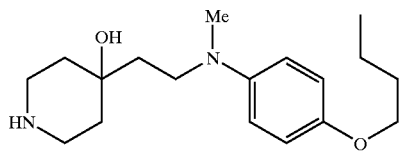
Example 19 Step 2
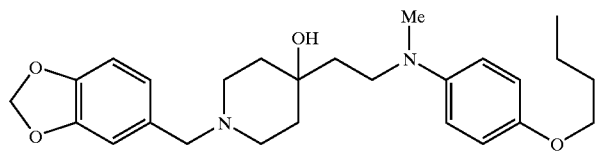
Example 20
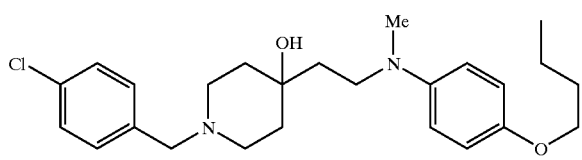
Example 21
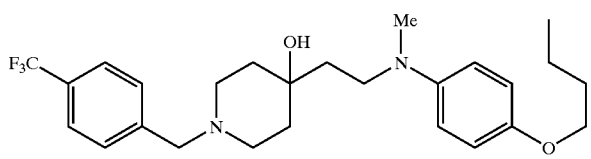
Example 22
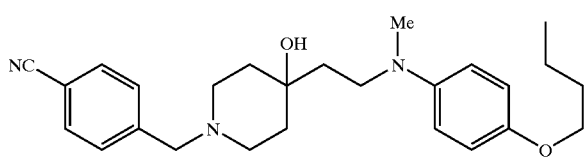
Example 23
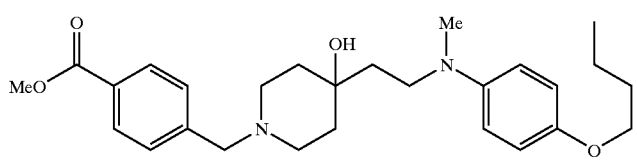
Example 24
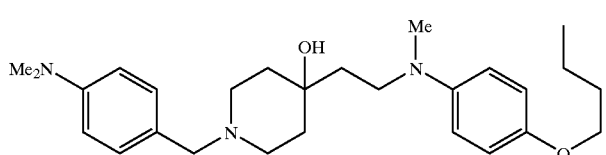
Example 25
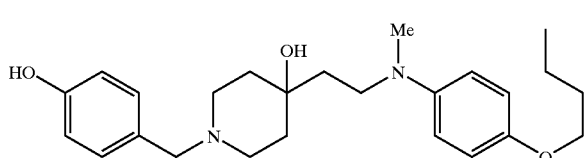
Example 26
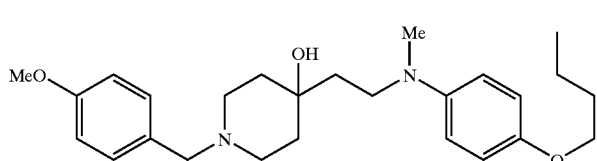

TABLE 7 (1)-continued
Example 27 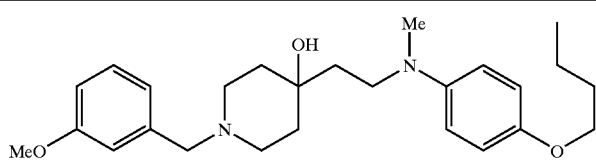
Example 28 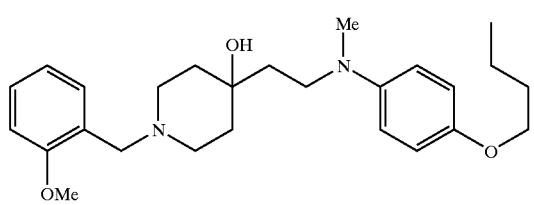
Example 29 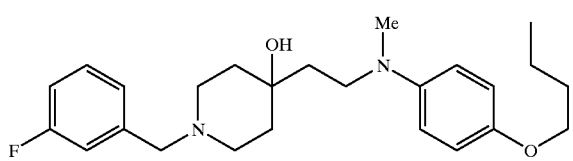
Example 30 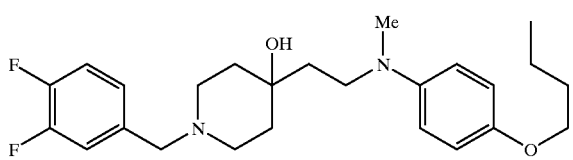
Example 31 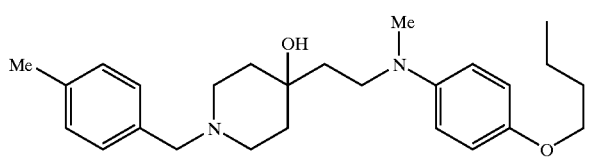
Example 32 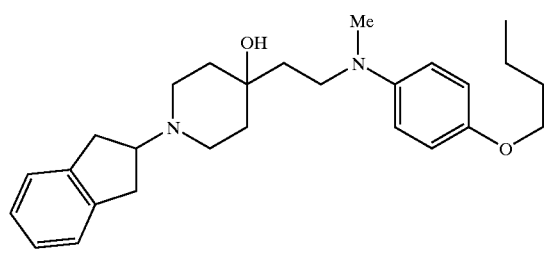
Example 33 Step 1 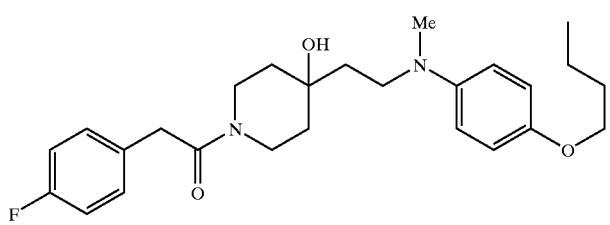
Example 33 Step 2 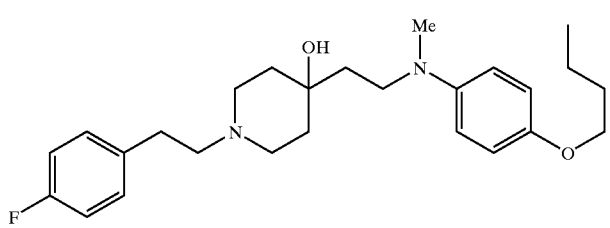

TABLE 7 (1)-continued
Example 34
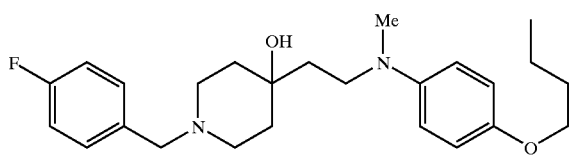
Example 35
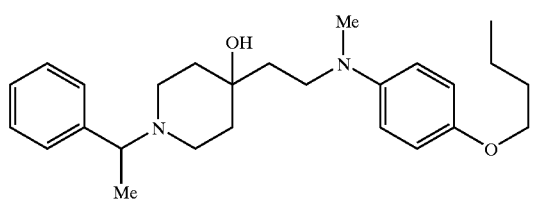
Example 36
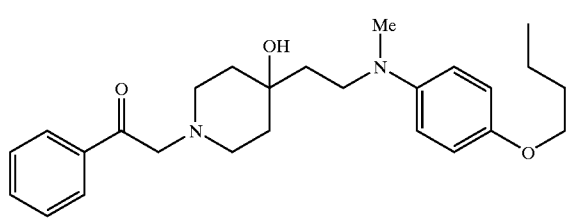
Example 37
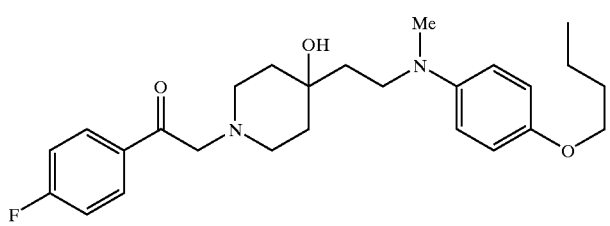
Example 38 Step 1
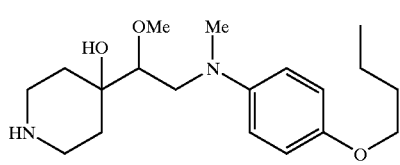
Example 38 Step 2
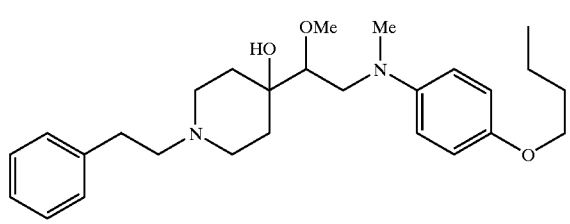
Example 39 Step 1
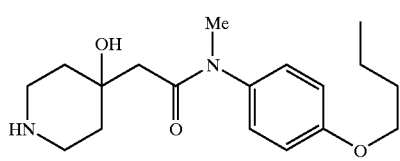
Example 39 Step 2
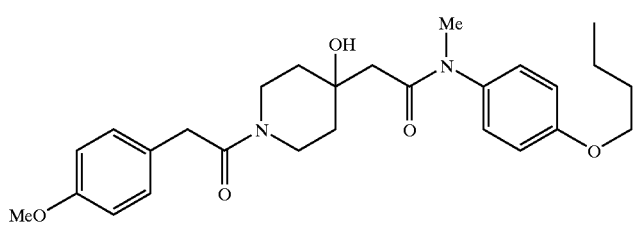

TABLE 7 (1)-continued
Example 39 Step 3
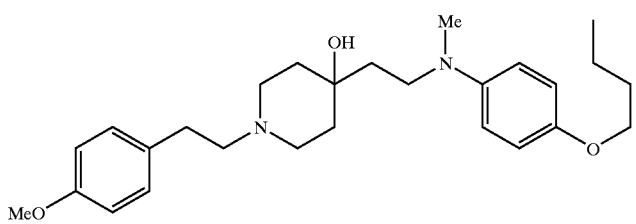
Example 40 Step 1
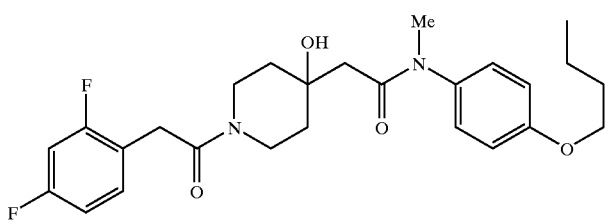
Example 40 Step 2
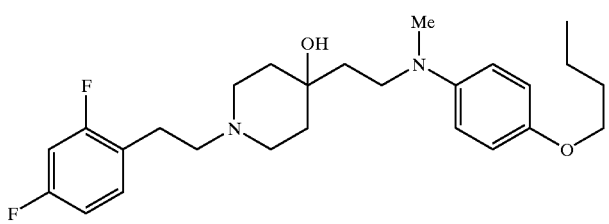
Example 41 Step 1
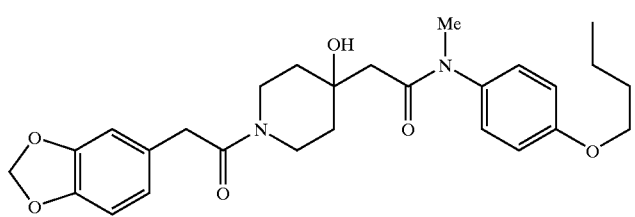
Example 41 Step 2
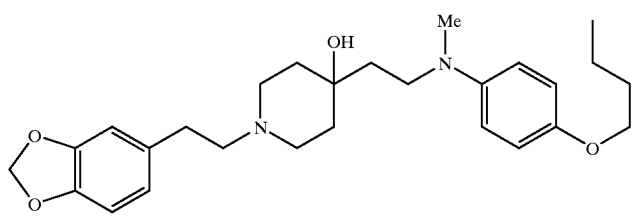
Example 42 Step 1
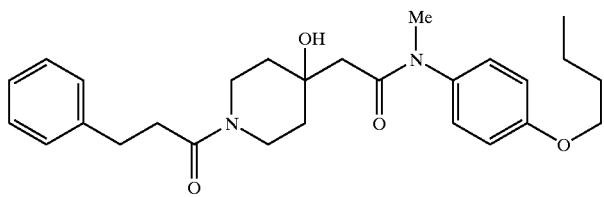
Example 42 Step 2
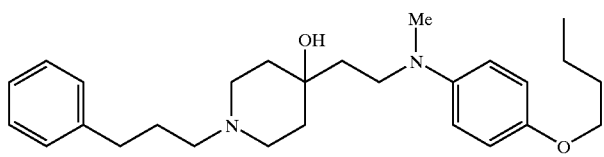

TABLE 7 (1)-continued
Example 43 Step 1 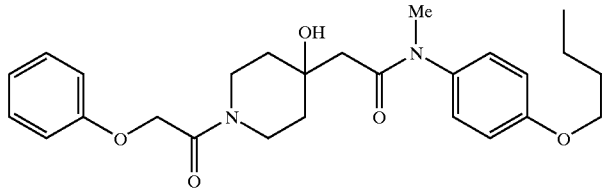
Example 43 Step 2 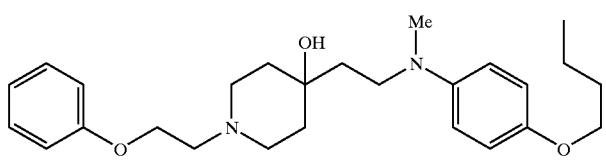
Example 44 Step 1 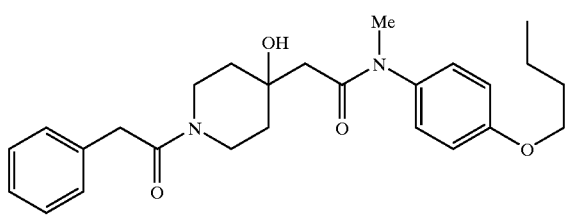
Example 44 Step 2 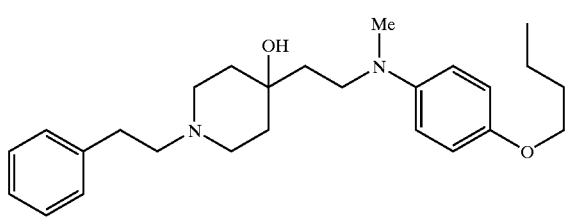
Example 45 Step 1 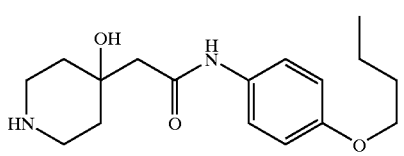
Example 45 Step 2 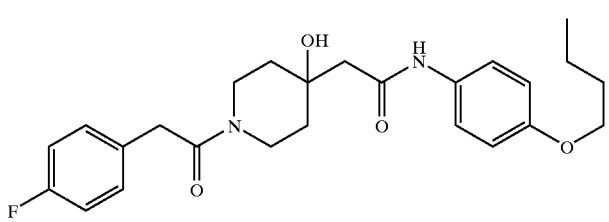
Example 45 Step 3 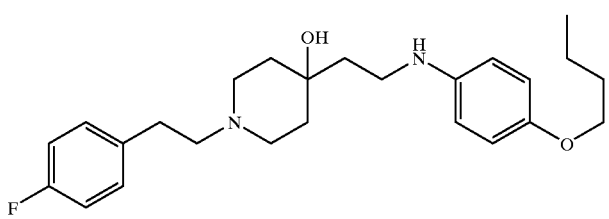
Example 46 Step 1 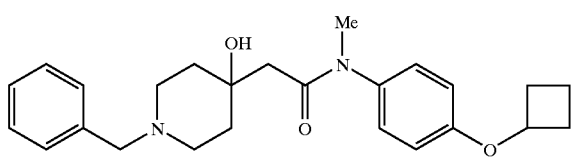

TABLE 7 (1)-continued
Example 46 Step 2
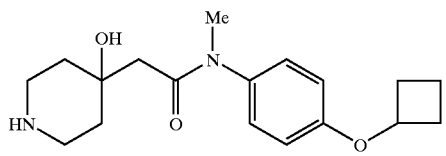
Example 46 Step 3
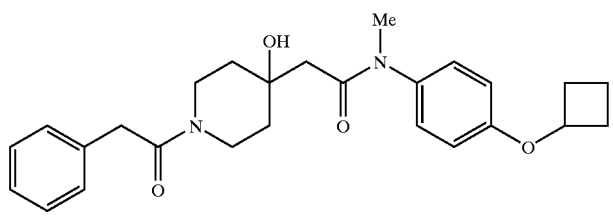
Example 46 Step 4
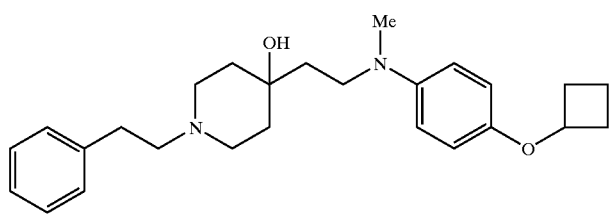
Example 47 Step 1
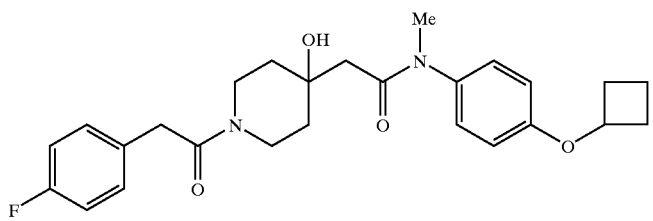
Example 47 Step 2
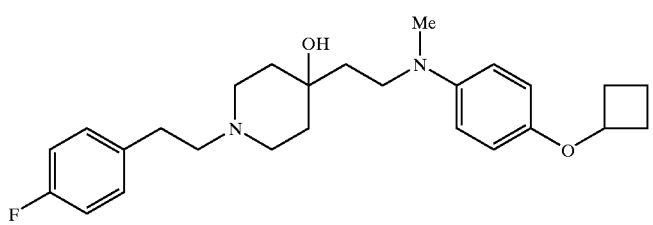
Example 48 Step 1
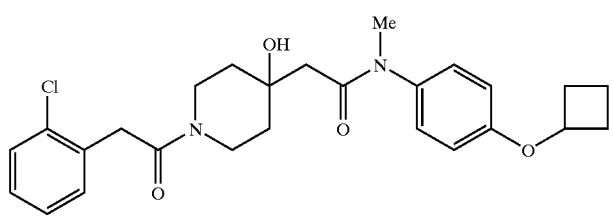
Example 48 Step 2
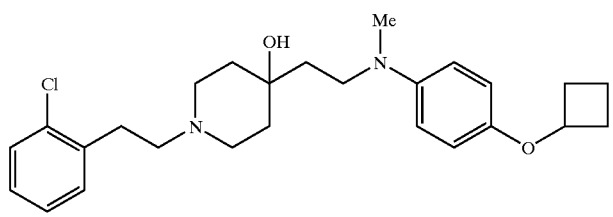

TABLE 7 (1)-continued
Example 49 Step 1 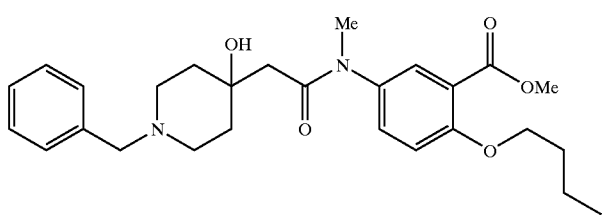
Example 49 Step 2 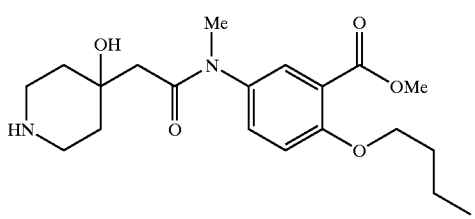
Example 49 Step 3 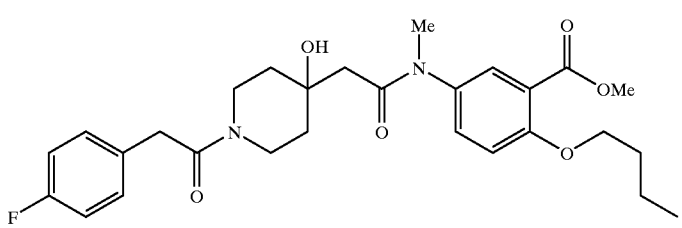
Example 49 Step 4 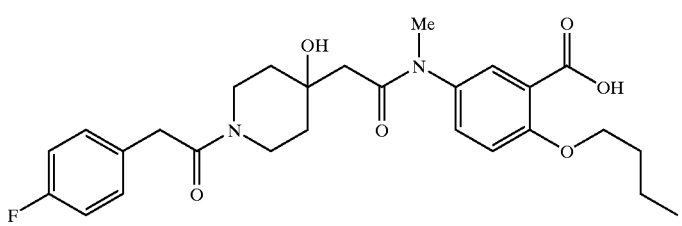
Example 49 Step 5 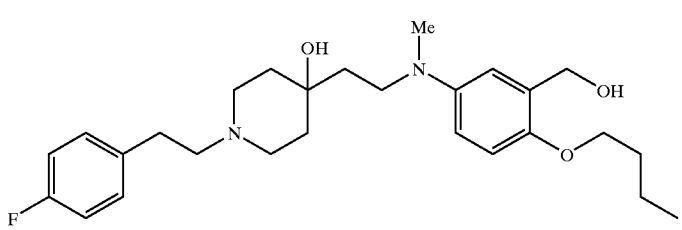
Example 50 Step 1 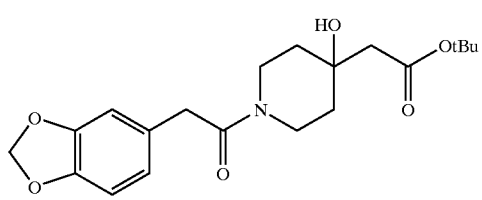
Example 50 Step 2 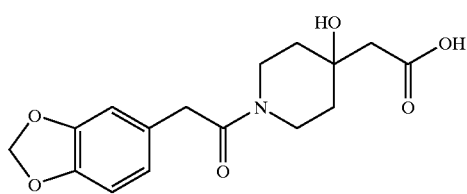

TABLE 7 (1)-continued
Example 50 Step 3
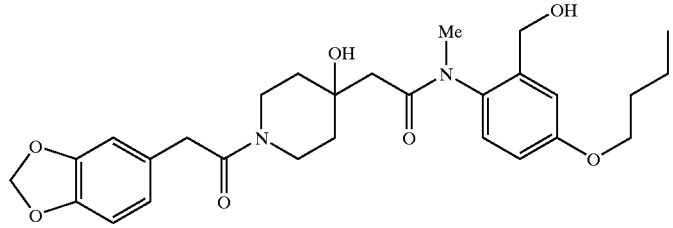
Example 50 Step 4
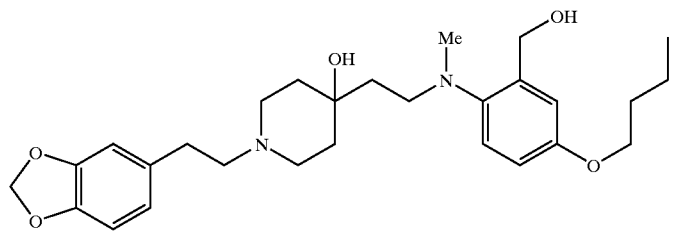
Example 51 Step 1
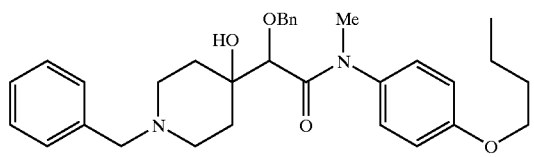
Example 51 Step 2
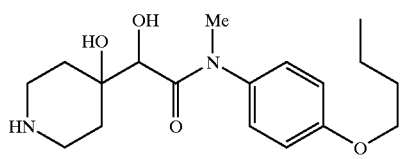
Example 51 Step 3
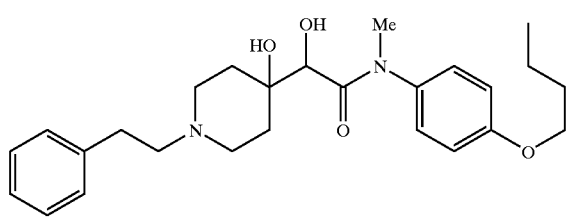
Example 51 Step 4
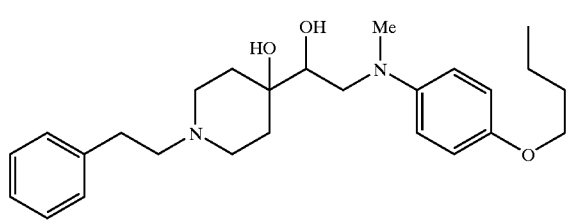
Example 52 Step 1
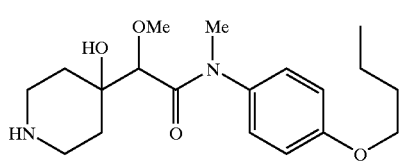

TABLE 7 (1)-continued
Example 52 Step 2 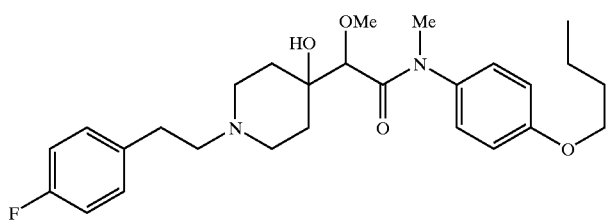
Example 52 Step 3 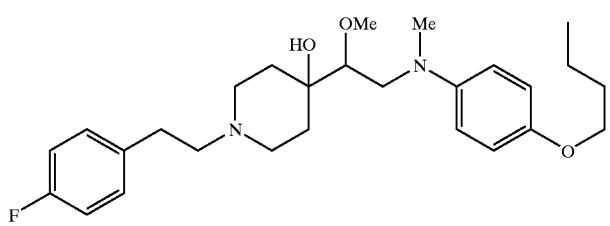
Example 53 Step 1 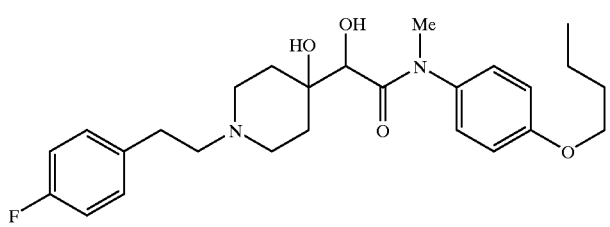
Example 53 Step 2 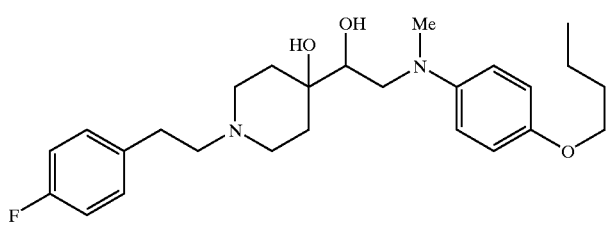
Example 54 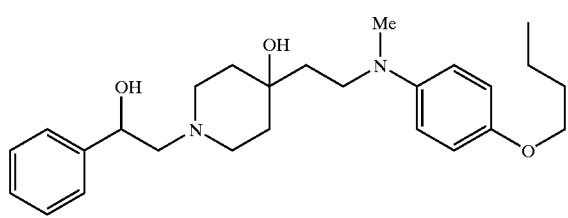
Example 55 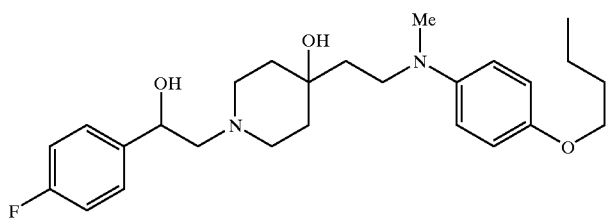
Example 56 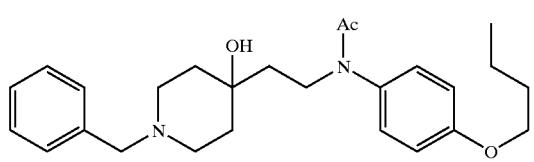

TABLE 7 (1)-continued
Example 57
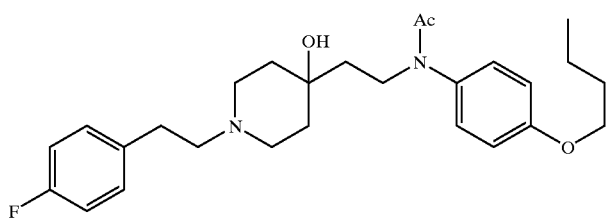
Example 58 Step 1
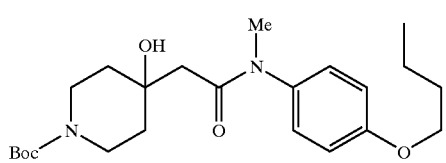
Example 58 Step 2
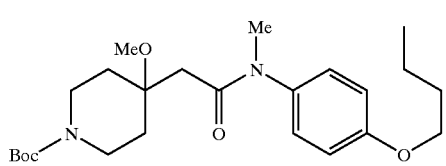
Example 58 Step 3
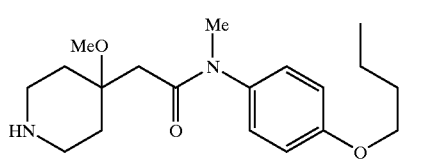
Example 58 Step 4
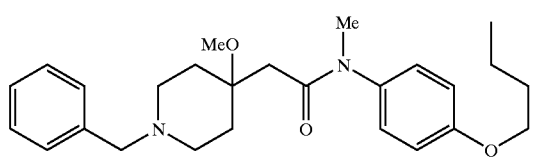
Example 58 Step 5
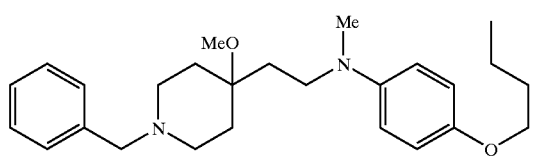
Example 59
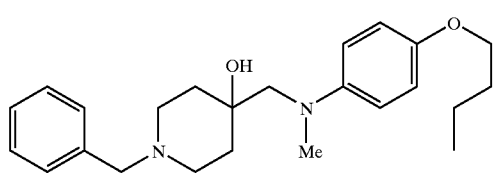
Example 60
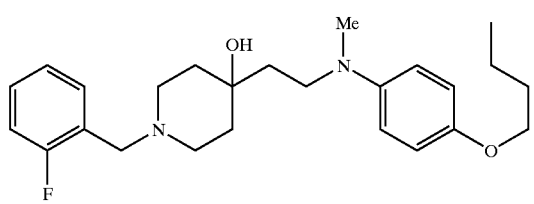
Example 61
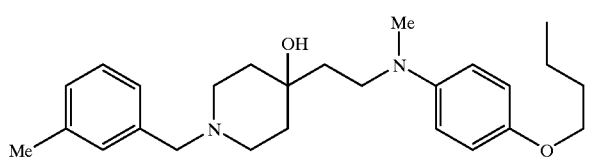

TABLE 7 (1)-continued
Example 62
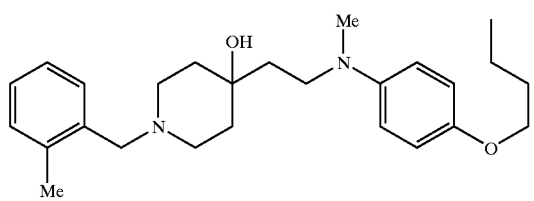
Example 63
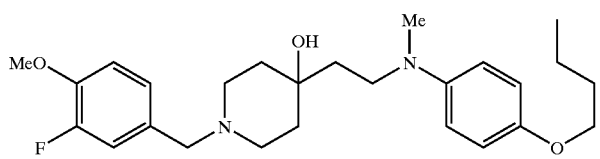
Example 64 Step 1
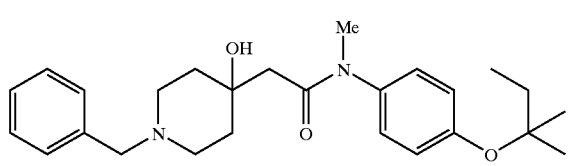
Example 64 Step 2
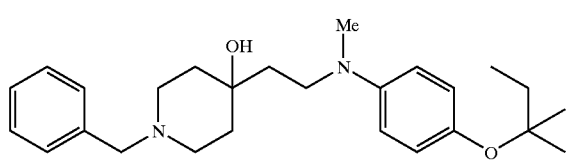
Example 65 Step 1
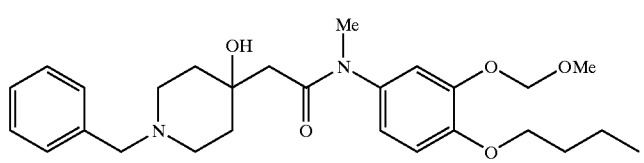
Example 65 Step 2
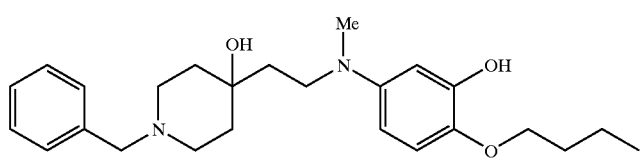
Example 66 Step 1
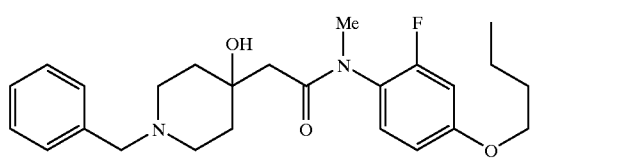
Example 66 Step 2
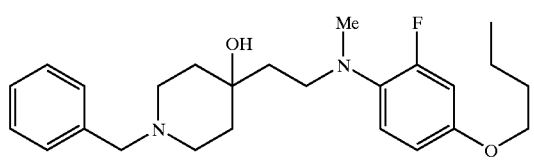
Example 67 Step 1
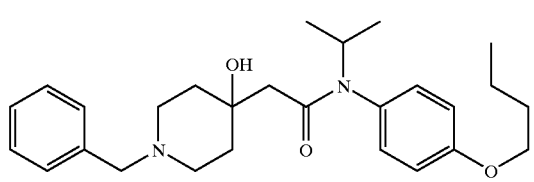

TABLE 7 (1)-continued
Example 67 Step 2
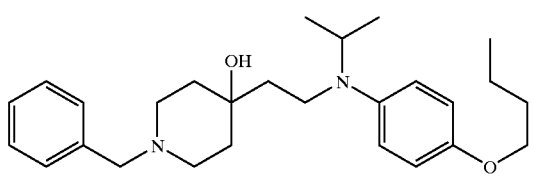
Example 68
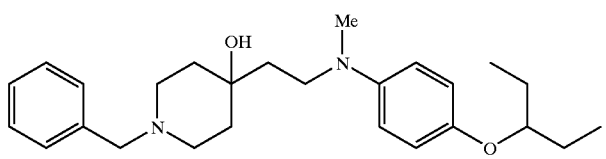
Example 69
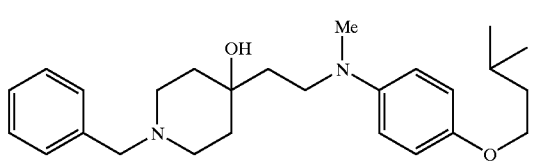
Example 70
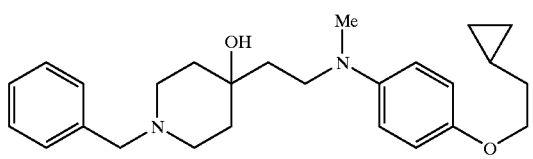
Example 71
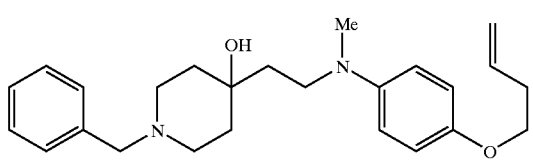
Example 72 Step 1
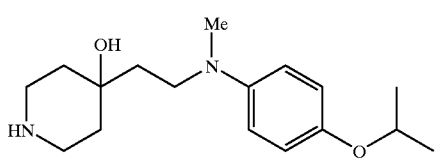
Example 72 Step 2
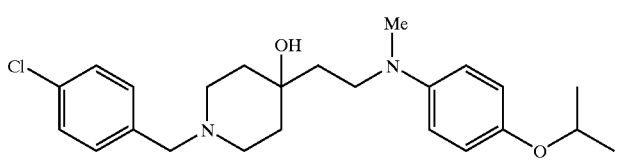
Example 73
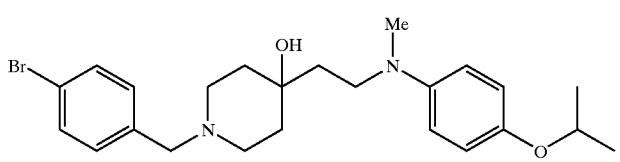
Example 74
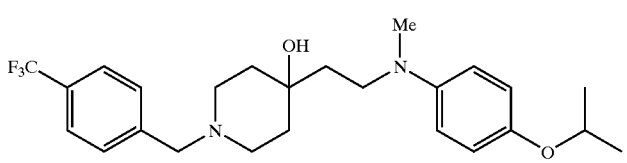

TABLE 7 (1)-continued
Example 75 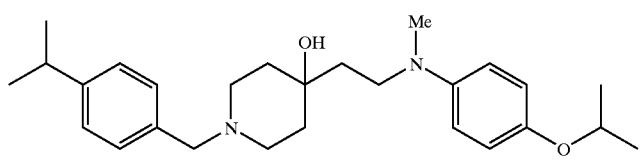
Example 76 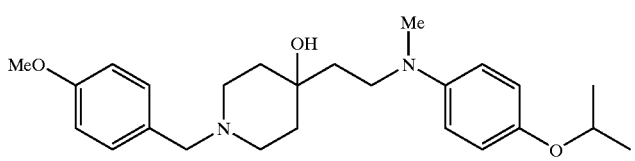
Example 77 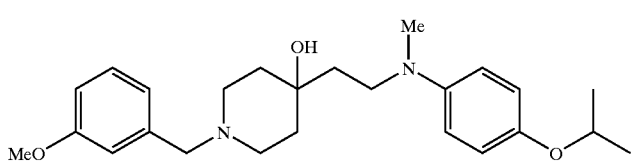
Example 78 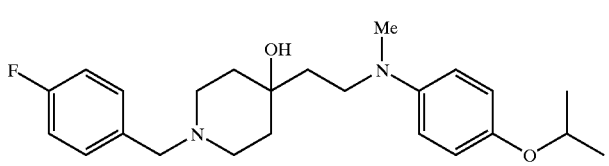
Example 79 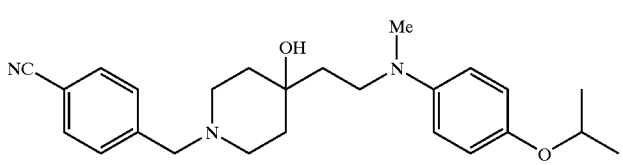
Example 80 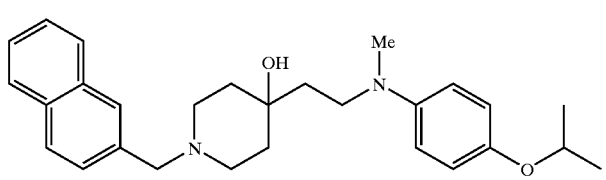
Example 81 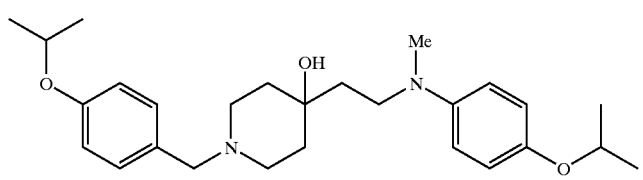
Example 82 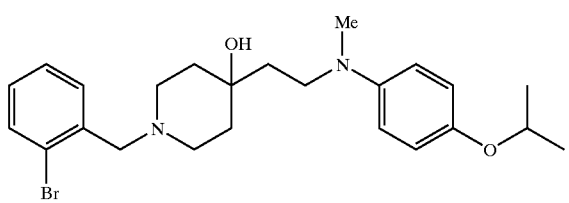
Example 83 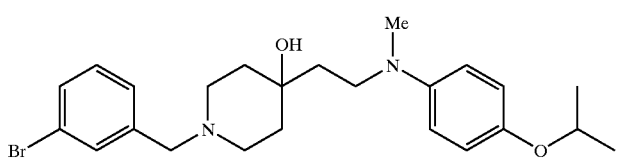

TABLE 7 (1)-continued
Example 84 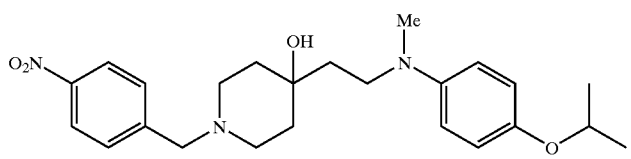
Example 85 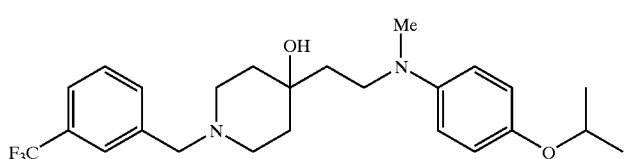
Example 86 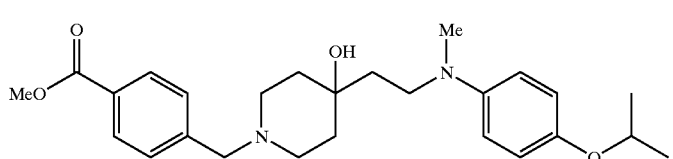
Example 87 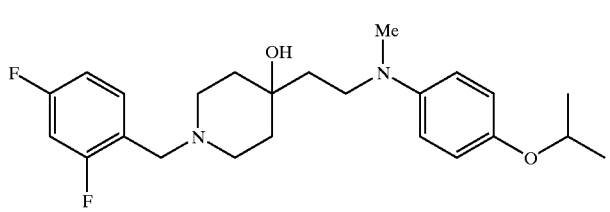
Example 88 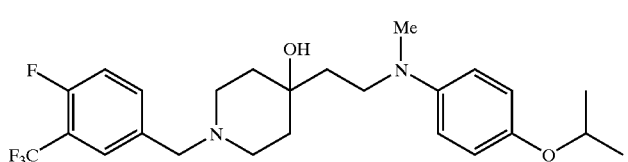
Example 89 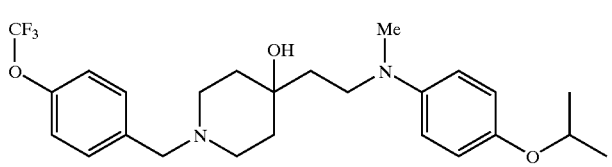
Example 90 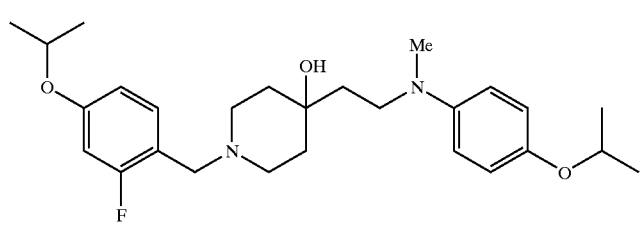
Example 91 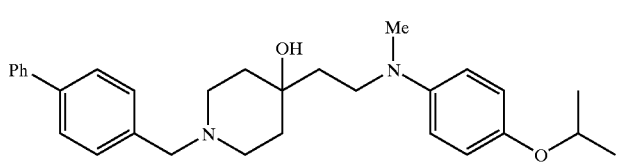
Example 92 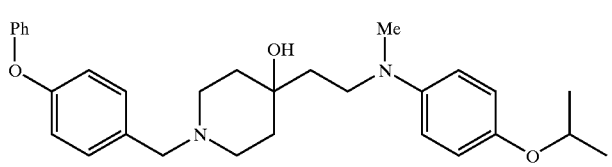

TABLE 7 (1)-continued
Example 93
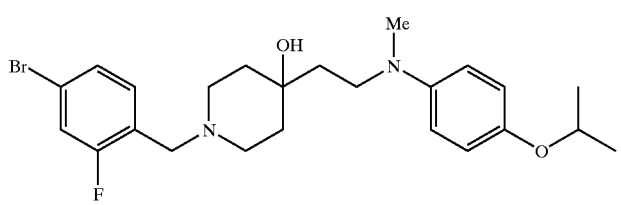
Example 94
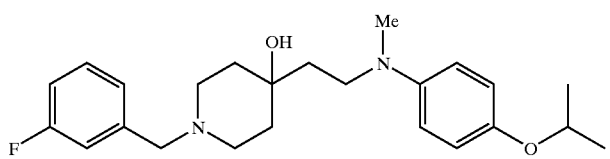
Example 95
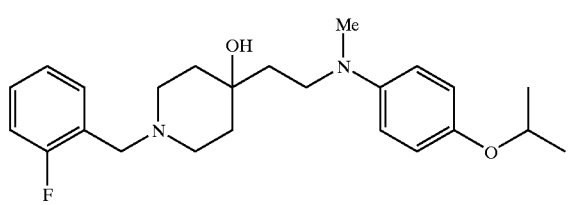
Example 96
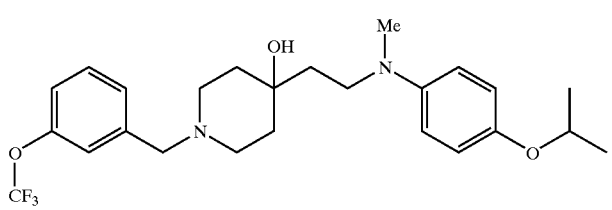
Example 97
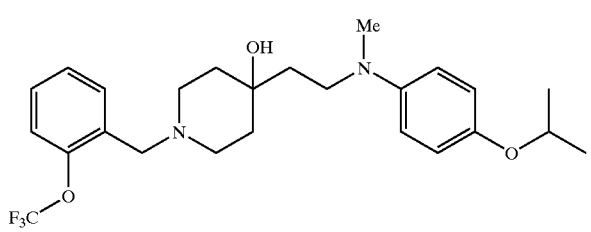
Example 98
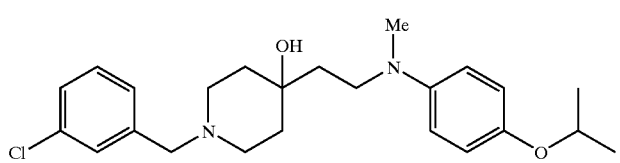
Example 99
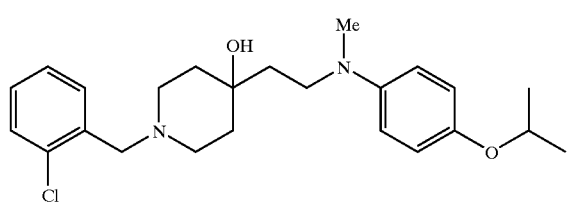
Example 100
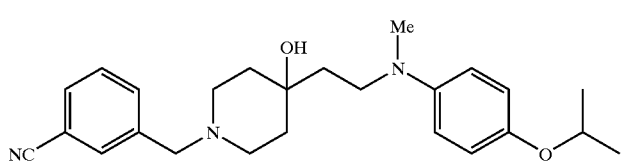

TABLE 7 (1)-continued
Example 101
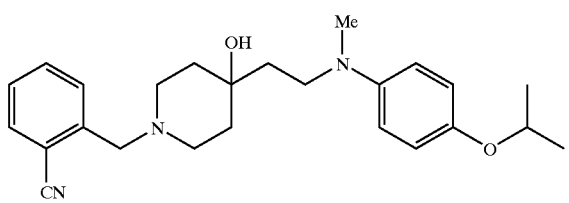
Example 102
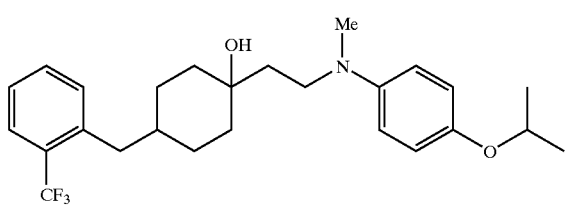
Example 103
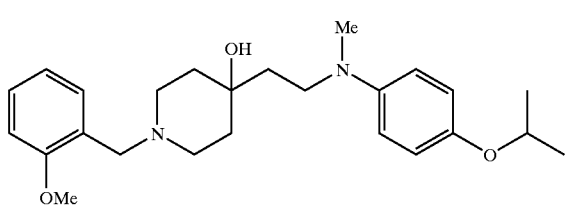
Example 104
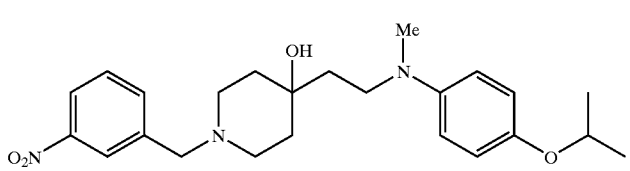
Example 105
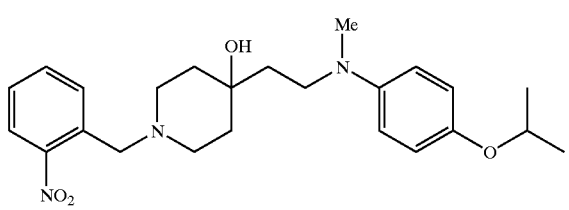
Example 106
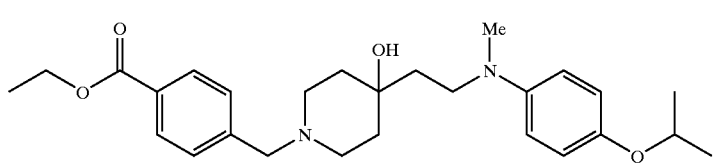
Example 107
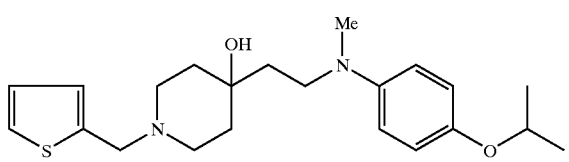
Example 108
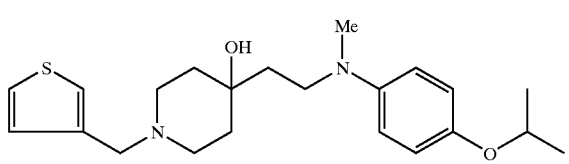

TABLE 7 (1)-continued
Example 109 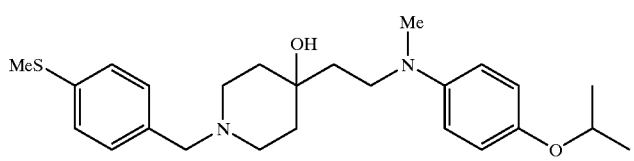
Example 110 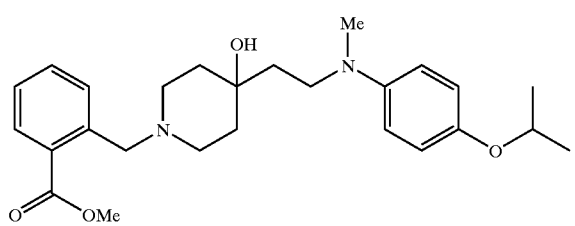
Example 111 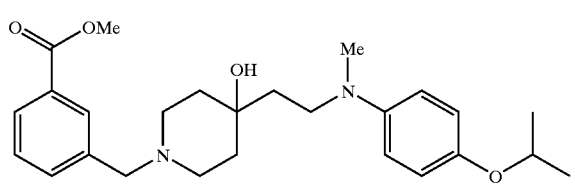
Example 112 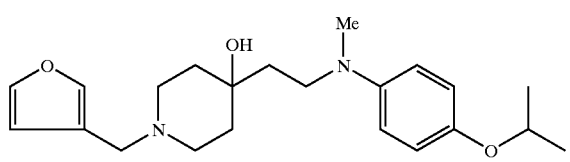
Example 113 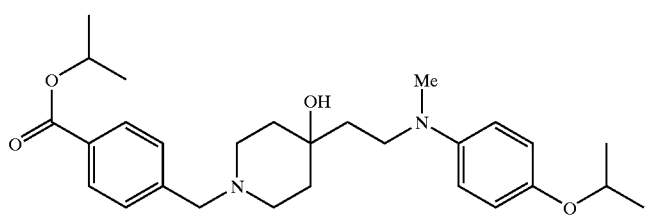
Example 114 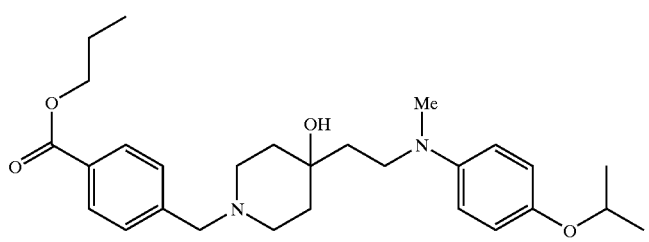
Example 115 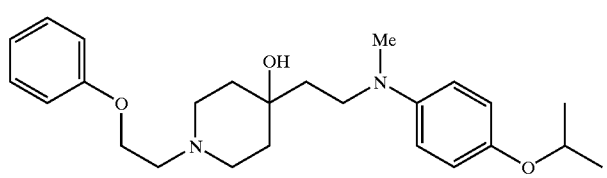
Example 116 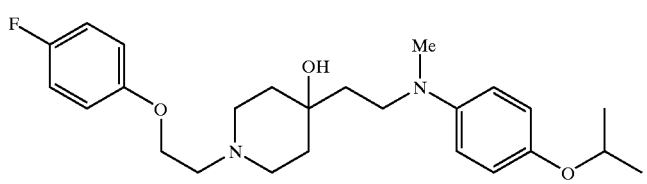

TABLE 7 (1)-continued
Example 117
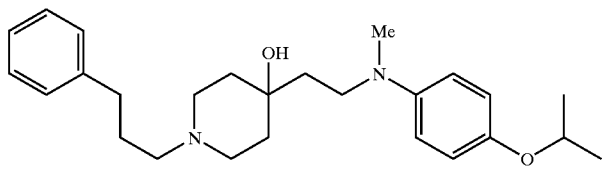
Example 118
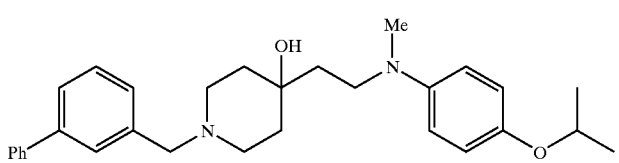
Example 119
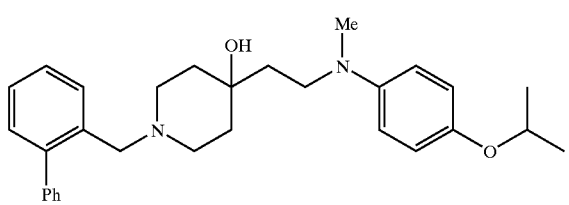
Example 120 Step 1
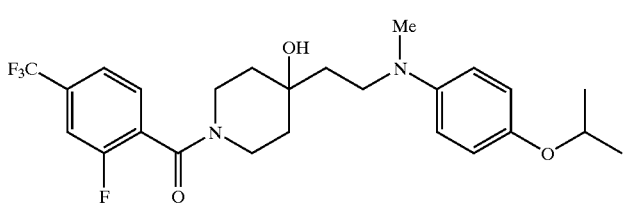
Example 120 Step 2
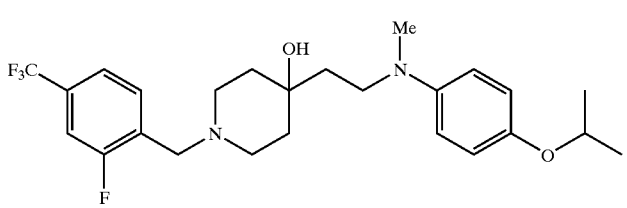
Example 121 Step 1
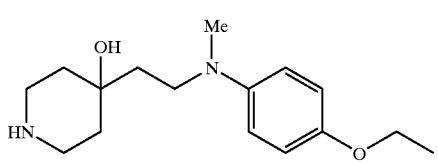
Example 121 Step 2
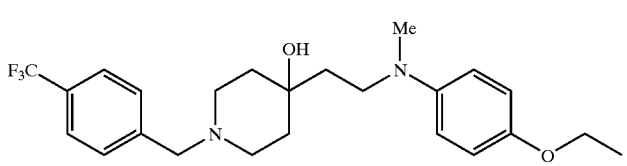
Example 122 Step 1
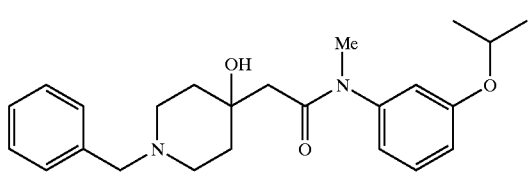

TABLE 7 (1)-continued
Example 122 Step 2
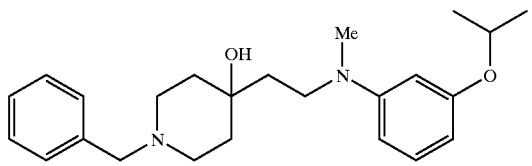
Example 122 Step 3
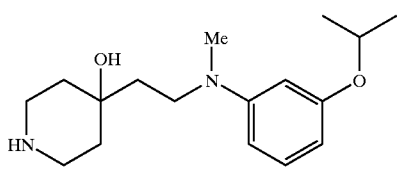
Example 122 Step 4
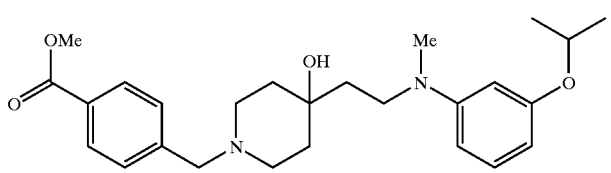
Example 123 Step 1
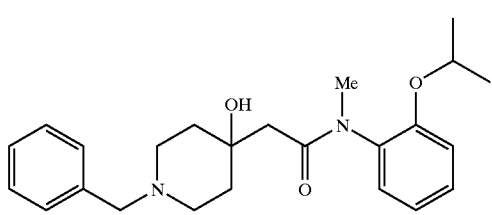
Example 123 Step 2
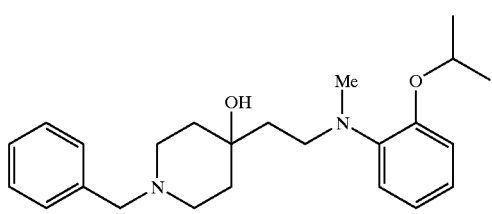
Example 123 Step 3
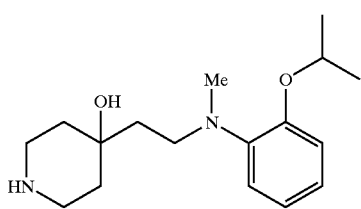
Example 123 Step 4
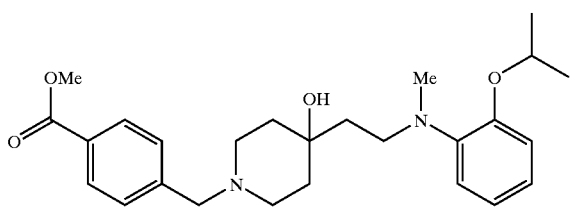
Example 124 Step 1
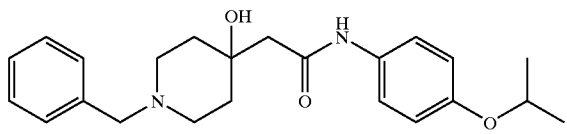

TABLE 7 (1)-continued
| Example 124 Step 2 | 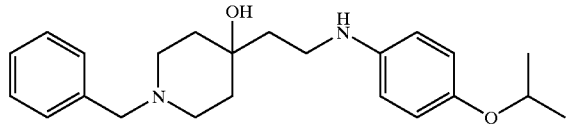 |
| Example 124 Step 3 | 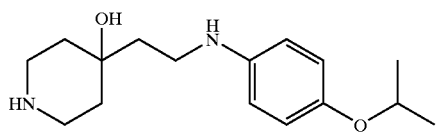 |
| Example 124 Step 4 | 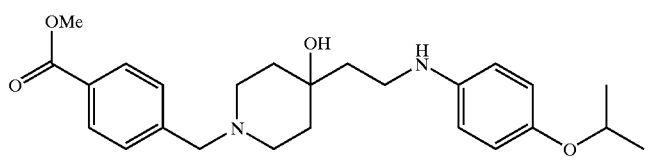 |
| Example 125 | 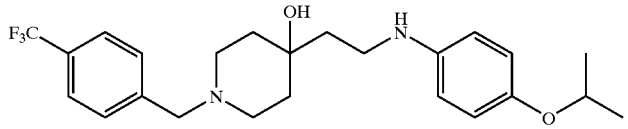 |
| Example 126 Step 1 | 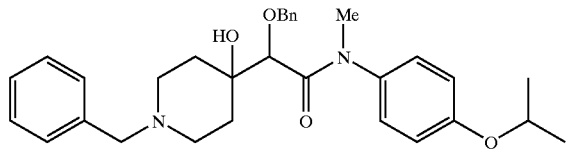 |
| Example 126 Step 2 | 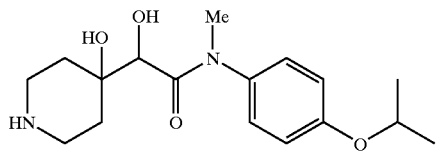 |
| Example 126 Step 3 | 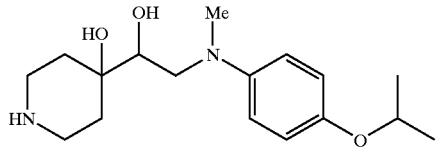 |
| Example 126 Step 4 | 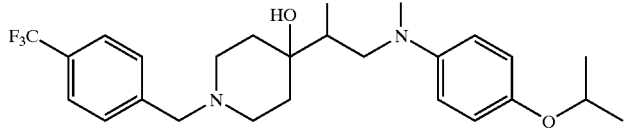 |
| Example 127 Step 1 | 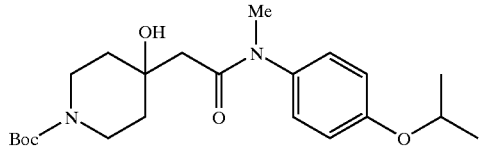 |
| Example 127 Step 2 | 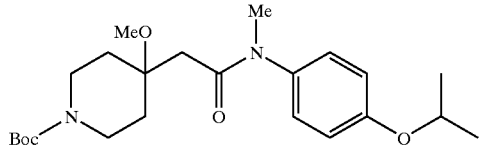 |

TABLE 7 (1)-continued
Example 127 Step 3
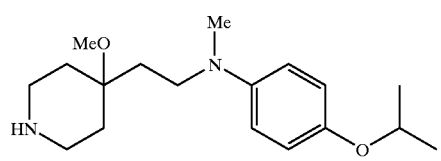
Example 127 Step 4
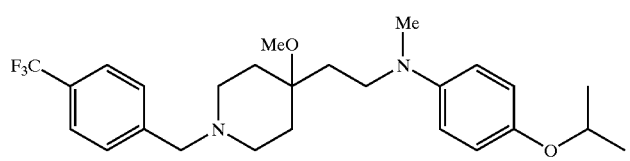
Example 128
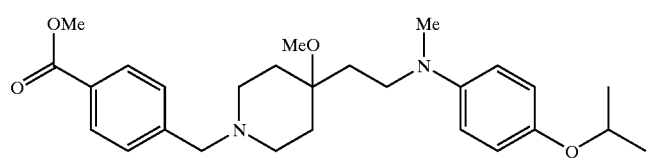
Example 129 Step 1
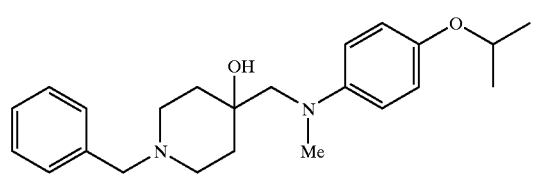
Example 129 Step 2
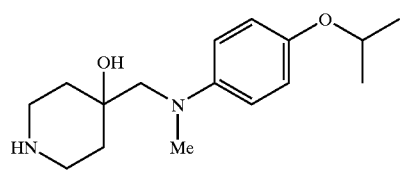
Example 129 Step 3
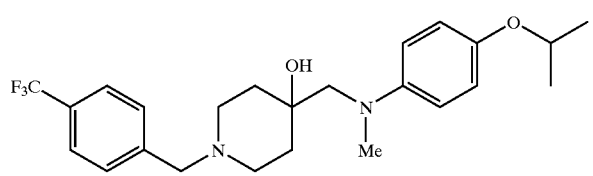
Example 130
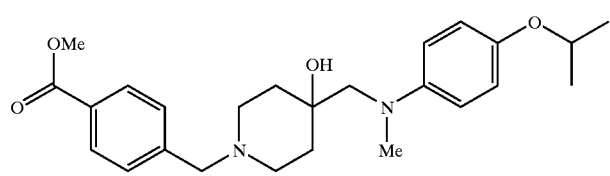
Example 131
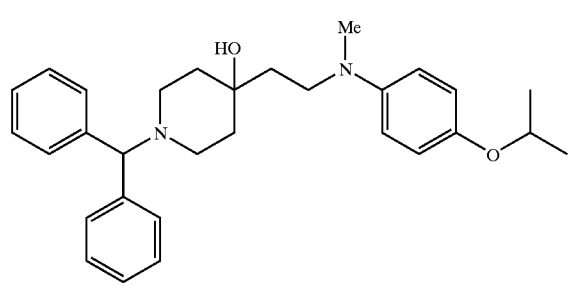

TABLE 7 (1)-continued
Example 132
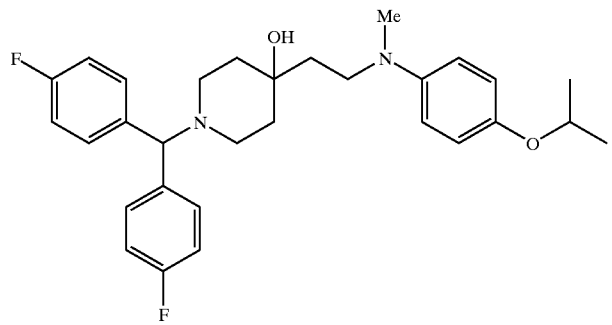
Example 133
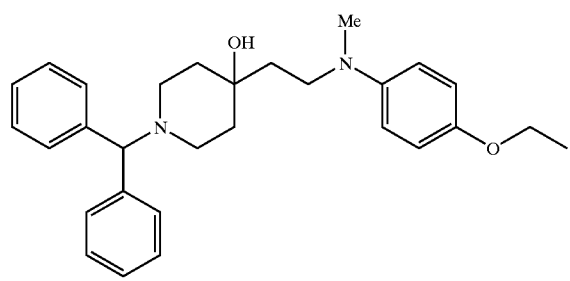
Example 134
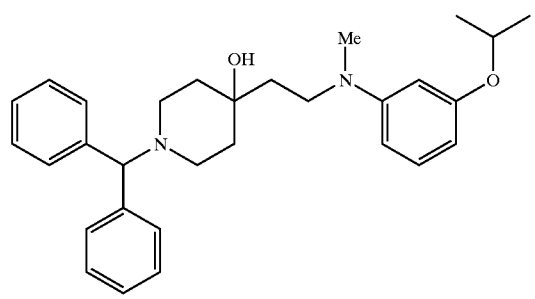
Example 135
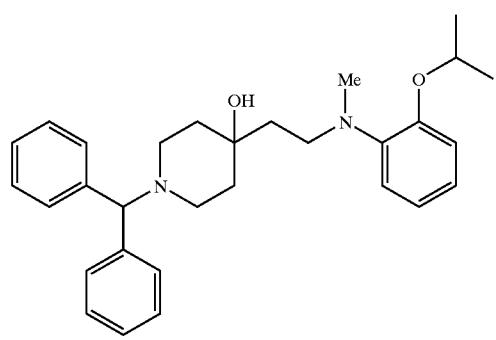
Example 136
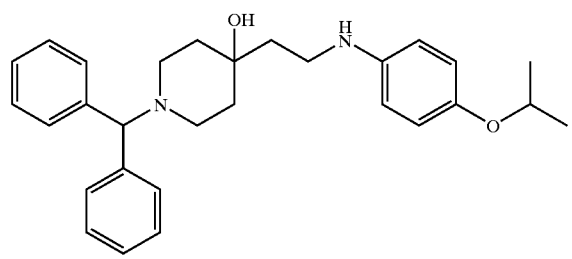

TABLE 7 (1)-continued
Example 137
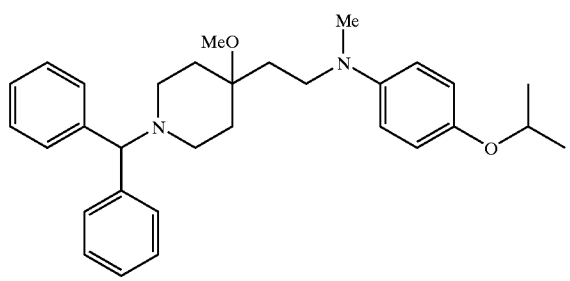
Example 138
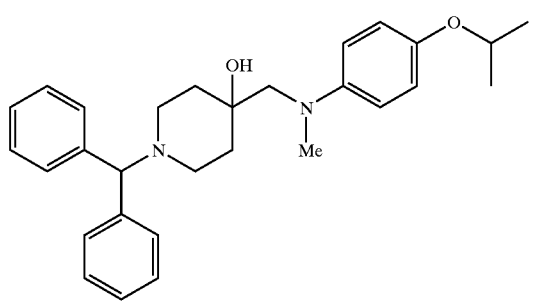
Example 139
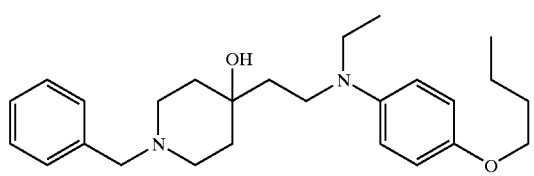
Example 140
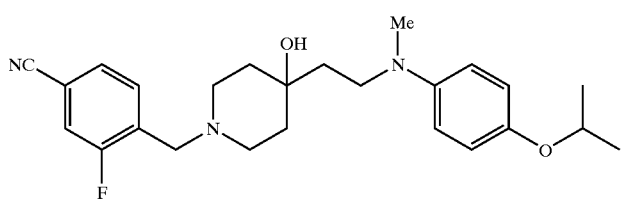
Example 141
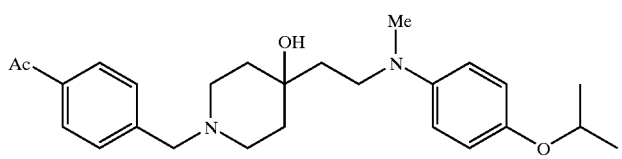
Example 142 Step 1
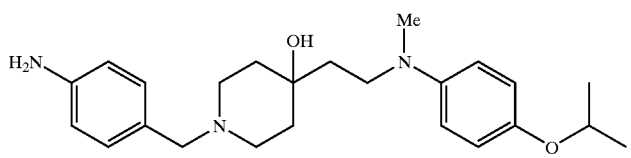
Example 142 Step 2
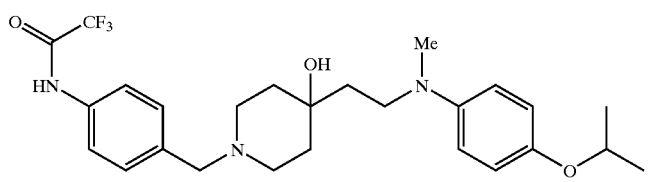

TABLE 7 (1)-continued

Example 143 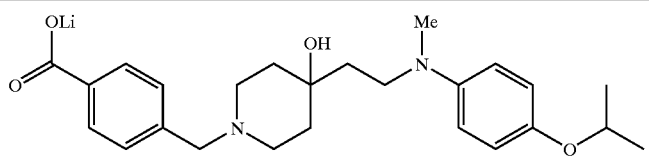

Example 144 dihydrochloride of compound of Example No. 1-2
Example 145 dihydrochloride of compound of Example No. 2-2
Example 146 dihydrochloride of compound of Example No. 3-2
Example 147 dihydrochloride of compound of Example No. 4-2
Example 148 dihydrochloride of compound of Example No. 5-2
Example 149 dihydrochloride of compound of Example No. 6-2
Example 150 dihydrochloride of compound of Example No. 7-2
Example 151 dihydrochloride of compound of Example No. 8-2
Example 152 dihydrochloride of compound of Example No. 9-2
Example 153 dihydrochloride of compound of Example No. 10-2
Example 154 dihydrochloride of compound of Example No. 11-2
Example 155 dihydrochloride of compound of Example No. 12-2
Example 156 dihydrochloride of compound of Example No. 13-2
Example 157 dihydrochloride of compound of Example No. 14-2
Example 158 dihydrochloride of compound of Example No. 15
Example 159 dihydrochloride of compound of Example No. 16
Example 160 dihydrochloride of compound of Example No. 17
Example 161 dihydrochlorlde of compound of Example No. 18
Example 162 dihydrochloride of compound of Example No. 19-2
Example 163 dihydrochloride of compound of Example No. 20
Example 164 dihydrochloride of compound of Example No. 21
Example 165 dihydrochloride of compound of Example No. 22
Example 166 dihydrochloride of compound of Example No. 23
Example 167 trihydrochloride of compound of Example No. 24
Example 168 dihydrochloride of compound of Example No. 25
Example 169 dihydrochloride of compound of Example No. 26
Example 170 dihydrochloride of compound of Example No. 27
Example 171 dihydrochloride of compound of Example No. 28
Example 172 dihydrochloride of compound of Example No. 29
Example 173 dihydrochloride of compound of Example No. 30
Example 174 dihydrochlorlde of compound of Example No. 31
Example 175 dihydrochloride of compound of Example No. 32
Example 176 dihydrochloride of compound of Example No. 33-2
Example 177 dihydrochloride of compound of Example No. 34
Example 178 dihydrochloride of compound of Example No. 35
Example 179 dihydrochloride of compound of Example No. 36
Example 180 dihydrochloride of compound of Example No. 37
Example 181 dihydrochloride of compound of Example No. 38-2
Example 182 dihydrochloride of compound of Example No. 39-3
Example 183 dihydrochloride of compound of Example No. 40-2
Example 184 dihydrochloride of compound of Example No. 41-2
Example 185 dihydrochloride of compound of Example No. 42-2
Example 186 dihydrochloride of compound of Example No. 43-2
Example 187 dihydrochloride of compound of Example No. 44-2
Example 188 dihydrochloride of compound of Example No. 45-3
Example 189 dihydrochloride of compound of Example No. 46-4
Example 190 dihydrochloride of compound of Example No. 47-2
Example 191 dihydrochloride of compound of Example No. 48-2
Example 192 dihydrochloride of compound of Example No. 49-5
Example 193 dihydrochloride of compound of Example No. 50-4
Example 194 dihydrochloride of compound of Example No. 51-4
Example 195 dihydrochloride of compound of Example No. 52-3
Example 196 dihydrochloride of compound of Example No. 53-2
Example 197 dihydrochloride of compound of Example No. 54
Example 198 dihydrochloride of compound of Example No. 55
Example 199 monohydrochloride of compound of Example No. 56
Example 200 monohydrochloride of compound of Example No. 57
Example 201 dihydrochloride of compound of Example No. 58-5
Example 202 dihydrochloride of compound of Example No. 59
Example 203 dihydrochloride of compound of Example No. 60
Example 204 dihydrochloride of compound of Example No. 61
Example 205 dihydrochloride of compound of Example No. 62
Example 206 dihydrochloride of compound of Example No. 63
Example 207 dimaleate of compound of Example No. 3-2
Example 208 monomaleate of compound of Example No. 3-2
Example 209 monomaleate of compound of Example No. 50-4
Example 210 monomaleate of compound of Example No. 59
Example 211 dihydrochloride of compound of Example No. 64-2
Example 212 dihydrochloride of compound of Example No. 65-2
Example 213 dihydrochloride of compound of Example No. 66-2

TABLE 7 (1)-continued

Example 214 dihydrochloride of compound of Example No. 67-2
Example 215 dihydrochloride of compound of Example No. 68
Example 216 dihydrochloride of compound of Example No. 69
Example 217 dihydrochloride of compound of Example No. 70
Example 218 dihydrochloride of compound of Example No. 71
Example 219 dihydrochloride of compound of Example No. 72-2
Example 220 dihydrochloride of compound of Example No. 73
Example 221 dihydrochloride of compound of Example No. 74
Example 222 dihydrochloride of compound of Example No. 75
Example 223 dihydrochloride of compound of Example No. 76
Example 224 dihydrochloride of compound of Example No. 77
Example 225 dihydrochloride of compound of Example No. 78
Example 226 dihydrochloride of compound of Example No. 79
Example 227 dihydrochloride of compound of Example No. 80
Example 228 dihydrochloride of compound of Example No. 81
Example 229 dihydrochloride of compound of Example No. 82
Example 230 dihydrochloride of compound of Example No. 83
Example 231 dihydrochloride of compound of Example No. 84
Example 232 dihydrochloride of compound of Example No. 85
Example 233 dihydrochloride of compound of Example No. 86
Example 234 dihydrochloride of compound of Example No. 87
Example 235 dihydrochloride of compound of Example No. 88
Example 236 dihydrochloride of compound of Example No. 89
Example 237 dihydrochloride of compound of Example No. 90
Example 238 dihydrochloride of compound of Example No. 91
Example 239 dihydrochloride of compound of Example No. 92
Example 240 dihydrochloride of compound of Example No. 93
Example 241 dihydrochloride of compound of Example No. 94
Example 242 dihydrochloride of compound of Example No. 95
Example 243 dihydrochloride of compound of Example No. 96
Example 244 dihydrochloride of compound of Example No. 97
Example 245 dihydrochloride of compound of Example No. 98
Example 246 dihydrochloride of compound of Example No. 99
Example 247 dihydrochloride of compound of Example No. 100
Example 248 dihydrochloride of compound of Example No. 101
Example 249 dihydrochloride of compound of Example No. 102
Example 250 dihydrochloride of compound of Example No. 103
Example 251 dihydrochloride of compound of Example No. 104
Example 252 dihydrochloride of compound of Example No. 105
Example 253 dihydrochloride of compound of Example No. 106
Example 254 dihydrochloride of compound of Example No. 107
Example 255 dihydrochloride of compound of Example No. 108
Example 256 dihydrochloride of compound of Example No. 109
Example 257 dihydrochloride of compound of Example No. 110
Example 258 dihydrochloride of compound of Example No. 111
Example 259 dihydrochloride of compound of Example No. 112
Example 260 dihydrochloride of compound of Example No. 113
Example 261 dihydrochloride of compound of Example No. 114
Example 262 dihydrochloride of compound of Example No. 115
Example 263 dihydrochloride of compound of Example No. 116
Example 264 dihydrochloride of compound of Example No. 117
Example 265 dihydrochloride of compound of Example No. 118
Example 266 dihydrochloride of compound of Example No. 119
Example 267 dihydrochloride of compound of Example No. 120-2
Example 268 dihydrochloride of compound of Example No. 121-2
Example 269 dihydrochloride of compound of Example No. 122-4
Example 270 dihydrochloride of compound of Example No. 123-4
Example 271 dihydrochloride of compound of Example No. 124-4
Example 272 dihydrochloride of compound of Example No. 125
Example 273 dihydrochloride of compound of Example No. 126-4
Example 274 dihydrochloride of compound of Example No. 127-4
Example 275 dihydrochloride of compound of Example No. 128
Example 276 dihydrochloride of compound of Example No. 129-3
Example 277 dihydrochloride of compound of Example No. 130
Example 278 dihydrochloride of compound of Example No. 131
Example 279 dihydrochloride of compound of Example No. 132
Example 280 dihydrochlorlde of compound of Example No. 133
Example 281 dihydrochloride of compound of Example No. 134
Example 282 dihydrochloride of compound of Example No. 135
Example 283 dihydrochloride of compound of Example No. 136
Example 284 dihydrochloride of compound of Example No. 137
Example 285 dihydrochloride of compound of Example No. 138
Example 286 dihydrochloride of compound of Example No. 139
Example 287 dihydrochloride of compound of Example No. 140
Example 288 dihydrochloride of compound of Example No. 141
Example 289 dihydrochloride of compound of Example No. 142-2

Example of Formulation

Examples of formulation containing the compounds according to the present invention are shown below. However, the present invention is by no means restricted to these examples.

(Formulation Example 1: Tablet)

| | |
|---|---|
| The compound in the Example 146 | 100 g |
| Lactose | 350 g |
| Potato starch | 120 g |
| Polyvinyl alcohol | 15 g |
| Magnesium stearate | 15 g |

After weighing each component above, the compound in the Example 146, lactose and potato starch are homogeneously mixed. An aqueous solution of polyvinyl alcohol is added to this mixture, and granules are prepared by a wet granulation method. The granules are dried, mixed with magnesium stearate, and formed into tablets each weighing 300 mg by press-molding.

(Formulation Example 2: Capsules)

| | |
|---|---|
| The compound in the Example 177 | 50 g |
| Lactose | 435 g |
| Magnesium stearate | 15 g |

The components above are homogeneously mixed after weighing. Three hundred milligram each of the mixture is filled in an appropriate hard capsule by using a capsule-encapsulating machine to prepare a capsule drug.

(Formulation Example 3: Injections)

| | |
|---|---|
| The compound in the Example 210 | 2 g |
| Propylene glycol | 200 g |
| Distilled water for injection | proper volume |

The compound in the example 210 is dissolved in propylene glycol after weighing each component. Aseptic water for injection is added to make a total volume of 1000 mL, and 5 mL each of the aqueous solution is dispensed in a 10 mL ampoule after aseptic filtration, followed by fusing the ampoule to prepare an injection.

(Formulation Example 4: Suppository)

| | |
|---|---|
| The compound in the Example 198 | 100 g |
| Polyethylene glycol 1500 | 180 g |
| Polyethylene glycol 4000 | 720 g |

After grinding the compound in the example 198 in a mortar into fine powder, suppositories each weighing 1 g are prepared by hot-melting.

(Formulation Example 5: Powder)

| | |
|---|---|
| The compound in the Example 162 | 200 g |
| Lactose | 790 g |
| magnesium stearate | 10 g |

A powder containing 20% of the effective ingredient is prepared by mixing each component homogeneously after weighing.

INDUSTRIAL APPLICABILITY

The compounds according to the present invention showed effectiveness in the arrhythimia model of animals and did not almost affect on the electrocardiogram of normal animals, and therefore they are useful as preventive and/or therapeutic agents of arrhythimia that do not suppress transient sodium current of the cardiac muscle and do not manifest proarrhythimic activity, and agents for preventing sudden death.

In the disease conditions of atrial flutter and atrial fibrillation, atrial flutter and atrial fibrillation are liable to occur by onset of electrical remodeling due to atrial flutter and atrial fibrillation themselves. No clinical applications of the drugs for suppressing electrical remodeling have been carried out, and excess influx of sodium and calcium is suggested as the cause of this phenomenon. Veratrine generates, or the other hand, a persistent sodium current by suppressing inactivation of the sodium channel incorporated in the cardiac muscle cells. Consequently, since veratrine causes contracture as a result of increased intracellular sodium concentration followed by increased intracellular calcium concentration through a sodium/calcium exchange transport system, the compounds according to the present invention seem to suppress the persistent sodium current. Judging from these facts, the compounds according to the present invention that suppress excess sodium influx caused by the persistent sodium current are useful for preventing progress of disease conditions of atrial flutter and atrial fibrillation.

The compounds according to the present invention has an action to suppress contracture of the isolated cardiac muscle cells as well as persistent sodium current. Therefore, the compounds according to the present invention are effective for therapy and alleviation of symptoms such as heart failure, angina pectoris, myocardial infarction, cardiovascular disorder accompanied with revascularization by PTCA/PTCR/CABG, injury of cardiomyocytes caused by ischemia-reperfusion (except severe arrhythimia), acute phase of cerebral infarction, cerebral hemorrhage transient cerebral ischemia, subarachnoid hemorrhage, head trauma, sequela of surgical operation of the brain, cerebrovascular disorder such as sequela of cerebral arteriosclerosis, disorder of implanted organs after implantation, syndromes caused by temporary shut-down of the flood stream in surgical operation of the organs, convulsion, epilepsy, cerebrovascular dementia and senile dementia, neuralgia, migraine, neuropathic pain, intoxication by digitalis, monkshood or pyrethroid insecticides. The compounds according to the present invention are also applicable to hyperkalemic periodic paralysis that is a congenital disease caused by the persistent sodium current, myotonia congenital and long QT syndrome.

What is claimed is:

1. A compound represented by the following formula (I):

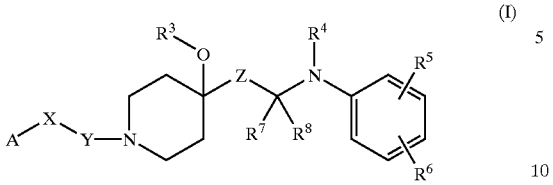

wherein

A represents a phenyl group, naphthyl group or monocyclic aromatic heterocyclic group each substituted by $R^1$ and $R^2$; $R^1$ and $R^2$ each independently represent hydrogen atom, halogen atom, trifluoromethyl group, cyano group, lower alkoxycarbonyl group, amino group unsubstituted or mono- or di-substituted by lower alkyl group, lower alkanoylamino group unsubstituted or substituted by fluorine atom, unprotected or protected hydroxyl group, lower alkoxy group, lower alkyl group, trifluoromethoxy group, nitro group, phenyl group, phenoxy group, unprotected or protected carboxyl group, carbamoyl group unsubstituted or mono- or di-substituted by lower alkyl group, lower alkanoyl group, lower alkylthio group, lower alkylsulfinyl group, lower alkylsulfonyl group and sulfamoyl group unsubstituted or mono- or di-substituted by lower alkyl group, or $R^1$ and $R^2$ together represent alkylenedioxy group;

$R^3$ represents hydrogen atom or Lower alkyl group;

$R^4$ represents hydrogen atom, lower alkyl group or lower alkanoyl group;

$R^5$ and $R^6$ each independently represent hydrogen atom, halogen atom, lower alkoxy group unsubstituted or mono-substituted by unprotected or protected hydroxyl group, lower alkyl group, unsubstituted or mono-substituted by unprotected or protected hydroxyl group, phenoxy group, lower alkenyloxy group or unprotected or protected hydroxyl group;

X represents a single bond, a group: —CH(OH)—, oxygen atom or carbonyl group;

Y represents lower alkylene group, lower alkylidene group or benzylidene group substituted by $R^1$, Y may form 5 or 6-membered ring together with X and carbon atoms on a benzene ring when A is phenyl group;

Z represents a single bond or methylene group unsubstituted or substituted by a group arbitrarily selected from a group comprising lower alkyl group, lower alkoxy group or unprotected or protected hydroxyl group; and $R^7$ and $R^8$ each independently represent hydrogen atom or lower alkyl groups, provided that $R^5$ and $R^6$ do not simultaneously represent hydrogen atoms, or a salt thereof.

2. A compound or a salt thereof as claimed in claim 1, wherein the binding position of $R^5$ is a para-position (4-position) relative to —$NR^4$, $R^7$ and $R^8$ each represent hydrogen atom, X is a single bond, and Y represents $C_1$ or $C_2$ alkylene group or benzylidene group substituted by $R^1$.

3. A compound or a salt thereof as claimed in claim 1, wherein A represents phenyl group or thienyl group each substituted by $R^1$ and $R^2$, and Z is a single bond or methylene group.

4. A compound or a salt thereof as claimed in claims 1, wherein $R^1$ represents hydrogen atom, halogen atom, trifluoromethyl group, cyano group, lower alkoxycarbonyl group or trifluoromethoxy group, $R^2$ represents hydrogen atom or halogen atom, $R^3$ represents hydrogen atom, $R^5$ represents $C_{2-6}$ alkoxy group, $R^6$ represents hydrogen atom, Y represents methylene group or benzylidene group substituted by $R^1$.

5. A compound or a salt thereof as claimed in claim 1, wherein the compound or the salt is selected from benzyl-4-[2-[N-(4-n-butoxyphenyl)-N-methylamino] ethyl]-piperidin-4-ol;

1-benzyl-4-[2-[N-methyl-N-(4-n-propoxylphenyl)amino] ethyl]-piperidin-4-ol;

4-(2-[N-(4-n-butoxyphenyl)-N-methylamino]ethyl]-1-(4-chlorophenylmethyl) piperidin-4-ol;

4-[2-[N-(4-n-butoxyphenyl)-N-methylamino]ethyl]-1-[4-(trifluoromethy) phenylmethyl]piperidin-4-ol;

4-[2-(N-(4-n-butoxyphenyl)-N-methylamino]ethyl]-1-(4-cyanophenylmethyl) piperidin-4-ol;

4-[2-[N-(4-n-butoxyphenyl)-N-methylamino]ethyl]-1-(4-methoxycarbonyl-phenylmethyl)piperidin-4-ol;

4-[2-[N-(4-n-butoxyphenyl)-N-methylamino]ethyl]-1-(3-florophenylmethyl) piperidin-4-ol;

4-[2-[N-(4-n-butoxyphenyl)-N-methylamino]ethyl]-1-(3,4-difluorophenyl-methyl)piperidin-4-ol;

4-[2-[N-(4-n-butoxyphenyl)-N-methylamino]ethyl]-1-(4-fluorophenylmethyl) piperidin-4-ol;

4-[2-[N-(4-n-butoxyphenyl)-N-methylamino]ethyl]-1-(2-fluorophenylmethyl) piperidin-4-ol;

1-(4-chlorophenylmethyl)-4-[2-[N-methyl-N-(4-isopropoxyphenyl)amino]ethyl]piperidin-4-ol;

1-(4-bromophenylmethyl)4-[2-[N-methyl-N-(4-isopropoxyphenyl)amino]ethyl]piperidin-4-ol;

4-[2-[N-methyl-N-(4-isopropoxyphenyl)amino]ethyl]-1-(4-trifluoromethyl) phenylmethyl]piperidin-4-ol;

1-(4-fluorophenylmethyl)-4-[2-[N-methyl-N-(4-isopropoxyphenyl)amino]ethyl]piperidin-4-ol;

1(4-cyanophenylmethyl)-4-[2-[N-methyl-N-(4-isopropoxyphenyl)amino]ethyl]piperidin-4-ol;

4-[2-[N-methyl-N-(4-isopropoxyphenyl)amino]ethyl]-1-(4 nitrophenylmethyl) piperidin-4-ol;

1-[4-(methoxycarbonyl)phenylmethyl)-4-[2-[N-methyl-N-(4-isopropoxy phenyl)amino]ethyl]piperidin-4-ol;

1-[4-fluoro-3-(trifluoromethyl)-4-[2-[N-menthyl-N-(4-isopropoxy phenyl)amino]ethyl]piperidin-4-ol;

1-(4-bromo-2-fluorophenylmethyl)-4-[2-[N-methyl-N-(4-iso-propoxyphenyl) amino]ethyl]piperidin-4-ol;

4-[2-[N-methyl-N-(4-isopropoxyphenyl)amino]ethyl]-1-(2-thienylmethyl) piperidin-4-ol;

4-[2-[N-methyl-N-(4-isopropoxyphenyl)amino]ethyl]-1-(3-thienylmethyl) piperidin-4-ol;

1-[2-(methoxycarbonyl)phenylmethyl)-4-[2-[N-methyl-N-(4-isopropoxy-phenyl)amino]ethyl]piperidin-4-ol;

1-[3-(methoxycarbonyl)phenylmethyl)-4-[2-[N-methyl-N-(4-isopropoxy-phenyl)amino]ethyl]piperidin-4-ol;

4-[2-[N-methyl-N-(4-isopropoxyphenyl)amino]ethyl]-1-(4-isopropoxy-carbonyl)phenylmethyl]piperidin-4-ol;

1-[2-fluoro-4-(trifluoromethyl)phenylmethyl]-4-[2-[N-methyl-N-(4-iso-propoxyphenyl)amino]ethyl) piperidin-4-ol;

4-[2-[N-methyl-N-(4-ethoxyphenyl)amino]ethyl]-1-[4-(trifluoromethyl) phenylmethyl]piperidin-4-ol;

1-diphenylmethyl-4-[2-[N-methyl-N-(4-isopropoxyphenyl)amino]ethyl]piperidin-4-ol;

1-bis(4-flourophenylmethyl-4-[2-[N-methyl-N-(4-isopropoxyphenyl) amino]ethyl]piperidin-4-ol; and diphenylmethyl-4-[2-[N-(4-ethoxyphenyl)-N-methylamino]ethyl]piperidin-4-ol.

6. Pharmaceutical compositions characterized by containing a therapeutically effective amount of a compound of claim 1 or pharmaceutically acceptable salt thereof.

7. A method for treating arrhythmia comprising administering to a patient in need thereof a therapeutically effective amount of a compound of claim 1 or pharmaceutically acceptable salt thereof.

8. A compound or a salt thereof as claimed in claim 2, wherein

A represents phenyl group or thienyl group each substitute by $R^1$ and $R^2$, and Z is a single bond or methylene group.

9. A compound or a salt thereof as c aimed in claim 2, wherein $R^1$ represents hydrogen atom, halogen atom, trifluoromethyl group, cyano group, lower alkoxycarbonyl group or trifluoromethoxy group, $R^2$ represents hydrogen atom or halogen atom, $R^3$ represents hydrogen atom, $R^5$ represents $C_{2-6}$ alkoxy group, $R^6$ represents hydrogen atom, and Y represents methylene group or benzylidene group substituted by $R^1$.

10. A compound or a salt thereof as claimed in claim 3, wherein $R^1$ represents hydrogen atom, halogen atom, trifluoromethyl group, cyano group, lower alkoxycarbonyl group or trifluoromethoxy group, $R^2$ represents hydrogen atom or halogen atom, $R^3$ represents hydrogen atom, $R^5$ represents $C_{2-6}$ alkoxy group, $R^6$ represents hydrogen atom, and Y represents methylene group or benzylidene group substituted by $R^1$.

* * * * *